US008404874B2

(12) United States Patent
DeLuca et al.

(10) Patent No.: US 8,404,874 B2

(45) Date of Patent: Mar. 26, 2013

(54) (20R,25S)-2-METHYLENE-19,26-DINOR-1α,25-DIHYDROXYVITAMIN $D_3$ IN CRYSTALLINE FORM

(75) Inventors: Hector F. DeLuca, Deerfield, WI (US); Pawel Grzywacz, Madison, WI (US); James B. Thoden, Madison, WI (US); Hazel Holden, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 19 days.

(21) Appl. No.: 13/247,600

(22) Filed: Sep. 28, 2011

(65) Prior Publication Data

US 2012/0083614 A1 Apr. 5, 2012

Related U.S. Application Data

(60) Provisional application No. 61/388,536, filed on Sep. 30, 2010.

(51) Int. Cl.
*C07C 401/00* (2006.01)
*A61K 31/59* (2006.01)

(52) U.S. Cl. ........................................ 552/653; 514/167

(58) Field of Classification Search .................. 514/167; 552/653

See application file for complete search history.

(56) References Cited

U.S. PATENT DOCUMENTS

| | | | | |
|---|---|---|---|---|
| 5,086,191 | A | 2/1992 | DeLuca et al. | |
| 5,536,713 | A | 7/1996 | DeLuca et al. | |
| 5,843,928 | A | 12/1998 | DeLuca et al. | |
| 5,969,156 | A * | 10/1999 | Briggs et al. | 548/537 |
| 6,673,372 | B1 * | 1/2004 | Radesca et al. | 424/489 |
| 7,528,122 | B2 | 5/2009 | DeLuca et al. | |
| 7,803,789 | B2 * | 9/2010 | Deluca et al. | 514/167 |
| 7,947,666 | B2 * | 5/2011 | DeLuca et al. | 514/167 |
| 8,114,901 | B2 * | 2/2012 | Bush et al. | 514/414 |
| 2004/0072886 | A1 * | 4/2004 | Reguri et al. | 514/381 |
| 2004/0132743 | A1 * | 7/2004 | Reddy et al. | 514/255.04 |
| 2007/0105885 | A1 * | 5/2007 | Pathi et al. | 514/283 |
| 2009/0170820 | A1 * | 7/2009 | DeLuca et al. | 514/167 |

OTHER PUBLICATIONS

Byrn et al., Pharmaceutical Solids: A Strategic Approach to Regulatory Considerations., Pharmaceutical Research., vol. 12, No. 7, 1995.

Baggiolini et al, Stereocontrolled Total Synthesis of 1 [alpha],25-Dihydroxycholecaliferol and 1 [alpha],25-Dihydroxyergocalciferol. J. Org. Chem., vol. 51, pp. 3098-3108, 1986.

Lythgoe et al, Calciferol and its Relatives. Part 22. A Direct Total Synthesis of Vitamin D2 and Vitamin D3. J. Chem. Soc. Perkin I., pp. 590, 1978.

Lythgoe, Synthetic Approaches to Vitamin D and its Relatives. Chem. Soc. Rev., vol. 9, pp. 449, 1983.

Perlman et al, Novel Synthesis of 19-Nor-Vitamin D Compounds, Tetrahedron Letters, vol. 32, No. 52, pp. 7663-7666, 1991.

(Continued)

*Primary Examiner* — Sabiha N Qazi

(74) *Attorney, Agent, or Firm* — Andrus, Sceales, Starke & Sawall, LLP

(57) ABSTRACT

A method of purifying (20R,25S)-2-methylene-19,26-dinor-1α,25-dihydroxyvitamin $D_3$ to obtain (20R,25S)-2-methylene-19,26-dinor-1α,25-dihydroxyvitamin $D_3$ in crystalline form. The method includes the steps of preparing a solvent of methanol and water, dissolving a product containing (20R,25S)-2-methylene-19,26-dinor-1α,25-dihydroxyvitamin $D_3$ to be purified in the solvent, cooling the solvent and dissolved product below ambient temperature for a sufficient amount of time to form a precipitate of (20R,25S)-2-methylene-19,26-dinor-1α,25-dihydroxyvitamin $D_3$ crystals, and recovering the (20R,25S)-2-methylene-19,26-dinor-1α,25-dihydroxyvitamin $D_3$ crystals.

16 Claims, 5 Drawing Sheets

O25A C21A C23A C25A C26A C12A C20A C18A C22A C24A C11A C13A C17A C9A C14A C16A C8A C15A C7A C6A C5A C4A C10A C3A C1A O2A C2A O1A C19A

OTHER PUBLICATIONS

Sicinski et al, New 1alpha,25-Dihydroxy-19-Norvitamin D3 Compounds of High Biological Activity Sunthesis and Biological Evaluation of 2-Hydroxymethyl, 2-Methyl, and 2-Methylene Analogs, J. Med. Chem, vol. 41, pp. 4662-4674, 1998.

Sardina et al, Studies on the Synthesis of Side-Chain Hydroxylated Metabolites of Vitamin D. 2. Stereocontrolled Synthesis of 25-Hydroxyvitamin D2. J. Org. Chem., vol. 51, pp. 1264-1269, 1986.

Toh et al, Studies on a Convergent Route to Side-Chain Analogues of Vitamin D:25-Hydroxy-23-oxavitamin D3. J. Org. Chem., vol. 48, pp. 1414-1417, 1988.

International Search Report and Written Opinion, PCT International Application No. PCT/US2012/042225, mailed Mar. 1, 2012.

* cited by examiner

(20R,25S)-2-METHYLENE-19,26-DINOR-1α,25-DIHYDROXYVITAMIN $D_3$ IN CRYSTALLINE FORM

STATEMENT REGARDING FEDERALLY SPONSORED RESEARCH OR DEVELOPMENT

This invention was made with government support under DK047814 awarded by the National Institutes of Health. The government has certain rights in the invention.

BACKGROUND OF THE INVENTION

The present invention relates to purification of organic compounds, and more particularly to the purification of (20R,25S)-2-Methylene-19,26-Dinor-1α,25-Dihydroxyvitamin $D_3$ (referred to herein as "NEL") by preparing it in crystalline form.

Purification of organic compounds, especially those designated for pharmaceutical use, is of considerable importance for chemists synthesizing such compounds. Preparation of the compound usually requires many synthetic steps and, therefore, the final product can be contaminated not only with side-products derived from the last synthetic step of the procedure but also with compounds that were formed in previous steps. Even chromatographic purification, which is a very efficient but relatively time-consuming process, does not usually provide compounds which are sufficiently pure to be used as drugs.

Depending on the method used to synthesize 1α-hydroxyvitamin D compounds, different minor undesirable compounds can accompany the final product. Thus, for example, if direct C-1 hydroxylation of 5,6-trans geometric isomer of vitamin D is performed, followed by $SeO^2$/NMO oxidation and photochemical irradiation [see Andrews et al., *J. Org. Chem.* 51, 1635 (1986); Calverley et al., *Tetrahedron* 43, 4609 (1987); Choudry et al, *J. Org. Chem.* 58, 1496 (1993)], the final 1α-hydroxyvitamin D product can be contaminated with 1β-hydroxy- as well as 5,6-trans isomers. If the method consists of C-1 allylic oxidation of the 4-phenyl-1,2,4-triazoline-3,5-dione adduct of the previtamin D compound, followed by cycloreversion of the modified adduct under basic conditions [Nevinckx et al., *Tetrahedron* 47, 9419 (1991); Vanmaele et al, *Tetrahedron* 41, 141 (1985) and 40, 1179 (1994); Vanmaele et al., *Tetrahedron Lett.* 23. 995 (1982)], one can expect that the desired 1α-hydroxyvitamin can be contaminated with the previtamin 5(10), 6,8-triene and 1β-hydroxy isomer. One of the most useful C-1 hydroxylation methods, of very broad scope and numerous applications, is the experimentally simple procedure elaborated by Paaren et al. [see *J. Org. Chem.* 45, 3253 (1980) and *Proc. Natl. Acad. Sci. U.S.A.* 75, 2080 (1978)]. This method consists of allylic oxidation of 3,5-cyclovitamin D derivatives, readily obtained from the buffered solvolysis of vitamin D tosylates, with $SeO_2$/t-BuOOH and subsequent acid-catalyzed cycloreversion to the desired 1αhydroxy compounds. Taking into account this synthetic path it is reasonable to assume that the final product can be contaminated with 1α-hydroxy epimer, 5,6-trans isomer and the previtamin D form. 1α-hydroxyvitamin $D_4$ is another undesirable contaminant found in 1α-hydroxyvitamin D compounds synthesized from vitamin $D_2$ or from ergosterol. 1α-hydroxyvitamin $D_4$ results from C-1 oxidation of vitamin $D_4$, which in turn is derived from contamination of the commercial ergosterol material. Typically, the final product may contain up to about 1.5% by weight 1α-hydroxyvitamin $D_4$. Thus, a purification technique that would eliminate or substantially reduce the amount of 1α-hydroxyvitamin $D_4$ in the final product to less than about 0.1-0.2% would be highly desirable.

The vitamin D conjugated triene system is not only heat- and light-sensitive but it is also prone to oxidation, leading to the complex mixture of very polar compounds. Oxidation usually happens when a vitamin D compound has been stored for a prolonged time. Other types of processes that can lead to a partial decomposition of vitamin D compounds consist of some water-elimination reactions; their driving force is allylic (1α-) and homoallylic (3β-) position of the hydroxy groups. The presence of such above-mentioned oxidation and elimination products can be easily detected by thin-layer chromatography.

Usually, all 1α-hydroxylatation procedures require at least one chromatographic purification. However, even chromatographically purified 1αhydroxyvitamin D compounds, although showing consistent spectroscopic data, suggesting homogeneity, do not meet the purity criteria required for therapeutic agents that can be orally, parenterally or transdermally administered. Therefore, it was evident that a suitable method of purification of the 1αhydroxylated vitamin D compound NEL is required.

SUMMARY OF THE INVENTION

The present invention relates to a method of purifying NEL by means of crystallization to obtain NEL in crystalline form. The solvent plays a crucial role in the crystallization process, and is typically an individual liquid substance or a suitable mixture of different liquids. For crystallizing NEL, the most appropriate solvent and/or solvent system is characterized by the following factors:

(1) low toxicity;

(2) low boiling point;

(3) significant dependence of solubility properties with regard to temperature (condition necessary for providing satisfactory crystallization yield); and (4) relatively low cost.

Interestingly, hexane, so frequently used for crystallization purposes, was found less suitable for crystallization of NEL. However, it was found that a mixture of two liquids, namely water and methanol, in amounts of from about 10% water with about 90% methanol to about 30% water with about 70% methanol, was most useful for the crystallization of NEL. In particular, it, was determined that a mixture of 20% water with 80% methanol (by volume) performed well. The water/methanol solvent mixture was also easy to remove by evaporation or other well known methods. In all cases the crystallization process occurred easily and efficiently; and the precipitated crystals were sufficiently large to assure their recovery by filtration or other means.

DETAILED DESCRIPTION OF THE INVENTION

The present invention provides (20R,25S)-2-methylene-19,26-dinor-1α,25-dihydroxyvitamin $D_3$ (NEL) in crystalline form, a pharmacologically important compound, characterized by the formula I shown below:

I

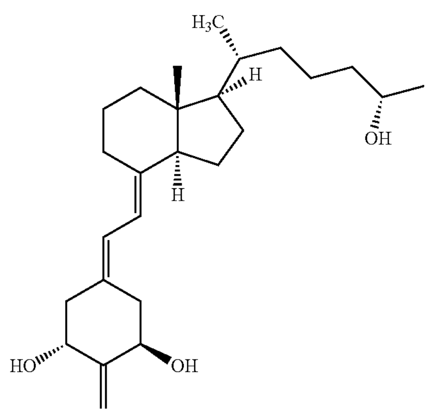

The present invention also provides a valuable method of purification of NEL. The purification technique involves obtaining the NEL product in crystalline form by utilizing a crystallization procedure wherein the NEL material to be purified is dissolved using as the solvent a mixture comprised of methanol and water in amounts of from about 10% water with about 90% methanol to about 30% water with about 70% methanol, by volume. Preferably the mixture comprises 80% methanol and 20% water (by volume). The solvent and dissolved product containing (20R,25S)-2-methylene-19,26-dinor-1α,25-dihydroxyvitamin D3 (NEL) to be purified may then be cooled to about −20° C., or may in a first step be maintained at ambient temperature for a period of time (1 hour to 1 week) and then cooled in a second step to about −20° C. In either case, the solution is then maintained at about −20° C. for up to 7 weeks. Thereafter, the solvent can be removed by evaporation, with or without vacuum, or other means as is well known, or the resultant crystals may be filtered from the mother liquor. The technique can be used to purify a wide range of final products containing NEL obtained from any known synthesis thereof, and in varying concentrations, i.e. from microgram amounts to kilogram amounts. As is well known to those skilled in this art, the amount of solvent utilized should be minimized and/or adjusted according to the amount of NEL to be purified.

Figure 2:
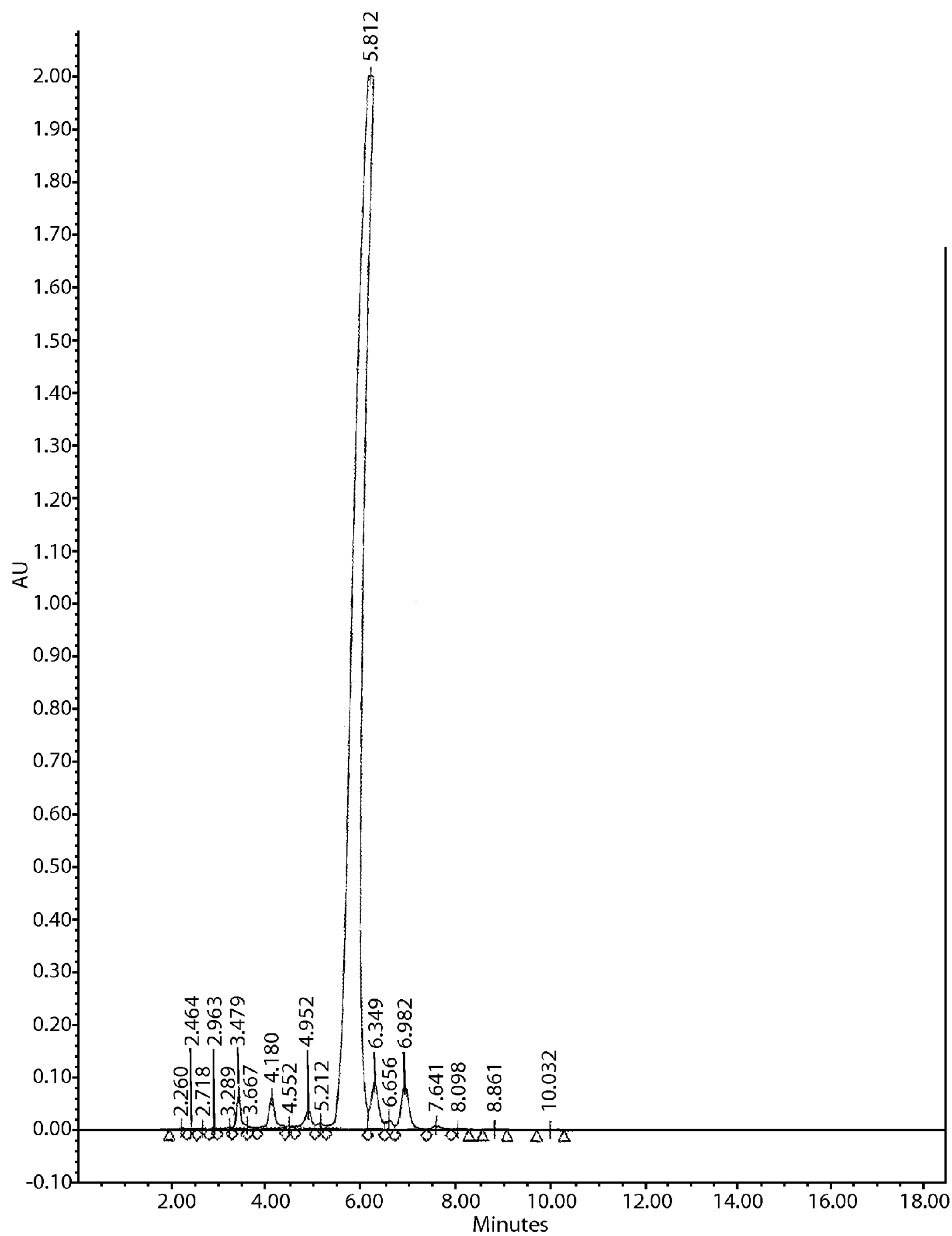
FIG. 2 is an HPLC (9.4 mm×25 cm Zorbax-Sil column, 15% 2-propanol in hexane; 6 mL/min; $R_t$=5.8 min.) profile of the solid material of NEL compound obtained after chemical synthesis; purity of the NEL compound before further HPLC purification was found to be 88.9%, checked by straight-phase HPLC.
Figure 3:
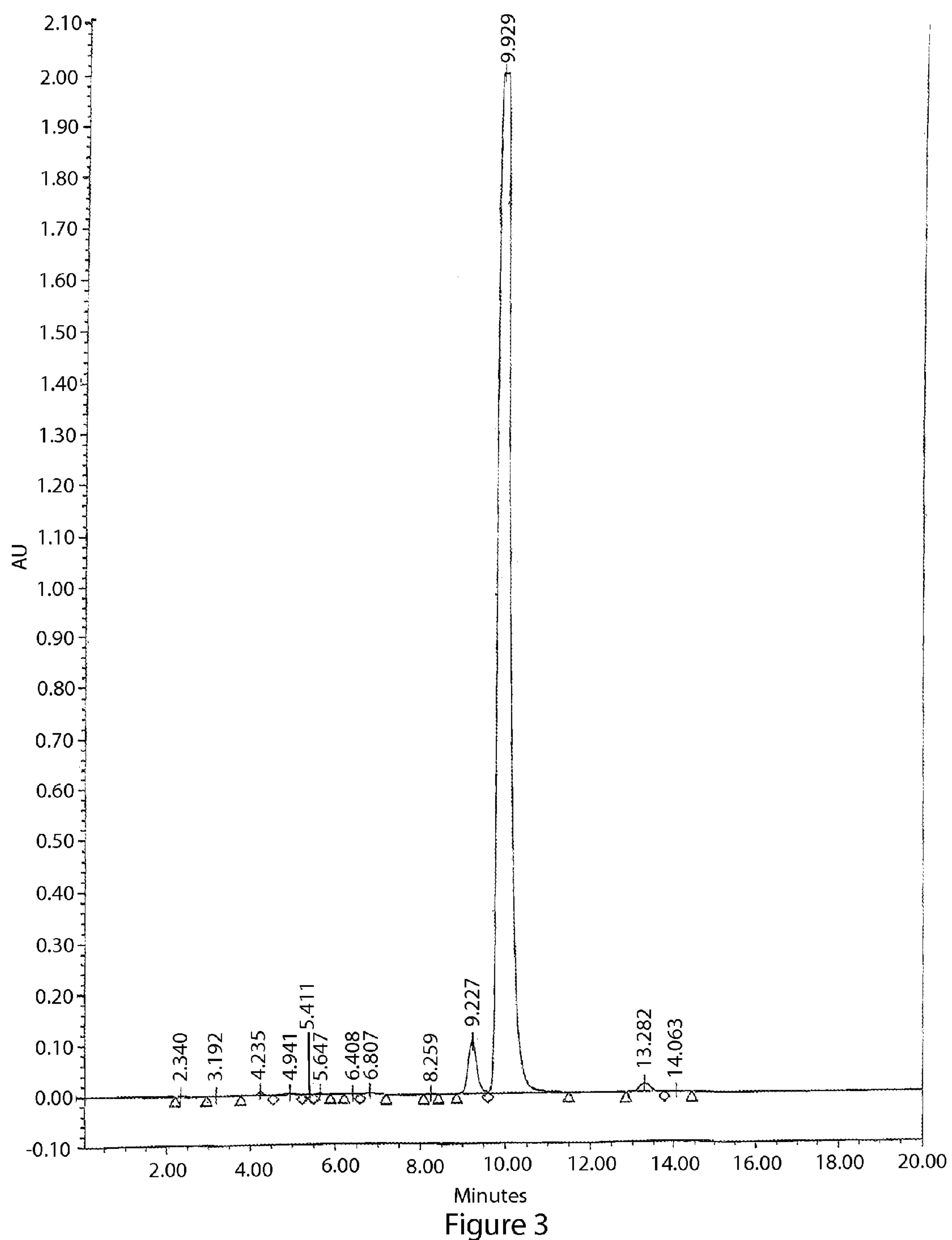
FIG. 3 is an HPLC (9.4 mm×25 cm Zorbax RX-C18 column, 15% water in methanol; 3 mL/min; $R_t$=9.9 min.) profile of the NEL compound obtained after a first, straight-phase HPLC purification of the solid NEL material; purity of the NEL compound after this first HPLC purification was found to be 95.3%, checked by reversed-phase HPLC.
Figure 4:
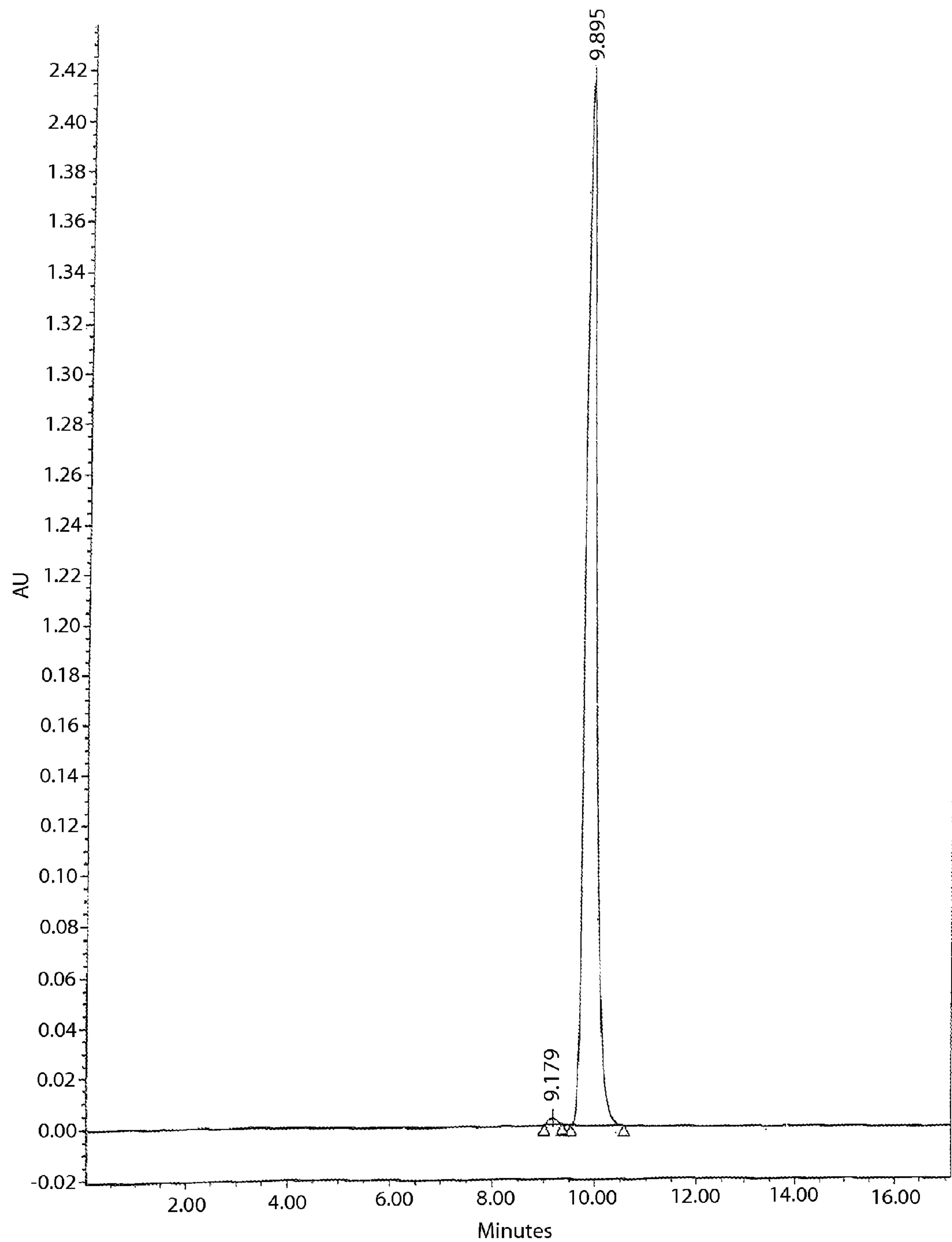
FIG. 4 is an HPLC (9.4 mm×25 cm Zorbax RX-C18 column, 15% water in methanol; 3 ml/min; $R_t$=9.9 min.) profile of the NEL compound obtained after a second reversed-phase HPLC purification of the NEL compound obtained from the first HPLC purification; purity of the NEL compound after this second HPLC purification was found to be 99.5%, checked by reversed-phase HPLC. Crystals of the NEL compound were obtained after reversed-phase HPLC purification by single crystallization using a 20% water/80% methanol solvent system.

The usefulness and advantages of the present crystallization procedure is shown in the following specific Examples 1 and 2. After crystallization, the precipitated material was observed under a microscope to confirm its crystalline form. Additionally, the crystals were then analyzed to determine their initial purity (88.9%; FIG. 2), and their significantly improved purity was confirmed after a first, straight-phase HPLC (95.3%, FIG. 3), as well as a second, reversed-phase HPLC (99.5%; FIG. 4). Yields of crystals were high and the obtained crystals showed a relatively sharp melting point of 154-155° C.

The described crystallization process of the synthetic NEL product represents a valuable purification method, which can remove most side products derived from the synthetic path. Such impurity is the result of the contamination of starting raw materials. The crystallization process occurred easily and efficiently; and the precipitated crystals were sufficiently large to assure their recovery by filtration, or other means.

EXAMPLE 1

Crystallization of (20R,25S)-2-methylene-19,26-dinor-1α,25-dihydroxyvitamin $D_3$ (NEL)

Crystals of the NEL analog were obtained from a solution of the compound in 20% water and 80% methanol (20% $H_2O$/80% MeOH) as follows:

14 mg of pure NEL compound was dissolved in 8 mL of water/methanol solvent mixture (water/methanol=2/8). The solution was kept at −20 degrees Celsius for 7 weeks. The precipitated crystals (M.p. 154-155° C.) were analyzed by straight phase HPLC (crystals: FIG. 2) and found to be 99.5% pure.

EXAMPLE 2

Experimental

A colorless prism-shaped crystal of dimensions 0.47×0.12×0.18 mm was selected for structural analysis. Intensity data were collected using a Bruker AXS Platinum 135 CCD detector controlled with the PROTEUM software suite (Bruker AXS Inc., Madison, Wis.). The x-ray source was CuKα radiation (1.54178 Å) from a Rigaku RU200 x-ray generator equipped with Montel optics, operated at 50 kV and 80 mA. The x-ray data were processed with SAINT version 7.06A (Bruker AXS Inc) and, internally scaled with SADABS version 2005/1 (Bruker AXS Inc.). The sample was mounted on a glass fiber using vacuum grease and cooled to 100° K. The intensity data were measured as a series of phi and omega oscillation frames each of 1° for 10-15 sec/frame. The detector was operated in 1024/1024 mode and was positioned 4.5 cm from the sample. Cell parameters were determined from a non-linear least squares fit of 9999 peaks in the range of 3.0<theta<64.8°. The data were merged to form a set of 6791 independent data with R(int)=0.0326.

The triclinic space group P1 was determined by systematic absences and statistical tests and verified by subsequent refinement. The structure was solved by direct methods, and refined by full matrix least-squares methods on $F^2$, (a) G. M. Sheldrick (1994), SHELXTL Version 5 Reference Manual, Bruker AXS Inc.; (b) *International Tables for Crystallography, Vol, C*, Kluwer: Boston (1995). The asymmetric unit was comprised of two molecules of NEL, designated with A and B. Hydrogen atom positions were determined from difference peaks and ultimately refined by a riding model with idealized geometry. Non-hydrogen atoms were refined with anisotropic displacement parameters. A total of 523 parameters were refined against 3 restraints and 6781 data to give wR2=0.0943 and S=1.066 for weights of $w=1/[s^2(F^2)+(0.0613P)^2]$, where $P=[F^2+2F_c^2]/3$. The final R(F) was 0.0342 for the 6781 observed data. The largest shift/s.u. was 0.001 in the final refinement cycle and the final difference map had maxima and minima of 0.217 and −0.177 e/Å$^3$, respectively. The absolute structure was determined by refinement of the Flack parameter, H. D. Flack, *Acta Cryst. A*, vol. 39, 876-881 (1983).

Figure 1A:
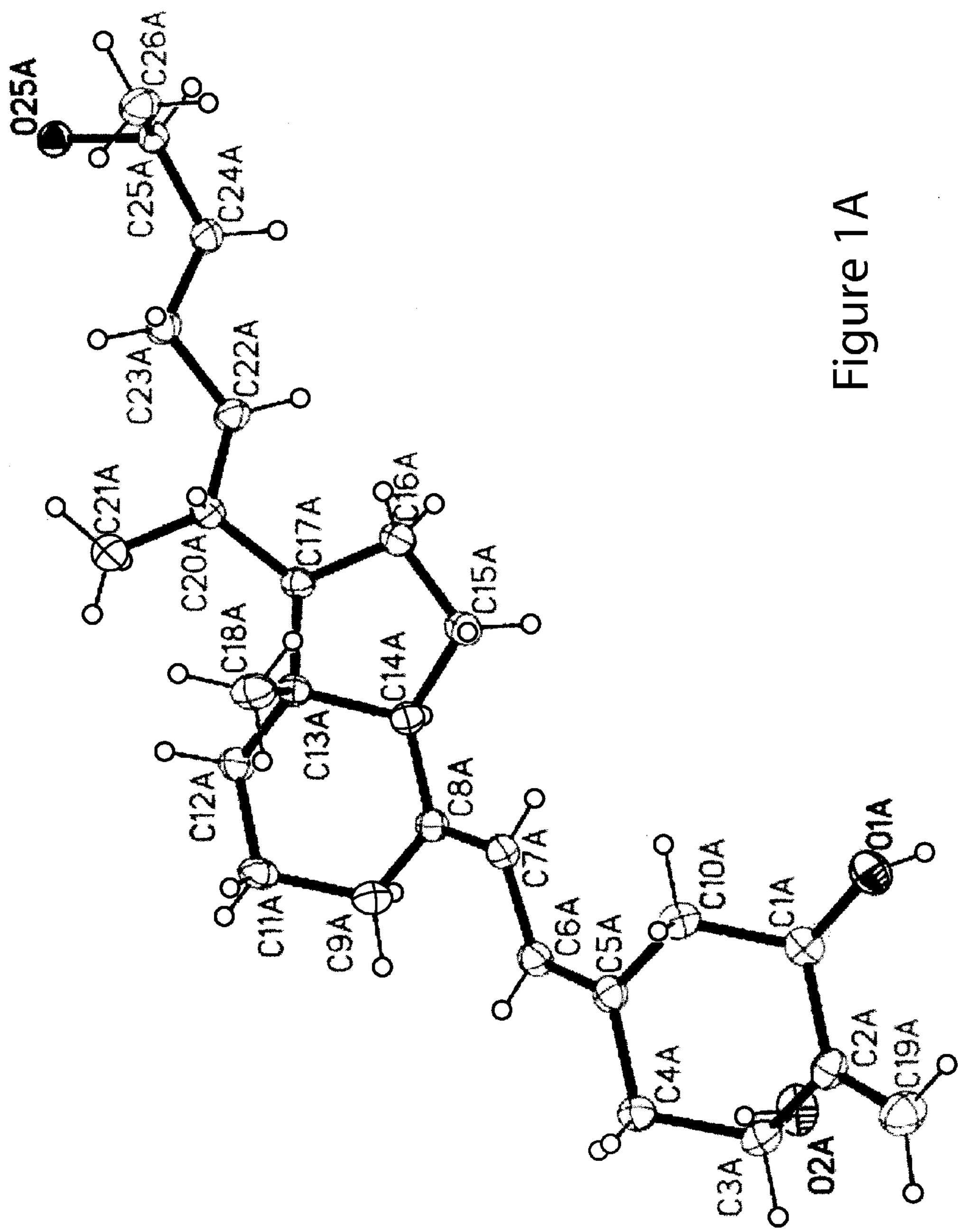
FIG. 1A is an illustration of the three dimensional structure of a first asymmetric molecular structure for NEL as defined by the atomic positional parameters discovered and set forth herein.
Figure 1B:
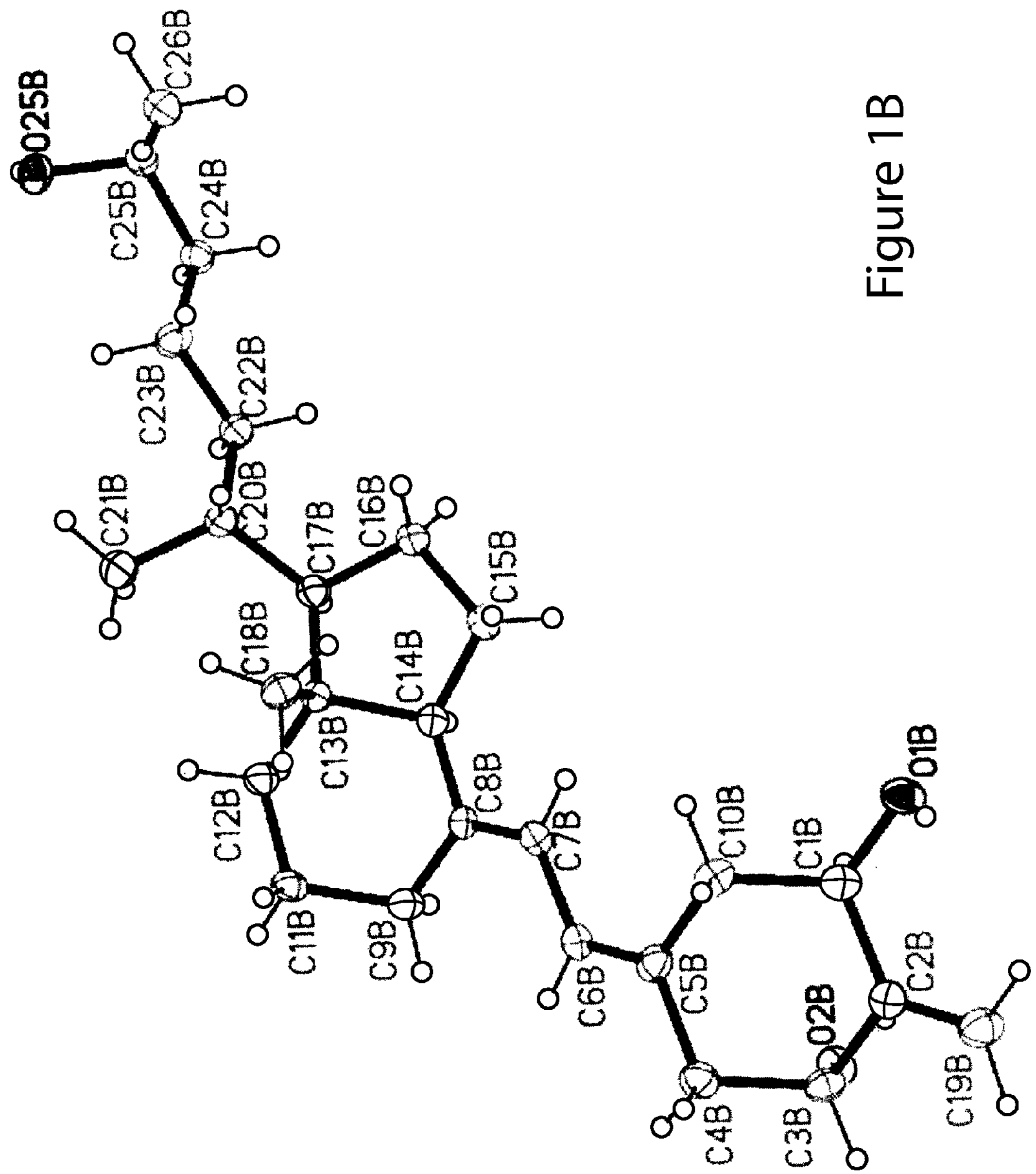
FIG. 1B is, an illustration of the three dimensional structure of a second asymmetric molecular structure for NEL as defined by the atomic positional parameters discovered and set forth herein.

The three dimensional structure of NEL as defined by the following physical data and atomic positional parameters described and calculated herein is illustrated in FIG. 1A and FIG. 1B.

TABLE 1

Crystal data and structure refinement for NEL.

| | |
|---|---|
| Identification code | NEL |
| Empirical formula | C26H42O3 |
| Formula weight | 402.60 |
| Temperature | 100(1) K |
| Wavelength | 1.54178 Å |
| Crystal system, space group | P1, |
| Unit cell dimensions | a = 6.3820(11) Å α = 110.920(5)° |
| | b = 12.594(2) Å β = 95.256(5)° |
| | c = 15.996(3)° Å γ = 90.609(5)° |
| Volume | 1194.6(4) Å$^3$ |
| Z, Calculated density | 2, 1.119 Mg/m$^3$ |
| Absorption coefficient | 0.549 mm$^{-1}$ |
| F(000) | 444 |
| Crystal size | 0.47 × 0.12 × 0.18 mm |
| Theta range for data collection | 2.97 to 64.82° |
| Limiting indices | −7 <= h <= 7, −14 <= k <= 14, −18 <= l <= 18 |
| Reflections collected/unique | 18206/6781 [R(int) = 0.0326] |
| Completeness to theta = 64.82 | 96.0% |
| Refinement method | Full-matrix least-squares on F$^2$ |
| Data/restraints/parameters | 6781/3/523 |
| Goodness-of-fit on F$^2$ | 1.066 |
| Final R indices [I > 2σ(I)] | R1 = 0.0336, wR2 = 0.0943 |
| R indices (all data) | R1 = 0.0342, wR2 = 0.0948 |
| Absolute structure parameter | −0.04(13) |
| Largest diff. peak and hole | 0.217 and −0.177 e/A$^3$ |

TABLE 2

Atomic coordinates (×10$^4$) and equivalent isotropic displacement parameters (A$^2$ × 10$^3$) for NEL. U(eq) is defined as one third of the trace of the orthogonalized Uij tensor.

| | x | y | z | U(eq) |
|---|---|---|---|---|
| O(1B) | 20004(2) | 17550(1) | 1623(1) | 24(1) |
| O(25A) | 17814(2) | 15531(1) | 1308(1) | 22(1) |
| O(1A) | 17343(2) | 13368(1) | 9956(1) | 25(1) |
| O(2B) | 26264(2) | 18348(1) | 1150(1) | 24(1) |
| O(25B) | 24669(2) | 16177(1) | 10298(1) | 25(1) |
| O(2A) | 23666(2) | 12775(1) | 10464(1) | 30(1) |
| C(12B) | 29763(3) | 18997(2) | 6571(1) | 21(1) |
| C(3B) | 24736(3) | 19211(2) | 1351(1) | 21(1) |
| C(14A) | 22676(3) | 13599(2) | 6215(1) | 20(1) |
| C(1A) | 19399(3) | 12961(2) | 9789(1) | 22(1) |
| C(1B) | 22059(3) | 18070(2) | 1796(1) | 20(1) |
| C(7B) | 26024(3) | 18595(2) | 4148(1) | 23(1) |
| C(9B) | 29674(3) | 19090(2) | 4995(1) | 21(1) |
| C(7A) | 22104(3) | 12709(2) | 7363(1) | 22(1) |
| C(8A) | 23258(3) | 12850(2) | 6750(1) | 20(1) |
| C(18B) | 25854(3) | 19292(2) | 6615(1) | 23(1) |

TABLE 2-continued

Atomic coordinates (×10$^4$) and equivalent isotropic displacement parameters (A$^2$ × 10$^3$) for NEL. U(eq) is defined as one third of the trace of the orthogonalized Uij tensor.

| | x | y | z | U(eq) |
|---|---|---|---|---|
| C(8B) | 27529(3) | 18497(2) | 4760(1) | 20(1) |
| C(4A) | 22392(3) | 11177(2) | 9084(1) | 22(1) |
| C(10B) | 22526(3) | 18874(2) | 2783(1) | 24(1) |
| C(13A) | 22519(3) | 12966(2) | 5181(1) | 21(1) |
| C(5A) | 21554(3) | 11878(2) | 8545(1) | 21(1) |
| C(13B) | 27557(3) | 18418(1) | 6337(1) | 18(1) |
| C(12A) | 24663(3) | 12455(2) | 4951(1) | 24(1) |
| C(4B) | 25235(3) | 19984(2) | 2339(1) | 23(1) |
| C(6B) | 26236(3) | 19238(2) | 3562(1) | 21(1) |
| C(5B) | 24742(3) | 19367(2) | 2960(1) | 22(1) |
| C(14B) | 27268(3) | 17751(2) | 5300(1) | 21(1) |
| C(10A) | 19424(3) | 12345(2) | 8773(1) | 24(1) |
| C(2B) | 22531(3) | 18696(2) | 1180(1) | 20(1) |
| C(11B) | 30116(3) | 19743(2) | 6014(1) | 22(1) |
| C(25A) | 16921(3) | 15954(2) | 2170(1) | 21(1) |
| C(11A) | 25307(3) | 11695(2) | 5489(1) | 26(1) |
| C(9A) | 25341(3) | 12322(2) | 6512(1) | 23(1) |
| C(2A) | 20095(3) | 12173(2) | 10275(1) | 22(1) |
| C(15B) | 25289(4) | 17009(2) | 5155(1) | 29(1) |
| C(19B) | 21153(3) | 18805(2) | 546(1) | 26(1) |
| C(22B) | 26528(3) | 16572(2) | 7829(1) | 24(1) |
| C(16A) | 20397(3) | 14647(2) | 5542(1) | 24(1) |
| C(19A) | 18923(3) | 11833(2) | 10779(1) | 29(1) |
| C(3A) | 22290(3) | 11784(2) | 10098(1) | 23(1) |
| C(6A) | 22665(3) | 12056(2) | 7932(1) | 22(1) |
| C(24A) | 18538(3) | 15914(2) | 2914(1) | 24(1) |
| C(15A) | 20687(3) | 14277(2) | 6365(1) | 28(1) |
| C(18A) | 20768(3) | 12036(2) | 4871(1) | 27(1) |
| C(20B) | 26644(3) | 17688(2) | 7646(1) | 22(1) |
| C(26B) | 21533(3) | 15634(2) | 9292(1) | 27(1) |
| C(25B) | 23829(3) | 15374(2) | 9433(1) | 21(1) |
| C(23B) | 25282(3) | 16605(2) | 8603(1) | 26(1) |
| C(16B) | 25461(3) | 16641(2) | 5984(1) | 26(1) |
| C(24B) | 25149(3) | 15444(2) | 8706(1) | 23(1) |
| C(23A) | 19136(3) | 14732(2) | 2894(1) | 26(1) |
| C(20A) | 21004(3) | 13700(2) | 3878(1) | 24(1) |
| C(17B) | 27207(3) | 17428(2) | 6678(1) | 20(1) |
| C(17A) | 21928(3) | 13962(1) | 4855(1) | 20(1) |
| C(22A) | 20565(3) | 14826(2) | 3734(1) | 24(1) |
| C(26A) | 14899(3) | 15287(2) | 2077(1) | 28(1) |
| C(21B) | 28182(4) | 18550(2) | 8366(1) | 33(1) |
| C(21A) | 22416(4) | 12988(2) | 3186(1) | 40(1) |

TABLE 3

Bond lengths [Å] for NEL.

| | |
|---|---|
| O(1B)—C(1B) | 1.419(2) |
| O(1B)—H(1BA) | 0.8200 |
| O(25A)—C(25A) | 1.461(2) |
| O(25A)—H(25A) | 0.8200 |
| O(1A)—C(1A) | 1.427(2) |
| O(1A)—H(1AA) | 0.8200 |
| O(2B)—C(3B) | 1.438(2) |
| O(2B)—H(2BA) | 0.8200 |
| O(25B)—C(25B) | 1.441(2) |
| O(25B)—H(25B) | 0.8200 |
| O(2A)—C(3A) | 1.426(2) |
| O(2A)—H(2AA) | 0.8200 |
| C(12B)—C(13B) | 1.529(3) |
| C(12B)—C(11B) | 1.536(3) |
| C(12B)—H(12A) | 0.9700 |
| C(12B)—H(12B) | 0.9700 |
| C(3B)—C(2B) | 1.503(3) |
| C(3B)—C(4B) | 1.533(2) |
| C(3B)—H(3BA) | 0.9800 |
| C(14A)—C(8A) | 1.511(3) |
| C(14A)—C(15A) | 1.527(3) |
| C(14A)—C(13A) | 1.552(2) |
| C(14A)—H(14A) | 0.9800 |

TABLE 3-continued

| Bond lengths [Å] for NEL. | |
|---|---|
| C(1A)—C(2A) | 1.511(3) |
| C(1A)—C(10A) | 1.532(3) |
| C(1A)—H(1AB) | 0.9800 |
| C(1B)—C(2B) | 1.513(3) |
| C(1B)—C(10B) | 1.540(3) |
| C(1B)—H(1BB) | 0.9800 |
| C(7B)—C(8B) | 1.346(3) |
| C(7B)—C(6B) | 1.454(3) |
| C(7B)—H(7BA) | 0.9300 |
| C(9B)—C(8B) | 1.502(3) |
| C(9B)—C(11B) | 1.538(3) |
| C(9B)—H(9BA) | 0.9700 |
| C(9B)—H(9BB) | 0.9700 |
| C(7A)—C(8A) | 1.338(3) |
| C(7A)—C(6A) | 1.453(3) |
| C(7A)—H(7AA) | 0.9300 |
| C(8A)—C(9A) | 1.512(3) |
| C(18B)—C(13B) | 1.535(2) |
| C(18B)—H(18A) | 0.9600 |
| C(18B)—H(18B) | 0.9600 |
| C(18B)—H(18C) | 0.9600 |
| C(8B)—C(14B) | 1.504(2) |
| C(4A)—C(5A) | 1.508(3) |
| C(4A)—C(3A) | 1.535(3) |
| C(4A)—H(4AA) | 0.9700 |
| C(4A)—H(4AB) | 0.9700 |
| C(10B)—C(5B) | 1.499(3) |
| C(10B)—H(10A) | 0.9700 |
| C(10B)—H(10B) | 0.9700 |
| C(13A)—C(18A) | 1.524(3) |
| C(13A)—C(12A) | 1.538(2) |
| C(13A)—C(17A) | 1.558(2) |
| C(5A)—C(6A) | 1.342(3) |
| C(5A)—C(10A) | 1.510(3) |
| C(13B)—C(17B) | 1.551(2) |
| C(13B)—C(14B) | 1.560(2) |
| C(12A)—C(11A) | 1.536(3) |
| C(12A)—H(12C) | 0.9700 |
| C(12A)—H(12D) | 0.9700 |
| C(4B)—C(5B) | 1.515(3) |
| C(4B)—H(4BA) | 0.9700 |
| C(4B)—H(4BB) | 0.9700 |
| C(6B)—C(5B) | 1.345(3) |
| C(6B)—H(6BA) | 0.9300 |
| C(14B)—C(15B) | 1.513(3) |
| C(14B)—H(14B) | 0.9800 |
| C(10A)—H(10C) | 0.9700 |
| C(10A)—H(10D) | 0.9700 |
| C(2B)—C(19B) | 1.326(3) |
| C(11B)—H(11A) | 0.9700 |
| C(11B)—H(11B) | 0.9700 |
| C(25A)—C(26A) | 1.499(3) |
| C(25A)—C(24A) | 1.518(3) |
| C(25A)—H(25C) | 0.9800 |
| C(11A)—C(9A) | 1.539(3) |
| C(11A)—H(11C) | 0.9700 |
| C(11A)—H(11D) | 0.9700 |
| C(9A)—H(9AA) | 0.9700 |
| C(9A)—H(9AB) | 0.9700 |
| C(2A)—C(19A) | 1.320(3) |
| C(2A)—C(3A) | 1.507(3) |
| C(15B)—C(16B) | 1.548(3) |
| C(15B)—H(15A) | 0.9700 |
| C(15B)—H(15B) | 0.9700 |
| C(19B)—H(19A) | 0.9300 |
| C(19B)—H(19B) | 0.9300 |
| C(22B)—C(23B) | 1.520(3) |
| C(22B)—C(20B) | 1.537(2) |
| C(22B)—H(22A) | 0.9700 |
| C(22B)—H(22B) | 0.9700 |
| C(16A)—C(15A) | 1.542(3) |
| C(16A)—C(17A) | 1.563(2) |
| C(16A)—H(16A) | 0.9700 |
| C(16A)—H(16B) | 0.9700 |
| C(19A)—H(19C) | 0.9300 |
| C(19A)—H(19D) | 0.9300 |
| C(3A)—H(3AA) | 0.9800 |
| C(6A)—H(6AA) | 0.9300 |
| C(24A)—C(23A) | 1.531(3) |
| C(24A)—H(24A) | 0.9700 |
| C(24A)—H(24B) | 0.9700 |
| C(15A)—H(15C) | 0.9700 |
| C(15A)—H(15D) | 0.9700 |
| C(18A)—H(18D) | 0.9600 |
| C(18A)—H(18E) | 0.9600 |
| C(18A)—H(18F) | 0.9600 |
| C(20B)—C(21B) | 1.532(3) |
| C(20B)—C(17B) | 1.541(2) |
| C(20B)—H(20A) | 0.9800 |
| C(26B)—C(25B) | 1.519(3) |
| C(26B)—H(26A) | 0.9600 |
| C(26B)—H(26B) | 0.9600 |
| C(26B)—H(26C) | 0.9600 |
| C(25B)—C(24B) | 1.523(3) |
| C(25B)—H(25D) | 0.9800 |
| C(23B)—C(24B) | 1.531(2) |
| C(23B)—H(23A) | 0.9700 |
| C(23B)—H(23B) | 0.9700 |
| C(16B)—C(17B) | 1.556(3) |
| C(16B)—H(16C) | 0.9700 |
| C(16B)—H(16D) | 0.9700 |
| C(24B)—H(24B) | 0.9700 |
| C(24B)—H(24C) | 0.9700 |
| C(23A)—C(22A) | 1.519(3) |
| C(23A)—H(23C) | 0.9700 |
| C(23A)—H(23D) | 0.9700 |
| C(20A)—C(21A) | 1.527(3) |
| C(20A)—C(17A) | 1.536(3) |
| C(20A)—C(22A) | 1.541(2) |
| C(20A)—H(20B) | 0.9800 |
| C(17B)—H(17A) | 0.9800 |
| C(17A)—H(17B) | 0.9800 |
| C(22A)—H(22C) | 0.9700 |
| C(22A)—H(22D) | 0.9700 |
| C(26A)—H(26D) | 0.9600 |
| C(26A)—H(26E) | 0.9600 |
| C(26A)—H(26F) | 0.9600 |
| C(21B)—H(21A) | 0.9600 |
| C(21B)—H(21B) | 0.9600 |
| C(21B)—H(21C) | 0.9600 |
| C(21A)—H(21D) | 0.9600 |
| C(21A)—H(21E) | 0.9600 |
| C(21A)—H(21F) | 0.9600 |

TABLE 4

| Bond angles [°] for NEL. | |
|---|---|
| C(1B)—O(1B)—H(1BA) | 109.5 |
| C(25A)—O(25A)—H(25A) | 109.5 |
| C(1A)—O(1A)—H(1AA) | 109.5 |
| C(3B)—O(2B)—H(2BA) | 109.5 |
| C(25B)—O(25B)—H(25B) | 109.5 |
| C(3A)—O(2A)—H(2AA) | 109.5 |
| C(13B)—C(12B)—C(11B) | 111.64(14) |
| C(13B)—C(12B)—H(12A) | 109.3 |
| C(11B)—C(12B)—H(12A) | 109.3 |
| C(13B)—C(12B)—H(12B) | 109.3 |
| C(11B)—C(12B)—H(12B) | 109.3 |
| H(12A)—C(12B)—H(12B) | 108.0 |
| O(2B)—C(3B)—C(2B) | 111.37(14) |
| O(2B)—C(3B)—C(4B) | 107.64(14) |
| C(2B)—C(3B)—C(4B) | 110.89(15) |
| O(2B)—C(3B)—H(3BA) | 109.0 |
| C(2B)—C(3B)—H(3BA) | 109.0 |
| C(4B)—C(3B)—H(3BA) | 109.0 |
| C(8A)—C(14A)—C(15A) | 120.67(16) |
| C(8A)—C(14A)—C(13A) | 113.85(14) |
| C(15A)—C(14A)—C(13A) | 104.06(14) |
| C(8A)—C(14A)—H(14A) | 105.7 |
| C(15A)—C(14A)—H(14A) | 105.7 |
| C(13A)—C(14A)—H(14A) | 105.7 |
| O(1A)—C(1A)—C(2A) | 113.69(15) |

TABLE 4-continued

| Bond angles [°] for NEL. | |
|---|---|
| O(1A)—C(1A)—C(10A) | 108.29(14) |
| C(2A)—C(1A)—C(10A) | 109.59(14) |
| O(1A)—C(1A)—H(1AB) | 108.4 |
| C(2A)—C(1A)—H(1AB) | 108.4 |
| C(10A)—C(1A)—H(1AB) | 108.4 |
| O(1B)—C(1B)—C(2B) | 114.49(15) |
| O(1B)—C(1B)—C(10B) | 111.74(15) |
| C(2B)—C(1B)—C(10B) | 109.51(15) |
| O(1B)—C(1B)—H(1BB) | 106.9 |
| C(2B)—C(1B)—H(1BB) | 106.9 |
| C(10B)—C(1B)—H(1BB) | 106.9 |
| C(8B)—C(7B)—C(6B) | 125.92(18) |
| C(8B)—C(7B)—H(7BA) | 117.0 |
| C(6B)—C(7B)—H(7BA) | 117.0 |
| C(8B)—C(9B)—C(11B) | 111.32(15) |
| C(8B)—C(9B)—H(9BA) | 109.4 |
| C(11B)—C(9B)—H(9BA) | 109.4 |
| C(8B)—C(9B)—H(9BB) | 109.4 |
| C(11B)—C(9B)—H(9BB) | 109.4 |
| H(9BA)—C(9B)—H(9BB) | 108.0 |
| C(8A)—C(7A)—C(6A) | 126.04(17) |
| C(8A)—C(7A)—H(7AA) | 117.0 |
| C(6A)—C(7A)—H(7AA) | 117.0 |
| C(7A)—C(8A)—C(14A) | 124.19(17) |
| C(7A)—C(8A)—C(9A) | 125.42(16) |
| C(14A)—C(8A)—C(9A) | 110.37(15) |
| C(13B)—C(18B)—H(18A) | 109.5 |
| C(13B)—C(18B)—H(18B) | 109.5 |
| H(18A)—C(18B)—H(18B) | 109.5 |
| C(13B)—C(18B)—H(18C) | 109.5 |
| H(18A)—C(18B)—H(18C) | 109.5 |
| H(18B)—C(18B)—H(18C) | 109.5 |
| C(7B)—C(8B)—C(9B) | 125.88(17) |
| C(7B)—C(8B)—C(14B) | 123.46(18) |
| C(9B)—C(8B)—C(14B) | 110.66(15) |
| C(5A)—C(4A)—C(3A) | 112.48(14) |
| C(5A)—C(4A)—H(4AA) | 109.1 |
| C(3A)—C(4A)—H(4AA) | 109.1 |
| C(5A)—C(4A)—H(4AB) | 109.1 |
| C(3A)—C(4A)—H(4AB) | 109.1 |
| H(4AA)—C(4A)—H(4AB) | 107.8 |
| C(5B)—C(10B)—C(1B) | 110.68(15) |
| C(5B)—C(10B)—H(10A) | 109.5 |
| C(1B)—C(10B)—H(10A) | 109.5 |
| C(5B)—C(10B)—H(10B) | 109.5 |
| C(1B)—C(10B)—H(10B) | 109.5 |
| H(10A)—C(10B)—H(10B) | 108.1 |
| C(18A)—C(13A)—C(12A) | 110.65(15) |
| C(18A)—C(13A)—C(14A) | 111.01(15) |
| C(12A)—C(13A)—C(14A) | 107.41(15) |
| C(18A)—C(13A)—C(17A) | 110.89(15) |
| C(12A)—C(13A)—C(17A) | 116.13(15) |
| C(14A)—C(13A)—C(17A) | 100.21(13) |
| C(6A)—C(5A)—C(4A) | 121.11(17) |
| C(6A)—C(5A)—C(10A) | 124.93(17) |
| C(4A)—C(5A)—C(10A) | 113.96(16) |
| C(12B)—C(13B)—C(18B) | 111.30(15) |
| C(12B)—C(13B)—C(17B) | 115.91(14) |
| C(18B)—C(13B)—C(17B) | 110.94(15) |
| C(12B)—C(13B)—C(14B) | 107.44(15) |
| C(18B)—C(13B)—C(14B) | 110.58(14) |
| C(17B)—C(13B)—C(14B) | 100.00(13) |
| C(11A)—C(12A)—C(13A) | 111.24(15) |
| C(11A)—C(12A)—H(12C) | 109.4 |
| C(13A)—C(12A)—H(12C) | 109.4 |
| C(11A)—C(12A)—H(12D) | 109.4 |
| C(13A)—C(12A)—H(12D) | 109.4 |
| H(12C)—C(12A)—H(12D) | 108.0 |
| C(5B)—C(4B)—C(3B) | 110.96(15) |
| C(5B)—C(4B)—H(4BA) | 109.4 |
| C(3B)—C(4B)—H(4BA) | 109.4 |
| C(5B)—C(4B)—H(4BB) | 109.4 |
| C(3B)—C(4B)—H(4BB) | 109.4 |
| H(4BA)—C(4B)—H(4BB) | 108.0 |
| C(5B)—C(6B)—C(7B) | 126.94(18) |
| C(5B)—C(6B)—H(6BA) | 116.5 |
| C(7B)—C(6B)—H(6BA) | 116.5 |
| C(6B)—C(5B)—C(10B) | 125.49(17) |

TABLE 4-continued

| Bond angles [°] for NEL. | |
|---|---|
| C(6B)—C(5B)—C(4B) | 121.22(18) |
| C(10B)—C(5B)—C(4B) | 113.17(15) |
| C(8B)—C(14B)—C(15B) | 121.27(16) |
| C(8B)—C(14B)—C(13B) | 113.18(14) |
| C(15B)—C(14B)—C(13B) | 104.01(15) |
| C(8B)—C(14B)—H(14B) | 105.7 |
| C(15B)—C(14B)—H(14B) | 105.7 |
| C(13B)—C(14B)—H(14B) | 105.7 |
| C(5A)—C(10A)—C(1A) | 111.36(15) |
| C(5A)—C(10A)—H(10C) | 109.4 |
| C(1A)—C(10A)—H(10C) | 109.4 |
| C(5A)—C(10A)—H(10D) | 109.4 |
| C(1A)—C(10A)—H(10D) | 109.4 |
| H(10C)—C(10A)—H(10D) | 108.0 |
| C(19B)—C(2B)—C(3B) | 121.69(17) |
| C(19B)—C(2B)—C(1B) | 124.35(18) |
| C(3B)—C(2B)—C(1B) | 113.96(15) |
| C(12B)—C(11B)—C(9B) | 112.84(15) |
| C(12B)—C(11B)—H(11A) | 109.0 |
| C(9B)—C(11B)—H(11A) | 109.0 |
| C(12B)—C(11B)—H(11B) | 109.0 |
| C(9B)—C(11B)—H(11B) | 109.0 |
| H(11A)—C(11B)—H(11B) | 107.8 |
| O(25A)—C(25A)—C(26A) | 108.17(15) |
| O(25A)—C(25A)—C(24A) | 109.76(15) |
| C(26A)—C(25A)—C(24A) | 114.61(16) |
| O(25A)—C(25A)—H(25C) | 108.0 |
| C(26A)—C(25A)—H(25C) | 108.0 |
| C(24A)—C(25A)—H(25C) | 108.0 |
| C(12A)—C(11A)—C(9A) | 112.71(15) |
| C(12A)—C(11A)—H(11C) | 109.0 |
| C(9A)—C(11A)—H(11C) | 109.0 |
| C(12A)—C(11A)—H(11D) | 109.0 |
| C(9A)—C(11A)—H(11D) | 109.0 |
| H(11C)—C(11A)—H(11D) | 107.8 |
| C(8A)—C(9A)—C(11A) | 110.93(15) |
| C(8A)—C(9A)—H(9AA) | 109.5 |
| C(11A)—C(9A)—H(9AA) | 109.5 |
| C(8A)—C(9A)—H(9AB) | 109.5 |
| C(11A)—C(9A)—H(9AB) | 109.5 |
| H(9AA)—C(9A)—H(9AB) | 108.0 |
| C(19A)—C(2A)—C(3A) | 123.23(17) |
| C(19A)—C(2A)—C(1A) | 124.78(18) |
| C(3A)—C(2A)—C(1A) | 111.96(16) |
| C(14B)—C(15B)—C(16B) | 103.37(15) |
| C(14B)—C(15B)—H(15A) | 111.1 |
| C(16B)—C(15B)—H(15A) | 111.1 |
| C(14B)—C(15B)—H(15B) | 111.1 |
| C(16B)—C(15B)—H(15B) | 111.1 |
| H(15A)—C(15B)—H(15B) | 109.1 |
| C(2B)—C(19B)—H(19A) | 120.0 |
| C(2B)—C(19B)—H(19B) | 120.0 |
| H(19A)—C(19B)—H(19B) | 120.0 |
| C(23B)—C(22B)—C(20B) | 115.28(16) |
| C(23B)—C(22B)—H(22A) | 108.5 |
| C(20B)—C(22B)—H(22A) | 108.5 |
| C(23B)—C(22B)—H(22B) | 108.5 |
| C(20B)—C(22B)—H(22B) | 108.5 |
| H(22A)—C(22B)—H(22B) | 107.5 |
| C(15A)—C(16A)—C(17A) | 107.70(14) |
| C(15A)—C(16A)—H(16A) | 110.2 |
| C(17A)—C(16A)—H(16A) | 110.2 |
| C(15A)—C(16A)—H(16B) | 110.2 |
| C(17A)—C(16A)—H(16B) | 110.2 |
| H(16A)—C(16A)—H(16B) | 108.5 |
| C(2A)—C(19A)—H(19C) | 120.0 |
| C(2A)—C(19A)—H(19D) | 120.0 |
| H(19C)—C(19A)—H(19D) | 120.0 |
| O(2A)—C(3A)—C(2A) | 106.68(15) |
| O(2A)—C(3A)—C(4A) | 112.30(15) |
| C(2A)—C(3A)—C(4A) | 109.87(15) |
| O(2A)—C(3A)—H(3AA) | 109.3 |
| C(2A)—C(3A)—H(3AA) | 109.3 |
| C(4A)—C(3A)—H(3AA) | 109.3 |
| C(5A)—C(6A)—C(7A) | 128.24(17) |
| C(5A)—C(6A)—H(6AA) | 115.9 |
| C(7A)—C(6A)—H(6AA) | 115.9 |
| C(25A)—C(24A)—C(23A) | 116.64(15) |

TABLE 4-continued

| Bond angles [°] for NEL. | |
|---|---|
| C(25A)—C(24A)—H(24A) | 108.1 |
| C(23A)—C(24A)—H(24A) | 108.1 |
| C(25A)—C(24A)—H(24B) | 108.1 |
| C(23A)—C(24A)—H(24B) | 108.1 |
| H(24A)—C(24A)—H(24B) | 107.3 |
| C(14A)—C(15A)—C(16A) | 103.22(15) |
| C(14A)—C(15A)—H(15C) | 111.1 |
| C(16A)—C(15A)—H(15C) | 111.1 |
| C(14A)—C(15A)—H(15D) | 111.1 |
| C(16A)—C(15A)—H(15D) | 111.1 |
| H(15C)—C(15A)—H(15D) | 109.1 |
| C(13A)—C(18A)—H(18D) | 109.5 |
| C(13A)—C(18A)—H(18E) | 109.5 |
| H(18D)—C(18A)—H(18E) | 109.5 |
| C(13A)—C(18A)—H(18F) | 109.5 |
| H(18D)—C(18A)—H(18F) | 109.5 |
| H(18E)—C(18A)—H(18F) | 109.5 |
| C(21B)—C(20B)—C(22B) | 109.89(15) |
| C(21B)—C(20B)—C(17B) | 113.74(16) |
| C(22B)—C(20B)—C(17B) | 109.14(14) |
| C(21B)—C(20B)—H(20A) | 108.0 |
| C(22B)—C(20B)—H(20A) | 108.0 |
| C(17B)—C(20B)—H(20A) | 108.0 |
| C(25B)—C(26B)—H(26A) | 109.5 |
| C(25B)—C(26B)—H(26B) | 109.5 |
| H(26A)—C(26B)—H(26B) | 109.5 |
| C(25B)—C(26B)—H(26C) | 109.5 |
| H(26A)—C(26B)—H(26C) | 109.5 |
| H(26B)—C(26B)—H(26C) | 109.5 |
| O(25B)—C(25B)—C(26B) | 106.88(15) |
| O(25B)—C(25B)—C(24B) | 109.97(15) |
| C(26B)—C(25B)—C(24B) | 113.97(15) |
| O(25B)—C(25B)—H(25D) | 108.6 |
| C(26B)—C(25B)—H(25D) | 108.6 |
| C(24B)—C(25B)—H(25D) | 108.6 |
| C(22B)—C(23B)—C(24B) | 111.82(15) |
| C(22B)—C(23B)—H(23A) | 109.3 |
| C(24B)—C(23B)—H(23A) | 109.3 |
| C(22B)—C(23B)—H(23B) | 109.3 |
| C(24B)—C(23B)—H(23B) | 109.3 |
| H(23A)—C(23B)—H(23B) | 107.9 |
| C(15B)—C(16B)—C(17B) | 107.10(15) |
| C(15B)—C(16B)—H(16C) | 110.3 |
| C(17B)—C(16B)—H(16C) | 110.3 |
| C(15B)—C(16B)—H(16D) | 110.3 |
| C(17B)—C(16B)—H(16D) | 110.3 |
| H(16C)—C(16B)—H(16D) | 108.6 |
| C(25B)—C(24B)—C(23B) | 115.78(15) |
| C(25B)—C(24B)—H(24B) | 108.3 |
| C(23B)—C(24B)—H(24B) | 108.3 |
| C(25B)—C(24B)—H(24C) | 108.3 |
| C(23B)—C(24B)—H(24C) | 108.3 |
| H(24B)—C(24B)—H(24C) | 107.4 |
| C(22A)—C(23A)—C(24A) | 110.47(15) |
| C(22A)—C(23A)—H(23C) | 109.6 |
| C(24A)—C(23A)—H(23C) | 109.6 |
| C(22A)—C(23A)—H(23D) | 109.6 |
| C(24A)—C(23A)—H(23D) | 109.6 |
| H(23C)—C(23A)—H(23D) | 108.1 |
| C(21A)—C(20A)—C(17A) | 113.40(17) |
| C(21A)—C(20A)—C(22A) | 110.07(17) |
| C(17A)—C(20A)—C(22A) | 109.15(14) |
| C(21A)—C(20A)—H(20B) | 108.0 |
| C(17A)—C(20A)—H(20B) | 108.0 |
| C(22A)—C(20A)—H(20B) | 108.0 |
| C(20B)—C(17B)—C(13B) | 119.83(14) |
| C(20B)—C(17B)—C(16B) | 110.64(15) |
| C(13B)—C(17B)—C(16B) | 104.20(14) |
| C(20B)—C(17B)—H(17A) | 107.2 |
| C(13B)—C(17B)—H(17A) | 107.2 |
| C(16B)—C(17B)—H(17A) | 107.2 |
| C(20A)—C(17A)—C(13A) | 119.67(14) |
| C(20A)—C(17A)—C(16A) | 111.84(15) |
| C(13A)—C(17A)—C(16A) | 103.18(14) |
| C(20A)—C(17A)—H(17B) | 107.2 |
| C(13A)—C(17A)—H(17B) | 107.2 |
| C(16A)—C(17A)—H(17B) | 107.2 |
| C(23A)—C(22A)—C(20A) | 116.00(16) |

TABLE 4-continued

| Bond angles [°] for NEL. | |
|---|---|
| C(23A)—C(22A)—H(22C) | 108.3 |
| C(20A)—C(22A)—H(22C) | 108.3 |
| C(23A)—C(22A)—H(22D) | 108.3 |
| C(20A)—C(22A)—H(22D) | 108.3 |
| H(22C)—C(22A)—H(22D) | 107.4 |
| C(25A)—C(26A)—H(26D) | 109.5 |
| C(25A)—C(26A)—H(26E) | 109.5 |
| H(26D)—C(26A)—H(26E) | 109.5 |
| C(25A)—C(26A)—H(26F) | 109.5 |
| H(26D)—C(26A)—B(26F) | 109.5 |
| H(26E)—C(26A)—H(26F) | 109.5 |
| C(20B)—C(21B)—H(21A) | 109.5 |
| C(20B)—C(21B)—H(21B) | 109.5 |
| H(21A)—C(21B)—H(21B) | 109.5 |
| C(20B)—C(21B)—H(21C) | 109.5 |
| H(21A)—C(21B)—H(21C) | 109.5 |
| H(21B)—C(21B)—H(21C) | 109.5 |
| C(20A)—C(21A)—H(21D) | 109.5 |
| C(20A)—C(21A)—H(21E) | 109.5 |
| H(21D)—C(21A)—H(21E) | 109.5 |
| C(20A)—C(21A)—H(21F) | 109.5 |
| H(21D)—C(21A)—H(21F) | 109.5 |
| H(21E)—C(21A)—H(21F) | 109.5 |

TABLE 5

Anisotropic displacement parameters ($Å^2 \times 10^3$) for NEL. The anisotropic displacement factor exponent takes the form: $-2\pi^2 [h^2 a^{*2} U_{11} + \ldots + 2hka^* b^* U_{12}]$

| | U11 | U22 | U33 | U23 | U13 | U12 |
|---|---|---|---|---|---|---|
| O(1B) | 17(1) | 27(1) | 31(1) | 16(1) | 0(1) | −2(1) |
| O(25A) | 26(1) | 23(1) | 20(1) | 9(1) | 4(1) | 1(1) |
| O(1A) | 20(1) | 26(1) | 28(1) | 8(1) | 5(1) | 3(1) |
| O(2B) | 19(1) | 24(1) | 26(1) | 6(1) | 2(1) | 2(1) |
| O(25B) | 30(1) | 24(1) | 20(1) | 9(1) | −2(1) | 4(1) |
| O(2A) | 21(1) | 34(1) | 29(1) | 4(1) | 2(1) | −6(1) |
| C(12B) | 18(1) | 24(1) | 22(1) | 11(1) | −3(1) | −4(1) |
| C(3B) | 22(1) | 22(1) | 23(1) | 13(1) | 2(1) | 4(1) |
| C(14A) | 21(1) | 19(1) | 20(1) | 7(1) | 3(1) | 1(1) |
| C(1A) | 20(1) | 20(1) | 25(1) | 7(1) | 2(1) | −2(1) |
| C(1B) | 18(1) | 21(1) | 24(1) | 11(1) | 3(1) | 2(1) |
| C(7B) | 23(1) | 22(1) | 20(1) | 5(1) | 1(1) | −5(1) |
| C(9B) | 20(1) | 22(1) | 23(1) | 11(1) | 2(1) | 0(1) |
| C(7A) | 23(1) | 20(1) | 20(1) | 5(1) | 2(1) | 3(1) |
| C(8A) | 21(1) | 18(1) | 19(1) | 5(1) | −1(1) | 1(1) |
| C(18B) | 24(1) | 26(1) | 24(1) | 13(1) | 3(1) | 4(1) |
| C(8B) | 25(1) | 18(1) | 15(1) | 3(1) | 2(1) | −1(1) |
| C(4A) | 24(1) | 21(1) | 23(1) | 10(1) | 3(1) | 2(1) |
| C(10B) | 26(1) | 27(1) | 22(1) | 13(1) | 5(1) | 3(1) |
| C(13A) | 23(1) | 19(1) | 22(1) | 9(1) | 2(1) | 1(1) |
| C(5A) | 24(1) | 17(1) | 18(1) | 4(1) | 0(1) | −1(1) |
| C(13B) | 20(1) | 19(1) | 17(1) | 7(1) | 0(1) | −1(1) |
| C(12A) | 26(1) | 26(1) | 24(1) | 12(1) | 9(1) | 7(1) |
| C(4B) | 24(1) | 20(1) | 25(1) | 9(1) | 2(1) | 1(1) |
| C(6B) | 25(1) | 19(1) | 17(1) | 4(1) | 1(1) | −2(1) |
| C(5B) | 27(1) | 20(1) | 18(1) | 6(1) | 5(1) | 3(1) |
| C(14B) | 24(1) | 19(1) | 18(1) | 7(1) | 1(1) | −2(1) |
| C(10A) | 25(1) | 25(1) | 24(1) | 13(1) | 1(1) | 1(1) |
| C(2B) | 20(1) | 19(1) | 20(1) | 6(1) | 2(1) | 3(1) |
| C(11B) | 17(1) | 24(1) | 25(1) | 12(1) | −2(1) | −4(1) |
| C(25A) | 27(1) | 21(1) | 17(1) | 8(1) | 4(1) | 5(1) |
| C(11A) | 24(1) | 29(1) | 31(1) | 17(1) | 11(1) | 11(1) |
| C(9A) | 21(1) | 26(1) | 27(1) | 14(1) | 2(1) | 2(1) |
| C(2A) | 24(1) | 23(1) | 17(1) | 6(1) | 0(1) | −3(1) |
| C(15B) | 35(1) | 28(1) | 22(1) | 9(1) | −4(1) | −13(1) |
| C(19B) | 22(1) | 31(1) | 29(1) | 17(1) | 2(1) | 1(1) |
| C(22B) | 26(1) | 24(1) | 22(1) | 9(1) | 0(1) | −2(1) |
| C(16A) | 26(1) | 23(1) | 25(1) | 10(1) | 4(1) | 5(1) |
| C(19A) | 26(1) | 37(1) | 29(1) | 17(1) | 5(1) | 2(1) |
| C(3A) | 23(1) | 24(1) | 21(1) | 11(1) | −2(1) | −1(1) |
| C(6A) | 24(1) | 18(1) | 22(1) | 6(1) | 1(1) | 2(1) |
| C(24A) | 33(1) | 19(1) | 20(1) | 6(1) | 1(1) | 3(1) |
| C(15A) | 34(1) | 27(1) | 27(1) | 13(1) | 10(1) | 12(1) |

TABLE 5-continued

Anisotropic displacement parameters ($Å^2 \times 10^3$) for NEL. The anisotropic displacement factor exponent takes the form: $-2\pi^2 [h^2 a*^2 U_{11} + \ldots + 2hka*b*U_{12}]$

| | U11 | U22 | U33 | U23 | U13 | U12 |
|---|---|---|---|---|---|---|
| C(18A) | 29(1) | 22(1) | 32(1) | 13(1) | −4(1) | −3(1) |
| C(20B) | 22(1) | 24(1) | 19(1) | 9(1) | 1(1) | −1(1) |
| C(26B) | 26(1) | 29(1) | 26(1) | 10(1) | 1(1) | −4(1) |
| C(25B) | 24(1) | 19(1) | 21(1) | 8(1) | −1(1) | −1(1) |
| C(23B) | 36(1) | 23(1) | 23(1) | 11(1) | 6(1) | 1(1) |
| C(16B) | 30(1) | 26(1) | 21(1) | 10(1) | −1(1) | −7(1) |
| C(24B) | 27(1) | 20(1) | 22(1) | 8(1) | 0(1) | −1(1) |
| C(23A) | 35(1) | 21(1) | 21(1) | 8(1) | −2(1) | 2(1) |
| C(20A) | 29(1) | 19(1) | 24(1) | 6(1) | 0(1) | 3(1) |
| C(17B) | 20(1) | 20(1) | 20(1) | 8(1) | 1(1) | 0(1) |
| C(17A) | 20(1) | 17(1) | 22(1) | 7(1) | 0(1) | 0(1) |
| C(22A) | 30(1) | 21(1) | 22(1) | 9(1) | −1(1) | 1(1) |
| C(26A) | 30(1) | 34(1) | 25(1) | 15(1) | 3(1) | 3(1) |
| C(21B) | 43(1) | 33(1) | 22(1) | 14(1) | −6(1) | −10(1) |
| C(21A) | 59(2) | 42(1) | 23(1) | 13(1) | 8(1) | 25(1) |

TABLE 6

Hydrogen coordinates ($\times 10^4$) and isotropic displacement parameters ($Å^2 \times 10^3$) for NEL.

| | x | y | z | U(eq) |
|---|---|---|---|---|
| H(1BA) | 19161 | 17964 | 1490 | 35 |
| H(25A) | 18570 | 16034 | 1263 | 33 |
| H(1AA) | 17440 | 14003 | 10350 | 38 |
| H(2BA) | 25660 | 17721 | 897 | 36 |
| H(25B) | 25582 | 15881 | 10525 | 37 |
| H(2AA) | 24659 | 12701 | 10160 | 45 |
| H(12A) | 30805 | 18420 | 6459 | 25 |
| H(12B) | 29951 | 19463 | 7205 | 25 |
| H(3BA) | 24872 | 19664 | 970 | 25 |
| H(14A) | 23849 | 14164 | 6358 | 24 |
| N(1AB) | 20405 | 13618 | 9985 | 26 |
| H(1BB) | 23051 | 17459 | 1699 | 24 |
| H(7BA) | 24730 | 18218 | 4096 | 27 |
| H(9BA) | 29766 | 19618 | 4680 | 25 |
| H(9BB) | 30734 | 18533 | 4798 | 25 |
| H(7AA) | 20824 | 13061 | 7432 | 26 |
| H(18A) | 26102 | 19896 | 6397 | 35 |
| H(18B) | 25900 | 19599 | 7259 | 35 |
| H(18C) | 24494 | 18928 | 6363 | 35 |
| H(4AA) | 23843 | 11012 | 8972 | 27 |
| H(4AB) | 21582 | 10459 | 8883 | 27 |
| H(10A) | 21552 | 19485 | 2912 | 29 |
| H(10B) | 22323 | 18458 | 3178 | 29 |
| H(12C) | 24585 | 12009 | 4312 | 29 |
| H(12D) | 25726 | 13065 | 5083 | 29 |
| H(4BA) | 26714 | 20228 | 2451 | 27 |
| H(4BB) | 24412 | 20656 | 2462 | 27 |
| H(6BA) | 27544 | 19598 | 3608 | 26 |
| H(14B) | 28424 | 17229 | 5174 | 25 |
| H(10C) | 18361 | 11726 | 8562 | 29 |

TABLE 6-continued

Hydrogen coordinates ($\times 10^4$) and isotropic displacement parameters ($Å^2 \times 10^3$) for NEL.

| | x | y | z | U(eq) |
|---|---|---|---|---|
| H(10D) | 19077 | 12870 | 8467 | 29 |
| H(11A) | 31562 | 20046 | 6148 | 26 |
| H(11B) | 29205 | 20381 | 6189 | 26 |
| H(25C) | 16590 | 16751 | 2294 | 25 |
| H(11C) | 26696 | 11421 | 5353 | 31 |
| H(11D) | 24327 | 11039 | 5303 | 31 |
| H(9AA) | 25631 | 11790 | 6817 | 28 |
| H(9AB) | 26460 | 12912 | 6716 | 28 |
| H(15A) | 25251 | 16354 | 4601 | 35 |
| H(15B) | 24038 | 17434 | 5137 | 35 |
| H(19A) | 21542 | 19209 | 194 | 39 |
| H(19B) | 19798 | 18479 | 454 | 39 |
| H(22A) | 25901 | 15976 | 7287 | 28 |
| H(22B) | 27952 | 16366 | 7953 | 28 |
| H(16A) | 20720 | 15457 | 5724 | 29 |
| H(16B) | 18952 | 14489 | 5269 | 29 |
| H(19C) | 19444 | 11330 | 11045 | 44 |
| H(19D) | 17576 | 12098 | 10868 | 44 |
| H(3AA) | 22660 | 11257 | 10408 | 27 |
| H(6AA) | 23960 | 11720 | 7861 | 26 |
| H(24A) | 18004 | 16316 | 3486 | 29 |
| H(24B) | 19810 | 16327 | 2892 | 29 |
| H(15C) | 20875 | 14932 | 6921 | 33 |
| H(15D) | 19488 | 13807 | 6380 | 33 |
| H(18D) | 19443 | 12371 | 5020 | 41 |
| H(18E) | 21043 | 11501 | 5166 | 41 |
| H(18F) | 20715 | 11650 | 4232 | 41 |
| H(20A) | 25243 | 18002 | 7690 | 26 |
| H(26A) | 20801 | 15579 | 9775 | 41 |
| H(26B) | 20899 | 15098 | 8731 | 41 |
| H(26C) | 21447 | 16391 | 9283 | 41 |
| H(25D) | 23893 | 14605 | 9451 | 26 |
| H(23A) | 23870 | 16840 | 8498 | 32 |
| H(23B) | 25948 | 17163 | 9157 | 32 |
| H(16C) | 25832 | 15852 | 5811 | 31 |
| H(16D) | 24128 | 16721 | 6241 | 31 |
| H(24B) | 24572 | 14884 | 8135 | 28 |
| H(24C) | 26567 | 15235 | 8835 | 28 |
| H(23C) | 17871 | 14278 | 2858 | 31 |
| H(23D) | 19853 | 14353 | 2365 | 31 |
| H(20B) | 19657 | 13272 | 3783 | 29 |
| H(17A) | 28500 | 17005 | 6615 | 24 |
| H(17B) | 23208 | 14447 | 4956 | 23 |
| H(22C) | 19938 | 15328 | 4253 | 29 |
| H(22D) | 21902 | 15184 | 3712 | 29 |
| H(26D) | 13962 | 15360 | 1598 | 43 |
| H(26E) | 14256 | 15574 | 2630 | 43 |
| H(26F) | 15183 | 14500 | 1945 | 43 |
| H(21A) | 28248 | 19245 | 8248 | 49 |
| H(21B) | 29556 | 18246 | 8354 | 49 |
| H(21C) | 27705 | 18701 | 8948 | 49 |
| H(21D) | 22673 | 12286 | 3278 | 61 |
| H(21E) | 23730 | 13402 | 3253 | 61 |
| H(21F) | 21731 | 12827 | 2591 | 61 |

TABLE 7

Observed and calculated structure factors for NEL

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 0 | 2 | −18 | 48 | 43 | 2 | 1 | 0 | −16 | 58 | 59 | 1 | 1 | 0 | −15 | 78 | 80 | 1 | 2 | −4 | −14 | 52 | 53 | 1 | 2 | 8 | −14 | 65 | 70 | 1 |
| 1 | 2 | −18 | 75 | 71 | 2 | 2 | 0 | −16 | 67 | 68 | 1 | 2 | 0 | −15 | 127 | 130 | 2 | 3 | −4 | −14 | 33 | 37 | 2 | 3 | 8 | −14 | 140 | 139 | 2 |
| 0 | 3 | −18 | 30 | 27 | 2 | 3 | 0 | −16 | 44 | 45 | 1 | 3 | 0 | −15 | 32 | 29 | 1 | −1 | −3 | −14 | 60 | 62 | 2 | 4 | 8 | −14 | 51 | 50 | 2 |
| 1 | 3 | −18 | 35 | 36 | 1 | −1 | 1 | −16 | 44 | 45 | 2 | 4 | 0 | −15 | 9 | 9 | 8 | 0 | −3 | −14 | 21 | 18 | 2 | −3 | 9 | −14 | 28 | 27 | 3 |
| 2 | 3 | −18 | 26 | 28 | 2 | 0 | 1 | −16 | 138 | 127 | 3 | −1 | 1 | −15 | 95 | 98 | 2 | 1 | −3 | −14 | 34 | 29 | 1 | −2 | 9 | −14 | 92 | 90 | 2 |
| −1 | 4 | −18 | 12 | 10 | 6 | 1 | 1 | −16 | 110 | 118 | 1 | 0 | 1 | −15 | 39 | 37 | 2 | 2 | −3 | −14 | 37 | 36 | 1 | −1 | 9 | −14 | 53 | 52 | 1 |
| 0 | 4 | −18 | 55 | 56 | 2 | 2 | 1 | −16 | 43 | 41 | 1 | 1 | 1 | −15 | 70 | 68 | 1 | 3 | −3 | −14 | 48 | 43 | 1 | 0 | 9 | −14 | 116 | 116 | 2 |
| 1 | 4 | −18 | 38 | 40 | 1 | 3 | 1 | −16 | 44 | 44 | 1 | 2 | 1 | −15 | 96 | 95 | 1 | −1 | −2 | −14 | 35 | 35 | 2 | 1 | 9 | −14 | 28 | 26 | 1 |
| 2 | 4 | −18 | 36 | 34 | 1 | 4 | 1 | −16 | 38 | 41 | 1 | 3 | 1 | −15 | 73 | 75 | 1 | 0 | −2 | −14 | 40 | 43 | 1 | 2 | 9 | −14 | 34 | 27 | 2 |
| −1 | 5 | −18 | 25 | 23 | 3 | −2 | 2 | −16 | 24 | 23 | 3 | 4 | 1 | −15 | 31 | 28 | 1 | 1 | −2 | −14 | 44 | 42 | 1 | 3 | 9 | −14 | 71 | 66 | 2 |
| 0 | 5 | −18 | 33 | 29 | 2 | −1 | 2 | −16 | 86 | 84 | 2 | −2 | 2 | −15 | 81 | 87 | 2 | 2 | −2 | −14 | 32 | 35 | 1 | −3 | 10 | −14 | 100 | 99 | 2 |
| 1 | 5 | −18 | 68 | 65 | 1 | 0 | 2 | −16 | 106 | 101 | 2 | −1 | 2 | −15 | 79 | 74 | 2 | 3 | −2 | −14 | 43 | 42 | 1 | −2 | 10 | −14 | 70 | 76 | 2 |
| 2 | 5 | −18 | 41 | 37 | 2 | 1 | 2 | −16 | 67 | 64 | 1 | 0 | 2 | −15 | 47 | 46 | 2 | 4 | −2 | −14 | 91 | 85 | 1 | −1 | 10 | −14 | 64 | 61 | 1 |
| −1 | 6 | −18 | 12 | 14 | 5 | 2 | 2 | −16 | 63 | 63 | 1 | 1 | 2 | −15 | 86 | 83 | 2 | −1 | −1 | −14 | 68 | 68 | 1 | 0 | 10 | −14 | 26 | 25 | 2 |
| 0 | 6 | −18 | 21 | 20 | 3 | 3 | 2 | −16 | 105 | 102 | 1 | 2 | 2 | −15 | 72 | 76 | 1 | 0 | −1 | −14 | 59 | 52 | 1 | 1 | 10 | −14 | 58 | 51 | 1 |
| 1 | 6 | −18 | 69 | 68 | 1 | 4 | 2 | −16 | 31 | 29 | 1 | 3 | 2 | −15 | 35 | 40 | 1 | 1 | −1 | −14 | 72 | 76 | 1 | 2 | 10 | −14 | 73 | 74 | 2 |
| 2 | 6 | −18 | 13 | 11 | 5 | −2 | 3 | −16 | 58 | 60 | 2 | 4 | 2 | −15 | 59 | 55 | 1 | 2 | −1 | −14 | 112 | 117 | 1 | 3 | 10 | −14 | 12 | 14 | 6 |
| −1 | 7 | −18 | 22 | 21 | 3 | −1 | 3 | −16 | 72 | 72 | 2 | −2 | 3 | −15 | 79 | 75 | 2 | 3 | −1 | −14 | 46 | 42 | 1 | −2 | 11 | −14 | 47 | 47 | 2 |
| 0 | 7 | −18 | 19 | 22 | 2 | 0 | 3 | −16 | 38 | 30 | 2 | −1 | 3 | −15 | 58 | 58 | 2 | 4 | −1 | −14 | 54 | 52 | 1 | −1 | 11 | −14 | 12 | 14 | 4 |
| 1 | 7 | −18 | 109 | 102 | 2 | 1 | 3 | −16 | 52 | 51 | 1 | 0 | 3 | −15 | 13 | 10 | 3 | −1 | 0 | −14 | 63 | 63 | 2 | 0 | 11 | −14 | 24 | 22 | 1 |
| 2 | 7 | −18 | 90 | 92 | 2 | 2 | 3 | −16 | 35 | 32 | 1 | 1 | 3 | −15 | 200 | 198 | 3 | 0 | 0 | −14 | 86 | 86 | 1 | 1 | 11 | −14 | 60 | 62 | 1 |
| 1 | 8 | −18 | 58 | 61 | 1 | 3 | 3 | −16 | 14 | 15 | 3 | 2 | 3 | −15 | 116 | 121 | 1 | 1 | 0 | −14 | 43 | 45 | 1 | 2 | 11 | −14 | 66 | 69 | 2 |
| 1 | −1 | −17 | 77 | 82 | 2 | 4 | 3 | −16 | 71 | 71 | 1 | 3 | 3 | −15 | 10 | 13 | 4 | 2 | 0 | −14 | 101 | 102 | 2 | −2 | 12 | −14 | 20 | 23 | 3 |
| 0 | 0 | −17 | 39 | 34 | 2 | −2 | 4 | −16 | 31 | 31 | 3 | 4 | 3 | −15 | 54 | 53 | 1 | 3 | 0 | −14 | 109 | 111 | 1 | −1 | 12 | −14 | 80 | 78 | 2 |
| 1 | 0 | −17 | 111 | 105 | 3 | −1 | 4 | −16 | 45 | 43 | 2 | 5 | 3 | −15 | 105 | 111 | 2 | 4 | 0 | −14 | 69 | 66 | 1 | 0 | 12 | −14 | 57 | 56 | 1 |
| 2 | 0 | −17 | 16 | 18 | 2 | 0 | 4 | −16 | 90 | 93 | 2 | −2 | 4 | −15 | 39 | 42 | 2 | −2 | 1 | −14 | 57 | 60 | 2 | 1 | 12 | −14 | 13 | 19 | 3 |
| −1 | 1 | −17 | 87 | 83 | 2 | 1 | 4 | −16 | 96 | 96 | 2 | −1 | 4 | −15 | 61 | 62 | 2 | −1 | 1 | −14 | 73 | 72 | 2 | 2 | 12 | −14 | 14 | 12 | 4 |
| 0 | 1 | −17 | 211 | 197 | 5 | 2 | 4 | −16 | 21 | 22 | 1 | 0 | 4 | −15 | 39 | 44 | 1 | 0 | 1 | −14 | 50 | 51 | 1 | 0 | 13 | −14 | 66 | 59 | 2 |
| 1 | 1 | −17 | 38 | 33 | 1 | 3 | 4 | −16 | 54 | 56 | 1 | 1 | 4 | −15 | 86 | 87 | 1 | 1 | 1 | −14 | 9 | 7 | 5 | 1 | 13 | −14 | 50 | 53 | 2 |
| 2 | 1 | −17 | 117 | 113 | 1 | 4 | 4 | −16 | 26 | 26 | 1 | 2 | 4 | −15 | 109 | 108 | 1 | 2 | 1 | −14 | 99 | 102 | 1 | 0 | −6 | −13 | 41 | 37 | 2 |
| 3 | 1 | −17 | 85 | 84 | 2 | −2 | 5 | −16 | 24 | 20 | 3 | 3 | 4 | −15 | 67 | 73 | 1 | 3 | 1 | −14 | 115 | 116 | 1 | 1 | −6 | −13 | 41 | 38 | 1 |
| −1 | 2 | −17 | 53 | 54 | 2 | −1 | 5 | −16 | 97 | 96 | 2 | 4 | 4 | −15 | 44 | 43 | 1 | 4 | 1 | −14 | 21 | 19 | 2 | −1 | −5 | −13 | 92 | 84 | 2 |
| 0 | 2 | −17 | 124 | 117 | 3 | 0 | 5 | −16 | 69 | 69 | 1 | 5 | 4 | −15 | 31 | 27 | 2 | 5 | 1 | −14 | 23 | 23 | 2 | 0 | −5 | −13 | 44 | 43 | 1 |
| 1 | 2 | −17 | 88 | 85 | 1 | 1 | 5 | −16 | 46 | 47 | 1 | −2 | 5 | −15 | 27 | 25 | 3 | −2 | 2 | −14 | 100 | 108 | 3 | 1 | −5 | −13 | 110 | 106 | 2 |
| 2 | 2 | −17 | 49 | 50 | 1 | 2 | 5 | −16 | 58 | 56 | 1 | −1 | 5 | −15 | 177 | 181 | 3 | −1 | 2 | −14 | 92 | 92 | 3 | 2 | −5 | −13 | 39 | 41 | 1 |
| 3 | 2 | −17 | 48 | 49 | 1 | 3 | 5 | −16 | 87 | 87 | 1 | 0 | 5 | −15 | 162 | 200 | 4 | 0 | 2 | −14 | 226 | 229 | 2 | 3 | −5 | −13 | 52 | 55 | 1 |
| −1 | 3 | −17 | 42 | 35 | 2 | 4 | 5 | −16 | 49 | 53 | 1 | 1 | 5 | −15 | 108 | 106 | 2 | 1 | 2 | −14 | 91 | 88 | 1 | −2 | −4 | −13 | 32 | 31 | 2 |
| 0 | 3 | −17 | 100 | 96 | 2 | −2 | 6 | −16 | 89 | 87 | 2 | 2 | 5 | −15 | 72 | 72 | 1 | 2 | 2 | −14 | 145 | 146 | 2 | −1 | −4 | −13 | 83 | 86 | 2 |
| 1 | 3 | −17 | 43 | 44 | 1 | −1 | 6 | −16 | 43 | 42 | 2 | 3 | 5 | −15 | 122 | 120 | 2 | 3 | 2 | −14 | 73 | 75 | 1 | 0 | −4 | −13 | 44 | 39 | 1 |
| 2 | 3 | −17 | 11 | 7 | 4 | 0 | 6 | −16 | 122 | 118 | 2 | 4 | 5 | −15 | 86 | 85 | 1 | 4 | 2 | −14 | 21 | 15 | 2 | 1 | −4 | −13 | 85 | 81 | 1 |
| 3 | 3 | −17 | 34 | 34 | 1 | 1 | 6 | −16 | 93 | 90 | 2 | −3 | 6 | −15 | 51 | 51 | 2 | 5 | 2 | −14 | 21 | 21 | 2 | 2 | −4 | −13 | 26 | 24 | 2 |
| −2 | 4 | −17 | 51 | 52 | 2 | 2 | 6 | −16 | 18 | 14 | 2 | −2 | 6 | −15 | 48 | 51 | 2 | −2 | 3 | −14 | 145 | 149 | 3 | 3 | −4 | −13 | 81 | 80 | 1 |
| −1 | 4 | −17 | 46 | 46 | 2 | 3 | 6 | −16 | 36 | 34 | 1 | −1 | 6 | −15 | 68 | 68 | 2 | −1 | 3 | −14 | 221 | 227 | 3 | 4 | −4 | −13 | 13 | 14 | 2 |
| 0 | 4 | −17 | 131 | 123 | 3 | 4 | 6 | −16 | 57 | 62 | 2 | 0 | 6 | −15 | 154 | 158 | 4 | 0 | 3 | −14 | 237 | 243 | 4 | −2 | −3 | −13 | 80 | 82 | 2 |
| 1 | 4 | −17 | 18 | 16 | 3 | −2 | 7 | −16 | 18 | 25 | 3 | 1 | 6 | −15 | 30 | 25 | 2 | 1 | 3 | −14 | 121 | 125 | 1 | −1 | −3 | −13 | 43 | 40 | 2 |
| 2 | 4 | −17 | 51 | 50 | 1 | −1 | 7 | −16 | 64 | 61 | 2 | 2 | 6 | −15 | 42 | 42 | 1 | 2 | 3 | −14 | 75 | 80 | 1 | 0 | −3 | −13 | 55 | 53 | 1 |
| 3 | 4 | −17 | 10 | 8 | 7 | 0 | 7 | −16 | 32 | 33 | 2 | 3 | 6 | −15 | 84 | 84 | 1 | 3 | 3 | −14 | 194 | 197 | 3 | 1 | −3 | −13 | 54 | 60 | 1 |

TABLE 7-continued

Observed and calculated structure factors for NEL

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −2 | 5 | −17 | 42 | 39 | 2 | 1 | 7 | −16 | 104 | 106 | 1 | 4 | 6 | −15 | 103 | 107 | 2 | 4 | 3 | −14 | 61 | 55 | 1 | 2 | −3 | −13 | 11 | 10 | 4 |
| −1 | 5 | −17 | 37 | 36 | 2 | 2 | 7 | −16 | 88 | 86 | 2 | −3 | 7 | −15 | 29 | 31 | 3 | 5 | 3 | −14 | 17 | 15 | 4 | 3 | −3 | −13 | 52 | 53 | 1 |
| 0 | 5 | −17 | 18 | 14 | 2 | 3 | 7 | −16 | 38 | 35 | 1 | −2 | 7 | −15 | 127 | 126 | 3 | −2 | 4 | −14 | 67 | 64 | 2 | 4 | −3 | −13 | 33 | 33 | 1 |
| 1 | 5 | −17 | 59 | 60 | 1 | −2 | 8 | −16 | 64 | 64 | 2 | −1 | 7 | −15 | 73 | 70 | 2 | −1 | 4 | −14 | 182 | 190 | 3 | −3 | −2 | −13 | 74 | 76 | 2 |
| 2 | 5 | −17 | 36 | 35 | 1 | −1 | 8 | −16 | 68 | 63 | 2 | 0 | 7 | −15 | 51 | 54 | 1 | 0 | 4 | −14 | 327 | 325 | 5 | −1 | −2 | −13 | 43 | 40 | 1 |
| 3 | 5 | −17 | 18 | 17 | 2 | 0 | 8 | −16 | 60 | 56 | 1 | 1 | 7 | −15 | 48 | 52 | 1 | 1 | 4 | −14 | 129 | 138 | 2 | 0 | −2 | −13 | 24 | 24 | 2 |
| −2 | 6 | −17 | 83 | 78 | 2 | 1 | 8 | −16 | 21 | 22 | 2 | 2 | 7 | −15 | 56 | 58 | 1 | 2 | 4 | −14 | 125 | 123 | 1 | 1 | −2 | −13 | 77 | 79 | 1 |
| −1 | 6 | −17 | 41 | 39 | 2 | 2 | 8 | −16 | 59 | 61 | 2 | 3 | 7 | −15 | 67 | 69 | 1 | 3 | 4 | −14 | 184 | 206 | 3 | 2 | −2 | −13 | 34 | 38 | 1 |
| 0 | 6 | −17 | 16 | 15 | 3 | 3 | 8 | −16 | 52 | 45 | 2 | 4 | 7 | −15 | 42 | 40 | 2 | 4 | 4 | −14 | 65 | 65 | 1 | 3 | −2 | −13 | 108 | 109 | 1 |
| 1 | 6 | −17 | 105 | 108 | 2 | −2 | 9 | −16 | 64 | 62 | 2 | −3 | 8 | −15 | 81 | 85 | 2 | 5 | 4 | −14 | 51 | 49 | 2 | 4 | −2 | −13 | 108 | 107 | 1 |
| 2 | 6 | −17 | 67 | 68 | 2 | −1 | 9 | −16 | 84 | 80 | 2 | −2 | 8 | −15 | 43 | 43 | 2 | −2 | 5 | −14 | 53 | 51 | 2 | 5 | −2 | −13 | 27 | 32 | 2 |
| 3 | 6 | −17 | 21 | 20 | 2 | 0 | 9 | −16 | 37 | 32 | 1 | −1 | 8 | −15 | 66 | 67 | 2 | −1 | 5 | −14 | 59 | 54 | 2 | −3 | −1 | −13 | 30 | 26 | 2 |
| −2 | 7 | −17 | 103 | 101 | 2 | 1 | 9 | −16 | 39 | 37 | 1 | 0 | 8 | −15 | 123 | 121 | 2 | 0 | 5 | −14 | 83 | 100 | 2 | −1 | −1 | −13 | 31 | 26 | 2 |
| −1 | 7 | −17 | 42 | 41 | 2 | 2 | 9 | −16 | 67 | 65 | 2 | 1 | 8 | −15 | 29 | 27 | 1 | 1 | 5 | −14 | 73 | 75 | 1 | 0 | −1 | −13 | 107 | 102 | 1 |
| 0 | 7 | −17 | 54 | 51 | 1 | 3 | 9 | −16 | 55 | 58 | 2 | 2 | 8 | −15 | 80 | 78 | 2 | 2 | 5 | −14 | 171 | 173 | 2 | 1 | −1 | −13 | 135 | 131 | 1 |
| 1 | 7 | −17 | 16 | 18 | 2 | −2 | 10 | −16 | 47 | 44 | 2 | 3 | 8 | −15 | 85 | 85 | 1 | 3 | 5 | −14 | 74 | 69 | 1 | 2 | −1 | −13 | 13 | 8 | 2 |
| 2 | 7 | −17 | 33 | 30 | 2 | −1 | 10 | −16 | 36 | 36 | 2 | −3 | 9 | −15 | 40 | 43 | 2 | 4 | 5 | −14 | 63 | 63 | 1 | 3 | −1 | −13 | 110 | 108 | 1 |
| 3 | 7 | −17 | 15 | 16 | 3 | 0 | 10 | −16 | 16 | 17 | 2 | −2 | 9 | −15 | 38 | 37 | 2 | 5 | 5 | −14 | 62 | 58 | 2 | 4 | −1 | −13 | 31 | 34 | 1 |
| −2 | 8 | −17 | 17 | 18 | 3 | 1 | 10 | −16 | 114 | 117 | 2 | −1 | 9 | −15 | 43 | 44 | 1 | −3 | 6 | −14 | 44 | 45 | 2 | 5 | −1 | −13 | 31 | 32 | 1 |
| −1 | 8 | −17 | 86 | 83 | 2 | 2 | 10 | −16 | 121 | 122 | 3 | 0 | 9 | −15 | 65 | 60 | 1 | −2 | 6 | −14 | 34 | 29 | 2 | −4 | 0 | −13 | 19 | 17 | 3 |
| 0 | 8 | −17 | 11 | 9 | 5 | −1 | 11 | −16 | 19 | 18 | 2 | 1 | 9 | −15 | 53 | 56 | 1 | −1 | 6 | −14 | 9 | 4 | 9 | −3 | 0 | −13 | 73 | 72 | 2 |
| 1 | 8 | −17 | 77 | 75 | 1 | 0 | 11 | −16 | 17 | 14 | 2 | 2 | 9 | −15 | 114 | 107 | 3 | 0 | 6 | −14 | 207 | 203 | 5 | −1 | 0 | −13 | 28 | 30 | 2 |
| 2 | 8 | −17 | 35 | 30 | 2 | 1 | 11 | −16 | 44 | 44 | 2 | 3 | 9 | −15 | 51 | 53 | 2 | 1 | 6 | −14 | 47 | 47 | 1 | 0 | 0 | −13 | 37 | 39 | 1 |
| 3 | 8 | −17 | 13 | 18 | 4 | 1 | −4 | −15 | 46 | 47 | 1 | −2 | 10 | −15 | 60 | 61 | 2 | 2 | 6 | −14 | 84 | 87 | 1 | 1 | 0 | −13 | 161 | 153 | 2 |
| −1 | 9 | −17 | 25 | 25 | 2 | 0 | −3 | −15 | 108 | 106 | 2 | −1 | 10 | −15 | 78 | 74 | 1 | 3 | 6 | −14 | 99 | 97 | 2 | 2 | 0 | −13 | 15 | 20 | 2 |
| 0 | 9 | −17 | 50 | 46 | 1 | 1 | −3 | −15 | 49 | 48 | 1 | 0 | 10 | −15 | 56 | 56 | 1 | 4 | 6 | −14 | 34 | 34 | 1 | 3 | 0 | −13 | 68 | 75 | 1 |
| 1 | 9 | −17 | 47 | 49 | 1 | 2 | −3 | −15 | 56 | 53 | 1 | 1 | 10 | −15 | 47 | 45 | 1 | 5 | 6 | −14 | 43 | 41 | 2 | 4 | 0 | −13 | 9 | 10 | 2 |
| 2 | 9 | −17 | 67 | 64 | 2 | −1 | −2 | −15 | 57 | 61 | 1 | 2 | 10 | −15 | 63 | 62 | 2 | −3 | 7 | −14 | 44 | 44 | 2 | 5 | 0 | −13 | 88 | 90 | 1 |
| 0 | 10 | −17 | 61 | 56 | 2 | 0 | −2 | −15 | 109 | 103 | 2 | −2 | 11 | −15 | 49 | 44 | 2 | −2 | 7 | −14 | 75 | 74 | 2 | −4 | 1 | −13 | 49 | 46 | 2 |
| 1 | 10 | −17 | 19 | 19 | 3 | 1 | −2 | −15 | 51 | 52 | 1 | −1 | 11 | −15 | 47 | 42 | 1 | −1 | 7 | −14 | 158 | 171 | 2 | −3 | 1 | −13 | 152 | 156 | 3 |
| 0 | −2 | −16 | 40 | 37 | 1 | 2 | −2 | −15 | 30 | 31 | 1 | 0 | 11 | −15 | 43 | 36 | 1 | 0 | 7 | −14 | 140 | 143 | 3 | −2 | 1 | −13 | 94 | 97 | 3 |
| 1 | −2 | −16 | 27 | 34 | 2 | 3 | −2 | −15 | 51 | 51 | 1 | 1 | 11 | −15 | 90 | 88 | 2 | 1 | 7 | −14 | 161 | 165 | 2 | −1 | 1 | −13 | 70 | 78 | 2 |
| 2 | −2 | −16 | 26 | 27 | 2 | −1 | −1 | −15 | 72 | 66 | 2 | 2 | 11 | −15 | 30 | 27 | 2 | 2 | 7 | −14 | 82 | 86 | 1 | 0 | 1 | −13 | 48 | 45 | 1 |
| −1 | −1 | −16 | 17 | 21 | 5 | 0 | −1 | −15 | 36 | 36 | 2 | 0 | 12 | −15 | 64 | 60 | 1 | 3 | 7 | −14 | 115 | 115 | 2 | 1 | 1 | −13 | 147 | 154 | 1 |
| 0 | −1 | −16 | 61 | 59 | 1 | 1 | −1 | −15 | 33 | 37 | 2 | 1 | 12 | −15 | 67 | 67 | 2 | 4 | 7 | −14 | 62 | 63 | 1 | 2 | 1 | −13 | 23 | 24 | 2 |
| 1 | −1 | −16 | 88 | 82 | 1 | 2 | −1 | −15 | 13 | 12 | 3 | 0 | −5 | −14 | 37 | 48 | 2 | −3 | 8 | −14 | 59 | 55 | 2 | 3 | 1 | −13 | 80 | 82 | 1 |
| 2 | −1 | −16 | 40 | 44 | 1 | 3 | −1 | −15 | 37 | 37 | 1 | 1 | −5 | −14 | 13 | 10 | 3 | −2 | 8 | −14 | 24 | 26 | 3 | 4 | 1 | −13 | 43 | 44 | 1 |
| 3 | −1 | −16 | 9 | 13 | 8 | 4 | −1 | −15 | 26 | 26 | 1 | −1 | −4 | −14 | 19 | 12 | 3 | −1 | 8 | −14 | 69 | 76 | 1 | 5 | 1 | −13 | 132 | 129 | 2 |
| −1 | 0 | −16 | 94 | 91 | 2 | −1 | 0 | −15 | 12 | 7 | 12 | 0 | −4 | −14 | 39 | 37 | 1 | 0 | 8 | −14 | 84 | 83 | 1 | −4 | 2 | −13 | 54 | 52 | 2 |
| 0 | 0 | −16 | 125 | 125 | 2 | 0 | 0 | −15 | 25 | 25 | 2 | 1 | −4 | −14 | 82 | 82 | 1 | 1 | 8 | −14 | 117 | 119 | 1 | −3 | 2 | −13 | 143 | 141 | 3 |
| −2 | 2 | −13 | 173 | 185 | 4 | −1 | 13 | −13 | 47 | 47 | 1 | −3 | 3 | −12 | 48 | 51 | 2 | 2 | 12 | −12 | 69 | 67 | 2 | 5 | 1 | −11 | 132 | 127 | 2 |
| −1 | 2 | −13 | 57 | 59 | 2 | 0 | 13 | −13 | 5 | 9 | 4 | −2 | 3 | −12 | 98 | 102 | 2 | −2 | 13 | −12 | 73 | 73 | 1 | −5 | 2 | −11 | 31 | 24 | 2 |
| 0 | 2 | −13 | 142 | 139 | 1 | 1 | 13 | −13 | 52 | 51 | 2 | −1 | 3 | −12 | 89 | 95 | 1 | −1 | 13 | −12 | 81 | 83 | 1 | −4 | 2 | −11 | 83 | 82 | 2 |
| 1 | 2 | −13 | 158 | 158 | 1 | 0 | −7 | −12 | 46 | 43 | 2 | 0 | 3 | −12 | 122 | 127 | 1 | 0 | 13 | −12 | 58 | 51 | 1 | −3 | 2 | −11 | 41 | 42 | 2 |
| 2 | 2 | −13 | 55 | 56 | 1 | 1 | −7 | −12 | 21 | 24 | 2 | 1 | 3 | −12 | 185 | 194 | 2 | 1 | 13 | −12 | 30 | 30 | 1 | −2 | 2 | −11 | 54 | 56 | 1 |
| 3 | 2 | −13 | 118 | 120 | 2 | −1 | −6 | −12 | 44 | 45 | 2 | 2 | 3 | −12 | 85 | 85 | 1 | 2 | 13 | −12 | 34 | 38 | 2 | −1 | 2 | −11 | 136 | 136 | 2 |
| 4 | 2 | −13 | 34 | 28 | 1 | 0 | −6 | −12 | 31 | 35 | 2 | 3 | 3 | −12 | 28 | 29 | 1 | −1 | −7 | −11 | 49 | 51 | 2 | 0 | 2 | −11 | 193 | 194 | 2 |
| 5 | 2 | −13 | 126 | 122 | 2 | 1 | −6 | −12 | 60 | 59 | 1 | 4 | 3 | −12 | 202 | 204 | 5 | 0 | −7 | −11 | 60 | 61 | 2 | 1 | 2 | −11 | 90 | 89 | 1 |
| −4 | 3 | −13 | 58 | 57 | 2 | 2 | −6 | −12 | 111 | 108 | 2 | 5 | 3 | −12 | 115 | 117 | 1 | 1 | −7 | −11 | 35 | 37 | 1 | 2 | 2 | −11 | 18 | 14 | 1 |

TABLE 7-continued

| Observed and calculated structure factors for NEL | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
| −3 | 3 | −13 | 119 | 120 | 3 | 3 | −6 | −12 | 75 | 76 | 2 | −5 | 4 | −12 | 95 | 97 | 2 | 2 | −7 | −11 | 79 | 80 | 2 | 3 | 2 | −11 | 114 | 119 | 1 |
| −2 | 3 | −13 | 57 | 51 | 2 | −2 | −5 | −12 | 44 | 43 | 2 | −4 | 4 | −12 | 32 | 26 | 2 | 3 | −7 | −11 | 47 | 49 | 2 | 4 | 2 | −11 | 115 | 111 | 2 |
| −1 | 3 | −13 | 29 | 34 | 2 | −1 | −5 | −12 | 28 | 24 | 3 | −3 | 4 | −12 | 103 | 107 | 2 | −2 | −6 | −11 | 101 | 97 | 2 | 5 | 2 | −11 | 94 | 93 | 1 |
| 0 | 3 | −13 | 311 | 310 | 3 | 0 | −5 | −12 | 24 | 27 | 2 | −2 | 4 | −12 | 22 | 20 | 2 | −1 | −6 | −11 | 55 | 54 | 2 | 6 | 2 | −11 | 38 | 38 | 1 |
| 1 | 3 | −13 | 23 | 20 | 1 | 1 | −5 | −12 | 88 | 88 | 1 | −1 | 4 | −12 | 132 | 131 | 2 | 0 | −6 | −11 | 95 | 88 | 2 | −5 | 3 | −11 | 37 | 36 | 2 |
| 2 | 3 | −13 | 125 | 127 | 1 | 2 | −5 | −12 | 29 | 30 | 2 | 0 | 4 | −12 | 42 | 41 | 1 | 1 | −6 | −11 | 42 | 38 | 1 | −4 | 3 | −11 | 143 | 144 | 3 |
| 3 | 3 | −13 | 102 | 103 | 2 | 3 | −5 | −12 | 139 | 138 | 2 | 1 | 4 | −12 | 180 | 179 | 2 | 2 | −6 | −11 | 68 | 67 | 1 | −3 | 3 | −11 | 84 | 87 | 2 |
| 4 | 3 | −13 | 129 | 134 | 2 | 4 | −5 | −12 | 71 | 78 | 2 | 2 | 4 | −12 | 94 | 96 | 1 | 3 | −6 | −11 | 37 | 37 | 1 | −2 | 3 | −11 | 93 | 97 | 1 |
| 5 | 3 | −13 | 127 | 119 | 3 | −3 | −4 | −12 | 72 | 74 | 2 | 3 | 4 | −12 | 61 | 63 | 1 | −3 | −5 | −11 | 112 | 115 | 3 | −1 | 3 | −11 | 127 | 134 | 1 |
| −2 | 4 | −13 | 138 | 137 | 3 | −2 | −4 | −12 | 69 | 69 | 2 | 4 | 4 | −12 | 30 | 28 | 1 | −2 | −5 | −11 | 49 | 47 | 1 | 0 | 3 | −11 | 458 | 460 | 4 |
| −1 | 4 | −13 | 131 | 130 | 2 | −1 | −4 | −12 | 79 | 76 | 2 | 5 | 4 | −12 | 158 | 161 | 1 | −1 | −5 | −11 | 88 | 82 | 2 | 1 | 3 | −11 | 58 | 63 | 1 |
| 0 | 4 | −13 | 63 | 69 | 1 | 0 | −4 | −12 | 45 | 42 | 1 | 6 | 4 | −12 | 38 | 37 | 1 | 0 | −5 | −11 | 24 | 26 | 2 | 2 | 3 | −11 | 114 | 113 | 1 |
| 1 | 4 | −13 | 13 | 14 | 2 | 1 | −4 | −12 | 85 | 92 | 2 | −4 | 5 | −12 | 99 | 99 | 2 | 1 | −5 | −11 | 79 | 78 | 1 | 3 | 3 | −11 | 97 | 98 | 1 |
| 2 | 4 | −13 | 80 | 82 | 1 | 2 | −4 | −12 | 70 | 65 | 1 | −2 | 5 | −12 | 55 | 53 | 2 | 2 | −5 | −11 | 51 | 53 | 1 | 4 | 3 | −11 | 186 | 183 | 2 |
| 3 | 4 | −13 | 26 | 30 | 1 | 3 | −4 | −12 | 67 | 66 | 1 | −1 | 5 | −12 | 220 | 225 | 2 | 3 | −5 | −11 | 57 | 54 | 1 | 5 | 3 | −11 | 25 | 21 | 1 |
| 4 | 4 | −13 | 27 | 22 | 2 | 4 | −4 | −12 | 27 | 28 | 1 | 0 | 5 | −12 | 116 | 112 | 1 | 4 | −5 | −11 | 67 | 66 | 1 | 6 | 3 | −11 | 90 | 93 | 1 |
| 5 | 4 | −13 | 123 | 116 | 3 | −3 | −3 | −12 | 22 | 22 | 3 | 1 | 5 | −12 | 145 | 147 | 1 | −4 | −4 | −11 | 53 | 50 | 2 | −5 | 4 | −11 | 40 | 35 | 2 |
| −2 | 5 | −13 | 104 | 103 | 3 | −2 | −3 | −12 | 52 | 52 | 1 | 2 | 5 | −12 | 110 | 114 | 1 | −3 | −4 | −11 | 61 | 57 | 2 | −4 | 4 | −11 | 203 | 194 | 5 |
| −1 | 5 | −13 | 234 | 233 | 3 | −1 | −3 | −12 | 79 | 82 | 1 | 3 | 5 | −12 | 184 | 182 | 3 | −2 | −4 | −11 | 82 | 79 | 1 | −3 | 4 | −11 | 66 | 63 | 2 |
| 0 | 5 | −13 | 430 | 428 | 5 | 0 | −3 | −12 | 90 | 86 | 2 | 4 | 5 | −12 | 144 | 145 | 1 | −1 | −4 | −11 | 66 | 67 | 1 | −2 | 4 | −11 | 59 | 59 | 1 |
| 1 | 5 | −13 | 199 | 204 | 2 | 1 | −3 | −12 | 124 | 121 | 2 | 5 | 5 | −12 | 40 | 42 | 1 | 0 | −4 | −11 | 88 | 90 | 2 | −1 | 4 | −11 | 164 | 167 | 2 |
| 2 | 5 | −13 | 48 | 49 | 1 | 2 | −3 | −12 | 41 | 47 | 1 | 6 | 5 | −12 | 24 | 25 | 1 | 1 | −4 | −11 | 60 | 65 | 2 | 0 | 4 | −11 | 108 | 105 | 1 |
| 3 | 5 | −13 | 96 | 98 | 2 | 3 | −3 | −12 | 77 | 79 | 1 | −3 | 6 | −12 | 69 | 70 | 2 | 2 | −4 | −11 | 137 | 139 | 2 | 1 | 4 | −11 | 16 | 19 | 1 |
| 4 | 5 | −13 | 122 | 123 | 2 | 4 | −3 | −12 | 79 | 76 | 1 | −2 | 6 | −12 | 154 | 151 | 3 | 3 | −4 | −11 | 15 | 14 | 2 | 2 | 4 | −11 | 80 | 81 | 1 |
| 5 | 5 | −13 | 30 | 25 | 1 | 5 | −3 | −12 | 42 | 43 | 2 | −1 | 6 | −12 | 152 | 152 | 2 | 4 | −4 | −11 | 23 | 23 | 1 | 3 | 4 | −11 | 62 | 61 | 1 |
| −3 | 6 | −13 | 55 | 53 | 2 | −4 | −2 | −12 | 50 | 47 | 2 | 0 | 6 | −12 | 121 | 117 | 1 | 5 | −4 | −11 | 22 | 21 | 3 | 4 | 4 | −11 | 107 | 107 | 1 |
| −2 | 6 | −13 | 108 | 108 | 3 | −3 | −2 | −12 | 121 | 120 | 3 | 1 | 6 | −12 | 161 | 164 | 2 | −4 | −3 | −11 | 16 | 13 | 4 | 5 | 4 | −11 | 73 | 73 | 1 |
| −1 | 6 | −13 | 104 | 103 | 2 | −2 | −2 | −12 | 67 | 65 | 1 | 2 | 6 | −12 | 64 | 62 | 1 | −3 | −3 | −11 | 104 | 103 | 2 | 6 | 4 | −11 | 82 | 75 | 1 |
| 0 | 6 | −13 | 285 | 317 | 12 | −1 | −2 | −12 | 128 | 124 | 2 | 3 | 6 | −12 | 153 | 157 | 2 | −2 | −3 | −11 | 77 | 81 | 1 | −5 | 5 | −11 | 19 | 21 | 4 |
| 1 | 6 | −13 | 156 | 148 | 2 | 0 | −2 | −12 | 234 | 230 | 3 | 4 | 6 | −12 | 80 | 84 | 1 | −1 | −3 | −11 | 79 | 74 | 1 | −4 | 5 | −11 | 85 | 85 | 2 |
| 2 | 6 | −13 | 58 | 63 | 1 | 1 | −2 | −12 | 101 | 109 | 1 | 5 | 6 | −12 | 30 | 30 | 1 | 0 | −3 | −11 | 41 | 29 | 1 | −3 | 5 | −11 | 109 | 110 | 2 |
| 3 | 6 | −13 | 110 | 112 | 2 | 2 | −2 | −12 | 96 | 127 | 1 | −3 | 7 | −12 | 122 | 129 | 3 | 1 | −3 | −11 | 54 | 53 | 1 | −2 | 5 | −11 | 93 | 96 | 2 |
| 4 | 6 | −13 | 103 | 105 | 1 | 3 | −2 | −12 | 160 | 159 | 2 | −2 | 7 | −12 | 70 | 66 | 2 | 2 | −3 | −11 | 87 | 89 | 1 | −1 | 5 | −11 | 85 | 86 | 1 |
| 5 | 6 | −13 | 47 | 46 | 1 | 4 | −2 | −12 | 77 | 78 | 1 | −1 | 7 | −12 | 188 | 186 | 2 | 3 | −3 | −11 | 95 | 94 | 1 | 0 | 5 | −11 | 109 | 110 | 1 |
| −3 | 7 | −13 | 98 | 103 | 3 | 5 | −2 | −12 | 71 | 72 | 2 | 0 | 7 | −12 | 123 | 124 | 1 | 4 | −3 | −11 | 12 | 12 | 3 | 1 | 5 | −11 | 124 | 125 | 1 |
| −2 | 7 | −13 | 93 | 93 | 2 | −4 | −1 | −12 | 28 | 28 | 3 | 1 | 7 | −12 | 159 | 158 | 2 | 5 | −3 | −11 | 40 | 38 | 2 | 2 | 5 | −11 | 160 | 158 | 1 |
| −1 | 7 | −13 | 31 | 32 | 2 | −3 | −1 | −12 | 78 | 78 | 2 | 2 | 7 | −12 | 128 | 129 | 1 | −4 | −2 | −11 | 39 | 34 | 2 | 3 | 5 | −11 | 33 | 32 | 1 |
| 0 | 7 | −13 | 172 | 160 | 4 | −2 | −1 | −12 | 99 | 100 | 2 | 3 | 7 | −12 | 115 | 117 | 1 | −3 | −2 | −11 | 164 | 161 | 4 | 4 | 5 | −11 | 148 | 147 | 1 |
| 1 | 7 | −13 | 87 | 81 | 1 | −1 | −1 | −12 | 37 | 33 | 2 | 4 | 7 | −12 | 85 | 82 | 1 | −2 | −2 | −11 | 131 | 130 | 2 | 5 | 5 | −11 | 17 | 16 | 1 |
| 2 | 7 | −13 | 156 | 166 | 2 | 0 | −1 | −12 | 241 | 249 | 2 | 5 | 7 | −12 | 119 | 121 | 1 | −1 | −2 | −11 | 98 | 96 | 1 | 6 | 5 | −11 | 25 | 24 | 1 |
| 3 | 7 | −13 | 26 | 24 | 2 | 1 | −1 | −12 | 81 | 83 | 1 | −3 | 8 | −12 | 107 | 106 | 3 | 0 | −2 | −11 | 75 | 71 | 1 | −5 | 6 | −11 | 37 | 38 | 2 |
| 4 | 7 | −13 | 92 | 93 | 1 | 2 | −1 | −12 | 208 | 209 | 4 | −2 | 8 | −12 | 50 | 54 | 2 | 1 | −2 | −11 | 84 | 88 | 1 | −4 | 6 | −11 | 100 | 101 | 2 |
| 5 | 7 | −13 | 51 | 51 | 1 | 3 | −1 | −12 | 57 | 60 | 1 | −1 | 8 | −12 | 219 | 223 | 4 | 2 | −2 | −11 | 74 | 72 | 1 | −3 | 6 | −11 | 93 | 96 | 2 |
| −3 | 8 | −13 | 21 | 16 | 4 | 4 | −1 | −12 | 44 | 43 | 1 | 0 | 8 | −12 | 109 | 109 | 2 | 3 | −2 | −11 | 27 | 27 | 1 | −2 | 6 | −11 | 155 | 152 | 2 |
| −2 | 8 | −13 | 132 | 131 | 3 | 5 | −1 | −12 | 94 | 92 | 1 | 1 | 8 | −12 | 196 | 208 | 3 | 4 | −2 | −11 | 121 | 121 | 1 | −1 | 6 | −11 | 140 | 145 | 2 |
| −1 | 8 | −13 | 98 | 104 | 2 | −4 | 0 | −12 | 45 | 41 | 2 | 2 | 8 | −12 | 85 | 89 | 1 | 5 | −2 | −11 | 51 | 49 | 1 | 0 | 6 | −11 | 121 | 112 | 1 |
| 0 | 8 | −13 | 56 | 63 | 1 | −3 | 0 | −12 | 80 | 82 | 2 | 3 | 8 | −12 | 157 | 153 | 2 | −5 | −1 | −11 | 12 | 20 | 7 | 1 | 6 | −11 | 203 | 207 | 2 |
| 1 | 8 | −13 | 70 | 66 | 1 | −2 | 0 | −12 | 48 | 44 | 2 | 4 | 8 | −12 | 87 | 89 | 1 | −4 | −1 | −11 | 28 | 21 | 3 | 2 | 6 | −11 | 113 | 108 | 1 |
| 2 | 8 | −13 | 63 | 60 | 1 | −1 | 0 | −12 | 89 | 86 | 1 | 5 | 8 | −12 | 45 | 44 | 1 | −3 | −1 | −11 | 99 | 95 | 2 | 3 | 6 | −11 | 140 | 140 | 1 |

TABLE 7-continued

Observed and calculated structure factors for NEL

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 3 | 8 | −13 | 43 | 43 | 1 | 0 | 0 | −12 | 88 | 88 | 1 | −3 | 9 | −12 | 64 | 69 | 2 | −2 | −1 | −11 | 245 | 244 | 5 | 4 | 6 | −11 | 131 | 129 | 1 |
| 4 | 8 | −13 | 60 | 58 | 1 | 1 | 0 | −12 | 120 | 119 | 1 | −2 | 9 | −12 | 55 | 55 | 2 | −1 | −1 | −11 | 162 | 167 | 1 | 5 | 6 | −11 | 106 | 108 | 1 |
| 5 | 8 | −13 | 21 | 18 | 1 | 2 | 0 | −12 | 67 | 71 | 1 | −1 | 9 | −12 | 56 | 54 | 1 | 0 | −1 | −11 | 87 | 85 | 1 | −3 | 7 | −11 | 35 | 31 | 2 |
| −3 | 9 | −13 | 108 | 109 | 3 | 3 | 0 | −12 | 105 | 108 | 1 | 0 | 9 | −12 | 70 | 75 | 1 | 1 | −1 | −11 | 238 | 237 | 2 | −2 | 7 | −11 | 259 | 264 | 6 |
| −2 | 9 | −13 | 147 | 145 | 3 | 4 | 0 | −12 | 24 | 23 | 1 | 1 | 9 | −12 | 118 | 122 | 2 | 2 | −1 | −11 | 158 | 157 | 1 | −1 | 7 | −11 | 53 | 52 | 1 |
| −1 | 9 | −13 | 24 | 25 | 2 | 5 | 0 | −12 | 148 | 142 | 2 | 2 | 9 | −12 | 63 | 65 | 2 | 3 | −1 | −11 | 136 | 135 | 1 | 0 | 7 | −11 | 87 | 84 | 1 |
| 0 | 9 | −13 | 102 | 99 | 2 | −5 | 1 | −12 | 90 | 87 | 2 | 3 | 9 | −12 | 12 | 15 | 5 | 4 | −1 | −11 | 140 | 141 | 1 | 1 | 7 | −11 | 80 | 83 | 1 |
| 1 | 9 | −13 | 63 | 61 | 1 | −4 | 1 | −12 | 33 | 27 | 2 | 4 | 9 | −12 | 48 | 52 | 1 | 5 | −1 | −11 | 40 | 40 | 1 | 2 | 7 | −11 | 281 | 289 | 2 |
| 2 | 9 | −13 | 127 | 141 | 3 | −3 | 1 | −12 | 182 | 179 | 4 | 5 | 9 | −12 | 35 | 36 | 1 | −5 | 0 | −11 | 64 | 63 | 2 | 3 | 7 | −11 | 38 | 36 | 1 |
| 3 | 9 | −13 | 45 | 42 | 2 | −2 | 1 | −12 | 59 | 58 | 2 | −3 | 10 | −12 | 67 | 65 | 2 | −4 | 0 | −11 | 44 | 41 | 2 | 4 | 7 | −11 | 37 | 33 | 1 |
| 4 | 9 | −13 | 40 | 40 | 1 | −1 | 1 | −12 | 141 | 146 | 2 | −2 | 10 | −12 | 60 | 64 | 2 | −3 | 0 | −11 | 121 | 120 | 3 | 5 | 7 | −11 | 35 | 31 | 1 |
| −3 | 10 | −13 | 26 | 26 | 3 | 0 | 1 | −12 | 52 | 51 | 1 | −1 | 10 | −12 | 3 | 4 | 3 | −2 | 0 | −11 | 135 | 143 | 2 | −3 | 8 | −11 | 79 | 75 | 2 |
| −2 | 10 | −13 | 71 | 68 | 2 | 1 | 1 | −12 | 257 | 259 | 2 | 0 | 10 | −12 | 23 | 19 | 2 | −1 | 0 | −11 | 130 | 132 | 1 | −2 | 8 | −11 | 97 | 97 | 3 |
| −1 | 10 | −13 | 36 | 36 | 1 | 2 | 1 | −12 | 113 | 112 | 1 | 1 | 10 | −12 | 47 | 50 | 1 | 0 | 0 | −11 | 225 | 221 | 2 | −1 | 8 | −11 | 59 | 63 | 1 |
| 0 | 10 | −13 | 69 | 69 | 1 | 3 | 1 | −12 | 88 | 93 | 2 | 2 | 10 | −12 | 37 | 36 | 2 | 1 | 0 | −11 | 155 | 148 | 1 | 0 | 8 | −11 | 163 | 157 | 2 |
| 1 | 10 | −13 | 39 | 37 | 1 | 4 | 1 | −12 | 97 | 95 | 2 | 3 | 10 | −12 | 30 | 28 | 2 | 2 | 0 | −11 | 68 | 62 | 1 | 1 | 8 | −11 | 215 | 214 | 2 |
| 2 | 10 | −13 | 88 | 81 | 2 | 5 | 1 | −12 | 90 | 88 | 1 | 4 | 10 | −12 | 67 | 66 | 1 | 3 | 0 | −11 | 89 | 89 | 1 | 2 | 8 | −11 | 128 | 122 | 1 |
| 3 | 10 | −13 | 61 | 62 | 2 | −5 | 2 | −12 | 95 | 91 | 2 | −3 | 11 | −12 | 53 | 56 | 2 | 4 | 0 | −11 | 35 | 36 | 1 | 3 | 8 | −11 | 34 | 31 | 1 |
| −3 | 11 | −13 | 21 | 25 | 3 | −4 | 2 | −12 | 45 | 40 | 2 | −2 | 11 | −12 | 10 | 1 | 10 | 5 | 0 | −11 | 65 | 61 | 1 | 4 | 8 | −11 | 87 | 83 | 1 |
| −2 | 11 | −13 | 52 | 51 | 2 | −3 | 2 | −12 | 41 | 41 | 2 | −1 | 11 | −12 | 84 | 84 | 1 | −5 | 1 | −11 | 54 | 54 | 2 | 5 | 8 | −11 | 39 | 39 | 1 |
| −1 | 11 | −13 | 97 | 90 | 2 | −2 | 2 | −12 | 136 | 140 | 2 | 0 | 11 | −12 | 26 | 25 | 2 | −4 | 1 | −11 | 42 | 40 | 2 | −3 | 9 | −11 | 50 | 49 | 2 |
| 0 | 11 | −13 | 25 | 22 | 2 | −1 | 2 | −12 | 104 | 106 | 2 | 1 | 11 | −12 | 41 | 45 | 1 | −3 | 1 | −11 | 76 | 72 | 2 | −2 | 9 | −11 | 118 | 117 | 3 |
| 1 | 11 | −13 | 78 | 77 | 1 | 0 | 2 | −12 | 48 | 45 | 1 | 2 | 11 | −12 | 66 | 63 | 2 | −2 | 1 | −11 | 55 | 52 | 1 | −1 | 9 | −11 | 136 | 145 | 2 |
| 2 | 11 | −13 | 124 | 121 | 3 | 1 | 2 | −12 | 80 | 83 | 1 | 3 | 11 | −12 | 68 | 67 | 2 | −1 | 1 | −11 | 154 | 165 | 1 | 0 | 9 | −11 | 184 | 188 | 3 |
| −2 | 12 | −13 | 19 | 22 | 3 | 2 | 2 | −12 | 33 | 29 | 1 | −3 | 12 | −12 | 29 | 31 | 2 | 0 | 1 | −11 | 117 | 117 | 1 | 1 | 9 | −11 | 47 | 51 | 1 |
| −1 | 12 | −13 | 17 | 12 | 2 | 3 | 2 | −12 | 28 | 26 | 1 | −2 | 12 | −12 | 49 | 49 | 2 | 1 | 1 | −11 | 18 | 12 | 1 | 2 | 9 | −11 | 144 | 141 | 3 |
| 0 | 12 | −13 | 66 | 62 | 1 | 4 | 2 | −12 | 59 | 61 | 1 | −1 | 12 | −12 | 38 | 37 | 1 | 2 | 1 | −11 | 176 | 164 | 1 | 3 | 9 | −11 | 104 | 102 | 1 |
| 1 | 12 | −13 | 85 | 80 | 1 | 5 | 2 | −12 | 184 | 178 | 3 | 0 | 12 | −12 | 62 | 61 | 1 | 3 | 1 | −11 | 94 | 96 | 1 | 4 | 9 | −11 | 52 | 48 | 1 |
| 2 | 12 | −13 | 18 | 16 | 3 | −4 | 3 | −12 | 37 | 31 | 2 | 1 | 12 | −12 | 12 | 15 | 1 | 4 | 1 | −11 | 35 | 35 | 1 | 5 | 9 | −11 | 45 | 48 | 1 |
| −3 | 10 | −11 | 16 | 20 | 4 | 6 | −2 | −10 | 20 | 27 | 2 | 1 | 6 | −10 | 88 | 84 | 1 | 2 | −6 | −9 | 73 | 71 | 1 | −3 | 2 | −9 | 19 | 19 | 2 |
| −2 | 10 | −11 | 149 | 157 | 3 | −5 | −1 | −10 | 71 | 70 | 2 | 2 | 6 | −10 | 64 | 66 | 1 | 3 | −6 | −9 | 58 | 59 | 1 | −2 | 2 | −9 | 18 | 15 | 2 |
| −1 | 10 | −11 | 153 | 151 | 4 | −4 | −1 | −10 | 65 | 69 | 2 | 3 | 6 | −10 | 78 | 73 | 1 | 4 | −6 | −9 | 50 | 52 | 1 | −1 | 2 | −9 | 105 | 113 | 1 |
| 0 | 10 | −11 | 42 | 44 | 1 | −3 | −1 | −10 | 72 | 83 | 2 | 4 | 6 | −10 | 50 | 50 | 1 | 5 | −6 | −9 | 18 | 18 | 4 | 0 | 2 | −9 | 91 | 99 | 1 |
| 1 | 10 | −11 | 169 | 173 | 3 | −2 | −1 | −10 | 92 | 96 | 1 | 5 | 6 | −10 | 89 | 88 | 1 | −4 | −5 | −9 | 39 | 38 | 2 | 1 | 2 | −9 | 192 | 194 | 2 |
| 2 | 10 | −11 | 104 | 102 | 2 | −1 | −1 | −10 | 86 | 86 | 1 | −5 | 7 | −10 | 77 | 82 | 2 | −3 | −5 | −9 | 62 | 57 | 2 | 2 | 2 | −9 | 99 | 104 | 1 |
| 3 | 10 | −11 | 29 | 30 | 2 | 0 | −1 | −10 | 68 | 66 | 1 | −4 | 7 | −10 | 50 | 47 | 2 | −2 | −5 | −9 | 106 | 103 | 3 | 3 | 2 | −9 | 99 | 101 | 1 |
| 4 | 10 | −11 | 59 | 58 | 1 | 1 | −1 | −10 | 72 | 69 | 1 | −3 | 7 | −10 | 120 | 124 | 3 | −1 | −5 | −9 | 117 | 118 | 3 | 4 | 2 | −9 | 106 | 106 | 1 |
| −3 | 11 | −11 | 14 | 10 | 4 | 2 | −1 | −10 | 116 | 115 | 1 | −2 | 7 | −10 | 244 | 241 | 4 | 0 | −5 | −9 | 9 | 6 | 4 | 5 | 2 | −9 | 14 | 17 | 2 |
| −2 | 11 | −11 | 129 | 124 | 3 | 3 | −1 | −10 | 53 | 55 | 1 | −1 | 7 | −10 | 159 | 164 | 2 | 1 | −5 | −9 | 116 | 116 | 1 | 6 | 2 | −9 | 30 | 23 | 1 |
| −1 | 11 | −11 | 46 | 46 | 1 | 4 | −1 | −10 | 79 | 78 | 1 | 0 | 7 | −10 | 288 | 271 | 3 | 2 | −5 | −9 | 81 | 80 | 1 | −6 | 3 | −9 | 81 | 78 | 2 |
| 0 | 11 | −11 | 72 | 73 | 1 | 5 | −1 | −10 | 39 | 41 | 1 | 1 | 7 | −10 | 117 | 118 | 1 | 3 | −5 | −9 | 133 | 130 | 2 | −5 | 3 | −9 | 97 | 95 | 3 |
| 1 | 11 | −11 | 103 | 99 | 1 | −5 | 0 | −10 | 151 | 149 | 3 | 2 | 7 | −10 | 252 | 251 | 1 | 4 | −5 | −9 | 22 | 19 | 2 | −4 | 3 | −9 | 67 | 78 | 2 |
| 2 | 11 | −11 | 147 | 145 | 3 | −4 | 0 | −10 | 37 | 47 | 2 | 3 | 7 | −10 | 100 | 98 | 1 | 5 | −5 | −9 | 100 | 100 | 2 | −3 | 3 | −9 | 68 | 66 | 1 |
| 3 | 11 | −11 | 29 | 32 | 2 | −3 | 0 | −10 | 153 | 162 | 4 | 4 | 7 | −10 | 48 | 48 | 1 | −5 | −4 | −9 | 24 | 23 | 3 | −2 | 3 | −9 | 109 | 106 | 1 |
| 4 | 11 | −11 | 61 | 61 | 1 | −2 | 0 | −10 | 99 | 95 | 2 | 5 | 7 | −10 | 75 | 74 | 1 | −4 | −4 | −9 | 23 | 21 | 3 | −1 | 3 | −9 | 243 | 248 | 2 |
| −3 | 12 | −11 | 54 | 54 | 2 | −1 | 0 | −10 | 107 | 108 | 1 | −3 | 8 | −10 | 92 | 89 | 2 | −2 | −4 | −9 | 120 | 123 | 3 | 0 | 3 | −9 | 129 | 121 | 1 |
| −2 | 12 | −11 | 62 | 69 | 2 | 0 | 0 | −10 | 36 | 31 | 1 | −2 | 8 | −10 | 29 | 30 | 2 | −1 | −4 | −9 | 88 | 86 | 1 | 1 | 3 | −9 | 21 | 15 | 1 |
| −1 | 12 | −11 | 64 | 62 | 1 | 1 | 0 | −10 | 169 | 171 | 1 | −1 | 8 | −10 | 116 | 108 | 1 | 0 | −4 | −9 | 43 | 46 | 1 | 2 | 3 | −9 | 170 | 172 | 1 |
| 0 | 12 | −11 | 57 | 55 | 1 | 2 | 0 | −10 | 105 | 105 | 1 | 0 | 8 | −10 | 148 | 139 | 2 | 1 | −4 | −9 | 62 | 61 | 1 | 3 | 3 | −9 | 119 | 122 | 1 |

TABLE 7-continued

Observed and calculated structure factors for NEL

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 1 | 12 | −11 | 72 | 71 | 1 | 3 | 0 | −10 | 44 | 41 | 1 | 1 | 8 | −10 | 158 | 156 | 1 | 2 | −4 | −9 | 56 | 59 | 1 | 4 | 3 | −9 | 74 | 76 | 1 |
| 2 | 12 | −11 | 18 | 19 | 3 | 4 | 0 | −10 | 158 | 158 | 1 | 2 | 8 | −10 | 76 | 78 | 1 | 3 | −4 | −9 | 136 | 138 | 2 | 5 | 3 | −9 | 98 | 94 | 1 |
| −2 | 13 | −11 | 13 | 17 | 3 | 5 | 0 | −10 | 50 | 47 | 1 | 3 | 8 | −10 | 139 | 140 | 1 | 4 | −4 | −9 | 134 | 126 | 1 | 6 | 3 | −9 | 28 | 30 | 1 |
| −1 | 13 | −11 | 53 | 54 | 1 | −5 | 1 | −10 | 164 | 153 | 4 | 4 | 8 | −10 | 60 | 60 | 1 | 5 | −4 | −9 | 85 | 84 | 2 | −6 | 4 | −9 | 40 | 38 | 2 |
| 0 | 13 | −11 | 28 | 25 | 1 | −4 | 1 | −10 | 65 | 76 | 2 | 5 | 8 | −10 | 22 | 17 | 1 | −5 | −3 | −9 | 26 | 22 | 2 | −5 | 4 | −9 | 100 | 96 | 2 |
| 1 | 13 | −11 | 58 | 55 | 1 | −3 | 1 | −10 | 158 | 167 | 2 | −3 | 9 | −10 | 60 | 57 | 2 | −4 | −3 | −9 | 91 | 89 | 2 | −3 | 4 | −9 | 192 | 192 | 3 |
| 2 | 13 | −11 | 19 | 18 | 3 | −2 | 1 | −10 | 154 | 147 | 2 | −2 | 9 | −10 | 97 | 92 | 3 | −3 | −3 | −9 | 98 | 115 | 3 | −2 | 4 | −9 | 49 | 57 | 1 |
| −1 | 14 | −11 | 5 | 7 | 5 | −1 | 1 | −10 | 133 | 133 | 1 | −1 | 9 | −10 | 76 | 79 | 1 | −2 | −3 | −9 | 45 | 46 | 1 | −1 | 4 | −9 | 60 | 64 | 1 |
| 0 | 14 | −11 | 30 | 33 | 1 | 0 | 1 | −10 | 84 | 87 | 1 | 0 | 9 | −10 | 58 | 55 | 1 | −1 | −3 | −9 | 142 | 141 | 2 | 0 | 4 | −9 | 92 | 92 | 1 |
| −1 | −8 | −10 | 61 | 60 | 2 | 1 | 1 | −10 | 275 | 283 | 2 | 1 | 9 | −10 | 59 | 66 | 1 | 0 | −3 | −9 | 31 | 30 | 1 | 1 | 4 | −9 | 151 | 142 | 1 |
| 0 | −8 | −10 | 86 | 87 | 2 | 2 | 1 | −10 | 117 | 114 | 1 | 2 | 9 | −10 | 42 | 37 | 2 | 1 | −3 | −9 | 39 | 37 | 1 | 2 | 4 | −9 | 62 | 61 | 1 |
| 1 | −8 | −10 | 29 | 29 | 2 | 3 | 1 | −10 | 14 | 16 | 1 | 3 | 9 | −10 | 31 | 29 | 1 | 2 | −3 | −9 | 115 | 114 | 1 | 3 | 4 | −9 | 157 | 157 | 1 |
| 2 | −8 | −10 | 29 | 27 | 2 | 4 | 1 | −10 | 193 | 189 | 2 | 4 | 9 | −10 | 99 | 98 | 1 | 3 | −3 | −9 | 267 | 267 | 2 | 4 | 4 | −9 | 143 | 143 | 1 |
| −2 | −7 | −10 | 55 | 51 | 2 | 5 | 1 | −10 | 116 | 117 | 1 | 5 | 9 | −10 | 107 | 108 | 2 | 4 | −3 | −9 | 140 | 137 | 1 | 5 | 4 | −9 | 221 | 216 | 2 |
| −1 | −7 | −10 | 72 | 73 | 2 | 6 | 1 | −10 | 75 | 75 | 1 | −3 | 10 | −10 | 57 | 57 | 2 | 5 | −3 | −9 | 47 | 42 | 1 | −6 | 5 | −9 | 18 | 18 | 3 |
| 0 | −7 | −10 | 69 | 65 | 2 | −5 | 2 | −10 | 154 | 155 | 3 | −2 | 10 | −10 | 62 | 64 | 2 | 6 | −3 | −9 | 76 | 75 | 2 | −5 | 5 | −9 | 57 | 57 | 2 |
| 1 | −7 | −10 | 62 | 61 | 1 | −3 | 2 | −10 | 73 | 79 | 1 | −1 | 10 | −10 | 136 | 142 | 2 | −5 | −2 | −9 | 23 | 23 | 3 | −4 | 5 | −9 | 124 | 116 | 3 |
| 2 | −7 | −10 | 101 | 97 | 2 | −2 | 2 | −10 | 64 | 65 | 1 | 0 | 10 | −10 | 125 | 120 | 2 | −4 | −2 | −9 | 104 | 108 | 3 | −3 | 5 | −9 | 111 | 111 | 2 |
| 3 | −7 | −10 | 35 | 39 | 2 | −1 | 2 | −10 | 110 | 116 | 1 | 1 | 10 | −10 | 107 | 104 | 1 | −3 | −2 | −9 | 63 | 77 | 2 | −2 | 5 | −9 | 65 | 68 | 1 |
| −3 | −6 | −10 | 97 | 97 | 1 | 0 | 2 | −10 | 67 | 64 | 1 | 2 | 10 | −10 | 149 | 148 | 2 | −2 | −2 | −9 | 121 | 120 | 2 | −1 | 5 | −9 | 164 | 176 | 2 |
| −2 | −6 | −10 | 75 | 76 | 1 | 1 | 2 | −10 | 52 | 58 | 1 | 3 | 10 | −10 | 13 | 13 | 2 | −1 | −2 | −9 | 70 | 69 | 1 | 0 | 5 | −9 | 91 | 93 | 1 |
| −1 | −6 | −10 | 53 | 51 | 1 | 2 | 2 | −10 | 42 | 44 | 1 | 4 | 10 | −10 | 18 | 17 | 1 | 0 | −2 | −9 | 228 | 221 | 2 | 1 | 5 | −9 | 249 | 260 | 2 |
| 0 | −6 | −10 | 64 | 62 | 1 | 3 | 2 | −10 | 93 | 95 | 1 | −4 | 11 | −10 | 45 | 44 | 2 | 1 | −2 | −9 | 58 | 59 | 1 | 2 | 5 | −9 | 50 | 42 | 1 |
| 1 | −6 | −10 | 68 | 68 | 1 | 4 | 2 | −10 | 121 | 118 | 1 | −3 | 11 | −10 | 79 | 77 | 2 | 2 | −2 | −9 | 212 | 205 | 2 | 3 | 5 | −9 | 138 | 144 | 1 |
| 2 | −6 | −10 | 70 | 68 | 1 | 5 | 2 | −10 | 102 | 103 | 1 | −2 | 11 | −10 | 58 | 55 | 2 | 3 | −2 | −9 | 162 | 157 | 1 | 4 | 5 | −9 | 141 | 148 | 1 |
| 3 | −6 | −10 | 53 | 52 | 1 | 6 | 2 | −10 | 48 | 49 | 1 | −1 | 11 | −10 | 94 | 94 | 2 | 4 | −2 | −9 | 90 | 90 | 1 | 5 | 5 | −9 | 146 | 146 | 2 |
| 4 | −6 | −10 | 64 | 63 | 1 | −5 | 3 | −10 | 233 | 224 | 5 | 0 | 11 | −10 | 122 | 127 | 2 | 5 | −2 | −9 | 19 | 18 | 2 | −5 | 6 | −9 | 30 | 26 | 2 |
| −4 | −5 | −10 | 29 | 28 | 2 | −4 | 3 | −10 | 173 | 184 | 4 | 1 | 11 | −10 | 25 | 29 | 1 | 6 | −2 | −9 | 110 | 102 | 3 | −4 | 6 | −9 | 125 | 122 | 3 |
| −3 | −5 | −10 | 126 | 122 | 2 | −3 | 3 | −10 | 60 | 56 | 1 | 2 | 11 | −10 | 100 | 103 | 1 | −5 | −1 | −9 | 44 | 47 | 2 | −3 | 6 | −9 | 78 | 74 | 1 |
| −2 | −5 | −10 | 82 | 76 | 2 | −2 | 3 | −10 | 128 | 126 | 1 | 3 | 11 | −10 | 33 | 34 | 2 | −3 | −1 | −9 | 126 | 130 | 2 | −2 | 6 | −9 | 187 | 190 | 2 |
| −1 | −5 | −10 | 142 | 145 | 2 | −1 | 3 | −10 | 24 | 25 | 1 | 4 | 11 | −10 | 62 | 63 | 1 | −2 | −1 | −9 | 116 | 121 | 2 | −1 | 6 | −9 | 126 | 127 | 1 |
| 0 | −5 | −10 | 20 | 23 | 2 | 0 | 3 | −10 | 9 | 8 | 2 | −3 | 12 | −10 | 38 | 35 | 2 | −1 | −1 | −9 | 133 | 129 | 1 | 0 | 6 | −9 | 102 | 100 | 1 |
| 1 | −5 | −10 | 117 | 118 | 1 | 1 | 3 | −10 | 198 | 209 | 2 | −2 | 12 | −10 | 44 | 42 | 2 | 0 | −1 | −9 | 93 | 85 | 1 | 1 | 6 | −9 | 71 | 76 | 1 |
| 2 | −5 | −10 | 93 | 95 | 1 | 2 | 3 | −10 | 85 | 84 | 1 | −1 | 12 | −10 | 42 | 46 | 1 | 1 | −1 | −9 | 36 | 33 | 1 | 2 | 6 | −9 | 57 | 59 | 1 |
| 3 | −5 | −10 | 60 | 62 | 1 | 3 | 3 | −10 | 31 | 26 | 1 | 0 | 12 | −10 | 65 | 64 | 1 | 2 | −1 | −9 | 108 | 105 | 1 | 3 | 6 | −9 | 94 | 91 | 1 |
| 4 | −5 | −10 | 49 | 51 | 1 | 4 | 3 | −10 | 57 | 55 | 1 | 1 | 12 | −10 | 44 | 43 | 1 | 3 | −1 | −9 | 213 | 213 | 2 | 4 | 6 | −9 | 101 | 102 | 1 |
| 5 | −5 | −10 | 27 | 25 | 2 | 5 | 3 | −10 | 53 | 51 | 1 | 2 | 12 | −10 | 27 | 25 | 2 | 4 | −1 | −9 | 155 | 153 | 1 | 5 | 6 | −9 | 105 | 112 | 2 |
| −4 | −4 | −10 | 17 | 18 | 5 | 6 | 3 | −10 | 12 | 12 | 2 | −2 | 13 | −10 | 48 | 44 | 1 | 5 | −1 | −9 | 30 | 28 | 1 | −5 | 7 | −9 | 14 | 7 | 5 |
| −3 | −4 | −10 | 52 | 47 | 1 | −5 | 4 | −10 | 74 | 72 | 2 | −1 | 13 | −10 | 69 | 65 | 1 | 6 | −1 | −9 | 17 | 18 | 2 | −4 | 7 | −9 | 83 | 84 | 2 |
| −2 | −4 | −10 | 80 | 79 | 2 | −4 | 4 | −10 | 17 | 16 | 4 | 0 | 13 | −10 | 98 | 93 | 1 | −6 | 0 | −9 | 32 | 32 | 2 | −3 | 7 | −9 | 14 | 14 | 4 |
| −1 | −4 | −10 | 46 | 44 | 1 | −3 | 4 | −10 | 102 | 103 | 2 | 1 | 13 | −10 | 66 | 65 | 1 | −5 | 0 | −9 | 119 | 122 | 3 | −2 | 7 | −9 | 187 | 182 | 3 |
| 0 | −4 | −10 | 171 | 176 | 2 | −2 | 4 | −10 | 75 | 77 | 1 | 2 | 13 | −10 | 21 | 15 | 3 | −4 | 0 | −9 | 22 | 22 | 3 | −1 | 7 | −9 | 135 | 131 | 2 |
| 1 | −4 | −10 | 29 | 31 | 1 | −1 | 4 | −10 | 73 | 66 | 1 | −1 | 14 | −10 | 101 | 101 | 1 | −3 | 0 | −9 | 15 | 13 | 3 | 0 | 7 | −9 | 116 | 107 | 1 |
| 2 | −4 | −10 | 224 | 230 | 2 | 0 | 4 | −10 | 126 | 124 | 1 | 0 | 14 | −10 | 72 | 73 | 1 | −2 | 0 | −9 | 105 | 110 | 2 | 1 | 7 | −9 | 154 | 152 | 1 |
| 3 | −4 | −10 | 109 | 107 | 2 | 1 | 4 | −10 | 92 | 99 | 1 | 1 | 14 | −10 | 58 | 59 | 2 | −1 | 0 | −9 | 327 | 333 | 3 | 2 | 7 | −9 | 92 | 92 | 1 |
| 4 | −4 | −10 | 57 | 58 | 1 | 2 | 4 | −10 | 98 | 100 | 1 | 0 | −9 | −9 | 32 | 31 | 2 | 0 | 0 | −9 | 79 | 77 | 1 | 3 | 7 | −9 | 85 | 75 | 1 |
| 5 | −4 | −10 | 86 | 85 | 2 | 3 | 4 | −10 | 68 | 68 | 1 | 2 | −9 | −9 | 58 | 59 | 2 | 1 | 0 | −9 | 236 | 243 | 2 | 4 | 7 | −9 | 124 | 126 | 1 |
| −4 | −3 | −10 | 51 | 51 | 2 | 4 | 4 | −10 | 29 | 28 | 1 | −2 | −8 | −9 | 89 | 81 | 2 | 2 | 0 | −9 | 162 | 166 | 1 | −4 | 8 | −9 | 24 | 23 | 3 |
| −3 | −3 | −10 | 33 | 35 | 2 | 5 | 4 | −10 | 77 | 80 | 1 | −1 | −8 | −9 | 27 | 28 | 2 | 3 | 0 | −9 | 236 | 236 | 2 | −3 | 8 | −9 | 60 | 60 | 2 |

TABLE 7-continued

| Observed and calculated structure factors for NEL | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
| −2 | −3 | −10 | 85 | 81 | 2 | 6 | 4 | −10 | 114 | 108 | 1 | 0 | −8 | −9 | 44 | 42 | 2 | 4 | 0 | −9 | 104 | 104 | 1 | −2 | 8 | −9 | 72 | 77 | 2 |
| −1 | −3 | −10 | 78 | 82 | 1 | −5 | 5 | −10 | 92 | 92 | 2 | 1 | −8 | −9 | 30 | 29 | 2 | 5 | 0 | −9 | 79 | 77 | 1 | −1 | 8 | −9 | 206 | 205 | 2 |
| 0 | −3 | −10 | 109 | 109 | 1 | −4 | 5 | −10 | 150 | 149 | 4 | 2 | −8 | −9 | 54 | 51 | 1 | −6 | 1 | −9 | 50 | 48 | 2 | 0 | 8 | −9 | 156 | 149 | 2 |
| 1 | −3 | −10 | 157 | 164 | 1 | −3 | 5 | −10 | 82 | 87 | 1 | 3 | −8 | −9 | 73 | 74 | 2 | −5 | 1 | −9 | 90 | 88 | 2 | 1 | 8 | −9 | 79 | 80 | 1 |
| 2 | −3 | −10 | 69 | 69 | 1 | −2 | 5 | −10 | 107 | 107 | 1 | −3 | −7 | −9 | 40 | 38 | 1 | −4 | 1 | −9 | 23 | 21 | 3 | 2 | 8 | −9 | 87 | 85 | 1 |
| 3 | −3 | −10 | 231 | 229 | 3 | −1 | 5 | −10 | 88 | 94 | 1 | −2 | −7 | −9 | 89 | 90 | 2 | −3 | 1 | −9 | 42 | 42 | 1 | 3 | 8 | −9 | 42 | 37 | 1 |
| 4 | −3 | −10 | 65 | 65 | 1 | 0 | 5 | −10 | 74 | 72 | 1 | −1 | −7 | −9 | 72 | 72 | 1 | −2 | 1 | −9 | 71 | 68 | 1 | 4 | 8 | −9 | 164 | 165 | 1 |
| 5 | −3 | −10 | 17 | 18 | 3 | 1 | 5 | −10 | 55 | 64 | 1 | 0 | −7 | −9 | 36 | 30 | 2 | −1 | 1 | −9 | 111 | 118 | 1 | −3 | 9 | −9 | 75 | 74 | 2 |
| −5 | −2 | −10 | 27 | 23 | 2 | 2 | 5 | −10 | 12 | 14 | 1 | 1 | −7 | −9 | 106 | 106 | 2 | 0 | 1 | −9 | 26 | 24 | 1 | −2 | 9 | −9 | 105 | 99 | 3 |
| −4 | −2 | −10 | 30 | 26 | 2 | 3 | 5 | −10 | 211 | 214 | 2 | 2 | −7 | −9 | 92 | 91 | 2 | 1 | 1 | −9 | 243 | 245 | 2 | −1 | 9 | −9 | 75 | 72 | 1 |
| −3 | −2 | −10 | 17 | 15 | 3 | 4 | 5 | −10 | 86 | 80 | 1 | 3 | −7 | −9 | 94 | 91 | 2 | 2 | 1 | −9 | 86 | 83 | 1 | 0 | 9 | −9 | 67 | 66 | 1 |
| −1 | −2 | −10 | 62 | 65 | 1 | 5 | 5 | −10 | 141 | 138 | 1 | 4 | −7 | −9 | 76 | 82 | 1 | 3 | 1 | −9 | 136 | 140 | 1 | 1 | 9 | −9 | 75 | 73 | 1 |
| 0 | −2 | −10 | 56 | 55 | 1 | −5 | 6 | −10 | 123 | 121 | 3 | −4 | −6 | −9 | 68 | 71 | 2 | 4 | 1 | −9 | 141 | 138 | 1 | 2 | 9 | −9 | 99 | 97 | 2 |
| 1 | −2 | −10 | 98 | 97 | 1 | −4 | 6 | −10 | 60 | 58 | 2 | −3 | −6 | −9 | 0 | 5 | 1 | 5 | 1 | −9 | 175 | 170 | 1 | 3 | 9 | −9 | 176 | 168 | 1 |
| 2 | −2 | −10 | 56 | 57 | 1 | −3 | 6 | −10 | 215 | 220 | 3 | −2 | −6 | −9 | 116 | 115 | 3 | 6 | 1 | −9 | 64 | 68 | 1 | 4 | 9 | −9 | 75 | 74 | 1 |
| 3 | −2 | −10 | 93 | 96 | 1 | −2 | 6 | −10 | 72 | 68 | 1 | −1 | −6 | −9 | 68 | 73 | 2 | −6 | 2 | −9 | 60 | 61 | 2 | −3 | 10 | −9 | 25 | 24 | 3 |
| 4 | −2 | −10 | 70 | 66 | 1 | −1 | 6 | −10 | 112 | 104 | 1 | 0 | −6 | −9 | 48 | 52 | 2 | −5 | 2 | −9 | 133 | 134 | 3 | −2 | 10 | −9 | 35 | 34 | 2 |
| 5 | −2 | −10 | 45 | 47 | 1 | 0 | 6 | −10 | 137 | 132 | 1 | 1 | −6 | −9 | 130 | 128 | 2 | −4 | 2 | −9 | 96 | 118 | 2 | −1 | 10 | −9 | 115 | 115 | 2 |
| 0 | 10 | −9 | 95 | 89 | 2 | −5 | −3 | −8 | 72 | 71 | 2 | 4 | 3 | −8 | 97 | 91 | 1 | 0 | 12 | −8 | 82 | 74 | 1 | −6 | −2 | −7 | 49 | 48 | 2 |
| 1 | 10 | −9 | 97 | 97 | 1 | −4 | −3 | −8 | 157 | 158 | 4 | 5 | 3 | −8 | 47 | 45 | 1 | 1 | 12 | −8 | 152 | 150 | 2 | −5 | −2 | −7 | 41 | 40 | 2 |
| 2 | 10 | −9 | 111 | 106 | 2 | −3 | −3 | −8 | 193 | 219 | 5 | 6 | 3 | −8 | 126 | 125 | 1 | 2 | 12 | −8 | 116 | 112 | 3 | −4 | −2 | −7 | 33 | 31 | 2 |
| 3 | 10 | −9 | 63 | 63 | 1 | −2 | −3 | −8 | 176 | 168 | 3 | −6 | 4 | −8 | 88 | 79 | 2 | 3 | 12 | −8 | 51 | 61 | 1 | −3 | −2 | −7 | 45 | 44 | 1 |
| 4 | 10 | −9 | 79 | 80 | 1 | −1 | −3 | −8 | 159 | 152 | 2 | −5 | 4 | −8 | 61 | 68 | 2 | 4 | 12 | −8 | 12 | 12 | 2 | −2 | −2 | −7 | 152 | 150 | 2 |
| −4 | 11 | −9 | 99 | 100 | 2 | 0 | −3 | −8 | 101 | 91 | 1 | −4 | 4 | −8 | 81 | 96 | 2 | −3 | 13 | −8 | 59 | 58 | 2 | −1 | −2 | −7 | 57 | 50 | 1 |
| −3 | 11 | −9 | 78 | 80 | 2 | 1 | −3 | −8 | 173 | 171 | 1 | −3 | 4 | −8 | 142 | 138 | 2 | −2 | 13 | −8 | 166 | 164 | 2 | 0 | −2 | −7 | 83 | 86 | 1 |
| −2 | 11 | −9 | 123 | 124 | 2 | 2 | −3 | −8 | 95 | 95 | 1 | −2 | 4 | −8 | 45 | 45 | 1 | −1 | 13 | −8 | 96 | 88 | 1 | 1 | −2 | −7 | 110 | 110 | 1 |
| −1 | 11 | −9 | 107 | 102 | 3 | 3 | −3 | −8 | 68 | 64 | 1 | −1 | 4 | −8 | 54 | 53 | 1 | 0 | 13 | −8 | 51 | 51 | 1 | 2 | −2 | −7 | 174 | 176 | 1 |
| 0 | 11 | −9 | 75 | 72 | 1 | 4 | −3 | −8 | 231 | 235 | 2 | 0 | 4 | −8 | 139 | 145 | 2 | 1 | 13 | −8 | 143 | 142 | 2 | 3 | −2 | −7 | 181 | 177 | 1 |
| 1 | 11 | −9 | 92 | 89 | 1 | 5 | −3 | −8 | 27 | 29 | 1 | 1 | 4 | −8 | 168 | 163 | 2 | 2 | 13 | −8 | 129 | 131 | 3 | 4 | −2 | −7 | 93 | 92 | 1 |
| 2 | 11 | −9 | 39 | 37 | 1 | 6 | −3 | −8 | 32 | 31 | 1 | 2 | 4 | −8 | 63 | 62 | 1 | −2 | 14 | −8 | 66 | 63 | 1 | 5 | −2 | −7 | 160 | 162 | 3 |
| 3 | 11 | −9 | 60 | 61 | 2 | −5 | −2 | −8 | 55 | 54 | 2 | 3 | 4 | −8 | 117 | 123 | 1 | −1 | 14 | −8 | 91 | 88 | 1 | 6 | −2 | −7 | 48 | 47 | 1 |
| 4 | 11 | −9 | 99 | 104 | 1 | −4 | −2 | −8 | 35 | 32 | 2 | 4 | 4 | −8 | 122 | 119 | 1 | 0 | 14 | −8 | 101 | 95 | 1 | −6 | −1 | −7 | 53 | 53 | 2 |
| −3 | 12 | −9 | 63 | 58 | 2 | −3 | −2 | −8 | 142 | 141 | 2 | 5 | 4 | −8 | 81 | 78 | 1 | 1 | 14 | −8 | 50 | 51 | 2 | −5 | −1 | −7 | 77 | 75 | 2 |
| −2 | 12 | −9 | 69 | 69 | 1 | −2 | −2 | −8 | 112 | 103 | 2 | −6 | 5 | −8 | 36 | 37 | 2 | −1 | −10 | −7 | 20 | 22 | 3 | −4 | −1 | −7 | 89 | 91 | 2 |
| −1 | 12 | −9 | 40 | 43 | 1 | −1 | −2 | −8 | 84 | 83 | 1 | −5 | 5 | −8 | 38 | 39 | 2 | 0 | −10 | −7 | 103 | 103 | 2 | −3 | −1 | −7 | 272 | 274 | 4 |
| 0 | 12 | −9 | 10 | 13 | 4 | 0 | −2 | −8 | 258 | 245 | 2 | −4 | 5 | −8 | 143 | 149 | 4 | 2 | −10 | −7 | 38 | 35 | 2 | −2 | −1 | −7 | 65 | 54 | 1 |
| 1 | 12 | −9 | 109 | 111 | 1 | 1 | −2 | −8 | 32 | 33 | 1 | −3 | 5 | −8 | 36 | 34 | 1 | −2 | −9 | −7 | 71 | 71 | 2 | −1 | −1 | −7 | 442 | 438 | 5 |
| 2 | 12 | −9 | 44 | 45 | 2 | 2 | −2 | −8 | 42 | 38 | 1 | −2 | 5 | −8 | 101 | 97 | 1 | −1 | −9 | −7 | 49 | 51 | 2 | 0 | −1 | −7 | 77 | 83 | 1 |
| 3 | 12 | −9 | 10 | 7 | 5 | 3 | −2 | −8 | 189 | 188 | 2 | −1 | 5 | −8 | 166 | 162 | 1 | 0 | −9 | −7 | 0 | 6 | 1 | 1 | −1 | −7 | 230 | 225 | 4 |
| −3 | 13 | −9 | 120 | 118 | 3 | 4 | −2 | −8 | 201 | 199 | 2 | 0 | 5 | −8 | 102 | 96 | 1 | 1 | −9 | −7 | 99 | 96 | 2 | 2 | −1 | −7 | 284 | 285 | 2 |
| −2 | 13 | −9 | 58 | 53 | 1 | 5 | −2 | −8 | 88 | 86 | 2 | 1 | 5 | −8 | 81 | 85 | 1 | 2 | −9 | −7 | 31 | 26 | 2 | 3 | −1 | −7 | 153 | 156 | 1 |
| −1 | 13 | −9 | 35 | 32 | 1 | 6 | −2 | −8 | 60 | 57 | 1 | 2 | 5 | −8 | 73 | 71 | 1 | 3 | −9 | −7 | 67 | 71 | 2 | 4 | −1 | −7 | 116 | 118 | 1 |
| 0 | 13 | −9 | 58 | 59 | 1 | −6 | −1 | −8 | 73 | 77 | 2 | 3 | 5 | −8 | 170 | 168 | 1 | −3 | −8 | −7 | 114 | 114 | 3 | 5 | −1 | −7 | 179 | 180 | 2 |
| 1 | 13 | −9 | 55 | 56 | 1 | −5 | −1 | −8 | 35 | 38 | 2 | 4 | 5 | −8 | 84 | 86 | 1 | −2 | −8 | −7 | 60 | 61 | 2 | 6 | −1 | −7 | 88 | 90 | 1 |
| 2 | 13 | −9 | 46 | 42 | 2 | −4 | −1 | −8 | 100 | 103 | 3 | 5 | 5 | −8 | 11 | 14 | 7 | −1 | −8 | −7 | 78 | 77 | 2 | −6 | 0 | −7 | 35 | 35 | 2 |
| −1 | 14 | −9 | 30 | 31 | 1 | −3 | −1 | −8 | 77 | 75 | 1 | −6 | 6 | −8 | 9 | 9 | 9 | 0 | −8 | −7 | 37 | 36 | 2 | −5 | 0 | −7 | 61 | 59 | 2 |
| 0 | 14 | −9 | 67 | 65 | 1 | −2 | −1 | −8 | 64 | 65 | 1 | −5 | 6 | −8 | 68 | 66 | 2 | 1 | −8 | −7 | 118 | 112 | 2 | −4 | 0 | −7 | 158 | 162 | 2 |
| 1 | 14 | −9 | 20 | 24 | 3 | −1 | −1 | −8 | 98 | 92 | 1 | −4 | 6 | −8 | 111 | 109 | 3 | 2 | −8 | −7 | 65 | 65 | 1 | −3 | 0 | −7 | 125 | 123 | 2 |
| −2 | −9 | −8 | 54 | 50 | 2 | 0 | −1 | −8 | 98 | 89 | 1 | −3 | 6 | −8 | 102 | 98 | 2 | 3 | −8 | −7 | 80 | 88 | 2 | −2 | 0 | −7 | 86 | 88 | 1 |

TABLE 7-continued

Observed and calculated structure factors for NEL

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −1 | −9 | −8 | 57 | 57 | 2 | 1 | −1 | −8 | 270 | 265 | 2 | −2 | 6 | −8 | 120 | 128 | 1 | 4 | −8 | −7 | 50 | 50 | 1 | −1 | 0 | −7 | 115 | 123 | 1 |
| 0 | −9 | −8 | 51 | 52 | 2 | 2 | −1 | −8 | 149 | 148 | 1 | −1 | 6 | −8 | 89 | 92 | 1 | −4 | −7 | −7 | 68 | 62 | 2 | 0 | 0 | −7 | 140 | 135 | 1 |
| 1 | −9 | −8 | 136 | 130 | 2 | 3 | −1 | −8 | 60 | 64 | 1 | 0 | 6 | −8 | 423 | 414 | 6 | −3 | −7 | −7 | 148 | 153 | 3 | 1 | 0 | −7 | 332 | 332 | 4 |
| 2 | −9 | −8 | 25 | 22 | 3 | 4 | −1 | −8 | 295 | 296 | 2 | 1 | 6 | −8 | 72 | 75 | 1 | −2 | −7 | −7 | 48 | 58 | 2 | 2 | 0 | −7 | 139 | 138 | 1 |
| 3 | −9 | −8 | 75 | 76 | 2 | 5 | −1 | −8 | 22 | 18 | 2 | 2 | 6 | −8 | 179 | 184 | 1 | 0 | −7 | −7 | 83 | 80 | 2 | 3 | 0 | −7 | 106 | 102 | 1 |
| −3 | −8 | −8 | 91 | 90 | 2 | 6 | −1 | −8 | 57 | 54 | 1 | 3 | 6 | −8 | 79 | 81 | 1 | 1 | −7 | −7 | 101 | 103 | 2 | 4 | 0 | −7 | 65 | 68 | 1 |
| −2 | −8 | −8 | 31 | 27 | 2 | −6 | 0 | −8 | 66 | 62 | 2 | 4 | 6 | −8 | 245 | 244 | 4 | 2 | −7 | −7 | 86 | 84 | 1 | 5 | 0 | −7 | 95 | 100 | 1 |
| −1 | −8 | −8 | 117 | 122 | 3 | −5 | 0 | −8 | 47 | 50 | 2 | 5 | 6 | −8 | 106 | 106 | 2 | 3 | −7 | −7 | 110 | 115 | 2 | 6 | 0 | −7 | 68 | 65 | 1 |
| 0 | −8 | −8 | 22 | 22 | 3 | −4 | 0 | −8 | 139 | 139 | 3 | −5 | 7 | −8 | 85 | 84 | 2 | 4 | −7 | −7 | 27 | 27 | 1 | 7 | 0 | −7 | 53 | 60 | 1 |
| 1 | −8 | −8 | 46 | 46 | 1 | −3 | 0 | −8 | 58 | 61 | 1 | −4 | 7 | −8 | 71 | 70 | 2 | 5 | −7 | −7 | 29 | 32 | 1 | −6 | 1 | −7 | 15 | 14 | 5 |
| 2 | −8 | −8 | 106 | 105 | 2 | −2 | 0 | −8 | 150 | 144 | 2 | −3 | 7 | −8 | 120 | 113 | 1 | −4 | −6 | −7 | 57 | 55 | 2 | −5 | 1 | −7 | 109 | 114 | 3 |
| 3 | −8 | −8 | 167 | 165 | 4 | −1 | 0 | −8 | 138 | 135 | 1 | −2 | 7 | −8 | 42 | 40 | 1 | −3 | −6 | −7 | 29 | 30 | 2 | −4 | 1 | −7 | 149 | 151 | 2 |
| 4 | −8 | −8 | 32 | 35 | 1 | 0 | 0 | −8 | 420 | 414 | 5 | −1 | 7 | −8 | 70 | 63 | 1 | −2 | −6 | −7 | 72 | 82 | 2 | −3 | 1 | −7 | 26 | 25 | 1 |
| −4 | −7 | −8 | 65 | 71 | 2 | 1 | 0 | −8 | 123 | 121 | 1 | 0 | 7 | −8 | 109 | 104 | 1 | −1 | −6 | −7 | 34 | 33 | 2 | −2 | 1 | −7 | 100 | 95 | 1 |
| −3 | −7 | −8 | 48 | 47 | 2 | 2 | 0 | −8 | 111 | 109 | 1 | 1 | 7 | −8 | 46 | 45 | 1 | 0 | −6 | −7 | 164 | 161 | 2 | −1 | 1 | −7 | 495 | 499 | 5 |
| −2 | −7 | −8 | 71 | 70 | 2 | 3 | 0 | −8 | 69 | 68 | 1 | 2 | 7 | −8 | 95 | 94 | 1 | 1 | −6 | −7 | 141 | 142 | 2 | 0 | 1 | −7 | 11 | 10 | 1 |
| −1 | −7 | −8 | 110 | 107 | 2 | 4 | 0 | −8 | 170 | 173 | 1 | 3 | 7 | −8 | 58 | 57 | 1 | 2 | −6 | −7 | 237 | 237 | 2 | 1 | 1 | −7 | 175 | 166 | 2 |
| 0 | −7 | −8 | 161 | 158 | 3 | 5 | 0 | −8 | 39 | 36 | 1 | 4 | 7 | −8 | 275 | 275 | 5 | 3 | −6 | −7 | 67 | 71 | 1 | 2 | 1 | −7 | 306 | 296 | 3 |
| 1 | −7 | −8 | 85 | 82 | 1 | 6 | 0 | −8 | 73 | 73 | 1 | −5 | 8 | −8 | 43 | 42 | 2 | 4 | −6 | −7 | 75 | 80 | 1 | 3 | 1 | −7 | 93 | 93 | 1 |
| 2 | −7 | −8 | 113 | 109 | 2 | −6 | 1 | −8 | 34 | 29 | 2 | −4 | 8 | −8 | 85 | 81 | 2 | 5 | −6 | −7 | 51 | 50 | 1 | 4 | 1 | −7 | 116 | 113 | 1 |
| 3 | −7 | −8 | 33 | 38 | 1 | −5 | 1 | −8 | 60 | 60 | 2 | −3 | 8 | −8 | 133 | 135 | 3 | −5 | −5 | −7 | 133 | 132 | 3 | 5 | 1 | −7 | 180 | 179 | 1 |
| 4 | −7 | −8 | 70 | 69 | 1 | −4 | 1 | −8 | 126 | 122 | 3 | −2 | 8 | −8 | 90 | 92 | 2 | −4 | −5 | −7 | 20 | 19 | 3 | 6 | 1 | −7 | 53 | 52 | 1 |
| 5 | −7 | −8 | 25 | 28 | 3 | −3 | 1 | −8 | 162 | 159 | 2 | −1 | 8 | −8 | 76 | 79 | 1 | −3 | −5 | −7 | 187 | 202 | 5 | 7 | 1 | −7 | 12 | 9 | 2 |
| −4 | −6 | −8 | 15 | 14 | 5 | −2 | 1 | −8 | 74 | 74 | 1 | 0 | 8 | −8 | 130 | 124 | 1 | −2 | −5 | −7 | 76 | 75 | 1 | −6 | 2 | −7 | 53 | 52 | 2 |
| −3 | −6 | −8 | 70 | 70 | 2 | −1 | 1 | −8 | 242 | 246 | 2 | 1 | 8 | −8 | 48 | 45 | 1 | −1 | −5 | −7 | 105 | 107 | 2 | −5 | 2 | −7 | 123 | 119 | 3 |
| −2 | −6 | −8 | 123 | 134 | 3 | 0 | 1 | −8 | 95 | 86 | 1 | 2 | 8 | −8 | 101 | 95 | 1 | 0 | −5 | −7 | 85 | 82 | 1 | −4 | 2 | −7 | 77 | 82 | 1 |
| −1 | −6 | −8 | 113 | 108 | 2 | 1 | 1 | −8 | 433 | 443 | 6 | 3 | 8 | −8 | 202 | 194 | 1 | 1 | −5 | −7 | 81 | 85 | 1 | −3 | 2 | −7 | 34 | 40 | 1 |
| 0 | −6 | −8 | 94 | 91 | 2 | 2 | 1 | −8 | 66 | 64 | 1 | 4 | 8 | −8 | 13 | 11 | 1 | 2 | −5 | −7 | 60 | 58 | 1 | −2 | 2 | −7 | 179 | 172 | 2 |
| 1 | −6 | −8 | 7 | 3 | 7 | 3 | 1 | −8 | 111 | 112 | 1 | −3 | 9 | −8 | 81 | 77 | 2 | 3 | −5 | −7 | 187 | 187 | 2 | −1 | 2 | −7 | 260 | 252 | 2 |
| 2 | −6 | −8 | 120 | 118 | 1 | 4 | 1 | −8 | 27 | 26 | 1 | −2 | 9 | −8 | 244 | 251 | 4 | 4 | −5 | −7 | 106 | 107 | 1 | 0 | 2 | −7 | 225 | 205 | 2 |
| 3 | −6 | −8 | 84 | 84 | 1 | 5 | 1 | −8 | 15 | 12 | 1 | −1 | 9 | −8 | 93 | 96 | 1 | 5 | −5 | −7 | 135 | 136 | 1 | 1 | 2 | −7 | 315 | 308 | 3 |
| 4 | −6 | −8 | 23 | 23 | 2 | 6 | 1 | −8 | 34 | 33 | 1 | 0 | 9 | −8 | 135 | 135 | 2 | 6 | −5 | −7 | 84 | 87 | 2 | 2 | 2 | −7 | 77 | 76 | 1 |
| 5 | −6 | −8 | 14 | 18 | 2 | −6 | 2 | −8 | 138 | 138 | 3 | 1 | 9 | −8 | 254 | 256 | 2 | −5 | −4 | −7 | 50 | 47 | 2 | 3 | 2 | −7 | 68 | 71 | 1 |
| −5 | −5 | −8 | 24 | 24 | 3 | −5 | 2 | −8 | 35 | 37 | 2 | 2 | 9 | −8 | 217 | 219 | 2 | −4 | −4 | −7 | 148 | 141 | 3 | 4 | 2 | −7 | 96 | 102 | 1 |
| −4 | −5 | −8 | 47 | 46 | 2 | −4 | 2 | −8 | 101 | 105 | 2 | 3 | 9 | −8 | 152 | 154 | 1 | −3 | −4 | −7 | 236 | 230 | 5 | 5 | 2 | −7 | 240 | 251 | 2 |
| −3 | −5 | −8 | 31 | 36 | 2 | −3 | 2 | −8 | 73 | 66 | 1 | 4 | 9 | −8 | 38 | 37 | 1 | −2 | −4 | −7 | 91 | 82 | 1 | 6 | 2 | −7 | 67 | 66 | 1 |
| −2 | −5 | −8 | 84 | 106 | 2 | −2 | 2 | −8 | 184 | 188 | 2 | −3 | 10 | −8 | 63 | 61 | 2 | −1 | −4 | −7 | 346 | 344 | 5 | 7 | 2 | −7 | 42 | 44 | 1 |
| −1 | −5 | −8 | 32 | 34 | 2 | −1 | 2 | −8 | 140 | 133 | 1 | −2 | 10 | −8 | 220 | 214 | 5 | 0 | −4 | −7 | 63 | 61 | 1 | −6 | 3 | −7 | 51 | 46 | 2 |
| 0 | −5 | −8 | 65 | 61 | 1 | 0 | 2 | −8 | 34 | 34 | 1 | −1 | 10 | −8 | 98 | 100 | 1 | 1 | −4 | −7 | 208 | 207 | 2 | −5 | 3 | −7 | 99 | 104 | 3 |
| 1 | −5 | −8 | 39 | 43 | 1 | 1 | 2 | −8 | 165 | 152 | 3 | 0 | 10 | −8 | 43 | 42 | 1 | 2 | −4 | −7 | 54 | 50 | 1 | −4 | 3 | −7 | 43 | 41 | 1 |
| 2 | −5 | −8 | 75 | 79 | 1 | 2 | 2 | −8 | 141 | 136 | 1 | 1 | 10 | −8 | 190 | 199 | 2 | 3 | −4 | −7 | 118 | 111 | 1 | −3 | 3 | −7 | 119 | 123 | 2 |
| 3 | −5 | −8 | 110 | 110 | 1 | 3 | 2 | −8 | 60 | 55 | 1 | 2 | 10 | −8 | 153 | 149 | 2 | 4 | −4 | −7 | 23 | 26 | 1 | −2 | 3 | −7 | 93 | 91 | 1 |
| 4 | −5 | −8 | 21 | 20 | 2 | 4 | 2 | −8 | 128 | 121 | 1 | 3 | 10 | −8 | 114 | 112 | 1 | 5 | −4 | −7 | 146 | 149 | 2 | −1 | 3 | −7 | 86 | 88 | 1 |
| 5 | −5 | −8 | 19 | 20 | 1 | 5 | 2 | −8 | 103 | 109 | 1 | 4 | 10 | −8 | 129 | 129 | 1 | 6 | −4 | −7 | 78 | 79 | 1 | 0 | 3 | −7 | 197 | 181 | 2 |
| −5 | −4 | −8 | 21 | 15 | 3 | 6 | 2 | −8 | 114 | 115 | 1 | −4 | 11 | −8 | 90 | 87 | 2 | −5 | −3 | −7 | 82 | 81 | 2 | 1 | 3 | −7 | 147 | 147 | 1 |
| −4 | −4 | −8 | 40 | 39 | 2 | 7 | 2 | −8 | 24 | 26 | 1 | −3 | 11 | −8 | 35 | 31 | 2 | −4 | −3 | −7 | 85 | 84 | 2 | 2 | 3 | −7 | 102 | 98 | 1 |
| −3 | −4 | −8 | 66 | 68 | 2 | −6 | 3 | −8 | 108 | 107 | 3 | −2 | 11 | −8 | 41 | 47 | 2 | −3 | −3 | −7 | 324 | 324 | 5 | 3 | 3 | −7 | 94 | 93 | 1 |
| −2 | −4 | −8 | 161 | 160 | 2 | −5 | 3 | −8 | 83 | 93 | 3 | −1 | 11 | −8 | 31 | 33 | 1 | −2 | −3 | −7 | 108 | 103 | 2 | 4 | 3 | −7 | 91 | 87 | 1 |
| −1 | −4 | −8 | 223 | 226 | 3 | −4 | 3 | −8 | 77 | 80 | 2 | 0 | 11 | −8 | 24 | 29 | 2 | −1 | −3 | −7 | 99 | 87 | 1 | 5 | 3 | −7 | 121 | 124 | 1 |

TABLE 7-continued

Observed and calculated structure factors for NEL

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 0 | −4 | −8 | 17 | 13 | 2 | −3 | 3 | −8 | 58 | 54 | 1 | 1 | 11 | −8 | 48 | 47 | 1 | 0 | −3 | −7 | 48 | 54 | 1 | −6 | 4 | −7 | 88 | 82 | 2 |
| 1 | −4 | −8 | 239 | 242 | 2 | −2 | 3 | −8 | 120 | 119 | 1 | 2 | 11 | −8 | 121 | 115 | 2 | 1 | −3 | −7 | 22 | 23 | 1 | −5 | 4 | −7 | 27 | 29 | 2 |
| 2 | −4 | −8 | 194 | 188 | 2 | −1 | 3 | −8 | 226 | 230 | 2 | 3 | 11 | −8 | 64 | 61 | 1 | 2 | −3 | −7 | 193 | 186 | 1 | −4 | 4 | −7 | 121 | 123 | 2 |
| 3 | −4 | −8 | 106 | 111 | 1 | 0 | 3 | −8 | 181 | 164 | 2 | 4 | 11 | −8 | 57 | 57 | 1 | 3 | −3 | −7 | 116 | 122 | 1 | −3 | 4 | −7 | 59 | 58 | 1 |
| 4 | −4 | −8 | 85 | 83 | 1 | 1 | 3 | −8 | 105 | 100 | 1 | −3 | 12 | −8 | 50 | 51 | 2 | 4 | −3 | −7 | 75 | 74 | 1 | −2 | 4 | −7 | 98 | 93 | 1 |
| 5 | −4 | −8 | 109 | 106 | 1 | 2 | 3 | −8 | 83 | 74 | 1 | −2 | 12 | −8 | 171 | 172 | 3 | 5 | −3 | −7 | 132 | 135 | 2 | −1 | 4 | −7 | 112 | 115 | 1 |
| 6 | −4 | −8 | 33 | 39 | 1 | 3 | 3 | −8 | 85 | 88 | 1 | −1 | 12 | −8 | 62 | 61 | 1 | 6 | −3 | −7 | 47 | 48 | 1 | 0 | 4 | −7 | 96 | 105 | 1 |
| 1 | 4 | −7 | 455 | 435 | 5 | −2 | 14 | −7 | 79 | 78 | 1 | −6 | −2 | −6 | 43 | 39 | 2 | 1 | 4 | −6 | 309 | 298 | 3 | −2 | 14 | −6 | 11 | 12 | 4 |
| 2 | 4 | −7 | 51 | 49 | 1 | −1 | 14 | −7 | 53 | 59 | 1 | −5 | −2 | −6 | 92 | 92 | 2 | 2 | 4 | −6 | 205 | 206 | 2 | −1 | 14 | −6 | 82 | 85 | 1 |
| 3 | 4 | −7 | 64 | 64 | 1 | 0 | 14 | −7 | 85 | 82 | 1 | −4 | −2 | −6 | 344 | 350 | 5 | 3 | 4 | −6 | 69 | 68 | 2 | 0 | 14 | −6 | 49 | 46 | 1 |
| 4 | 4 | −7 | 98 | 91 | 2 | 1 | 14 | −7 | 59 | 57 | 2 | −3 | −2 | −6 | 28 | 23 | 1 | 4 | 4 | −6 | 57 | 62 | 1 | 1 | 14 | −6 | 76 | 74 | 2 |
| 5 | 4 | −7 | 113 | 111 | 3 | 2 | 14 | −7 | 36 | 43 | 2 | −2 | −2 | −6 | 257 | 262 | 3 | 5 | 4 | −6 | 97 | 92 | 2 | 2 | 14 | −6 | 39 | 43 | 2 |
| −6 | 5 | −7 | 32 | 31 | 2 | −2 | −10 | −6 | 16 | 79 | 2 | −1 | −2 | −6 | 229 | 236 | 3 | −6 | 5 | −6 | 25 | 22 | 2 | −1 | −11 | −5 | 73 | 72 | 2 |
| −4 | 5 | −7 | 128 | 137 | 2 | −1 | −10 | −6 | 78 | 77 | 2 | 0 | −2 | −6 | 587 | 573 | 6 | −5 | 5 | −6 | 146 | 168 | 4 | 2 | −11 | −5 | 18 | 18 | 4 |
| −3 | 5 | −7 | 226 | 231 | 3 | 0 | −10 | −6 | 169 | 162 | 4 | 1 | −2 | −6 | 115 | 120 | 1 | −4 | 5 | −6 | 157 | 159 | 2 | −3 | −10 | −5 | 39 | 39 | 2 |
| −2 | 5 | −7 | 88 | 84 | 1 | 2 | −10 | −6 | 107 | 110 | 3 | 2 | −2 | −6 | 187 | 182 | 2 | −3 | 5 | −6 | 179 | 170 | 3 | −2 | −10 | −5 | 92 | 89 | 2 |
| −1 | 5 | −7 | 46 | 48 | 1 | 3 | −10 | −6 | 64 | 60 | 2 | 3 | −2 | −6 | 37 | 40 | 1 | −2 | 5 | −6 | 112 | 114 | 1 | −1 | −10 | −5 | 107 | 108 | 3 |
| 0 | 5 | −7 | 238 | 212 | 3 | −3 | −9 | −6 | 0 | 9 | 1 | 4 | −2 | −6 | 203 | 209 | 1 | −1 | 5 | −6 | 392 | 368 | 5 | 0 | −10 | −5 | 50 | 45 | 2 |
| 1 | 5 | −7 | 191 | 180 | 2 | −2 | −9 | −6 | 75 | 77 | 2 | 5 | −2 | −6 | 202 | 199 | 5 | 0 | 5 | −6 | 126 | 112 | 1 | 2 | −10 | −5 | 54 | 53 | 1 |
| 2 | 5 | −7 | 99 | 103 | 1 | −1 | −9 | −6 | 120 | 118 | 3 | 6 | −2 | −6 | 57 | 55 | 1 | 1 | 5 | −6 | 358 | 343 | 4 | 3 | −10 | −5 | 21 | 20 | 3 |
| 3 | 5 | −7 | 134 | 129 | 1 | 0 | −9 | −6 | 101 | 103 | 2 | −6 | −1 | −6 | 46 | 45 | 2 | 2 | 5 | −6 | 63 | 65 | 1 | 4 | −10 | −5 | 68 | 71 | 2 |
| 4 | 5 | −7 | 176 | 177 | 4 | 1 | −9 | −6 | 108 | 107 | 2 | −5 | −1 | −6 | 15 | 13 | 4 | 3 | 5 | −6 | 139 | 139 | 2 | −3 | −9 | −5 | 26 | 24 | 3 |
| 5 | 5 | −7 | 168 | 173 | 4 | 2 | −9 | −6 | 191 | 192 | 3 | −4 | −1 | −6 | 182 | 178 | 3 | 4 | 5 | −6 | 168 | 174 | 4 | −2 | −9 | −5 | 118 | 120 | 3 |
| −6 | 6 | −7 | 32 | 30 | 2 | 3 | −9 | −6 | 101 | 97 | 2 | −3 | −1 | −6 | 51 | 55 | 1 | −6 | 6 | −6 | 35 | 34 | 2 | −1 | −9 | −5 | 116 | 114 | 3 |
| −5 | 6 | −7 | 170 | 162 | 4 | 4 | −9 | −6 | 17 | 18 | 3 | −2 | −1 | −6 | 147 | 139 | 2 | −5 | 6 | −6 | 113 | 125 | 3 | 0 | −9 | −5 | 105 | 100 | 2 |
| −4 | 6 | −7 | 43 | 45 | 2 | −4 | −8 | −6 | 62 | 61 | 2 | −1 | −1 | −6 | 24 | 17 | 1 | −4 | 6 | −6 | 153 | 157 | 2 | 1 | −9 | −5 | 66 | 64 | 1 |
| −3 | 6 | −7 | 93 | 89 | 1 | −3 | −8 | −6 | 120 | 122 | 3 | 0 | −1 | −6 | 208 | 202 | 2 | −3 | 6 | −6 | 153 | 158 | 2 | 2 | −9 | −5 | 134 | 141 | 2 |
| −2 | 6 | −7 | 201 | 205 | 2 | −2 | −8 | −6 | 103 | 111 | 3 | 1 | −1 | −6 | 71 | 71 | 1 | −2 | 6 | −6 | 149 | 151 | 1 | 3 | −9 | −5 | 108 | 107 | 2 |
| −1 | 6 | −7 | 34 | 27 | 1 | −1 | −8 | −6 | 40 | 37 | 2 | 2 | −1 | −6 | 253 | 259 | 2 | −1 | 6 | −6 | 79 | 84 | 1 | 4 | −9 | −5 | 32 | 30 | 1 |
| 0 | 6 | −7 | 41 | 40 | 1 | 0 | −8 | −6 | 140 | 139 | 3 | 3 | −1 | −6 | 115 | 114 | 1 | 0 | 6 | −6 | 274 | 261 | 3 | −4 | −8 | −5 | 40 | 40 | 2 |
| 1 | 6 | −7 | 142 | 140 | 1 | 1 | −8 | −6 | 126 | 125 | 2 | 4 | −1 | −6 | 154 | 152 | 1 | 1 | 6 | −6 | 263 | 271 | 2 | −3 | −8 | −5 | 24 | 19 | 3 |
| 2 | 6 | −7 | 103 | 99 | 1 | 2 | −8 | −6 | 151 | 154 | 2 | 5 | −1 | −6 | 79 | 81 | 1 | 2 | 6 | −6 | 61 | 69 | 1 | −2 | −8 | −5 | 67 | 78 | 2 |
| 3 | 6 | −7 | 146 | 139 | 2 | 3 | −8 | −6 | 104 | 106 | 2 | 6 | −1 | −6 | 27 | 27 | 1 | 3 | 6 | −6 | 253 | 253 | 3 | 0 | −8 | −5 | 106 | 104 | 2 |
| 4 | 6 | −7 | 94 | 90 | 2 | 4 | −8 | −6 | 49 | 44 | 1 | −6 | 0 | −6 | 82 | 83 | 2 | 4 | 6 | −6 | 53 | 57 | 2 | 1 | −8 | −5 | 111 | 113 | 1 |
| −6 | 7 | −7 | 129 | 129 | 3 | 5 | −8 | −6 | 26 | 25 | 1 | −5 | 0 | −6 | 132 | 131 | 3 | −6 | 7 | −6 | 50 | 45 | 2 | 2 | −8 | −5 | 28 | 23 | 2 |
| −5 | 7 | −7 | 123 | 118 | 3 | −4 | −7 | −6 | 55 | 56 | 2 | −4 | 0 | −6 | 165 | 166 | 2 | −5 | 7 | −6 | 100 | 100 | 2 | 3 | −8 | −5 | 129 | 136 | 1 |
| −4 | 7 | −7 | 164 | 159 | 4 | −3 | −7 | −6 | 33 | 35 | 2 | −3 | 0 | −6 | 77 | 74 | 1 | −4 | 7 | −6 | 67 | 64 | 2 | 4 | −8 | −5 | 65 | 59 | 1 |
| −3 | 7 | −7 | 56 | 51 | 1 | −2 | −7 | −6 | 110 | 127 | 3 | −2 | 0 | −6 | 155 | 154 | 2 | −3 | 7 | −6 | 109 | 108 | 1 | 5 | −8 | −5 | 29 | 33 | 1 |
| −2 | 7 | −7 | 44 | 46 | 1 | −1 | −7 | −6 | 57 | 57 | 2 | −1 | 0 | −6 | 106 | 108 | 1 | −2 | 7 | −6 | 47 | 54 | 1 | −4 | −7 | −5 | 36 | 33 | 2 |
| −1 | 7 | −7 | 40 | 38 | 1 | 0 | −7 | −6 | 130 | 125 | 2 | 0 | 0 | −6 | 379 | 387 | 3 | −1 | 7 | −6 | 330 | 331 | 3 | −3 | −7 | −5 | 89 | 92 | 2 |
| 0 | 7 | −7 | 224 | 214 | 2 | 1 | −7 | −6 | 151 | 153 | 2 | 1 | 0 | −6 | 165 | 172 | 1 | 0 | 7 | −6 | 169 | 163 | 1 | −2 | −7 | −5 | 172 | 188 | 4 |
| 1 | 7 | −7 | 193 | 188 | 1 | 2 | −7 | −6 | 174 | 172 | 2 | 2 | 0 | −6 | 322 | 317 | 4 | 1 | 7 | −6 | 176 | 180 | 1 | −1 | −7 | −5 | 187 | 192 | 3 |
| 2 | 7 | −7 | 41 | 35 | 1 | 3 | −7 | −6 | 130 | 134 | 1 | 3 | 0 | −6 | 112 | 115 | 1 | 2 | 7 | −6 | 163 | 168 | 1 | 0 | −7 | −5 | 122 | 127 | 2 |
| 3 | 7 | −7 | 205 | 200 | 2 | 4 | −7 | −6 | 47 | 47 | 1 | 4 | 0 | −6 | 200 | 201 | 1 | 3 | 7 | −6 | 249 | 249 | 3 | 1 | −7 | −5 | 60 | 62 | 1 |
| −5 | 8 | −7 | 149 | 147 | 3 | 5 | −7 | −6 | 76 | 77 | 1 | 5 | 0 | −6 | 47 | 52 | 1 | −5 | 8 | −6 | 140 | 135 | 3 | 2 | −7 | −5 | 250 | 254 | 2 |
| −4 | 8 | −7 | 80 | 78 | 2 | −5 | −6 | −6 | 42 | 40 | 2 | 6 | 0 | −6 | 127 | 128 | 1 | −4 | 8 | −6 | 22 | 25 | 3 | 3 | −7 | −5 | 159 | 163 | 2 |
| −3 | 8 | −7 | 88 | 84 | 2 | −4 | −6 | −6 | 86 | 88 | 2 | 7 | 0 | −6 | 39 | 41 | 1 | −3 | 8 | −6 | 264 | 270 | 3 | 4 | −7 | −5 | 43 | 44 | 1 |
| −2 | 8 | −7 | 152 | 155 | 2 | −3 | −6 | −6 | 82 | 84 | 2 | −6 | 1 | −6 | 44 | 43 | 2 | −2 | 8 | −6 | 98 | 94 | 1 | 5 | −7 | −5 | 46 | 46 | 1 |
| −1 | 8 | −7 | 116 | 116 | 1 | −2 | −6 | −6 | 317 | 328 | 8 | −5 | 1 | −6 | 209 | 209 | 4 | −1 | 8 | −6 | 134 | 132 | 1 | −5 | −6 | −5 | 53 | 49 | 2 |

TABLE 7-continued

Observed and calculated structure factors for NEL

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 0 | 8 | −7 | 136 | 134 | 1 | −1 | −6 | −6 | 171 | 174 | 3 | −4 | 1 | −6 | 105 | 105 | 2 | 0 | 8 | −6 | 65 | 61 | 1 | −4 | −6 | −5 | 25 | 24 | 3 |
| 1 | 8 | −7 | 76 | 71 | 1 | 0 | −6 | −6 | 13 | 5 | 3 | −3 | 1 | −6 | 108 | 105 | 1 | 1 | 8 | −6 | 165 | 163 | 1 | −3 | −6 | −5 | 20 | 15 | 3 |
| 2 | 8 | −7 | 83 | 83 | 1 | 1 | −6 | −6 | 61 | 63 | 1 | −2 | 1 | −6 | 220 | 217 | 2 | 2 | 8 | −6 | 119 | 117 | 1 | −2 | −6 | −5 | 201 | 194 | 3 |
| 3 | 8 | −7 | 230 | 219 | 2 | 2 | −6 | −6 | 328 | 333 | 3 | −1 | 1 | −6 | 345 | 343 | 4 | 3 | 8 | −6 | 222 | 227 | 2 | −1 | −6 | −5 | 144 | 136 | 2 |
| 4 | 8 | −7 | 242 | 249 | 3 | 3 | −6 | −6 | 201 | 203 | 2 | 0 | 1 | −6 | 280 | 279 | 2 | 4 | 8 | −6 | 65 | 70 | 1 | 0 | −6 | −5 | 61 | 58 | 1 |
| −3 | 9 | −7 | 133 | 123 | 3 | 4 | −6 | −6 | 134 | 132 | 2 | 1 | 1 | −6 | 332 | 335 | 3 | −5 | 9 | −6 | 67 | 70 | 2 | 1 | −6 | −5 | 111 | 111 | 1 |
| −2 | 9 | −7 | 316 | 319 | 5 | 5 | −6 | −6 | 65 | 67 | 1 | 2 | 1 | −6 | 253 | 245 | 3 | −3 | 9 | −6 | 138 | 141 | 3 | 2 | −6 | −5 | 31 | 29 | 1 |
| −1 | 9 | −7 | 65 | 63 | 1 | 6 | −6 | −6 | 29 | 34 | 1 | 3 | 1 | −6 | 113 | 110 | 1 | −2 | 9 | −6 | 21 | 16 | 4 | 3 | −6 | −5 | 143 | 145 | 1 |
| 0 | 9 | −7 | 67 | 69 | 1 | −5 | −5 | −6 | 23 | 25 | 3 | 4 | 1 | −6 | 126 | 121 | 1 | −1 | 9 | −6 | 157 | 160 | 1 | 4 | −6 | −5 | 39 | 39 | 1 |
| 1 | 9 | −7 | 77 | 75 | 1 | −4 | −5 | −6 | 75 | 73 | 2 | 5 | 1 | −6 | 131 | 134 | 1 | 0 | 9 | −6 | 55 | 54 | 1 | 5 | −6 | −5 | 53 | 54 | 1 |
| 2 | 9 | −7 | 226 | 235 | 1 | −3 | −5 | −6 | 121 | 122 | 3 | 6 | 1 | −6 | 70 | 76 | 1 | 1 | 9 | −6 | 217 | 222 | 2 | 6 | −6 | −5 | 46 | 42 | 1 |
| 3 | 9 | −7 | 176 | 169 | 1 | −2 | −5 | −6 | 195 | 190 | 3 | 7 | 1 | −6 | 37 | 42 | 1 | 2 | 9 | −6 | 92 | 94 | 1 | −5 | −5 | −5 | 112 | 122 | 3 |
| 4 | 9 | −7 | 86 | 84 | 1 | −1 | −5 | −6 | 37 | 38 | 1 | −6 | 2 | −6 | 61 | 63 | 2 | 3 | 9 | −6 | 225 | 224 | 2 | −4 | −5 | −5 | 102 | 107 | 3 |
| −3 | 10 | −7 | 10 | 11 | 10 | 0 | −5 | −6 | 72 | 76 | 1 | −5 | 2 | −6 | 45 | 46 | 2 | 4 | 9 | −6 | 29 | 32 | 1 | −3 | −5 | −5 | 267 | 266 | 4 |
| −2 | 10 | −7 | 128 | 123 | 3 | 1 | −5 | −6 | 52 | 51 | 1 | −4 | 2 | −6 | 49 | 41 | 1 | −3 | 10 | −6 | 149 | 150 | 3 | −2 | −5 | −5 | 171 | 168 | 2 |
| −1 | 10 | −7 | 62 | 58 | 1 | 2 | −5 | −6 | 224 | 222 | 2 | −3 | 2 | −6 | 72 | 69 | 1 | −2 | 10 | −6 | 136 | 140 | 3 | −1 | −5 | −5 | 170 | 164 | 2 |
| 0 | 10 | −7 | 99 | 101 | 1 | 3 | −5 | −6 | 89 | 89 | 1 | −2 | 2 | −6 | 98 | 97 | 1 | −1 | 10 | −6 | 82 | 83 | 1 | 0 | −5 | −5 | 96 | 99 | 1 |
| 1 | 10 | −7 | 54 | 54 | 1 | 4 | −5 | −6 | 100 | 100 | 1 | −1 | 2 | −6 | 139 | 136 | 1 | 0 | 10 | −6 | 39 | 39 | 1 | 1 | −5 | −5 | 259 | 265 | 2 |
| 2 | 10 | −7 | 18 | 12 | 2 | 5 | −5 | −6 | 105 | 102 | 1 | 0 | 2 | −6 | 181 | 172 | 1 | 1 | 10 | −6 | 146 | 143 | 1 | 2 | −5 | −5 | 86 | 84 | 1 |
| 3 | 10 | −7 | 129 | 133 | 1 | 6 | −5 | −6 | 74 | 74 | 1 | 1 | 2 | −6 | 414 | 421 | 4 | 2 | 10 | −6 | 114 | 116 | 2 | 3 | −5 | −5 | 78 | 80 | 1 |
| 4 | 10 | −7 | 20 | 27 | 1 | −5 | −4 | −6 | 40 | 37 | 2 | 2 | 2 | −6 | 185 | 180 | 2 | 3 | 10 | −6 | 226 | 226 | 2 | 4 | −5 | −5 | 125 | 129 | 1 |
| −4 | 11 | −7 | 85 | 90 | 2 | −4 | −4 | −6 | 190 | 187 | 4 | 3 | 2 | −6 | 229 | 236 | 2 | 4 | 10 | −6 | 87 | 86 | 1 | 5 | −5 | −5 | 107 | 116 | 1 |
| −3 | 11 | −7 | 43 | 43 | 2 | −3 | −4 | −6 | 49 | 45 | 1 | 4 | 2 | −6 | 150 | 154 | 1 | −4 | 11 | −6 | 33 | 31 | 3 | 6 | −5 | −5 | 11 | 12 | 5 |
| −2 | 11 | −7 | 174 | 180 | 2 | −2 | −4 | −6 | 113 | 115 | 2 | 5 | 2 | −6 | 85 | 91 | 1 | −3 | 11 | −6 | 180 | 183 | 4 | −6 | −4 | −5 | 20 | 24 | 3 |
| −1 | 11 | −7 | 82 | 89 | 2 | −1 | −4 | −6 | 106 | 96 | 2 | 6 | 2 | −6 | 57 | 56 | 1 | −2 | 11 | −6 | 78 | 74 | 1 | −5 | −4 | −5 | 207 | 209 | 5 |
| 0 | 11 | −7 | 47 | 52 | 2 | 0 | −4 | −6 | 82 | 86 | 1 | 7 | 2 | −6 | 38 | 44 | 1 | −1 | 11 | −6 | 25 | 24 | 1 | −4 | −4 | −5 | 122 | 127 | 3 |
| 1 | 11 | −7 | 46 | 46 | 1 | 1 | −4 | −6 | 129 | 130 | 1 | −6 | 3 | −6 | 95 | 92 | 2 | 0 | 11 | −6 | 90 | 91 | 2 | −3 | −4 | −5 | 142 | 140 | 2 |
| 2 | 11 | −7 | 282 | 282 | 4 | 2 | −4 | −6 | 266 | 266 | 2 | −5 | 3 | −6 | 42 | 41 | 2 | 1 | 11 | −6 | 181 | 186 | 2 | −2 | −4 | −5 | 202 | 195 | 3 |
| 3 | 11 | −7 | 108 | 107 | 1 | 3 | −4 | −6 | 109 | 108 | 1 | −4 | 3 | −6 | 21 | 19 | 2 | 2 | 11 | −6 | 7 | 15 | 7 | −1 | −4 | −5 | 293 | 304 | 3 |
| 4 | 11 | −7 | 67 | 68 | 1 | 4 | −4 | −6 | 48 | 51 | 1 | −3 | 3 | −6 | 9 | 2 | 4 | 3 | 11 | −6 | 120 | 120 | 1 | 0 | −4 | −5 | 159 | 159 | 1 |
| −4 | 12 | −7 | 17 | 18 | 4 | 5 | −4 | −6 | 36 | 38 | 1 | −2 | 3 | −6 | 121 | 111 | 2 | 4 | 11 | −6 | 60 | 59 | 1 | 1 | −4 | −5 | 275 | 283 | 3 |
| −3 | 12 | −7 | 117 | 117 | 3 | 6 | −4 | −6 | 15 | 20 | 3 | −1 | 3 | −6 | 283 | 281 | 3 | −3 | 12 | −6 | 145 | 143 | 3 | 2 | −4 | −5 | 157 | 151 | 1 |
| −2 | 12 | −7 | 89 | 86 | 1 | −6 | −3 | −6 | 72 | 70 | 2 | 0 | 3 | −6 | 164 | 155 | 1 | −2 | 12 | −6 | 38 | 40 | 1 | 3 | −4 | −5 | 65 | 65 | 1 |
| −1 | 12 | −7 | 103 | 109 | 2 | −5 | −3 | −6 | 25 | 14 | 2 | 1 | 3 | −6 | 257 | 254 | 2 | −1 | 12 | −6 | 29 | 31 | 1 | 4 | −4 | −5 | 42 | 42 | 1 |
| 0 | 12 | −7 | 15 | 11 | 2 | −4 | −3 | −6 | 128 | 129 | 3 | 2 | 3 | −6 | 271 | 263 | 3 | 0 | 12 | −6 | 85 | 80 | 1 | 5 | −4 | −5 | 119 | 119 | 2 |
| 1 | 12 | −7 | 81 | 80 | 1 | −3 | −3 | −6 | 77 | 79 | 1 | 3 | 3 | −6 | 83 | 82 | 1 | 1 | 12 | −6 | 40 | 43 | 1 | 6 | −4 | −5 | 6 | 9 | 5 |
| 2 | 12 | −7 | 108 | 106 | 3 | −2 | −3 | −6 | 182 | 173 | 3 | 4 | 3 | −6 | 99 | 98 | 1 | 2 | 12 | −6 | 91 | 89 | 2 | −6 | −3 | −5 | 17 | 24 | 4 |
| 3 | 12 | −7 | 52 | 55 | 2 | −1 | −3 | −6 | 97 | 102 | 1 | 5 | 3 | −6 | 47 | 45 | 1 | 3 | 12 | −6 | 90 | 99 | 2 | −5 | −3 | −5 | 115 | 117 | 3 |
| 4 | 12 | −7 | 73 | 77 | 1 | 0 | −3 | −6 | 59 | 55 | 1 | −6 | 4 | −6 | 31 | 29 | 2 | 4 | 12 | −6 | 83 | 89 | 1 | −4 | −3 | −5 | 52 | 50 | 1 |
| −3 | 13 | −7 | 11 | 12 | 8 | 1 | −3 | −6 | 121 | 115 | 1 | −5 | 4 | −6 | 163 | 192 | 4 | −3 | 13 | −6 | 30 | 27 | 2 | −3 | −3 | −5 | 118 | 125 | 2 |
| −2 | 13 | −7 | 58 | 57 | 1 | 2 | −3 | −6 | 176 | 173 | 1 | −4 | 4 | −6 | 28 | 26 | 1 | −2 | 13 | −6 | 77 | 78 | 1 | −2 | −3 | −5 | 235 | 226 | 3 |
| −1 | 13 | −7 | 88 | 84 | 1 | 3 | −3 | −6 | 206 | 215 | 2 | −3 | 4 | −6 | 91 | 88 | 1 | −1 | 13 | −6 | 64 | 67 | 1 | −1 | −3 | −5 | 290 | 287 | 3 |
| 0 | 13 | −7 | 126 | 134 | 1 | 4 | −3 | −6 | 101 | 102 | 1 | −2 | 4 | −6 | 63 | 57 | 1 | 0 | 13 | −6 | 80 | 85 | 1 | 0 | −3 | −5 | 413 | 400 | 4 |
| 1 | 13 | −7 | 22 | 28 | 1 | 5 | −3 | −6 | 88 | 96 | 1 | −1 | 4 | −6 | 343 | 332 | 3 | 1 | 13 | −6 | 63 | 70 | 1 | 1 | −3 | −5 | 214 | 209 | 2 |
| 2 | 13 | −7 | 80 | 80 | 2 | 6 | −3 | −6 | 71 | 68 | 1 | 0 | 4 | −6 | 294 | 281 | 2 | 2 | 13 | −6 | 79 | 77 | 2 | 2 | −3 | −5 | 144 | 147 | 1 |
| 3 | −3 | −5 | 135 | 130 | 1 | −5 | 4 | −5 | 76 | 79 | 2 | −3 | 13 | −5 | 116 | 113 | 3 | 3 | −4 | −4 | 166 | 165 | 1 | −5 | 3 | −4 | 103 | 98 | 2 |
| 4 | −3 | −5 | 60 | 58 | 1 | −4 | 4 | −5 | 52 | 49 | 1 | −2 | 13 | −5 | 48 | 45 | 1 | 4 | −4 | −4 | 55 | 53 | 1 | −4 | 3 | −4 | 29 | 27 | 1 |
| 5 | −3 | −5 | 66 | 73 | 1 | −3 | 4 | −5 | 143 | 143 | 2 | −1 | 13 | −5 | 37 | 39 | 1 | 5 | −4 | −4 | 66 | 72 | 1 | −3 | 3 | −4 | 116 | 119 | 2 |
| 6 | −3 | −5 | 31 | 33 | 2 | −2 | 4 | −5 | 183 | 188 | 3 | 0 | 13 | −5 | 81 | 78 | 1 | 6 | −4 | −4 | 64 | 59 | 1 | −2 | 3 | −4 | 185 | 193 | 3 |

TABLE 7-continued

Observed and calculated structure factors for NEL

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 7 | −3 | −5 | 18 | 16 | 4 | −1 | 4 | −5 | 223 | 216 | 3 | 1 | 13 | −5 | 49 | 52 | 1 | −5 | −3 | −4 | 162 | 169 | 4 | −1 | 3 | −4 | 587 | 613 | 6 |
| −6 | −2 | −5 | 36 | 35 | 2 | 0 | 4 | −5 | 368 | 363 | 3 | 2 | 13 | −5 | 40 | 39 | 2 | −4 | −3 | −4 | 50 | 50 | 2 | 0 | 3 | −4 | 129 | 136 | 1 |
| −5 | −2 | −5 | 94 | 97 | 2 | 1 | 4 | −5 | 271 | 265 | 2 | −2 | 14 | −5 | 71 | 70 | 1 | −3 | −3 | −4 | 84 | 87 | 1 | 1 | 3 | −4 | 386 | 384 | 4 |
| −4 | −2 | −5 | 250 | 263 | 4 | 2 | 4 | −5 | 144 | 141 | 3 | −1 | 14 | −5 | 45 | 44 | 1 | −2 | −3 | −4 | 142 | 135 | 2 | 4 | 3 | −4 | 148 | 144 | 2 |
| −3 | −2 | −5 | 253 | 268 | 4 | 3 | 4 | −5 | 79 | 81 | 1 | 0 | 14 | −5 | 61 | 55 | 1 | −1 | −3 | −4 | 332 | 336 | 4 | 5 | 3 | −4 | 165 | 165 | 2 |
| −2 | −2 | −5 | 164 | 162 | 2 | 4 | 4 | −5 | 240 | 224 | 3 | 1 | 14 | −5 | 37 | 38 | 2 | 0 | −3 | −4 | 322 | 314 | 3 | 6 | 3 | −4 | 21 | 21 | 3 |
| −1 | −2 | −5 | 178 | 174 | 2 | 5 | 4 | −5 | 69 | 72 | 1 | 2 | 14 | −5 | 57 | 63 | 2 | 1 | −3 | −4 | 330 | 324 | 3 | −7 | 4 | −4 | 89 | 90 | 2 |
| 0 | −2 | −5 | 69 | 69 | 1 | −6 | 5 | −5 | 67 | 65 | 2 | −2 | −11 | −4 | 44 | 40 | 2 | 2 | −3 | −4 | 96 | 87 | 1 | −6 | 4 | −4 | 79 | 79 | 2 |
| 1 | −2 | −5 | 213 | 204 | 2 | −5 | 5 | −5 | 79 | 92 | 2 | −1 | −11 | −4 | 130 | 127 | 3 | 3 | −3 | −4 | 99 | 90 | 1 | −5 | 4 | −4 | 146 | 146 | 3 |
| 2 | −2 | −5 | 93 | 91 | 1 | −4 | 5 | −5 | 243 | 241 | 4 | 0 | −11 | −4 | 89 | 88 | 2 | 4 | −3 | −4 | 53 | 55 | 1 | −4 | 4 | −4 | 112 | 116 | 2 |
| 3 | −2 | −5 | 208 | 213 | 1 | −3 | 5 | −5 | 85 | 86 | 1 | 1 | −11 | −4 | 72 | 68 | 2 | 5 | −3 | −4 | 33 | 34 | 1 | −3 | 4 | −4 | 56 | 57 | 1 |
| 4 | −2 | −5 | 140 | 143 | 1 | −2 | 5 | −5 | 52 | 48 | 1 | 2 | −11 | −4 | 35 | 36 | 2 | 6 | −3 | −4 | 47 | 50 | 1 | −2 | 4 | −4 | 165 | 166 | 3 |
| 5 | −2 | −5 | 107 | 108 | 1 | −1 | 5 | −5 | 338 | 331 | 5 | 3 | −11 | −4 | 92 | 92 | 2 | 7 | −3 | −4 | 46 | 46 | 2 | −1 | 4 | −4 | 287 | 295 | 3 |
| 6 | −2 | −5 | 78 | 76 | 1 | 0 | 5 | −5 | 608 | 595 | 6 | −3 | −10 | −4 | 120 | 117 | 3 | −6 | −2 | −4 | 83 | 85 | 2 | 0 | 4 | −4 | 221 | 221 | 2 |
| −6 | −1 | −5 | 39 | 40 | 2 | 1 | 5 | −5 | 46 | 38 | 1 | −2 | −10 | −4 | 48 | 49 | 2 | −5 | −2 | −4 | 185 | 189 | 4 | 1 | 4 | −4 | 157 | 160 | 1 |
| −5 | −1 | −5 | 130 | 127 | 3 | 2 | 5 | −5 | 104 | 88 | 2 | −1 | −10 | −4 | 58 | 57 | 2 | −4 | −2 | −4 | 125 | 122 | 3 | 3 | 4 | −4 | 148 | 158 | 2 |
| −4 | −1 | −5 | 101 | 101 | 2 | 3 | 5 | −5 | 35 | 24 | 2 | 0 | −10 | −4 | 223 | 211 | 5 | −3 | −2 | −4 | 68 | 69 | 1 | 4 | 4 | −4 | 82 | 81 | 1 |
| −3 | −1 | −5 | 263 | 266 | 4 | 4 | 5 | −5 | 149 | 142 | 2 | 1 | −10 | −4 | 73 | 68 | 3 | −2 | −2 | −4 | 151 | 151 | 2 | 5 | 4 | −4 | 32 | 30 | 2 |
| −2 | −1 | −5 | 176 | 184 | 2 | −6 | 6 | −5 | 71 | 67 | 2 | 2 | −10 | −4 | 30 | 27 | 2 | −1 | −2 | −4 | 162 | 159 | 2 | 6 | 4 | −4 | 73 | 78 | 2 |
| −1 | −1 | −5 | 199 | 206 | 2 | −5 | 6 | −5 | 58 | 69 | 2 | 3 | −10 | −4 | 59 | 57 | 1 | 0 | −2 | −4 | 300 | 292 | 3 | −6 | 5 | −4 | 29 | 30 | 2 |
| 0 | −1 | −5 | 315 | 324 | 3 | −4 | 6 | −5 | 242 | 235 | 4 | 4 | −10 | −4 | 103 | 102 | 2 | 1 | −2 | −4 | 32 | 23 | 1 | −5 | 5 | −4 | 70 | 83 | 2 |
| 1 | −1 | −5 | 332 | 325 | 3 | −3 | 6 | −5 | 204 | 203 | 2 | −3 | −9 | −4 | 61 | 62 | 2 | 2 | −2 | −4 | 248 | 247 | 2 | −4 | 5 | −4 | 8 | 13 | 7 |
| 2 | −1 | −5 | 96 | 95 | 1 | −2 | 6 | −5 | 111 | 119 | 1 | −2 | −9 | −4 | 111 | 117 | 3 | 3 | −2 | −4 | 149 | 152 | 1 | −3 | 5 | −4 | 156 | 154 | 2 |
| 3 | −1 | −5 | 101 | 104 | 1 | −1 | 6 | −5 | 286 | 278 | 3 | −1 | −9 | −4 | 75 | 87 | 2 | 4 | −2 | −4 | 28 | 29 | 1 | −2 | 5 | −4 | 90 | 93 | 1 |
| 4 | −1 | −5 | 119 | 119 | 1 | 0 | 6 | −5 | 514 | 492 | 6 | 0 | −9 | −4 | 29 | 29 | 3 | 5 | −2 | −4 | 147 | 144 | 1 | −1 | 5 | −4 | 159 | 153 | 3 |
| 5 | −1 | −5 | 111 | 113 | 1 | 1 | 6 | −5 | 75 | 76 | 1 | 1 | −9 | −4 | 74 | 70 | 1 | 6 | −2 | −4 | 55 | 52 | 1 | 0 | 5 | −4 | 230 | 230 | 2 |
| 6 | −1 | −5 | 113 | 115 | 1 | 2 | 6 | −5 | 78 | 82 | 1 | 2 | −9 | −4 | 133 | 133 | 2 | 7 | −2 | −4 | 97 | 98 | 2 | 1 | 5 | −4 | 278 | 284 | 3 |
| 7 | −1 | −5 | 68 | 63 | 1 | 3 | 6 | −5 | 33 | 24 | 2 | 3 | −9 | −4 | 80 | 80 | 2 | −6 | −1 | −4 | 25 | 21 | 3 | 3 | 5 | −4 | 14 | 17 | 2 |
| −6 | 0 | −5 | 37 | 38 | 2 | −5 | 7 | −5 | 101 | 102 | 3 | 4 | −9 | −4 | 32 | 34 | 1 | −5 | −1 | −4 | 130 | 135 | 3 | 4 | 5 | −4 | 57 | 56 | 1 |
| −5 | 0 | −5 | 124 | 123 | 3 | −4 | 7 | −5 | 275 | 265 | 6 | 5 | −9 | −4 | 52 | 55 | 2 | −4 | −1 | −4 | 188 | 195 | 3 | 5 | 5 | −4 | 90 | 92 | 2 |
| −4 | 0 | −5 | 42 | 39 | 1 | −3 | 7 | −5 | 182 | 187 | 2 | −4 | −8 | −4 | 78 | 78 | 2 | −3 | −1 | −4 | 183 | 196 | 4 | −6 | 6 | −4 | 10 | 13 | 10 |
| −3 | 0 | −5 | 96 | 101 | 1 | −2 | 7 | −5 | 129 | 136 | 1 | −3 | −8 | −4 | 76 | 76 | 2 | −2 | −1 | −4 | 48 | 46 | 1 | −5 | 6 | −4 | 70 | 79 | 2 |
| −2 | 0 | −5 | 314 | 302 | 3 | −1 | 7 | −5 | 131 | 130 | 1 | −1 | −8 | −4 | 80 | 89 | 2 | −1 | −1 | −4 | 166 | 166 | 2 | −4 | 6 | −4 | 144 | 138 | 2 |
| −1 | 0 | −5 | 113 | 115 | 1 | 0 | 7 | −5 | 179 | 166 | 1 | 0 | −8 | −4 | 38 | 31 | 1 | 0 | −1 | −4 | 399 | 409 | 3 | −3 | 6 | −4 | 146 | 146 | 2 |
| 0 | 0 | −5 | 307 | 311 | 2 | 1 | 7 | −5 | 135 | 135 | 1 | 1 | −8 | −4 | 78 | 82 | 1 | 1 | −1 | −4 | 133 | 135 | 1 | −2 | 6 | −4 | 72 | 79 | 1 |
| 1 | 0 | −5 | 36 | 42 | 1 | 2 | 7 | −5 | 25 | 27 | 1 | 2 | −8 | −4 | 100 | 103 | 1 | 2 | −1 | −4 | 229 | 223 | 2 | −1 | 6 | −4 | 166 | 170 | 2 |
| 2 | 0 | −5 | 21 | 23 | 1 | 3 | 7 | −5 | 51 | 57 | 1 | 3 | −8 | −4 | 86 | 86 | 1 | 3 | −1 | −4 | 145 | 147 | 1 | 0 | 6 | −4 | 398 | 389 | 5 |
| 3 | 0 | −5 | 288 | 285 | 3 | −6 | 8 | −5 | 78 | 79 | 2 | 4 | −8 | −4 | 98 | 100 | 1 | 4 | −1 | −4 | 87 | 92 | 1 | 1 | 6 | −4 | 10 | 9 | 2 |
| 4 | 0 | −5 | 84 | 79 | 1 | −5 | 8 | −5 | 24 | 20 | 3 | 5 | −8 | −4 | 62 | 62 | 1 | 5 | −1 | −4 | 143 | 138 | 1 | 2 | 6 | −4 | 75 | 78 | 1 |
| 5 | 0 | −5 | 138 | 138 | 1 | −4 | 8 | −5 | 285 | 281 | 7 | −5 | −7 | −4 | 58 | 62 | 2 | 6 | −1 | −4 | 37 | 34 | 1 | −5 | 7 | −4 | 88 | 88 | 2 |
| 6 | 0 | −5 | 40 | 43 | 1 | −3 | 8 | −5 | 43 | 37 | 1 | −4 | −7 | −4 | 57 | 56 | 2 | 7 | −1 | −4 | 68 | 71 | 1 | −4 | 7 | −4 | 71 | 73 | 2 |
| 7 | 0 | −5 | 48 | 45 | 1 | −2 | 8 | −5 | 185 | 188 | 2 | −3 | −7 | −4 | 92 | 89 | 2 | −6 | 0 | −4 | 66 | 65 | 2 | −3 | 7 | −4 | 300 | 302 | 3 |
| −6 | 1 | −5 | 110 | 111 | 3 | −1 | 8 | −5 | 69 | 67 | 1 | −2 | −7 | −4 | 122 | 122 | 2 | −5 | 0 | −4 | 168 | 169 | 4 | −2 | 7 | −4 | 85 | 82 | 1 |
| −5 | 1 | −5 | 129 | 128 | 3 | 0 | 8 | −5 | 173 | 164 | 2 | −1 | −7 | −4 | 24 | 19 | 2 | −4 | 0 | −4 | 192 | 194 | 3 | −1 | 7 | −4 | 359 | 355 | 4 |
| −4 | 1 | −5 | 160 | 164 | 2 | 1 | 8 | −5 | 134 | 130 | 1 | 0 | −7 | −4 | 128 | 129 | 2 | −3 | 0 | −4 | 63 | 56 | 1 | 0 | 7 | −4 | 344 | 333 | 3 |
| −3 | 1 | −5 | 116 | 114 | 1 | 2 | 8 | −5 | 193 | 202 | 1 | 1 | −7 | −4 | 89 | 85 | 1 | −2 | 0 | −4 | 83 | 87 | 1 | 1 | 7 | −4 | 172 | 171 | 1 |
| −2 | 1 | −5 | 109 | 105 | 1 | 3 | 8 | −5 | 46 | 46 | 1 | 2 | −7 | −4 | 83 | 80 | 1 | −1 | 0 | −4 | 97 | 102 | 1 | 2 | 7 | −4 | 102 | 101 | 1 |
| −1 | 1 | −5 | 222 | 228 | 2 | 4 | 8 | −5 | 88 | 88 | 1 | 3 | −7 | −4 | 29 | 29 | 1 | 0 | 0 | −4 | 189 | 195 | 1 | 3 | 7 | −4 | 201 | 204 | 2 |
| 0 | 1 | −5 | 190 | 186 | 1 | −5 | 9 | −5 | 26 | 27 | 3 | 4 | −7 | −4 | 50 | 53 | 1 | 1 | 0 | −4 | 127 | 128 | 1 | −6 | 8 | −4 | 30 | 29 | 2 |

TABLE 7-continued

Observed and calculated structure factors for NEL

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 1 | 1 | −5 | 247 | 254 | 2 | −4 | 9 | −5 | 49 | 49 | 2 | 5 | −7 | −4 | 66 | 66 | 1 | 2 | 0 | −4 | 243 | 243 | 2 | −5 | 8 | −4 | 82 | 76 | 2 |
| 2 | 1 | −5 | 87 | 86 | 1 | −3 | 9 | −5 | 291 | 296 | 7 | 6 | −7 | −4 | 80 | 78 | 2 | 3 | 0 | −4 | 141 | 144 | 1 | −4 | 8 | −4 | 123 | 122 | 3 |
| 3 | 1 | −5 | 92 | 87 | 1 | −2 | 9 | −5 | 257 | 258 | 4 | −5 | −6 | −4 | 21 | 20 | 3 | 4 | 0 | −4 | 210 | 206 | 1 | −3 | 8 | −4 | 229 | 231 | 2 |
| 4 | 1 | −5 | 168 | 172 | 1 | −1 | 9 | −5 | 66 | 67 | 1 | −4 | −6 | −4 | 33 | 33 | 2 | 5 | 0 | −4 | 90 | 90 | 1 | −2 | 8 | −4 | 179 | 184 | 2 |
| 5 | 1 | −5 | 163 | 160 | 1 | 0 | 9 | −5 | 45 | 43 | 1 | −3 | −6 | −4 | 142 | 144 | 2 | 6 | 0 | −4 | 71 | 69 | 1 | −1 | 8 | −4 | 264 | 257 | 3 |
| 6 | 1 | −5 | 127 | 126 | 1 | 1 | 9 | −5 | 83 | 88 | 1 | −2 | −6 | −4 | 60 | 53 | 1 | 7 | 0 | −4 | 36 | 38 | 1 | 0 | 8 | −4 | 108 | 98 | 1 |
| 7 | 1 | −5 | 52 | 58 | 1 | 2 | 9 | −5 | 321 | 321 | 2 | −1 | −6 | −4 | 114 | 112 | 2 | −6 | 1 | −4 | 124 | 121 | 3 | 1 | 8 | −4 | 308 | 306 | 2 |
| −6 | 2 | −5 | 28 | 30 | 2 | 3 | 9 | −5 | 73 | 77 | 1 | 0 | −6 | −4 | 49 | 48 | 1 | −5 | 1 | −4 | 187 | 192 | 3 | 2 | 8 | −4 | 122 | 119 | 1 |
| −5 | 2 | −5 | 117 | 117 | 3 | 4 | 9 | −5 | 68 | 68 | 1 | 1 | −6 | −4 | 166 | 170 | 2 | −4 | 1 | −4 | 150 | 144 | 2 | 3 | 8 | −4 | 139 | 145 | 1 |
| −4 | 2 | −5 | 21 | 24 | 2 | −3 | 10 | −5 | 159 | 160 | 4 | 2 | −6 | −4 | 210 | 207 | 2 | −3 | 1 | −4 | 77 | 77 | 1 | 4 | 8 | −4 | 18 | 19 | 1 |
| −3 | 2 | −5 | 85 | 88 | 1 | −2 | 10 | −5 | 141 | 144 | 2 | 3 | −6 | −4 | 43 | 40 | 1 | −2 | 1 | −4 | 67 | 72 | 1 | −5 | 9 | −4 | 61 | 65 | 2 |
| −2 | 2 | −5 | 157 | 157 | 2 | −1 | 10 | −5 | 49 | 52 | 1 | 4 | −6 | −4 | 79 | 81 | 1 | −1 | 1 | −4 | 264 | 272 | 3 | −4 | 9 | −4 | 110 | 110 | 3 |
| −1 | 2 | −5 | 212 | 209 | 2 | 0 | 10 | −5 | 79 | 79 | 1 | 5 | −6 | −4 | 73 | 74 | 1 | 0 | 1 | −4 | 239 | 249 | 1 | −3 | 9 | −4 | 264 | 260 | 6 |
| 0 | 2 | −5 | 113 | 106 | 1 | 1 | 10 | −5 | 96 | 100 | 1 | 6 | −6 | −4 | 41 | 43 | 1 | 1 | 1 | −4 | 339 | 346 | 3 | −2 | 9 | −4 | 89 | 81 | 1 |
| 1 | 2 | −5 | 325 | 328 | 3 | 2 | 10 | −5 | 151 | 152 | 2 | −5 | −5 | −4 | 94 | 98 | 2 | 2 | 1 | −4 | 32 | 31 | 1 | −1 | 9 | −4 | 136 | 132 | 1 |
| 2 | 2 | −5 | 302 | 291 | 4 | 3 | 10 | −5 | 24 | 28 | 1 | −4 | −5 | −4 | 77 | 79 | 2 | 4 | 1 | −4 | 206 | 218 | 2 | 0 | 9 | −4 | 43 | 45 | 1 |
| 4 | 2 | −5 | 82 | 83 | 1 | 4 | 10 | −5 | 80 | 98 | 1 | −3 | −5 | −4 | 46 | 47 | 1 | 5 | 1 | −4 | 87 | 75 | 1 | 1 | 9 | −4 | 186 | 179 | 1 |
| 5 | 2 | −5 | 173 | 177 | 2 | 5 | 10 | −5 | 76 | 76 | 1 | −2 | −5 | −4 | 136 | 132 | 2 | 6 | 1 | −4 | 64 | 65 | 1 | 2 | 9 | −4 | 175 | 172 | 1 |
| 6 | 2 | −5 | 80 | 82 | 1 | −3 | 11 | −5 | 85 | 86 | 2 | −1 | −5 | −4 | 142 | 142 | 2 | 7 | 1 | −4 | 72 | 77 | 1 | 3 | 9 | −4 | 139 | 140 | 1 |
| 7 | 2 | −5 | 55 | 54 | 1 | −2 | 11 | −5 | 121 | 124 | 2 | 0 | −5 | −4 | 110 | 111 | 1 | −7 | 2 | −4 | 35 | 32 | 2 | 4 | 9 | −4 | 81 | 80 | 1 |
| −6 | 3 | −5 | 198 | 190 | 4 | −1 | 11 | −5 | 90 | 95 | 2 | 1 | −5 | −4 | 173 | 178 | 2 | −6 | 2 | −4 | 14 | 14 | 5 | −3 | 10 | −4 | 78 | 76 | 2 |
| −5 | 3 | −5 | 35 | 36 | 2 | 0 | 11 | −5 | 70 | 73 | 1 | 2 | −5 | −4 | 135 | 138 | 1 | −5 | 2 | −4 | 167 | 163 | 2 | −2 | 10 | −4 | 68 | 63 | 1 |
| −4 | 3 | −5 | 95 | 89 | 1 | 1 | 11 | −5 | 54 | 56 | 1 | 3 | −5 | −4 | 56 | 57 | 1 | −4 | 2 | −4 | 95 | 96 | 1 | −1 | 10 | −4 | 47 | 46 | 1 |
| −3 | 3 | −5 | 118 | 117 | 1 | 2 | 11 | −5 | 96 | 95 | 1 | 4 | −5 | −4 | 36 | 36 | 1 | −3 | 2 | −4 | 252 | 258 | 3 | 0 | 10 | −4 | 95 | 90 | 1 |
| −2 | 3 | −5 | 237 | 231 | 3 | 3 | 11 | −5 | 82 | 85 | 1 | 5 | −5 | −4 | 37 | 35 | 1 | −2 | 2 | −4 | 329 | 324 | 4 | 1 | 10 | −4 | 43 | 41 | 1 |
| −1 | 3 | −5 | 496 | 510 | 4 | 4 | 11 | −5 | 37 | 36 | 1 | 6 | −5 | −4 | 51 | 47 | 1 | −1 | 2 | −4 | 130 | 133 | 1 | 2 | 10 | −4 | 114 | 114 | 1 |
| 0 | 3 | −5 | 219 | 210 | 1 | −3 | 12 | −5 | 51 | 52 | 2 | −5 | −4 | −4 | 19 | 20 | 4 | 0 | 2 | −4 | 315 | 325 | 2 | 3 | 10 | −4 | 93 | 94 | 1 |
| 1 | 3 | −5 | 175 | 176 | 1 | −2 | 12 | −5 | 100 | 100 | 2 | −4 | −4 | −4 | 62 | 64 | 2 | 1 | 2 | −4 | 560 | 572 | 5 | 4 | 10 | −4 | 82 | 81 | 1 |
| 2 | 3 | −5 | 224 | 220 | 3 | −1 | 12 | −5 | 59 | 61 | 1 | −3 | −4 | −4 | 89 | 92 | 1 | 2 | 2 | −4 | 143 | 152 | 2 | 5 | 10 | −4 | 27 | 27 | 1 |
| 3 | 3 | −5 | 59 | 56 | 1 | 0 | 12 | −5 | 62 | 60 | 1 | −2 | −4 | −4 | 48 | 43 | 1 | 4 | 2 | −4 | 164 | 154 | 2 | −3 | 11 | −4 | 137 | 135 | 3 |
| 4 | 3 | −5 | 74 | 71 | 1 | 1 | 12 | −5 | 27 | 26 | 1 | −1 | −4 | −4 | 129 | 131 | 1 | 5 | 2 | −4 | 177 | 178 | 2 | −2 | 11 | −4 | 25 | 26 | 2 |
| 5 | 3 | −5 | 53 | 53 | 1 | 2 | 12 | −5 | 137 | 136 | 3 | 0 | −4 | −4 | 325 | 314 | 4 | 6 | 2 | −4 | 76 | 85 | 2 | −1 | 11 | −4 | 93 | 90 | 2 |
| 6 | 3 | −5 | 69 | 81 | 2 | 3 | 12 | −5 | 49 | 53 | 2 | 1 | −4 | −4 | 140 | 136 | 1 | −7 | 3 | −4 | 37 | 36 | 2 | 0 | 11 | −4 | 58 | 72 | 2 |
| −6 | 4 | −5 | 68 | 62 | 2 | 4 | 12 | −5 | 45 | 46 | 2 | 2 | −4 | −4 | 58 | 50 | 1 | −6 | 3 | −4 | 45 | 45 | 2 | 1 | 11 | −4 | 196 | 199 | 2 |
| 2 | 11 | −4 | 145 | 145 | 2 | 3 | −5 | −3 | 121 | 118 | 1 | 6 | 2 | −3 | 87 | 107 | 2 | 3 | 10 | −3 | 15 | 16 | 2 | 2 | −6 | −2 | 174 | 179 | 1 |
| 3 | 11 | −4 | 52 | 49 | 2 | 4 | −5 | −3 | 70 | 76 | 1 | 7 | 3 | −3 | 0 | 8 | 1 | 4 | 10 | −3 | 75 | 72 | 1 | 3 | −6 | −2 | 96 | 89 | 1 |
| 4 | 11 | −4 | 29 | 32 | 1 | 5 | −5 | −3 | 43 | 46 | 1 | −6 | 3 | −3 | 50 | 49 | 2 | 5 | 10 | −3 | 59 | 59 | 1 | 4 | −6 | −2 | 141 | 148 | 1 |
| −3 | 12 | −4 | 16 | 14 | 5 | 6 | −5 | −3 | 26 | 25 | 2 | −5 | 3 | −3 | 55 | 57 | 1 | −3 | 11 | −3 | 71 | 71 | 2 | 5 | −6 | −2 | 40 | 47 | 1 |
| −2 | 12 | −4 | 91 | 90 | 2 | −3 | −4 | −3 | 19 | 22 | 3 | −4 | 3 | −3 | 127 | 124 | 2 | −2 | 11 | −3 | 85 | 82 | 1 | 6 | −6 | −2 | 60 | 56 | 1 |
| −1 | 12 | −4 | 48 | 47 | 1 | −2 | −4 | −3 | 183 | 168 | 2 | −3 | 3 | −3 | 84 | 75 | 2 | −1 | 11 | −3 | 52 | 55 | 1 | −2 | −5 | −2 | 99 | 92 | 1 |
| 0 | 12 | −4 | 57 | 59 | 1 | −1 | −4 | −3 | 136 | 145 | 1 | −2 | 3 | −3 | 89 | 84 | 2 | 0 | 11 | −3 | 77 | 79 | 1 | −1 | −5 | −2 | 277 | 268 | 4 |
| 1 | 12 | −4 | 43 | 44 | 1 | 0 | −4 | −3 | 127 | 123 | 2 | −1 | 3 | −3 | 279 | 295 | 3 | 1 | 11 | −3 | 81 | 78 | 1 | 0 | −5 | −2 | 94 | 96 | 1 |
| 2 | 12 | −4 | 101 | 100 | 1 | 1 | −4 | −3 | 208 | 213 | 2 | 0 | 3 | −3 | 320 | 320 | 3 | 2 | 11 | −3 | 116 | 113 | 2 | 1 | −5 | −2 | 31 | 27 | 1 |
| 3 | 12 | −4 | 160 | 164 | 4 | 2 | −4 | −3 | 351 | 355 | 5 | 1 | 3 | −3 | 259 | 259 | 2 | 3 | 11 | −3 | 175 | 179 | 4 | 2 | −5 | −2 | 237 | 239 | 2 |
| −3 | 13 | −4 | 55 | 55 | 2 | 3 | −4 | −3 | 73 | 72 | 1 | 3 | 3 | −3 | 44 | 38 | 2 | 4 | 11 | −3 | 24 | 23 | 1 | 3 | −5 | −2 | 45 | 48 | 1 |
| −2 | 13 | −4 | 90 | 89 | 1 | 4 | −4 | −3 | 125 | 122 | 1 | 4 | 3 | −3 | 58 | 59 | 1 | −4 | 12 | −3 | 53 | 52 | 2 | 4 | −5 | −2 | 143 | 147 | 1 |
| −1 | 13 | −4 | 77 | 79 | 1 | 5 | −4 | −3 | 52 | 58 | 1 | 5 | 3 | −3 | 176 | 181 | 4 | −3 | 12 | −3 | 21 | 24 | 4 | 5 | −5 | −2 | 112 | 120 | 1 |
| 0 | 13 | −4 | 58 | 56 | 1 | 6 | −4 | −3 | 68 | 70 | 1 | 6 | 3 | −3 | 154 | 171 | 3 | −2 | 12 | −3 | 93 | 94 | 2 | 6 | −5 | −2 | 29 | 26 | 2 |
| 1 | 13 | −4 | 55 | 55 | 1 | 7 | −4 | −3 | 50 | 52 | 2 | −7 | 4 | −3 | 33 | 33 | 2 | −1 | 12 | −3 | 60 | 62 | 1 | −2 | −4 | −2 | 338 | 315 | 5 |

TABLE 7-continued

Observed and calculated structure factors for NEL

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 2 | 13 | −4 | 47 | 48 | 2 | −3 | −3 | −3 | 181 | 177 | 4 | −6 | 4 | −3 | 53 | 48 | 2 | 0 | 12 | −3 | 42 | 47 | 1 | −1 | −4 | −2 | 221 | 222 | 2 |
| −2 | 14 | −4 | 46 | 49 | 1 | −2 | −3 | −3 | 175 | 171 | 2 | −5 | 4 | −3 | 28 | 29 | 2 | 1 | 12 | −3 | 55 | 53 | 1 | 0 | −4 | −2 | 174 | 176 | 2 |
| −1 | 14 | −4 | 41 | 39 | 1 | −1 | −3 | −3 | 84 | 78 | 1 | −4 | 4 | −3 | 197 | 191 | 3 | 2 | 12 | −3 | 71 | 70 | 1 | 1 | −4 | −2 | 103 | 101 | 1 |
| 0 | 14 | −4 | 11 | 10 | 2 | 0 | −3 | −3 | 533 | 535 | 6 | −3 | 4 | −3 | 106 | 101 | 1 | 3 | 12 | −3 | 104 | 109 | 2 | 2 | −4 | −2 | 230 | 210 | 4 |
| 1 | 14 | −4 | 56 | 57 | 2 | 1 | −3 | −3 | 101 | 99 | 1 | −2 | 4 | −3 | 142 | 145 | 3 | −3 | 13 | −3 | 72 | 71 | 2 | 3 | −4 | −2 | 147 | 148 | 1 |
| −2 | −12 | −3 | 71 | 68 | 2 | 2 | −3 | −3 | 242 | 237 | 3 | −1 | 4 | −3 | 111 | 117 | 1 | −2 | 13 | −3 | 49 | 45 | 1 | 4 | −4 | −2 | 83 | 81 | 1 |
| −1 | −12 | −3 | 85 | 83 | 2 | 3 | −3 | −3 | 280 | 275 | 2 | 0 | 4 | −3 | 134 | 139 | 1 | −1 | 13 | −3 | 3 | 12 | 2 | 5 | −4 | −2 | 65 | 66 | 1 |
| 1 | −12 | −3 | 39 | 38 | 3 | 4 | −3 | −3 | 19 | 22 | 1 | 1 | 4 | −3 | 178 | 170 | 1 | 0 | 13 | −3 | 20 | 22 | 1 | 6 | −4 | −2 | 76 | 75 | 1 |
| −3 | −11 | −3 | 24 | 22 | 2 | 5 | −3 | −3 | 124 | 122 | 1 | 3 | 4 | −3 | 91 | 89 | 1 | 1 | 13 | −3 | 17 | 18 | 1 | 7 | −4 | −2 | 114 | 113 | 3 |
| −2 | −11 | −3 | 38 | 34 | 2 | 6 | −3 | −3 | 79 | 81 | 1 | 4 | 4 | −3 | 39 | 42 | 1 | 2 | 13 | −3 | 64 | 61 | 2 | −3 | −3 | −2 | 82 | 78 | 2 |
| −1 | −11 | −3 | 60 | 60 | 2 | 7 | −3 | −3 | 138 | 125 | 3 | 5 | 4 | −3 | 246 | 241 | 5 | −2 | 14 | −3 | 63 | 62 | 2 | −2 | −3 | −2 | 311 | 313 | 6 |
| 0 | −11 | −3 | 29 | 26 | 2 | −3 | −2 | −3 | 196 | 202 | 3 | 6 | 4 | −3 | 123 | 112 | 3 | −1 | 14 | −3 | 33 | 34 | 1 | −1 | −3 | −2 | 309 | 295 | 3 |
| 1 | −11 | −3 | 67 | 68 | 3 | −2 | −2 | −3 | 322 | 335 | 5 | −7 | 5 | −3 | 27 | 22 | 2 | 0 | 14 | −3 | 34 | 30 | 1 | 0 | −3 | −2 | 116 | 120 | 1 |
| 2 | −11 | −3 | 121 | 118 | 2 | −1 | −2 | −3 | 126 | 119 | 1 | −6 | 5 | −3 | 148 | 140 | 3 | 1 | 14 | −3 | 91 | 93 | 2 | 1 | −3 | −2 | 190 | 186 | 1 |
| 3 | −11 | −3 | 25 | 18 | 2 | 0 | −2 | −3 | 706 | 721 | 7 | −5 | 5 | −3 | 103 | 126 | 3 | −2 | −12 | −2 | 54 | 53 | 2 | 2 | −3 | −2 | 40 | 39 | 1 |
| 4 | −11 | −3 | 34 | 40 | 2 | 1 | −2 | −3 | 101 | 104 | 1 | −4 | 5 | −3 | 119 | 113 | 2 | −1 | −12 | −2 | 68 | 65 | 2 | 3 | −3 | −2 | 209 | 203 | 2 |
| −4 | −10 | −3 | 71 | 70 | 2 | 2 | −2 | −3 | 443 | 435 | 4 | −3 | 5 | −3 | 45 | 43 | 1 | 0 | −12 | −2 | 70 | 71 | 1 | 4 | −3 | −2 | 126 | 123 | 1 |
| −3 | −10 | −3 | 43 | 38 | 2 | 3 | −2 | −3 | 153 | 145 | 1 | −2 | 5 | −3 | 169 | 171 | 2 | 1 | −12 | −2 | 49 | 48 | 3 | 5 | −3 | −2 | 47 | 44 | 1 |
| −2 | −10 | −3 | 22 | 19 | 3 | 4 | −2 | −3 | 198 | 203 | 1 | −1 | 5 | −3 | 206 | 201 | 4 | 2 | −12 | −2 | 43 | 41 | 2 | 6 | −3 | −2 | 67 | 67 | 1 |
| −1 | −10 | −3 | 63 | 65 | 2 | 5 | −2 | −3 | 61 | 60 | 1 | 0 | 5 | −3 | 92 | 91 | 1 | 3 | −12 | −2 | 39 | 37 | 1 | 7 | −3 | −2 | 55 | 55 | 2 |
| 0 | −10 | −3 | 45 | 38 | 2 | 6 | −2 | −3 | 21 | 20 | 1 | 1 | 5 | −3 | 385 | 374 | 4 | −3 | −11 | −2 | 28 | 27 | 2 | −3 | −2 | −2 | 314 | 315 | 6 |
| 1 | −10 | −3 | 28 | 23 | 4 | −3 | −1 | −3 | 121 | 124 | 2 | 3 | 5 | −3 | 205 | 195 | 3 | −2 | −11 | −2 | 85 | 81 | 2 | −2 | −2 | −2 | 399 | 379 | 6 |
| 2 | −10 | −3 | 123 | 119 | 2 | −2 | −1 | −3 | 229 | 233 | 2 | 4 | 5 | −3 | 43 | 39 | 2 | −1 | −11 | −2 | 135 | 133 | 3 | −1 | −2 | −2 | 430 | 439 | 5 |
| 3 | −10 | −3 | 94 | 95 | 2 | −1 | −1 | −3 | 248 | 259 | 3 | 5 | 5 | −3 | 161 | 157 | 3 | 0 | −11 | −2 | 56 | 53 | 2 | 0 | −2 | −2 | 168 | 169 | 2 |
| 4 | −10 | −3 | 22 | 22 | 2 | 0 | −1 | −3 | 538 | 566 | 5 | −6 | 6 | −3 | 44 | 42 | 2 | 1 | −11 | −2 | 57 | 56 | 3 | 1 | −2 | −2 | 624 | 638 | 5 |
| −4 | −9 | −3 | 83 | 80 | 2 | 1 | −1 | −3 | 385 | 400 | 3 | −5 | 6 | −3 | 32 | 37 | 2 | 2 | −11 | −2 | 50 | 48 | 1 | 2 | −2 | −2 | 291 | 284 | 2 |
| −3 | −9 | −3 | 58 | 59 | 2 | 2 | −1 | −3 | 259 | 257 | 2 | −4 | 6 | −3 | 186 | 186 | 3 | 3 | −11 | −2 | 67 | 66 | 1 | 3 | −2 | −2 | 143 | 142 | 1 |
| −2 | −9 | −3 | 82 | 83 | 2 | 3 | −1 | −3 | 366 | 349 | 4 | −3 | 6 | −3 | 80 | 78 | 1 | 4 | −11 | −2 | 27 | 26 | 2 | 4 | −2 | −2 | 95 | 96 | 1 |
| −1 | −9 | −3 | 89 | 116 | 2 | 4 | −1 | −3 | 47 | 52 | 1 | −2 | 6 | −3 | 48 | 50 | 1 | −4 | −10 | −2 | 98 | 102 | 2 | 5 | −2 | −2 | 188 | 185 | 1 |
| 0 | −9 | −3 | 50 | 48 | 2 | 5 | −1 | −3 | 35 | 33 | 1 | −1 | 6 | −3 | 391 | 391 | 5 | −3 | −10 | −2 | 79 | 83 | 2 | 6 | −2 | −2 | 17 | 17 | 1 |
| 1 | −9 | −3 | 74 | 77 | 1 | 6 | −1 | −3 | 141 | 144 | 1 | 0 | 6 | −3 | 176 | 170 | 2 | −2 | −10 | −2 | 59 | 59 | 2 | 7 | −2 | −2 | 20 | 18 | 3 |
| 2 | −9 | −3 | 96 | 101 | 2 | 7 | −1 | −3 | 42 | 40 | 1 | 1 | 6 | −3 | 315 | 315 | 3 | −1 | −10 | −2 | 54 | 63 | 2 | −3 | −1 | −2 | 158 | 165 | 4 |
| 3 | −9 | −3 | 67 | 66 | 1 | −7 | 0 | 3 | 17 | 22 | 4 | 2 | 6 | −3 | 160 | 156 | 1 | 0 | −10 | −2 | 12 | 12 | 6 | −2 | −1 | −2 | 288 | 287 | 4 |
| 4 | −9 | −3 | 38 | 37 | 1 | −6 | 0 | −3 | 16 | 7 | 4 | 3 | 6 | −3 | 96 | 104 | 1 | 1 | −10 | −2 | 61 | 62 | 2 | −1 | −1 | −2 | 422 | 425 | 6 |
| 5 | −9 | −3 | 30 | 37 | 1 | −4 | 0 | −3 | 151 | 151 | 3 | 4 | 6 | −3 | 135 | 137 | 3 | 2 | −10 | −2 | 105 | 102 | 2 | 0 | −1 | −2 | 605 | 633 | 7 |
| −5 | −8 | −3 | 28 | 31 | 2 | −3 | 0 | −3 | 179 | 173 | 2 | −6 | 7 | −3 | 13 | 12 | 5 | 3 | −10 | −2 | 91 | 91 | 2 | 1 | −1 | −2 | 474 | 489 | 4 |
| −4 | −8 | −3 | 56 | 54 | 2 | −2 | 0 | −3 | 205 | 208 | 2 | −5 | 7 | −3 | 40 | 43 | 2 | 4 | −10 | −2 | 40 | 40 | 1 | 2 | −1 | −2 | 110 | 105 | 1 |
| −3 | −8 | −3 | 99 | 103 | 2 | −1 | 0 | −3 | 179 | 189 | 2 | −4 | 7 | −3 | 135 | 133 | 2 | 5 | −10 | −2 | 27 | 26 | 3 | 3 | −1 | −2 | 121 | 115 | 1 |
| −2 | −8 | −3 | 76 | 76 | 2 | 0 | 0 | −3 | 181 | 191 | 1 | −3 | 7 | −3 | 128 | 127 | 1 | −4 | −9 | −2 | 75 | 80 | 2 | 4 | −1 | −2 | 147 | 142 | 1 |
| 0 | −8 | −3 | 21 | 14 | 2 | 1 | 0 | −3 | 90 | 91 | 1 | −2 | 7 | −3 | 149 | 152 | 1 | −3 | −9 | −2 | 91 | 96 | 2 | 5 | −1 | −2 | 36 | 34 | 1 |
| 1 | −8 | −3 | 61 | 63 | 1 | 2 | 0 | −3 | 98 | 91 | 1 | −1 | 7 | −3 | 190 | 193 | 2 | −1 | −9 | −2 | 149 | 155 | 4 | 6 | −1 | −2 | 98 | 102 | 1 |
| 2 | −8 | −3 | 96 | 96 | 1 | 3 | 0 | −3 | 229 | 225 | 2 | 0 | 7 | −3 | 214 | 209 | 2 | 1 | −9 | −2 | 172 | 178 | 2 | 7 | −1 | −2 | 14 | 9 | 2 |
| 3 | −8 | −3 | 42 | 50 | 1 | 4 | 0 | −3 | 209 | 208 | 2 | 1 | 7 | −3 | 183 | 192 | 1 | 2 | −9 | −2 | 61 | 60 | 2 | −3 | 0 | −2 | 327 | 320 | 5 |
| 4 | −8 | −3 | 151 | 183 | 3 | 5 | 0 | −3 | 113 | 113 | 1 | 2 | 7 | −3 | 80 | 70 | 1 | 3 | −9 | −2 | 189 | 193 | 3 | −2 | 0 | −2 | 194 | 195 | 2 |
| 5 | −8 | −3 | 63 | 62 | 1 | 6 | 0 | −3 | 180 | 178 | 1 | 3 | 7 | −3 | 68 | 63 | 1 | 4 | −9 | −2 | 63 | 62 | 1 | −1 | 0 | −2 | 283 | 295 | 4 |
| −5 | −7 | −3 | 22 | 21 | 3 | 7 | 0 | −3 | 113 | 111 | 1 | −5 | 8 | −3 | 38 | 33 | 2 | 5 | −9 | −2 | 9 | 10 | 5 | 0 | 0 | −2 | 448 | 469 | 4 |
| −4 | −7 | −3 | 43 | 40 | 2 | −7 | 1 | −3 | 58 | 58 | 2 | −4 | 8 | −3 | 39 | 39 | 2 | −4 | −8 | −2 | 67 | 72 | 2 | 1 | 0 | −2 | 255 | 264 | 2 |
| −3 | −7 | −3 | 133 | 135 | 3 | −6 | 1 | −3 | 108 | 101 | 2 | −3 | 8 | −3 | 139 | 141 | 1 | −3 | −8 | −2 | 41 | 47 | 2 | 2 | 0 | −2 | 197 | 198 | 2 |
| −1 | −7 | −3 | 153 | 152 | 2 | −5 | 1 | −3 | 138 | 128 | 3 | −2 | 8 | −3 | 195 | 197 | 2 | −2 | −8 | −2 | 84 | 84 | 1 | 3 | 0 | −2 | 53 | 62 | 1 |

TABLE 7-continued

Observed and calculated structure factors for NEL

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 1 | −7 | −3 | 136 | 138 | 1 | −4 | 1 | −3 | 167 | 166 | 2 | −1 | 8 | −3 | 76 | 80 | 1 | −1 | −8 | −2 | 184 | 182 | 3 | 4 | 0 | −2 | 200 | 199 | 2 |
| 2 | −7 | −3 | 145 | 144 | 1 | −3 | 1 | −3 | 119 | 108 | 2 | 0 | 8 | −3 | 141 | 129 | 1 | 0 | −8 | −2 | 57 | 56 | 1 | 5 | 0 | −2 | 126 | 125 | 1 |
| 3 | −7 | −3 | 79 | 82 | 1 | −2 | 1 | −3 | 136 | 140 | 1 | 1 | 8 | −3 | 52 | 54 | 1 | 1 | −8 | −2 | 23 | 23 | 1 | 6 | 0 | −2 | 49 | 48 | 1 |
| 4 | −7 | −3 | 127 | 146 | 2 | −1 | 1 | −3 | 156 | 169 | 2 | 2 | 8 | −3 | 84 | 79 | 1 | 2 | −8 | −2 | 123 | 120 | 1 | 7 | 0 | −2 | 39 | 35 | 1 |
| 5 | −7 | −3 | 42 | 47 | 1 | 0 | 1 | −3 | 193 | 195 | 1 | 3 | 8 | −3 | 168 | 165 | 1 | 3 | −8 | −2 | 78 | 79 | 1 | −7 | 1 | −2 | 33 | 37 | 2 |
| 6 | −7 | −3 | 58 | 59 | 1 | 1 | 1 | −3 | 93 | 95 | 1 | 4 | 8 | −3 | 86 | 92 | 1 | 4 | −8 | −2 | 65 | 72 | 1 | −6 | 1 | −2 | 65 | 62 | 2 |
| −4 | −6 | −3 | 178 | 174 | 4 | 2 | 1 | −3 | 131 | 133 | 1 | −5 | 9 | −3 | 72 | 73 | 2 | 5 | −8 | −2 | 102 | 102 | 1 | −5 | 1 | −2 | 41 | 42 | 2 |
| −3 | −6 | −3 | 162 | 164 | 2 | 4 | 1 | −3 | 229 | 226 | 2 | −4 | 9 | −3 | 67 | 71 | 2 | 6 | −8 | −2 | 78 | 77 | 2 | −4 | 1 | −2 | 149 | 149 | 3 |
| −2 | −6 | −3 | 200 | 196 | 3 | 5 | 1 | −3 | 98 | 97 | 1 | −3 | 9 | −3 | 145 | 145 | 3 | −4 | −7 | −2 | 103 | 105 | 2 | −3 | 1 | −2 | 179 | 168 | 2 |
| −1 | −6 | −3 | 163 | 164 | 2 | 6 | 1 | −3 | 135 | 136 | 1 | −2 | 9 | −3 | 101 | 100 | 1 | −2 | −7 | −2 | 119 | 122 | 2 | −2 | 1 | −2 | 97 | 101 | 1 |
| 0 | −6 | −3 | 174 | 169 | 1 | 7 | 1 | −3 | 56 | 51 | 1 | −1 | 9 | −3 | 120 | 113 | 1 | −1 | −7 | −2 | 91 | 88 | 1 | −1 | 1 | −2 | 299 | 306 | 4 |
| 1 | −6 | −3 | 111 | 114 | 1 | −7 | 2 | −3 | 68 | 70 | 2 | 0 | 9 | −3 | 255 | 256 | 2 | 0 | −7 | −2 | 92 | 92 | 1 | 0 | 1 | −2 | 381 | 397 | 3 |
| 2 | −6 | −3 | 83 | 81 | 1 | −6 | 2 | −3 | 135 | 129 | 3 | 1 | 9 | −3 | 46 | 43 | 1 | 1 | −7 | −2 | 91 | 86 | 1 | 1 | 1 | −2 | 226 | 235 | 2 |
| 3 | −6 | −3 | 69 | 71 | 1 | −5 | 2 | −3 | 154 | 154 | 2 | 2 | 9 | −3 | 74 | 74 | 1 | 2 | −7 | −2 | 29 | 27 | 1 | 2 | 1 | −2 | 361 | 374 | 8 |
| 4 | −6 | −3 | 41 | 46 | 1 | −4 | 2 | −3 | 49 | 51 | 1 | 3 | 9 | −3 | 42 | 41 | 1 | 3 | −7 | −2 | 107 | 113 | 1 | 3 | 1 | −2 | 69 | 65 | 2 |
| 5 | −6 | −3 | 74 | 79 | 1 | −3 | 2 | −3 | 4 | 4 | 4 | 4 | 9 | −3 | 75 | 74 | 1 | 4 | −7 | −2 | 45 | 48 | 1 | 4 | 1 | −2 | 180 | 184 | 1 |
| 6 | −6 | −3 | 56 | 55 | 1 | −2 | 2 | −3 | 160 | 156 | 2 | 5 | 9 | −3 | 35 | 36 | 1 | 5 | −7 | −2 | 78 | 75 | 1 | 5 | 1 | −2 | 172 | 172 | 2 |
| −3 | −5 | −3 | 61 | 60 | 1 | −1 | 2 | −3 | 458 | 468 | 6 | −3 | 10 | −3 | 61 | 64 | 2 | 6 | −7 | −2 | 39 | 39 | 1 | 6 | 1 | −2 | 37 | 33 | 1 |
| −2 | −5 | −3 | 230 | 233 | 3 | 0 | 2 | −3 | 143 | 147 | 1 | −2 | 10 | −3 | 218 | 213 | 3 | −3 | −6 | −2 | 143 | 146 | 3 | 7 | 1 | −2 | 64 | 64 | 1 |
| −1 | −5 | −3 | 115 | 118 | 1 | 1 | 2 | −3 | 177 | 183 | 1 | −1 | 10 | −3 | 139 | 142 | 1 | −2 | −6 | −2 | 133 | 131 | 2 | −7 | 2 | −2 | 25 | 28 | 3 |
| 0 | −5 | −3 | 251 | 244 | 3 | 3 | 2 | −3 | 133 | 128 | 3 | 0 | 10 | −3 | 29 | 30 | 1 | −1 | −6 | −2 | 19 | 19 | 1 | −6 | 2 | −2 | 120 | 119 | 3 |
| 1 | −5 | −3 | 206 | 202 | 2 | 4 | 2 | −3 | 158 | 159 | 2 | 1 | 10 | −3 | 230 | 240 | 2 | 0 | −6 | −2 | 129 | 131 | 1 | −5 | 2 | −2 | 109 | 99 | 2 |
| 2 | −5 | −3 | 231 | 236 | 2 | 5 | 2 | −3 | 233 | 227 | 3 | 2 | 10 | −3 | 140 | 138 | 2 | 1 | −6 | −2 | 75 | 74 | 1 | −4 | 2 | −2 | 53 | 50 | 1 |
| −3 | 2 | −2 | 115 | 119 | 2 | −4 | 9 | −2 | 32 | 35 | 2 | −1 | −7 | −1 | 61 | 62 | 1 | 4 | 1 | −1 | 94 | 96 | 1 | −5 | 8 | −1 | 55 | 54 | 2 |
| −2 | 2 | −2 | 228 | 229 | 3 | −3 | 9 | −2 | 65 | 64 | 1 | 0 | −7 | −1 | 83 | 86 | 1 | 5 | 1 | −1 | 177 | 182 | 2 | −4 | 8 | −1 | 121 | 116 | 3 |
| −1 | 2 | −2 | 436 | 445 | 6 | −2 | 9 | −2 | 74 | 75 | 1 | 1 | −7 | −1 | 99 | 100 | 1 | 6 | 1 | −1 | 76 | 79 | 1 | −3 | 8 | −1 | 80 | 77 | 1 |
| 0 | 2 | −2 | 578 | 596 | 5 | −1 | 9 | −2 | 133 | 129 | 1 | 2 | −7 | −1 | 109 | 109 | 1 | 7 | 1 | −1 | 49 | 44 | 1 | −2 | 8 | −1 | 61 | 62 | 1 |
| 1 | 2 | −2 | 378 | 390 | 3 | 0 | 9 | −2 | 29 | 32 | 1 | 3 | −7 | −1 | 132 | 134 | 1 | −7 | 2 | −1 | 94 | 93 | 2 | −1 | 8 | −1 | 150 | 149 | 1 |
| 2 | 2 | −2 | 191 | 219 | 4 | 1 | 9 | −2 | 147 | 145 | 1 | 4 | −7 | −1 | 130 | 136 | 1 | −6 | 2 | −1 | 43 | 40 | 2 | 0 | 8 | −1 | 108 | 109 | 1 |
| 3 | 2 | −2 | 163 | 164 | 4 | 2 | 9 | −2 | 53 | 52 | 1 | 5 | −7 | −1 | 12 | 13 | 3 | −5 | 2 | −1 | 218 | 218 | 5 | 1 | 8 | −1 | 70 | 73 | 1 |
| 4 | 2 | −2 | 136 | 132 | 1 | 3 | 9 | −2 | 80 | 77 | 1 | 6 | −7 | −1 | 54 | 55 | 1 | −4 | 2 | −1 | 69 | 71 | 1 | 2 | 8 | −1 | 150 | 149 | 1 |
| 5 | 2 | −2 | 32 | 36 | 2 | 4 | 9 | −2 | 14 | 9 | 2 | −2 | −6 | −1 | 133 | 142 | 3 | −3 | 2 | −1 | 237 | 242 | 5 | 3 | 8 | −1 | 91 | 95 | 1 |
| 6 | 2 | −2 | 49 | 56 | 2 | 5 | 9 | −2 | 80 | 79 | 1 | −1 | −6 | −1 | 70 | 66 | 2 | −2 | 2 | −1 | 222 | 217 | 2 | 4 | 8 | −1 | 126 | 116 | 1 |
| 7 | 2 | −2 | 18 | 13 | 1 | −3 | 10 | −2 | 65 | 59 | 2 | 0 | −6 | −1 | 64 | 62 | 1 | −1 | 2 | −1 | 665 | 679 | 7 | 5 | 8 | −1 | 45 | 40 | 1 |
| −7 | 3 | −2 | 62 | 59 | 2 | −2 | 10 | −2 | 182 | 182 | 3 | 1 | −6 | −1 | 180 | 175 | 2 | 0 | 2 | −1 | 273 | 281 | 2 | −5 | 9 | −1 | 0 | 8 | 1 |
| −6 | 3 | −2 | 31 | 30 | 2 | −1 | 10 | −2 | 88 | 89 | 1 | 2 | −6 | −1 | 55 | 51 | 1 | 1 | 2 | −1 | 600 | 624 | 5 | −4 | 9 | −1 | 51 | 50 | 2 |
| −5 | 3 | −2 | 26 | 23 | 2 | 0 | 10 | −2 | 24 | 28 | 1 | 3 | −6 | −1 | 162 | 158 | 1 | 2 | 2 | −1 | 213 | 253 | 5 | −3 | 9 | −1 | 46 | 47 | 2 |
| −4 | 3 | −2 | 154 | 155 | 2 | 1 | 10 | −2 | 58 | 60 | 1 | 4 | −6 | −1 | 117 | 111 | 1 | 3 | 2 | −1 | 913 | 392 | 9 | −2 | 9 | −1 | 98 | 96 | 1 |
| −3 | 3 | −2 | 111 | 110 | 2 | 2 | 10 | −2 | 96 | 97 | 1 | 5 | −6 | −1 | 21 | 23 | 1 | 4 | 2 | −1 | 133 | 137 | 1 | −1 | 9 | −1 | 13 | 8 | 2 |
| −2 | 3 | −2 | 182 | 183 | 2 | 3 | 10 | −2 | 98 | 95 | 1 | 6 | −6 | −1 | 77 | 71 | 1 | 5 | 2 | −1 | 197 | 189 | 4 | 0 | 9 | −1 | 149 | 147 | 1 |
| −1 | 3 | −2 | 77 | 75 | 1 | 4 | 10 | −2 | 32 | 33 | 1 | −2 | −5 | −1 | 153 | 147 | 2 | 6 | 2 | −1 | 19 | 19 | 1 | 1 | 9 | −1 | 123 | 117 | 1 |
| 0 | 3 | −2 | 68 | 70 | 1 | 5 | 10 | −2 | 61 | 55 | 1 | −1 | −5 | −1 | 131 | 137 | 2 | 7 | 2 | −1 | 37 | 27 | 1 | 2 | 9 | −1 | 188 | 192 | 1 |
| 1 | 3 | −2 | 293 | 307 | 2 | −3 | 11 | −2 | 92 | 90 | 2 | 0 | −5 | −1 | 160 | 162 | 2 | −7 | 3 | −1 | 57 | 54 | 2 | 3 | 9 | −1 | 127 | 125 | 1 |
| 3 | 3 | −2 | 194 | 193 | 4 | −2 | 11 | −2 | 111 | 112 | 2 | 1 | −5 | −1 | 76 | 77 | 1 | −6 | 3 | −1 | 62 | 63 | 2 | 4 | 9 | −1 | 42 | 45 | 1 |
| 4 | 3 | −2 | 46 | 50 | 1 | −1 | 11 | −2 | 158 | 163 | 2 | 2 | −5 | −1 | 164 | 157 | 2 | −5 | 3 | −1 | 277 | 279 | 4 | 5 | 9 | −1 | 70 | 65 | 1 |
| 5 | 3 | −2 | 53 | 55 | 2 | 0 | 11 | −2 | 105 | 103 | 2 | 3 | −5 | −1 | 189 | 173 | 2 | −4 | 3 | −1 | 76 | 71 | 1 | −3 | 10 | −1 | 41 | 46 | 3 |
| 6 | 3 | −2 | 52 | 45 | 2 | 1 | 11 | −2 | 107 | 109 | 1 | 4 | −5 | −1 | 127 | 123 | 1 | −3 | 3 | −1 | 221 | 210 | 4 | −2 | 10 | −1 | 44 | 38 | 1 |
| −7 | 4 | −2 | 30 | 26 | 2 | 2 | 11 | −2 | 104 | 104 | 2 | 5 | −5 | −1 | 35 | 32 | 1 | −2 | 3 | −1 | 377 | 386 | 4 | −1 | 10 | −1 | 88 | 91 | 1 |
| −6 | 4 | −2 | 130 | 127 | 3 | 3 | 11 | −2 | 75 | 75 | 2 | 6 | −5 | −1 | 134 | 133 | 2 | −1 | 3 | −1 | 145 | 148 | 1 | 0 | 10 | −1 | 20 | 19 | 1 |

TABLE 7-continued

| Observed and calculated structure factors for NEL | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
| −5 | 4 | −2 | 111 | 116 | 2 | −3 | 12 | −2 | 69 | 65 | 2 | −3 | −4 | −1 | 25 | 31 | 2 | 0 | 3 | −1 | 292 | 296 | 2 | 1 | 10 | −1 | 117 | 121 | 1 |
| −4 | 4 | −2 | 195 | 194 | 3 | −2 | 12 | −2 | 102 | 105 | 2 | −2 | −4 | −1 | 213 | 190 | 3 | 1 | 3 | −1 | 296 | 295 | 2 | 2 | 10 | −1 | 100 | 94 | 1 |
| −3 | 4 | −2 | 147 | 150 | 2 | −1 | 12 | −2 | 43 | 40 | 1 | −1 | −4 | −1 | 155 | 152 | 2 | 2 | 3 | −1 | 188 | 198 | 4 | 3 | 10 | −1 | 91 | 90 | 2 |
| −2 | 4 | −2 | 320 | 304 | 6 | 0 | 12 | −2 | 80 | 81 | 1 | 0 | −4 | −1 | 341 | 354 | 5 | 3 | 3 | −1 | 497 | 472 | 11 | 4 | 10 | −1 | 18 | 10 | 2 |
| −1 | 4 | −2 | 55 | 52 | 1 | 1 | 12 | −2 | 39 | 34 | 1 | 1 | −4 | −1 | 31 | 32 | 1 | 4 | 3 | −1 | 65 | 66 | 1 | −3 | 11 | −1 | 95 | 98 | 3 |
| 0 | 4 | −2 | 208 | 208 | 1 | 2 | 12 | −2 | 93 | 96 | 1 | 2 | −4 | −1 | 476 | 461 | 5 | 5 | 3 | −1 | 117 | 116 | 2 | −2 | 11 | −1 | 59 | 59 | 1 |
| 1 | 4 | −2 | 181 | 186 | 2 | 3 | 12 | −2 | 23 | 25 | 2 | 3 | −4 | −1 | 150 | 148 | 1 | 6 | 3 | −1 | 28 | 27 | 2 | −1 | 11 | −1 | 57 | 60 | 1 |
| 3 | 4 | −2 | 210 | 212 | 3 | −3 | 13 | −2 | 53 | 54 | 2 | 4 | −4 | −1 | 57 | 57 | 1 | 7 | 3 | −1 | 62 | 61 | 2 | 0 | 11 | −1 | 35 | 36 | 1 |
| 4 | 4 | −2 | 33 | 30 | 1 | −2 | 13 | −2 | 72 | 73 | 1 | 5 | −4 | −1 | 179 | 179 | 1 | −7 | 4 | −1 | 26 | 30 | 2 | 1 | 11 | −1 | 65 | 68 | 1 |
| 5 | 4 | −2 | 90 | 85 | 2 | −1 | 13 | −2 | 38 | 42 | 1 | 6 | −4 | −1 | 87 | 81 | 2 | −6 | 4 | −1 | 37 | 34 | 2 | 2 | 11 | −1 | 90 | 89 | 1 |
| 6 | 4 | −2 | 199 | 197 | 4 | 0 | 13 | −2 | 67 | 64 | 1 | −3 | −3 | −1 | 338 | 340 | 7 | −5 | 4 | −1 | 145 | 147 | 2 | 3 | 11 | −1 | 75 | 77 | 2 |
| −7 | 5 | −2 | 25 | 28 | 2 | 1 | 13 | −2 | 14 | 14 | 1 | −2 | −3 | −1 | 72 | 72 | 1 | −4 | 4 | −1 | 140 | 142 | 2 | −3 | 12 | −1 | 55 | 52 | 2 |
| −6 | 5 | −2 | 118 | 116 | 3 | 2 | 13 | −2 | 96 | 97 | 2 | −1 | −3 | −1 | 421 | 421 | 5 | −3 | 4 | −1 | 213 | 211 | 3 | −2 | 12 | −1 | 56 | 59 | 1 |
| −5 | 5 | −2 | 86 | 98 | 2 | −1 | 14 | −2 | 28 | 30 | 1 | 0 | −3 | −1 | 376 | 382 | 4 | −2 | 4 | −1 | 226 | 220 | 4 | −1 | 12 | −1 | 82 | 84 | 1 |
| −4 | 5 | −2 | 49 | 50 | 1 | 0 | 14 | −2 | 44 | 45 | 1 | 1 | −3 | −1 | 398 | 401 | 3 | −1 | 4 | −1 | 58 | 58 | 1 | 0 | 12 | −1 | 43 | 45 | 1 |
| −3 | 5 | −2 | 103 | 97 | 1 | 1 | 14 | −2 | 82 | 83 | 2 | 2 | −3 | −1 | 63 | 56 | 1 | 0 | 4 | −1 | 462 | 464 | 4 | 1 | 12 | −1 | 53 | 54 | 1 |
| −2 | 5 | −2 | 65 | 61 | 1 | −1 | −13 | −1 | 42 | 42 | 2 | 3 | −3 | −1 | 339 | 317 | 4 | 1 | 4 | −1 | 152 | 147 | 1 | 2 | 12 | −1 | 80 | 78 | 2 |
| −1 | 5 | −2 | 350 | 355 | 7 | 0 | −13 | −1 | 101 | 101 | 3 | 4 | −3 | −1 | 118 | 118 | 1 | 2 | 4 | −1 | 160 | 146 | 2 | 3 | 12 | −1 | 34 | 35 | 2 |
| 0 | 5 | −2 | 106 | 113 | 1 | 1 | −13 | −1 | 64 | 64 | 2 | 5 | −3 | −1 | 130 | 132 | 1 | 3 | 4 | −1 | 81 | 77 | 2 | −3 | 13 | −1 | 51 | 51 | 2 |
| 1 | 5 | −2 | 227 | 219 | 2 | −3 | −12 | −1 | 34 | 37 | 2 | 6 | −3 | −1 | 70 | 74 | 1 | 4 | 4 | −1 | 58 | 53 | 1 | −2 | 13 | −1 | 23 | 20 | 2 |
| 2 | 5 | −2 | 321 | 322 | 5 | −2 | −12 | −1 | 89 | 88 | 2 | −3 | −2 | −1 | 272 | 260 | 5 | 5 | 4 | −1 | 200 | 201 | 4 | −1 | 13 | −1 | 51 | 51 | 1 |
| 3 | 5 | −2 | 211 | 206 | 3 | −1 | −12 | −1 | 48 | 46 | 2 | −2 | −2 | −1 | 123 | 120 | 2 | 6 | 4 | −1 | 18 | 16 | 4 | 0 | 13 | −1 | 35 | 35 | 1 |
| 4 | 5 | −2 | 109 | 107 | 2 | 0 | −12 | −1 | 32 | 29 | 2 | −1 | −2 | −1 | 659 | 682 | 10 | −7 | 5 | −1 | 10 | 10 | 9 | 1 | 13 | −1 | 86 | 83 | 1 |
| 5 | 5 | −2 | 25 | 27 | 2 | 1 | −12 | −1 | 132 | 130 | 3 | 0 | −2 | −1 | 808 | 843 | 10 | −6 | 5 | −1 | 94 | 96 | 2 | 2 | 13 | −1 | 167 | 170 | 4 |
| 6 | 5 | −2 | 122 | 113 | 2 | 2 | −12 | −1 | 164 | 162 | 3 | 1 | −2 | −1 | 784 | 818 | 6 | −5 | 5 | −1 | 127 | 132 | 3 | 0 | 14 | −1 | 12 | 10 | 2 |
| −6 | 6 | −2 | 34 | 33 | 2 | 3 | −12 | −1 | 42 | 45 | 1 | 2 | −2 | −1 | 412 | 405 | 3 | −4 | 5 | −1 | 37 | 37 | 1 | −2 | −13 | 0 | 83 | 79 | 2 |
| −5 | 6 | −2 | 73 | 82 | 2 | −3 | −11 | −1 | 46 | 45 | 2 | 3 | −2 | −1 | 380 | 360 | 4 | −3 | 5 | −1 | 287 | 275 | 4 | −1 | −13 | 0 | 138 | 143 | 3 |
| −4 | 6 | −2 | 147 | 148 | 2 | −2 | −11 | −1 | 128 | 130 | 3 | 4 | −2 | −1 | 133 | 130 | 1 | −2 | 5 | −1 | 39 | 45 | 1 | 0 | −13 | 0 | 77 | 75 | 1 |
| −3 | 6 | −2 | 152 | 151 | 2 | −1 | −11 | −1 | 73 | 78 | 2 | 5 | −2 | −1 | 117 | 112 | 1 | −1 | 5 | −1 | 137 | 134 | 2 | 1 | −13 | 0 | 109 | 110 | 3 |
| −2 | 6 | −2 | 105 | 93 | 1 | 0 | −11 | −1 | 74 | 72 | 2 | 6 | −2 | −1 | 72 | 72 | 1 | 0 | 5 | −1 | 130 | 138 | 1 | 2 | −13 | 0 | 105 | 103 | 3 |
| −1 | 6 | −2 | 338 | 327 | 5 | 2 | −11 | −1 | 152 | 153 | 2 | 7 | −2 | −1 | 7 | 12 | 6 | 1 | 5 | −1 | 178 | 179 | 1 | −3 | −12 | 0 | 29 | 25 | 2 |
| 0 | 6 | −2 | 232 | 232 | 2 | 3 | −11 | −1 | 114 | 113 | 2 | −3 | −1 | −1 | 151 | 147 | 3 | 2 | 5 | −1 | 152 | 141 | 1 | −2 | −12 | 0 | 47 | 42 | 2 |
| 1 | 6 | −2 | 97 | 96 | 1 | 4 | −11 | −1 | 11 | 9 | 5 | −2 | −1 | −1 | 121 | 114 | 2 | 3 | 5 | −1 | 211 | 205 | 2 | −1 | −12 | 0 | 255 | 240 | 6 |
| 2 | 6 | −2 | 265 | 270 | 2 | −4 | −10 | −1 | 73 | 77 | 2 | −1 | −1 | −1 | 608 | 629 | 12 | 4 | 5 | −1 | 97 | 98 | 2 | 0 | −12 | 0 | 64 | 64 | 2 |
| 3 | 6 | −2 | 120 | 115 | 1 | −3 | −10 | −1 | 6 | 8 | 6 | 0 | −1 | −1 | 146 | 147 | 2 | 5 | 5 | −1 | 36 | 26 | 2 | 1 | −12 | 0 | 100 | 97 | 3 |
| 4 | 6 | −2 | 98 | 91 | 2 | 1 | −10 | −1 | 35 | 35 | 2 | 1 | −1 | −1 | 821 | 845 | 7 | 6 | 5 | −1 | 68 | 68 | 2 | 2 | −12 | 0 | 121 | 121 | 2 |
| 5 | 6 | −2 | 63 | 63 | 2 | 2 | −10 | −1 | 57 | 51 | 1 | 2 | −1 | −1 | 215 | 215 | 1 | −6 | 6 | −1 | 70 | 72 | 2 | 3 | −12 | 0 | 36 | 37 | 1 |
| −6 | 7 | −2 | 23 | 18 | 3 | 3 | −10 | −1 | 21 | 22 | 2 | 3 | −1 | −1 | 426 | 407 | 4 | −5 | 6 | −1 | 62 | 67 | 2 | −4 | −11 | 0 | 44 | 44 | 2 |
| −5 | 7 | −2 | 48 | 52 | 2 | 4 | −10 | −1 | 42 | 43 | 2 | 4 | −1 | −1 | 48 | 51 | 1 | −4 | 6 | −1 | 72 | 72 | 1 | −3 | −11 | 0 | 34 | 31 | 2 |
| −4 | 7 | −2 | 135 | 142 | 2 | 5 | −10 | −1 | 28 | 34 | 2 | 5 | −1 | −1 | 195 | 195 | 1 | −3 | 6 | −1 | 174 | 160 | 2 | 1 | −11 | 0 | 74 | 74 | 2 |
| −3 | 7 | −2 | 81 | 79 | 1 | −4 | −9 | −1 | 79 | 85 | 2 | 6 | −1 | −1 | 63 | 65 | 1 | −2 | 6 | −1 | 230 | 224 | 3 | 2 | −11 | 0 | 77 | 81 | 2 |
| −2 | 7 | −2 | 117 | 116 | 1 | −2 | −9 | −1 | 124 | 122 | 3 | 7 | −1 | −1 | 11 | 3 | 3 | −1 | 6 | −1 | 177 | 175 | 2 | 3 | −11 | 0 | 95 | 93 | 2 |
| −1 | 7 | −2 | 138 | 141 | 1 | −1 | −9 | −1 | 79 | 77 | 1 | −3 | 0 | −1 | 90 | 92 | 1 | 0 | 6 | −1 | 95 | 88 | 1 | 4 | −11 | 0 | 21 | 22 | 2 |
| 0 | 7 | −2 | 155 | 152 | 1 | 0 | −9 | −1 | 146 | 151 | 2 | −1 | 0 | −1 | 120 | 127 | 2 | 1 | 6 | −1 | 26 | 25 | 1 | −4 | −10 | 0 | 19 | 17 | 3 |
| 1 | 7 | −2 | 49 | 53 | 1 | 1 | −9 | −1 | 42 | 35 | 2 | 0 | 0 | −1 | 76 | 82 | 1 | 2 | 6 | −1 | 86 | 81 | 1 | −2 | −10 | 0 | 57 | 56 | 2 |
| 2 | 7 | −2 | 90 | 96 | 1 | 2 | −9 | −1 | 178 | 178 | 2 | 1 | 0 | −1 | 53 | 54 | 1 | 3 | 6 | −1 | 52 | 48 | 1 | 0 | −10 | 0 | 76 | 77 | 2 |
| 3 | 7 | −2 | 221 | 221 | 2 | 3 | −9 | −1 | 28 | 32 | 2 | 2 | 0 | −1 | 406 | 401 | 3 | 4 | 6 | −1 | 115 | 97 | 1 | 1 | −10 | 0 | 241 | 243 | 5 |
| 4 | 7 | −2 | 12 | 12 | 6 | 4 | −9 | −1 | 129 | 136 | 2 | 3 | 0 | −1 | 101 | 98 | 1 | 5 | 6 | −1 | 88 | 91 | 2 | 2 | −10 | 0 | 104 | 102 | 3 |
| −6 | 8 | −2 | 20 | 20 | 3 | 5 | −9 | −1 | 98 | 97 | 1 | 4 | 0 | −1 | 219 | 221 | 2 | −6 | 7 | −1 | 58 | 52 | 2 | 3 | −10 | 0 | 94 | 93 | 2 |

TABLE 7-continued

Observed and calculated structure factors for NEL

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −5 | 8 | −2 | 34 | 34 | 2 | −3 | −8 | −1 | 65 | 67 | 2 | 5 | 0 | −1 | 136 | 137 | 1 | −5 | 7 | −1 | 34 | 40 | 2 | 4 | −10 | 0 | 92 | 88 | 2 |
| −4 | 8 | −2 | 86 | 87 | 2 | −2 | −8 | −1 | 182 | 181 | 3 | 6 | 0 | −1 | 38 | 32 | 1 | −4 | 7 | −1 | 114 | 117 | 2 | 5 | −10 | 0 | 24 | 24 | 1 |
| −3 | 8 | −2 | 167 | 167 | 2 | −1 | −8 | −1 | 140 | 141 | 2 | 7 | 0 | −1 | 20 | 21 | 1 | −3 | 7 | −1 | 176 | 173 | 3 | −3 | −9 | 0 | 69 | 70 | 2 |
| −2 | 8 | −2 | 84 | 84 | 1 | 0 | −8 | −1 | 53 | 53 | 1 | −7 | 1 | −1 | 84 | 79 | 2 | −2 | 7 | −1 | 107 | 102 | 1 | −2 | −9 | 0 | 120 | 114 | 3 |
| −1 | 8 | −2 | 58 | 60 | 1 | 1 | −8 | −1 | 61 | 62 | 1 | −4 | 1 | −1 | 173 | 167 | 4 | −1 | 7 | −1 | 155 | 159 | 1 | −1 | −9 | 0 | 76 | 76 | 2 |
| 0 | 8 | −2 | 39 | 41 | 1 | 2 | −8 | −1 | 131 | 131 | 2 | −3 | 1 | −1 | 127 | 118 | 2 | 0 | 7 | −1 | 139 | 138 | 1 | 0 | −9 | 0 | 97 | 95 | 2 |
| 1 | 8 | −2 | 126 | 123 | 1 | 3 | −8 | −1 | 142 | 143 | 1 | −2 | 1 | −1 | 458 | 459 | 7 | 1 | 7 | −1 | 134 | 136 | 1 | 1 | −9 | 0 | 33 | 35 | 1 |
| 2 | 8 | −2 | 181 | 183 | 1 | 4 | −8 | −1 | 106 | 102 | 2 | −1 | 1 | −1 | 566 | 583 | 8 | 2 | 7 | −1 | 72 | 75 | 1 | 2 | −9 | 0 | 52 | 52 | 2 |
| 3 | 8 | −2 | 25 | 21 | 1 | 5 | −8 | −1 | 86 | 87 | 1 | 0 | 1 | −1 | 368 | 385 | 3 | 3 | 7 | −1 | 226 | 218 | 2 | 3 | −9 | 0 | 45 | 48 | 1 |
| 4 | 8 | −2 | 113 | 114 | 1 | 6 | −8 | −1 | 65 | 65 | 1 | 1 | 1 | −1 | 930 | 924 | 21 | 4 | 7 | −1 | 63 | 65 | 1 | 4 | −9 | 0 | 87 | 92 | 1 |
| 5 | 8 | −2 | 43 | 38 | 1 | −3 | −7 | −1 | 64 | 74 | 2 | 2 | 1 | −1 | 280 | 280 | 6 | 5 | 7 | −1 | 25 | 27 | 4 | 5 | −9 | 0 | 24 | 19 | 1 |
| −5 | 9 | −2 | 29 | 27 | 2 | −2 | −7 | −1 | 91 | 91 | 2 | 3 | 1 | −1 | 227 | 201 | 5 | −6 | 8 | −1 | 35 | 37 | 2 | −3 | −8 | 0 | 126 | 129 | 3 |
| −2 | −8 | 0 | 23 | 24 | 2 | 0 | 1 | 0 | 140 | 148 | 1 | 5 | 7 | 0 | 115 | 114 | 1 | 4 | −9 | 1 | 51 | 50 | 1 | 0 | 1 | 1 | 144 | 147 | 1 |
| −1 | −8 | 0 | 138 | 136 | 3 | 1 | 1 | 0 | 828 | 873 | 7 | 6 | 7 | 0 | 12 | 6 | 3 | 5 | −9 | 1 | 12 | 8 | 3 | 1 | 1 | 1 | 601 | 629 | 5 |
| 0 | −8 | 0 | 47 | 43 | 1 | 2 | 1 | 0 | 225 | 227 | 3 | −6 | 8 | 0 | 64 | 66 | 2 | −2 | −8 | 1 | 148 | 148 | 3 | 2 | 1 | 1 | 125 | 114 | 1 |
| 1 | −8 | 0 | 215 | 216 | 2 | 3 | 1 | 0 | 264 | 260 | 6 | −5 | 8 | 0 | 76 | 75 | 2 | −1 | −8 | 1 | 72 | 74 | 2 | 3 | 1 | 1 | 153 | 146 | 1 |
| 2 | −8 | 0 | 38 | 36 | 1 | 4 | 1 | 0 | 68 | 67 | 1 | −4 | 8 | 0 | 13 | 9 | 8 | 0 | −8 | 1 | 111 | 109 | 2 | 4 | 1 | 1 | 107 | 111 | 1 |
| 3 | −8 | 0 | 61 | 64 | 1 | 5 | 1 | 0 | 104 | 103 | 1 | −3 | 8 | 0 | 61 | 64 | 1 | 1 | −8 | 1 | 150 | 150 | 1 | 5 | 1 | 1 | 183 | 181 | 1 |
| 4 | −8 | 0 | 7 | 9 | 6 | 6 | 1 | 0 | 165 | 171 | 1 | −2 | 8 | 0 | 41 | 36 | 1 | 2 | −8 | 1 | 60 | 62 | 1 | 6 | 1 | 1 | 84 | 81 | 1 |
| 5 | −8 | 0 | 76 | 75 | 1 | 7 | 1 | 0 | 72 | 70 | 1 | −1 | 8 | 0 | 215 | 216 | 2 | 3 | −8 | 1 | 80 | 76 | 1 | 7 | 1 | 1 | 39 | 37 | 1 |
| 6 | −8 | 0 | 66 | 65 | 1 | −7 | 2 | 0 | 66 | 63 | 2 | 0 | 8 | 0 | 47 | 43 | 1 | 4 | −8 | 1 | 120 | 117 | 1 | −7 | 2 | 1 | 16 | 12 | 4 |
| −2 | −7 | 0 | 178 | 176 | 4 | −6 | 2 | 0 | 182 | 183 | 4 | 1 | 8 | 0 | 137 | 137 | 1 | 5 | −8 | 1 | 53 | 54 | 1 | −6 | 2 | 1 | 70 | 72 | 2 |
| −1 | −7 | 0 | 224 | 222 | 5 | −5 | 2 | 0 | 121 | 119 | 3 | 2 | 8 | 0 | 25 | 24 | 1 | 6 | −8 | 1 | 35 | 37 | 1 | −5 | 2 | 1 | 112 | 111 | 3 |
| 0 | −7 | 0 | 71 | 74 | 1 | −4 | 2 | 0 | 142 | 138 | 2 | 3 | 8 | 0 | 130 | 129 | 1 | −2 | −7 | 1 | 71 | 76 | 2 | −4 | 2 | 1 | 130 | 130 | 3 |
| 1 | −7 | 0 | 164 | 168 | 2 | −3 | 2 | 0 | 412 | 403 | 9 | 4 | 8 | 0 | 127 | 125 | 1 | −1 | −7 | 1 | 136 | 136 | 1 | −3 | 2 | 1 | 377 | 360 | 8 |
| 2 | −7 | 0 | 195 | 195 | 2 | −2 | 2 | 0 | 270 | 259 | 3 | 5 | 8 | 0 | 66 | 62 | 1 | 0 | −7 | 1 | 141 | 138 | 1 | −2 | 2 | 1 | 414 | 405 | 5 |
| 3 | −7 | 0 | 125 | 116 | 1 | −1 | 2 | 0 | 243 | 250 | 3 | −5 | 9 | 0 | 22 | 20 | 3 | 1 | −7 | 1 | 157 | 158 | 2 | −1 | 2 | 1 | 795 | 818 | 9 |
| 4 | −7 | 0 | 70 | 70 | 1 | 0 | 2 | 0 | 597 | 604 | 5 | −4 | 9 | 0 | 89 | 92 | 2 | 2 | −7 | 1 | 106 | 102 | 1 | 0 | 2 | 1 | 808 | 842 | 7 |
| 5 | −7 | 0 | 100 | 94 | 1 | 1 | 2 | 0 | 350 | 368 | 3 | −3 | 9 | 0 | 46 | 49 | 2 | 3 | −7 | 1 | 176 | 173 | 1 | 1 | 2 | 1 | 660 | 682 | 5 |
| 6 | −7 | 0 | 73 | 71 | 1 | 3 | 2 | 0 | 142 | 144 | 3 | −2 | 9 | 0 | 54 | 52 | 1 | 4 | −7 | 1 | 112 | 117 | 1 | 2 | 2 | 1 | 127 | 120 | 1 |
| −2 | −6 | 0 | 143 | 137 | 3 | 4 | 2 | 0 | 80 | 76 | 1 | −1 | 9 | 0 | 33 | 35 | 1 | 5 | −7 | 1 | 41 | 40 | 1 | 3 | 2 | 1 | 274 | 259 | 6 |
| −1 | −6 | 0 | 50 | 52 | 1 | 5 | 2 | 0 | 34 | 30 | 1 | 0 | 9 | 0 | 99 | 95 | 1 | 6 | −7 | 1 | 58 | 52 | 1 | 4 | 2 | 1 | 167 | 167 | 2 |
| 0 | −6 | 0 | 65 | 66 | 1 | 6 | 2 | 0 | 76 | 80 | 1 | 1 | 9 | 0 | 77 | 76 | 1 | −2 | −6 | 1 | 88 | 81 | 1 | 5 | 2 | 1 | 132 | 128 | 1 |
| 1 | −6 | 0 | 111 | 108 | 1 | 7 | 2 | 0 | 60 | 59 | 1 | 2 | 9 | 0 | 114 | 113 | 1 | −1 | −6 | 1 | 25 | 25 | 1 | 6 | 2 | 1 | 31 | 31 | 1 |
| 2 | −6 | 0 | 142 | 135 | 1 | −7 | 3 | 0 | 77 | 74 | 2 | 3 | 9 | 0 | 73 | 70 | 2 | 0 | −6 | 1 | 91 | 87 | 1 | 7 | 2 | 1 | 90 | 89 | 1 |
| 3 | −6 | 0 | 69 | 68 | 1 | −6 | 3 | 0 | 171 | 167 | 4 | 4 | 9 | 0 | 108 | 105 | 1 | 1 | −6 | 1 | 175 | 174 | 2 | −7 | 3 | 1 | 67 | 65 | 2 |
| 4 | −6 | 0 | 108 | 106 | 1 | −5 | 3 | 0 | 47 | 48 | 1 | 5 | 9 | 0 | 55 | 58 | 1 | 2 | −6 | 1 | 229 | 224 | 2 | −6 | 3 | 1 | 68 | 74 | 2 |
| 5 | −6 | 0 | 91 | 92 | 1 | −4 | 3 | 0 | 44 | 39 | 1 | −3 | 10 | 0 | 90 | 93 | 2 | 3 | −6 | 1 | 170 | 160 | 1 | −5 | 3 | 1 | 126 | 132 | 2 |
| 6 | −6 | 0 | 138 | 136 | 2 | −3 | 3 | 0 | 229 | 213 | 5 | −2 | 10 | 0 | 107 | 103 | 2 | 4 | −6 | 1 | 74 | 72 | 1 | −4 | 3 | 1 | 116 | 118 | 2 |
| −2 | −5 | 0 | 177 | 166 | 2 | −2 | 3 | 0 | 201 | 196 | 2 | −1 | 10 | 0 | 239 | 243 | 4 | 5 | −6 | 1 | 68 | 67 | 1 | −3 | 3 | 1 | 345 | 318 | 7 |
| −1 | −5 | 0 | 133 | 132 | 1 | −1 | 3 | 0 | 411 | 416 | 5 | 0 | 10 | 0 | 80 | 78 | 1 | 6 | −6 | 1 | 67 | 72 | 1 | −2 | 3 | 1 | 63 | 56 | 1 |
| 0 | −5 | 0 | 26 | 26 | 1 | 0 | 3 | 0 | 882 | 918 | 7 | 1 | 10 | 0 | 134 | 157 | 2 | −2 | −5 | 1 | 149 | 140 | 3 | −1 | 3 | 1 | 394 | 401 | 4 |
| 1 | −5 | 0 | 161 | 165 | 1 | 1 | 3 | 0 | 295 | 292 | 2 | 2 | 10 | 0 | 58 | 56 | 1 | −1 | −5 | 1 | 177 | 179 | 2 | 0 | 3 | 1 | 375 | 381 | 3 |
| 2 | −5 | 0 | 94 | 85 | 1 | 2 | 3 | 0 | 201 | 201 | 2 | 3 | 10 | 0 | 102 | 104 | 2 | 0 | −5 | 1 | 129 | 138 | 2 | 1 | 3 | 1 | 426 | 422 | 3 |
| 3 | −5 | 0 | 191 | 183 | 2 | 3 | 3 | 0 | 108 | 109 | 3 | −3 | 11 | 0 | 95 | 93 | 2 | 1 | −5 | 1 | 134 | 133 | 1 | 2 | 3 | 1 | 73 | 71 | 1 |
| 4 | −5 | 0 | 61 | 55 | 1 | 4 | 3 | 0 | 50 | 48 | 1 | −2 | 11 | 0 | 80 | 80 | 1 | 3 | −5 | 1 | 282 | 276 | 2 | 3 | 3 | 1 | 338 | 340 | 5 |
| 5 | −5 | 0 | 15 | 17 | 2 | 5 | 3 | 0 | 110 | 103 | 2 | −1 | 11 | 0 | 72 | 75 | 1 | 4 | −5 | 1 | 39 | 38 | 1 | 4 | 3 | 1 | 35 | 30 | 1 |
| 6 | −5 | 0 | 100 | 98 | 2 | 6 | 3 | 0 | 43 | 47 | 1 | 0 | 11 | 0 | 166 | 165 | 3 | 5 | −5 | 1 | 131 | 132 | 1 | 5 | 3 | 1 | 146 | 142 | 1 |
| −2 | −4 | 0 | 647 | 625 | 10 | 7 | 3 | 0 | 20 | 19 | 1 | 1 | 11 | 0 | 115 | 119 | 1 | 6 | −5 | 1 | 94 | 95 | 2 | 6 | 3 | 1 | 38 | 31 | 1 |

TABLE 7-continued

Observed and calculated structure factors for NEL

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −1 | −4 | 0 | 121 | 120 | 1 | −7 | 4 | 0 | 52 | 53 | 2 | 2 | 11 | 0 | 73 | 72 | 1 | −2 | −4 | 1 | 160 | 147 | 2 | 7 | 3 | 1 | 105 | 102 | 1 |
| 0 | −4 | 0 | 63 | 66 | 1 | −6 | 4 | 0 | 133 | 131 | 3 | 3 | 11 | 0 | 35 | 32 | 2 | −1 | −4 | 1 | 154 | 147 | 1 | −7 | 4 | 1 | 71 | 73 | 2 |
| 1 | −4 | 0 | 131 | 134 | 1 | −5 | 4 | 0 | 106 | 104 | 2 | −3 | 12 | 0 | 35 | 36 | 2 | 0 | −4 | 1 | 456 | 464 | 5 | −6 | 4 | 1 | 87 | 82 | 2 |
| 2 | −4 | 0 | 348 | 337 | 4 | −4 | 4 | 0 | 27 | 29 | 1 | −2 | 12 | 0 | 121 | 122 | 2 | 1 | −4 | 1 | 57 | 58 | 1 | −5 | 4 | 1 | 175 | 179 | 3 |
| 3 | −4 | 0 | 219 | 217 | 2 | −3 | 4 | 0 | 220 | 216 | 3 | −1 | 12 | 0 | 99 | 98 | 1 | 2 | −4 | 1 | 218 | 219 | 2 | −4 | 4 | 1 | 57 | 57 | 1 |
| 4 | −4 | 0 | 27 | 29 | 1 | −2 | 4 | 0 | 352 | 337 | 7 | 0 | 12 | 0 | 66 | 65 | 1 | 3 | −4 | 1 | 207 | 210 | 2 | −3 | 4 | 1 | 149 | 147 | 2 |
| 5 | −4 | 0 | 105 | 104 | 1 | −1 | 4 | 0 | 130 | 134 | 1 | 1 | 12 | 0 | 247 | 240 | 3 | 4 | −4 | 1 | 140 | 142 | 1 | −2 | 4 | 1 | 477 | 461 | 10 |
| 6 | −4 | 0 | 134 | 130 | 2 | 0 | 4 | 0 | 65 | 67 | 1 | 2 | 12 | 0 | 44 | 41 | 2 | 5 | −4 | 1 | 145 | 147 | 1 | −1 | 4 | 1 | 28 | 32 | 1 |
| −2 | −3 | 0 | 202 | 200 | 3 | 1 | 4 | 0 | 120 | 120 | 1 | 3 | 12 | 0 | 25 | 25 | 2 | 6 | −4 | 1 | 36 | 33 | 1 | 0 | 4 | 1 | 344 | 355 | 2 |
| −1 | −3 | 0 | 292 | 291 | 3 | 2 | 4 | 0 | 658 | 625 | 8 | −2 | 13 | 0 | 105 | 104 | 2 | −2 | −3 | 1 | 199 | 197 | 4 | 1 | 4 | 1 | 156 | 151 | 1 |
| 0 | −3 | 0 | 888 | 919 | 9 | 3 | 4 | 0 | 100 | 94 | 2 | −1 | 13 | 0 | 110 | 109 | 1 | −1 | −3 | 1 | 296 | 296 | 3 | 2 | 4 | 1 | 215 | 191 | 2 |
| 1 | −3 | 0 | 407 | 416 | 3 | 4 | 4 | 0 | 101 | 95 | 2 | 0 | 13 | 0 | 78 | 75 | 1 | 0 | −3 | 1 | 298 | 297 | 4 | 3 | 4 | 1 | 28 | 31 | 1 |
| 2 | −3 | 0 | 206 | 198 | 2 | 5 | 4 | 0 | 38 | 40 | 1 | 1 | 13 | 0 | 138 | 143 | 2 | 1 | −3 | 1 | 142 | 148 | 1 | 4 | 4 | 1 | 146 | 140 | 1 |
| 3 | −3 | 0 | 224 | 213 | 2 | 6 | 4 | 0 | 110 | 116 | 1 | 2 | 13 | 0 | 78 | 79 | 2 | 2 | −3 | 1 | 384 | 387 | 3 | 5 | 4 | 1 | 111 | 119 | 1 |
| 4 | −3 | 0 | 45 | 39 | 1 | −7 | 5 | 0 | 113 | 103 | 3 | 0 | −14 | 1 | 13 | 11 | 8 | 3 | −3 | 1 | 215 | 210 | 2 | 6 | 4 | 1 | 19 | 17 | 1 |
| 5 | −3 | 0 | 45 | 48 | 1 | −6 | 5 | 0 | 96 | 97 | 2 | 1 | −14 | 1 | 57 | 62 | 2 | 4 | −3 | 1 | 77 | 71 | 1 | −7 | 5 | 1 | 67 | 69 | 2 |
| 6 | −3 | 0 | 172 | 167 | 2 | −5 | 5 | 0 | 11 | 18 | 7 | −2 | −13 | 1 | 172 | 170 | 4 | 5 | −3 | 1 | 277 | 280 | 2 | −6 | 5 | 1 | 133 | 133 | 3 |
| 7 | −3 | 0 | 74 | 74 | 2 | −4 | 5 | 0 | 59 | 55 | 1 | −1 | −13 | 1 | 89 | 83 | 2 | 6 | −3 | 1 | 60 | 63 | 1 | −5 | 5 | 1 | 33 | 32 | 2 |
| 0 | −2 | 0 | 599 | 604 | 7 | −3 | 5 | 0 | 195 | 183 | 3 | 0 | −13 | 1 | 36 | 35 | 2 | 7 | −3 | 1 | 58 | 54 | 2 | −4 | 5 | 1 | 126 | 123 | 2 |
| 1 | −2 | 0 | 242 | 250 | 2 | −2 | 5 | 0 | 91 | 84 | 2 | 1 | −13 | 1 | 54 | 51 | 3 | −1 | −2 | 1 | 590 | 624 | 14 | −3 | 5 | 1 | 193 | 173 | 3 |
| 2 | −2 | 0 | 271 | 260 | 2 | −1 | 5 | 0 | 167 | 166 | 2 | 2 | −13 | 1 | 19 | 20 | 5 | 0 | −2 | 1 | −281 | 281 | 3 | −2 | 5 | 1 | 165 | 157 | 2 |
| 3 | −2 | 0 | 413 | 402 | 4 | 0 | 5 | 0 | 26 | 26 | 1 | 3 | −13 | 1 | 48 | 50 | 2 | 1 | −2 | 1 | 642 | 679 | 6 | −1 | 5 | 1 | 77 | 78 | 1 |
| 4 | −2 | 0 | 146 | 138 | 1 | 1 | 5 | 0 | 135 | 133 | 1 | −3 | −12 | 1 | 35 | 35 | 2 | 2 | −2 | 1 | 220 | 217 | 2 | 0 | 5 | 1 | 159 | 161 | 1 |
| 5 | −2 | 0 | 124 | 119 | 1 | 2 | 5 | 0 | 178 | 166 | 2 | −1 | −12 | 1 | 53 | 54 | 2 | 3 | −2 | 1 | 239 | 241 | 2 | 1 | 5 | 1 | 133 | 138 | 1 |
| 6 | −2 | 0 | 185 | 184 | 1 | 3 | 5 | 0 | 90 | 79 | 1 | 2 | −12 | 1 | 57 | 59 | 1 | 4 | −2 | 1 | 69 | 72 | 1 | 2 | 5 | 1 | 153 | 147 | 1 |
| 7 | −2 | 0 | 63 | 63 | 2 | 4 | 5 | 0 | 106 | 107 | 1 | 3 | −12 | 1 | 55 | 53 | 1 | 5 | −2 | 1 | 220 | 218 | 2 | 3 | 5 | 1 | 19 | 13 | 1 |
| −3 | −1 | 0 | 263 | 260 | 3 | 5 | 5 | 0 | 58 | 58 | 1 | 4 | −12 | 1 | 53 | 51 | 1 | 6 | −2 | 1 | 40 | 39 | 1 | 4 | 5 | 1 | 119 | 123 | 1 |
| −2 | −1 | 0 | 224 | 227 | 4 | 6 | 5 | 0 | 48 | 56 | 1 | −4 | −11 | 1 | 18 | 22 | 3 | 7 | −2 | 1 | 92 | 94 | 2 | 5 | 5 | 1 | 54 | 54 | 1 |
| −1 | −1 | 0 | 761 | 873 | 18 | −6 | 6 | 0 | 143 | 136 | 3 | −2 | −11 | 1 | 91 | 89 | 2 | 0 | −1 | 1 | 377 | 385 | 8 | 6 | 5 | 1 | 54 | 52 | 1 |
| 0 | −1 | 0 | 138 | 148 | 1 | −4 | 6 | 0 | 106 | 105 | 2 | −1 | −11 | 1 | 57 | 68 | 2 | 1 | −1 | 1 | 556 | 583 | 5 | −6 | 6 | 1 | 81 | 72 | 2 |
| 1 | −1 | 0 | 787 | 821 | 7 | −3 | 6 | 0 | 68 | 68 | 1 | 0 | −11 | 1 | 37 | 36 | 2 | 2 | −1 | 1 | 458 | 459 | 4 | −5 | 6 | 1 | 15 | 23 | 4 |
| 2 | −1 | 0 | 307 | 298 | 2 | −2 | 6 | 0 | 142 | 135 | 2 | 2 | −11 | 1 | 57 | 60 | 2 | 3 | −1 | 1 | 126 | 118 | 1 | −4 | 6 | 1 | 116 | 111 | 2 |
| 3 | −1 | 0 | 219 | 217 | 2 | −1 | 6 | 0 | 113 | 108 | 1 | 3 | −11 | 1 | 98 | 98 | 2 | 4 | −1 | 1 | 176 | 167 | 1 | −3 | 6 | 1 | 163 | 158 | 2 |
| 4 | −1 | 0 | 62 | 60 | 1 | 0 | 6 | 0 | 67 | 65 | 1 | 4 | −11 | 1 | 59 | 56 | 1 | 5 | −1 | 1 | 243 | 241 | 2 | −2 | 6 | 1 | 57 | 52 | 1 |
| 5 | −1 | 0 | 108 | 105 | 1 | 1 | 6 | 0 | 51 | 52 | 1 | −4 | −10 | 1 | 12 | 10 | 9 | 6 | −1 | 1 | 126 | 121 | 1 | −1 | 6 | 1 | 182 | 175 | 2 |
| 6 | −1 | 0 | 44 | 45 | 1 | 2 | 6 | 0 | 142 | 136 | 1 | −3 | −10 | 1 | 89 | 90 | 2 | 7 | −1 | 1 | 86 | 80 | 2 | 0 | 6 | 1 | 66 | 63 | 1 |
| 7 | −1 | 0 | 38 | 43 | 1 | 3 | 6 | 0 | 180 | 177 | 1 | −2 | −10 | 1 | 101 | 94 | 2 | −3 | 0 | 1 | 98 | 98 | 2 | 1 | 6 | 1 | 71 | 66 | 1 |
| −3 | 0 | 0 | 118 | 117 | 2 | 4 | 6 | 0 | 125 | 133 | 1 | −1 | −10 | 1 | 116 | 121 | 3 | −2 | 0 | 1 | 411 | 402 | 8 | 2 | 6 | 1 | 138 | 143 | 1 |
| −2 | 0 | 0 | 348 | 341 | 7 | 5 | 6 | 0 | 28 | 33 | 1 | 0 | −10 | 1 | 17 | 18 | 3 | −1 | 0 | 1 | 52 | 55 | 1 | 3 | 6 | 1 | 23 | 19 | 1 |
| −1 | 0 | 0 | 126 | 133 | 2 | 6 | 6 | 0 | 28 | 18 | 1 | 1 | −10 | 1 | 87 | 92 | 1 | 0 | 0 | 1 | 76 | 82 | 1 | 4 | 6 | 1 | 115 | 120 | 1 |
| 1 | 0 | 0 | 127 | 132 | 1 | −6 | 7 | 0 | 71 | 71 | 2 | 2 | −10 | 1 | 44 | 38 | 2 | 1 | 0 | 1 | 123 | 127 | 1 | 5 | 6 | 1 | 6 | 8 | 6 |
| 2 | 0 | 0 | 344 | 341 | 3 | −4 | 7 | 0 | 69 | 71 | 2 | 3 | −10 | 1 | 47 | 46 | 1 | 2 | 0 | 1 | 195 | 197 | 2 | 6 | 6 | 1 | 27 | 27 | 1 |
| 3 | 0 | 0 | 119 | 117 | 1 | −3 | 7 | 0 | 125 | 117 | 2 | 4 | −10 | 1 | 106 | 103 | 2 | 3 | 0 | 1 | 92 | 93 | 1 | −6 | 7 | 1 | 53 | 55 | 2 |
| 4 | 0 | 0 | 307 | 302 | 3 | −2 | 7 | 0 | 196 | 196 | 2 | 5 | −10 | 1 | 6 | 5 | 6 | 4 | 0 | 1 | 146 | 146 | 1 | −5 | 7 | 1 | 0 | 14 | 1 |
| 5 | 0 | 0 | 12 | 8 | 2 | −1 | 7 | 0 | 165 | 168 | 1 | −3 | −9 | 1 | 124 | 125 | 3 | 5 | 0 | 1 | 74 | 78 | 1 | −4 | 7 | 1 | 130 | 135 | 3 |
| 6 | 0 | 0 | 45 | 38 | 1 | 0 | 7 | 0 | 71 | 74 | 1 | −1 | −9 | 1 | 123 | 117 | 3 | 6 | 0 | 1 | 94 | 91 | 1 | −3 | 7 | 1 | 135 | 134 | 2 |
| 7 | 0 | 0 | 64 | 63 | 1 | 1 | 7 | 0 | 219 | 222 | 2 | 0 | −9 | 1 | 143 | 147 | 2 | 7 | 0 | 1 | 96 | 91 | 1 | −2 | 7 | 1 | 110 | 110 | 1 |
| −3 | 1 | 0 | 214 | 218 | 5 | 2 | 7 | 0 | 184 | 177 | 1 | 1 | −9 | 1 | 14 | 8 | 3 | −3 | 1 | 1 | 420 | 408 | 9 | −1 | 7 | 1 | 99 | 101 | 1 |
| −2 | 1 | 0 | 304 | 297 | 3 | 3 | 7 | 0 | 88 | 88 | 1 | 2 | −9 | 1 | 97 | 95 | 2 | −2 | 1 | 1 | 212 | 214 | 2 | 0 | 7 | 1 | 83 | 86 | 1 |

TABLE 7-continued

| Observed and calculated structure factors for NEL | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
| −1 | 1 | 0 | 792 | 821 | 9 | 4 | 7 | 0 | 68 | 72 | 1 | 3 | −9 | 1 | 47 | 46 | 1 | −1 | 1 | 1 | 814 | 844 | 9 | 1 | 7 | 1 | 61 | 62 | 1 |
| 2 | 7 | 1 | 92 | 91 | 1 | 2 | −9 | 2 | 73 | 75 | 1 | 7 | 0 | 2 | 60 | 64 | 1 | 0 | 7 | 2 | 90 | 92 | 1 | 2 | −9 | 3 | 99 | 100 | 2 |
| 3 | 7 | 1 | 68 | 74 | 1 | 3 | −9 | 2 | 69 | 64 | 1 | −3 | 1 | 2 | 117 | 115 | 2 | 1 | 7 | 2 | 91 | 88 | 1 | 3 | −9 | 3 | 146 | 144 | 2 |
| 4 | 7 | 1 | 71 | 74 | 1 | 4 | −9 | 2 | 37 | 36 | 1 | −2 | 1 | 2 | 110 | 105 | 1 | 2 | 7 | 2 | 120 | 121 | 1 | 4 | −9 | 3 | 69 | 70 | 1 |
| 5 | 7 | 1 | 63 | 60 | 1 | 5 | −9 | 2 | 29 | 27 | 1 | −1 | 1 | 2 | 479 | 489 | 5 | 3 | 7 | 2 | 101 | 103 | 1 | 5 | −9 | 3 | 73 | 74 | 1 |
| 6 | 7 | 1 | 66 | 69 | 1 | −2 | −8 | 2 | 179 | 183 | 3 | 0 | 1 | 2 | 604 | 633 | 5 | 4 | 7 | 2 | 103 | 105 | 1 | −2 | −8 | 3 | 80 | 78 | 1 |
| −5 | 8 | 1 | 83 | 87 | 2 | −1 | −8 | 2 | 123 | 123 | 2 | 1 | 1 | 2 | 417 | 426 | 3 | 5 | 7 | 2 | 63 | 65 | 1 | −1 | −8 | 3 | 53 | 55 | 1 |
| −4 | 8 | 1 | 107 | 101 | 3 | 0 | −8 | 2 | 38 | 41 | 1 | 2 | 1 | 2 | 295 | 287 | 3 | −5 | 8 | 2 | 101 | 102 | 2 | 0 | −8 | 3 | 142 | 129 | 2 |
| −3 | 8 | 1 | 140 | 142 | 2 | 1 | −8 | 2 | 59 | 61 | 1 | 3 | 1 | 2 | 167 | 165 | 1 | −4 | 8 | 2 | 75 | 72 | 2 | 1 | −8 | 3 | 74 | 80 | 1 |
| −2 | 8 | 1 | 130 | 131 | 1 | 2 | −8 | 2 | 86 | 84 | 1 | 4 | 1 | 2 | 182 | 181 | 1 | −3 | 8 | 2 | 80 | 80 | 1 | 2 | −8 | 3 | 194 | 196 | 2 |
| −1 | 8 | 1 | 60 | 62 | 1 | 3 | −8 | 2 | 170 | 167 | 1 | 5 | 1 | 2 | 31 | 30 | 1 | −2 | 8 | 2 | 124 | 120 | 1 | 3 | −8 | 3 | 142 | 142 | 1 |
| 0 | 8 | 1 | 52 | 53 | 1 | 4 | −8 | 2 | 85 | 88 | 1 | 6 | 1 | 2 | 112 | 107 | 1 | −1 | 8 | 2 | 20 | 23 | 1 | 4 | −8 | 3 | 37 | 39 | 1 |
| 1 | 8 | 1 | 137 | 141 | 1 | 5 | −8 | 2 | 33 | 33 | 1 | 7 | 1 | 2 | 51 | 52 | 1 | 0 | 8 | 2 | 57 | 56 | 1 | 5 | −8 | 3 | 37 | 33 | 1 |
| 2 | 8 | 1 | 181 | 181 | 1 | 6 | −8 | 2 | 25 | 20 | 2 | −7 | 2 | 2 | 25 | 18 | 3 | 1 | 8 | 2 | 184 | 182 | 2 | 6 | −8 | 3 | 48 | 61 | 1 |
| 3 | 8 | 1 | 67 | 67 | 1 | −2 | −7 | 2 | 93 | 95 | 2 | −6 | 2 | 2 | 17 | 17 | 4 | 2 | 8 | 2 | 83 | 83 | 1 | −1 | −7 | 3 | 188 | 192 | 4 |
| 4 | 8 | 1 | 152 | 162 | 1 | −1 | −7 | 2 | 46 | 52 | 2 | −5 | 2 | 2 | 185 | 186 | 4 | 3 | 8 | 2 | 41 | 46 | 1 | 0 | −7 | 3 | 215 | 209 | 3 |
| 5 | 8 | 1 | 4 | 4 | 3 | 0 | −7 | 2 | 154 | 152 | 2 | −4 | 2 | 2 | 93 | 96 | 1 | 4 | 8 | 2 | 69 | 72 | 2 | 1 | −7 | 3 | 192 | 194 | 2 |
| −5 | 9 | 1 | 95 | 97 | 2 | 1 | −7 | 2 | 139 | 142 | 1 | −3 | 2 | 2 | 140 | 142 | 3 | 5 | 8 | 2 | 81 | 82 | 1 | 2 | −7 | 3 | 148 | 151 | 1 |
| −4 | 9 | 1 | 133 | 135 | 3 | 2 | −7 | 2 | 116 | 116 | 1 | −2 | 2 | 2 | 292 | 283 | 3 | −5 | 9 | 2 | 3 | 10 | 3 | 3 | −7 | 3 | 128 | 128 | 1 |
| −3 | 9 | 1 | 33 | 33 | 2 | 3 | −7 | 2 | 82 | 79 | 1 | −1 | 2 | 2 | 630 | 638 | 7 | −4 | 9 | 2 | 62 | 62 | 2 | 4 | −7 | 3 | 137 | 133 | 1 |
| −2 | 9 | 1 | 178 | 179 | 2 | 4 | −7 | 2 | 140 | 142 | 1 | 0 | 2 | 2 | 169 | 169 | 1 | −3 | 9 | 2 | 190 | 193 | 4 | 5 | −7 | 3 | 43 | 43 | 1 |
| −1 | 9 | 1 | 36 | 34 | 1 | 5 | −7 | 2 | 55 | 52 | 1 | 1 | 2 | 2 | 430 | 439 | 3 | −2 | 9 | 2 | 60 | 60 | 1 | 6 | −7 | 3 | 10 | 11 | 2 |
| 0 | 9 | 1 | 150 | 151 | 1 | 6 | −7 | 2 | 11 | 17 | 1 | 2 | 2 | 2 | 403 | 380 | 4 | −1 | 9 | 2 | 175 | 177 | 2 | −1 | −6 | 3 | 320 | 315 | 7 |
| 1 | 9 | 1 | 80 | 78 | 1 | −1 | −6 | 2 | 97 | 96 | 2 | 3 | 2 | 2 | 324 | 316 | 4 | 0 | 9 | 2 | 65 | 64 | 1 | 0 | −6 | 3 | 170 | 171 | 2 |
| 2 | 9 | 1 | 120 | 122 | 1 | 0 | −6 | 2 | 232 | 231 | 3 | 4 | 2 | 2 | 44 | 46 | 1 | 1 | 9 | 2 | 153 | 155 | 2 | 1 | −6 | 3 | 383 | 392 | 4 |
| 3 | 9 | 1 | 85 | 90 | 2 | 1 | −6 | 2 | 333 | 327 | 4 | 5 | 2 | 2 | 60 | 57 | 1 | 2 | 9 | 2 | 64 | 65 | 1 | 2 | −6 | 3 | 47 | 51 | 1 |
| 5 | 9 | 1 | 75 | 77 | 1 | 2 | −6 | 2 | 106 | 94 | 1 | 6 | 2 | 2 | 119 | 119 | 1 | 3 | 9 | 2 | 90 | 96 | 1 | 3 | −6 | 3 | 79 | 78 | 1 |
| −3 | 10 | 1 | 26 | 23 | 3 | 3 | −6 | 2 | 151 | 151 | 1 | 7 | 2 | 2 | 59 | 55 | 1 | −3 | 10 | 2 | 89 | 91 | 2 | 4 | −6 | 3 | 186 | 185 | 2 |
| −2 | 10 | 1 | 58 | 51 | 1 | 4 | −6 | 2 | 150 | 148 | 1 | −7 | 3 | 2 | 54 | 55 | 2 | −2 | 10 | 2 | 104 | 102 | 2 | 5 | −6 | 3 | 35 | 37 | 1 |
| −1 | 10 | 1 | 29 | 35 | 1 | 5 | −6 | 2 | 81 | 82 | 1 | −6 | 3 | 2 | 65 | 67 | 2 | −1 | 10 | 2 | 59 | 62 | 1 | 6 | −6 | 3 | 43 | 42 | 2 |
| 0 | 10 | 1 | 100 | 121 | 2 | 6 | −6 | 2 | 35 | 33 | 2 | −5 | 3 | 2 | 47 | 44 | 1 | 0 | 10 | 2 | 14 | 12 | 3 | −1 | −5 | 3 | 381 | 374 | 8 |
| 1 | 10 | 1 | 119 | 124 | 1 | −1 | −5 | 2 | 225 | 220 | 3 | −4 | 3 | 2 | 126 | 123 | 2 | 1 | 10 | 2 | 62 | 63 | 1 | 0 | −5 | 3 | 90 | 91 | 1 |
| 2 | 10 | 1 | 55 | 53 | 1 | 0 | −5 | 2 | 107 | 113 | 1 | −3 | 3 | 2 | 213 | 202 | 4 | 2 | 10 | 2 | 61 | 59 | 1 | 1 | −5 | 3 | 202 | 201 | 3 |
| 3 | 10 | 1 | 8 | 8 | 7 | 1 | −5 | 2 | 363 | 354 | 5 | −2 | 3 | 2 | 40 | 40 | 1 | 3 | 10 | 2 | 81 | 84 | 2 | 2 | −5 | 3 | 175 | 171 | 2 |
| −3 | 11 | 1 | 114 | 114 | 3 | 2 | −5 | 2 | 68 | 61 | 1 | −1 | 3 | 2 | 191 | 186 | 2 | −3 | 11 | 2 | 66 | 66 | 2 | 3 | −5 | 3 | 43 | 43 | 1 |
| −2 | 11 | 1 | 152 | 153 | 2 | 3 | −5 | 2 | 101 | 97 | 1 | 0 | 3 | 2 | 115 | 119 | 1 | −2 | 11 | 2 | 51 | 48 | 1 | 4 | −5 | 3 | 119 | 114 | 1 |
| −1 | 11 | 1 | 168 | 164 | 3 | 4 | −5 | 2 | 51 | 50 | 1 | 1 | 3 | 2 | 307 | 295 | 2 | −1 | 11 | 2 | 56 | 57 | 1 | 5 | −5 | 3 | 115 | 126 | 2 |
| 0 | 11 | 1 | 72 | 72 | 1 | 5 | −5 | 2 | 99 | 98 | 1 | 2 | 3 | 2 | 317 | 314 | 3 | 0 | 11 | 2 | 56 | 53 | 1 | 6 | −5 | 3 | 144 | 140 | 2 |
| 1 | 11 | 1 | 82 | 78 | 1 | 6 | −5 | 2 | 116 | 115 | 2 | 3 | 3 | 2 | 84 | 78 | 1 | 1 | 11 | 2 | 133 | 133 | 1 | −3 | −4 | 3 | 89 | 89 | 2 |
| 2 | 11 | 1 | 124 | 130 | 2 | −3 | −4 | 2 | 210 | 211 | 5 | 4 | 3 | 2 | 26 | 24 | 1 | 2 | 11 | 2 | 83 | 81 | 1 | −2 | −4 | 3 | 283 | 270 | 6 |
| 3 | 11 | 1 | 44 | 46 | 2 | −2 | −4 | 2 | 232 | 232 | 5 | 5 | 3 | 2 | 57 | 55 | 1 | 3 | 11 | 2 | 25 | 27 | 2 | −1 | −4 | 3 | 177 | 170 | 2 |
| −3 | 12 | 1 | 47 | 45 | 2 | −1 | −4 | 2 | 178 | 186 | 2 | 6 | 3 | 2 | 68 | 68 | 1 | −3 | 12 | 2 | 42 | 37 | 2 | 0 | −4 | 3 | 138 | 139 | 2 |
| −2 | 12 | 1 | 164 | 162 | 2 | 0 | −4 | 2 | 211 | 208 | 3 | −7 | 4 | 2 | 114 | 113 | 3 | −2 | 12 | 2 | 47 | 41 | 1 | 1 | −4 | 3 | 109 | 118 | 1 |
| −1 | 12 | 1 | 131 | 129 | 2 | 1 | −4 | 2 | 53 | 52 | 1 | −6 | 4 | 2 | 76 | 75 | 2 | −1 | 12 | 2 | 50 | 49 | 1 | 2 | −4 | 3 | 141 | 146 | 1 |
| 0 | 12 | 1 | 28 | 29 | 1 | 2 | −4 | 2 | 314 | 304 | 3 | −5 | 4 | 2 | 67 | 66 | 2 | 0 | 12 | 2 | 76 | 72 | 1 | 3 | −4 | 3 | 105 | 101 | 1 |
| 1 | 12 | 1 | 47 | 46 | 1 | 3 | −4 | 2 | 149 | 150 | 1 | −4 | 4 | 2 | 81 | 82 | 1 | 1 | 12 | 2 | 70 | 65 | 1 | 4 | −4 | 3 | 194 | 190 | 2 |
| 2 | 12 | 1 | 90 | 89 | 2 | 4 | −4 | 2 | 195 | 194 | 2 | −3 | 4 | 2 | 145 | 147 | 2 | 2 | 12 | 2 | 55 | 54 | 2 | 5 | −4 | 3 | 28 | 30 | 1 |
| −2 | 13 | 1 | 105 | 105 | 2 | 5 | −4 | 2 | 113 | 117 | 1 | −2 | 4 | 2 | 230 | 210 | 5 | −1 | 13 | 2 | 76 | 76 | 2 | 6 | −4 | 3 | 52 | 48 | 1 |
| −1 | 13 | 1 | 66 | 64 | 1 | 6 | −4 | 2 | 131 | 127 | 2 | −1 | 4 | 2 | 102 | 101 | 1 | 0 | 13 | 2 | 108 | 109 | 2 | 7 | −4 | 3 | 29 | 32 | 2 |

TABLE 7-continued

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| Observed and calculated structure factors for NEL | | | | | | | | | | | | | | | | | | | | | | | | | | | | | |
| 0 | 13 | 1 | 102 | 102 | 1 | 7 | −4 | 2 | 28 | 26 | 2 | 0 | 4 | 2 | 176 | 176 | 1 | −1 | −14 | 3 | 94 | 93 | 2 | −3 | −3 | 3 | 38 | 38 | 2 |
| 1 | 13 | 1 | 41 | 43 | 2 | −3 | −3 | 2 | 197 | 194 | 4 | 1 | 4 | 2 | 222 | 221 | 2 | 0 | −14 | 3 | 34 | 30 | 2 | −2 | −3 | 3 | 99 | 93 | 2 |
| −1 | −14 | 2 | 85 | 83 | 2 | −1 | −3 | 2 | 296 | 307 | 4 | 2 | 4 | 2 | 338 | 315 | 3 | 1 | −14 | 3 | 35 | 34 | 2 | −1 | −3 | 3 | 251 | 259 | 4 |
| 0 | −14 | 2 | 45 | 45 | 2 | 0 | −3 | 2 | 69 | 70 | 1 | 3 | 4 | 2 | 96 | 94 | 1 | 2 | −14 | 3 | 60 | 62 | 2 | 0 | −3 | 3 | 320 | 319 | 5 |
| 1 | −14 | 2 | 29 | 30 | 3 | 1 | −3 | 2 | 73 | 74 | 1 | 4 | 4 | 2 | 79 | 77 | 1 | −3 | −13 | 3 | 31 | 32 | 2 | 1 | −3 | 3 | 285 | 295 | 3 |
| −2 | −13 | 2 | 99 | 97 | 2 | 2 | −3 | 2 | 188 | 184 | 1 | 5 | 4 | 2 | 91 | 92 | 1 | −2 | −13 | 3 | 65 | 61 | 2 | 2 | −3 | 3 | 88 | 84 | 1 |
| 0 | −13 | 2 | 68 | 64 | 2 | 3 | −3 | 2 | 107 | 111 | 1 | 6 | 4 | 2 | 69 | 63 | 1 | −1 | −13 | 3 | 20 | 18 | 3 | 3 | −3 | 3 | 78 | 75 | 1 |
| 1 | −13 | 2 | 41 | 42 | 3 | 4 | −3 | 2 | 154 | 154 | 1 | −6 | 5 | 2 | 29 | 26 | 2 | 0 | −13 | 3 | 19 | 22 | 3 | 4 | −3 | 3 | 124 | 124 | 1 |
| 2 | −13 | 2 | 73 | 73 | 2 | 5 | −3 | 2 | 27 | 23 | 1 | −5 | 5 | 2 | 105 | 120 | 3 | 2 | −13 | 3 | 44 | 45 | 3 | 5 | −3 | 3 | 55 | 57 | 1 |
| 3 | −13 | 2 | 54 | 54 | 1 | 6 | −3 | 2 | 35 | 29 | 1 | −4 | 5 | 2 | 142 | 147 | 2 | 3 | −13 | 3 | 73 | 72 | 1 | 6 | −3 | 3 | 51 | 48 | 1 |
| −3 | −12 | 2 | 26 | 25 | 2 | 7 | −3 | 2 | 58 | 59 | 2 | −3 | 5 | 2 | 45 | 47 | 1 | −3 | −12 | 3 | 106 | 108 | 2 | 7 | −3 | 3 | 8 | 8 | 6 |
| −2 | −12 | 2 | 97 | 96 | 2 | −1 | −2 | 2 | 365 | 390 | 9 | −2 | 5 | 2 | 240 | 239 | 3 | −2 | −12 | 3 | 73 | 71 | 2 | −2 | −2 | 3 | 207 | 210 | 5 |
| −1 | −12 | 2 | 38 | 35 | 2 | 0 | −2 | 2 | 596 | 596 | 8 | −1 | 5 | 2 | 29 | 26 | 1 | −1 | −12 | 3 | 50 | 53 | 2 | −1 | −2 | 3 | 174 | 183 | 2 |
| 0 | −12 | 2 | 83 | 81 | 2 | 1 | −2 | 2 | 430 | 446 | 4 | 0 | 5 | 2 | 92 | 96 | 1 | 0 | −12 | 3 | 45 | 47 | 2 | 0 | −2 | 3 | 144 | 147 | 2 |
| 2 | −12 | 2 | 103 | 105 | 2 | 2 | −2 | 2 | 224 | 227 | 2 | 1 | 5 | 2 | 275 | 268 | 2 | 1 | −12 | 3 | 63 | 62 | 2 | 1 | −2 | 3 | 446 | 467 | 4 |
| 3 | −12 | 2 | 65 | 64 | 1 | 3 | −2 | 2 | 112 | 118 | 1 | 2 | 5 | 2 | 100 | 92 | 1 | 2 | −12 | 3 | 92 | 93 | 2 | 2 | −2 | 3 | 156 | 155 | 1 |
| 4 | −12 | 2 | 53 | 52 | 1 | 4 | −2 | 2 | 53 | 50 | 1 | 3 | 5 | 2 | 57 | 56 | 1 | 3 | −12 | 3 | 26 | 25 | 2 | 3 | −2 | 3 | 6 | 4 | 3 |
| −4 | −11 | 2 | 53 | 54 | 2 | 5 | −2 | 2 | 106 | 99 | 1 | 4 | 5 | 2 | 90 | 86 | 1 | 4 | −12 | 3 | 56 | 52 | 2 | 4 | −2 | 3 | 48 | 52 | 1 |
| −3 | −11 | 2 | 74 | 75 | 2 | 6 | −2 | 2 | 115 | 119 | 2 | 5 | 5 | 2 | 78 | 83 | 1 | −3 | −11 | 3 | 172 | 179 | 4 | 5 | −2 | 3 | 154 | 154 | 2 |
| −2 | −11 | 2 | 106 | 104 | 2 | 7 | −2 | 2 | 29 | 28 | 2 | 6 | 5 | 2 | 30 | 29 | 1 | −2 | −11 | 3 | 116 | 113 | 3 | 6 | −2 | 3 | 128 | 129 | 2 |
| −1 | −11 | 2 | 93 | 109 | 3 | −1 | −1 | 2 | 223 | 236 | 4 | −6 | 6 | 2 | 58 | 57 | 2 | −1 | −11 | 3 | 73 | 77 | 2 | 7 | −2 | 3 | 66 | 70 | 2 |
| 0 | −11 | 2 | 95 | 104 | 3 | 0 | −1 | 2 | 377 | 397 | 4 | −5 | 6 | 2 | 35 | 47 | 2 | 0 | −11 | 3 | 68 | 78 | 2 | −2 | −1 | 3 | 136 | 133 | 2 |
| 1 | −11 | 2 | 156 | 163 | 4 | 1 | −1 | 2 | 295 | 306 | 2 | −4 | 6 | 2 | 139 | 148 | 2 | 1 | −11 | 3 | 54 | 55 | 2 | −1 | −1 | 3 | 90 | 94 | 1 |
| 2 | −11 | 2 | 110 | 112 | 3 | 2 | −1 | 2 | 96 | 100 | 1 | −3 | 6 | 2 | 100 | 90 | 1 | 2 | −11 | 3 | 89 | 82 | 2 | 0 | −1 | 3 | 190 | 195 | 2 |
| 3 | −11 | 2 | 95 | 91 | 2 | 3 | −1 | 2 | 179 | 168 | 1 | −2 | 6 | 2 | 176 | 178 | 2 | 3 | −11 | 3 | 73 | 71 | 2 | 1 | −1 | 3 | 158 | 169 | 1 |
| 4 | −11 | 2 | 52 | 53 | 1 | 4 | −1 | 2 | 149 | 149 | 1 | −1 | 6 | 2 | 75 | 74 | 1 | 4 | −11 | 3 | 9 | 5 | 9 | 2 | −1 | 3 | 132 | 139 | 1 |
| −3 | −10 | 2 | 97 | 96 | 2 | 5 | −1 | 2 | 44 | 43 | 1 | 0 | 6 | 2 | 129 | 131 | 1 | −3 | −10 | 3 | 13 | 16 | 6 | 3 | −1 | 3 | 120 | 108 | 1 |
| −2 | −10 | 2 | 94 | 97 | 2 | 6 | −1 | 2 | 64 | 62 | 1 | 1 | 6 | 2 | 18 | 19 | 1 | −2 | −10 | 3 | 140 | 138 | 3 | 4 | −1 | 3 | 168 | 166 | 1 |
| −1 | −10 | 2 | 57 | 60 | 2 | 7 | −1 | 2 | 38 | 37 | 2 | 2 | 6 | 2 | 133 | 130 | 1 | −1 | −10 | 3 | 235 | 240 | 5 | 5 | −1 | 3 | 136 | 128 | 1 |
| 0 | −10 | 2 | 25 | 28 | 2 | −3 | 0 | 2 | 52 | 61 | 1 | 3 | 6 | 2 | 145 | 146 | 1 | 0 | −10 | 3 | 27 | 30 | 2 | 6 | −1 | 3 | 101 | 101 | 2 |
| 1 | −10 | 2 | 89 | 90 | 1 | −2 | 0 | 2 | 191 | 198 | 4 | 4 | 6 | 2 | 56 | 57 | 1 | 1 | −10 | 3 | 140 | 142 | 2 | 7 | −1 | 3 | 61 | 58 | 2 |
| 2 | −10 | 2 | 182 | 182 | 4 | −1 | 0 | 2 | 253 | 265 | 3 | 5 | 6 | 2 | 12 | 11 | 3 | 2 | −10 | 3 | 216 | 213 | 5 | −2 | 0 | 3 | 96 | 91 | 1 |
| 3 | −10 | 2 | 61 | 59 | 1 | 0 | 0 | 2 | 450 | 469 | 4 | 6 | 6 | 2 | 57 | 56 | 1 | 3 | −10 | 3 | 65 | 64 | 1 | −1 | 0 | 3 | 90 | 92 | 1 |
| 4 | −10 | 2 | 84 | 80 | 2 | 1 | 0 | 2 | 284 | 295 | 3 | −6 | 7 | 2 | 35 | 39 | 2 | 4 | −10 | 3 | 40 | 38 | 2 | 0 | 0 | 3 | 182 | 191 | 1 |
| 5 | −10 | 2 | 57 | 55 | 1 | 2 | 0 | 2 | 195 | 195 | 1 | −5 | 7 | 2 | 78 | 75 | 2 | 5 | −10 | 3 | 37 | 38 | 1 | 1 | 0 | 3 | 178 | 189 | 1 |
| −2 | −9 | 2 | 52 | 52 | 1 | 3 | 0 | 2 | 326 | 319 | 3 | −4 | 7 | 2 | 48 | 48 | 2 | −2 | −9 | 3 | 74 | 74 | 1 | 2 | 0 | 3 | 207 | 207 | 1 |
| −1 | −9 | 2 | 147 | 145 | 2 | 4 | 0 | 2 | 173 | 165 | 1 | −3 | 7 | 2 | 110 | 113 | 2 | −1 | −9 | 3 | 48 | 43 | 1 | 3 | 0 | 3 | 179 | 173 | 2 |
| 0 | −9 | 2 | 28 | 31 | 2 | 5 | 0 | 2 | 90 | 83 | 1 | −2 | 7 | 2 | 28 | 28 | 1 | 0 | −9 | 3 | 251 | 256 | 4 | 4 | 0 | 3 | 154 | 150 | 1 |
| 1 | −9 | 2 | 132 | 129 | 3 | 6 | 0 | 2 | 114 | 115 | 1 | −1 | 7 | 2 | 89 | 85 | 1 | 1 | −9 | 3 | 120 | 114 | 3 | 5 | 0 | 3 | 100 | 101 | 1 |
| 6 | 0 | 3 | 11 | 7 | 2 | 1 | 7 | 3 | 151 | 152 | 1 | 5 | −8 | 4 | 81 | 76 | 1 | 6 | 1 | 4 | 24 | 21 | 1 | −1 | 9 | 4 | 73 | 70 | 1 |
| 7 | 0 | 3 | 23 | 21 | 3 | 2 | 7 | 3 | 100 | 95 | 1 | 6 | −8 | 4 | 26 | 29 | 1 | −7 | 2 | 4 | 94 | 98 | 2 | 0 | 9 | 4 | 26 | 29 | 1 |
| −3 | 1 | 3 | 357 | 349 | 8 | 3 | 7 | 3 | 135 | 135 | 2 | −1 | −7 | 4 | 176 | 171 | 4 | −6 | 2 | 4 | 54 | 52 | 2 | 1 | 9 | 4 | 82 | 87 | 2 |
| −2 | 1 | 3 | 258 | 256 | 3 | 4 | 7 | 3 | 44 | 41 | 2 | 0 | −7 | 4 | 349 | 334 | 4 | −5 | 2 | 4 | 146 | 145 | 3 | 2 | 9 | 4 | 118 | 117 | 1 |
| −1 | 1 | 3 | 391 | 401 | 4 | 5 | 7 | 3 | 28 | 21 | 1 | 1 | −7 | 4 | 357 | 355 | 4 | −4 | 2 | 4 | 28 | 29 | 1 | 3 | 9 | 4 | 59 | 62 | 1 |
| 0 | 1 | 3 | 544 | 566 | 4 | −5 | 8 | 3 | 60 | 62 | 2 | 2 | −7 | 4 | 84 | 82 | 1 | −3 | 2 | 4 | 151 | 152 | 3 | 4 | 9 | 4 | 46 | 57 | 1 |
| 1 | 1 | 3 | 244 | 258 | 2 | −4 | 8 | 3 | 180 | 184 | 3 | 3 | −7 | 4 | 300 | 302 | 3 | −2 | 2 | 4 | 248 | 247 | 3 | −3 | 10 | 4 | 59 | 58 | 2 |
| 2 | 1 | 3 | 230 | 232 | 2 | −3 | 8 | 3 | 46 | 50 | 1 | 4 | −7 | 4 | 72 | 73 | 1 | −1 | 2 | 4 | 31 | 23 | 1 | −2 | 10 | 4 | 29 | 28 | 2 |
| 3 | 1 | 3 | 123 | 123 | 1 | −2 | 8 | 3 | 95 | 95 | 1 | 5 | −7 | 4 | 87 | 88 | 2 | 0 | 2 | 4 | 290 | 292 | 2 | −1 | 10 | 4 | 70 | 68 | 1 |
| 4 | 1 | 3 | 26 | 20 | 1 | −1 | 8 | 3 | 63 | 63 | 1 | 6 | −7 | 4 | 105 | 115 | 2 | 1 | 2 | 4 | 165 | 159 | 1 | 0 | 10 | 4 | 218 | 211 | 3 |

TABLE 7-continued

Observed and calculated structure factors for NEL

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 5 | 1 | 3 | 94 | 94 | 1 | 0 | 8 | 3 | 19 | 14 | 1 | −1 | −6 | 4 | 7 | 10 | 7 | 2 | 2 | 4 | 155 | 152 | 1 | 1 | 10 | 4 | 59 | 57 | 1 |
| 6 | 1 | 3 | 73 | 72 | 1 | 1 | 8 | 3 | 184 | 190 | 2 | 0 | −6 | 4 | 398 | 389 | 6 | 3 | 2 | 4 | 69 | 70 | 1 | 2 | 10 | 4 | 47 | 49 | 1 |
| 7 | 1 | 3 | 23 | 23 | 2 | 2 | 8 | 3 | 74 | 76 | 1 | 1 | −6 | 4 | 165 | 170 | 2 | 4 | 2 | 4 | 130 | 122 | 1 | 3 | 10 | 4 | 119 | 117 | 3 |
| −7 | 2 | 3 | 49 | 55 | 2 | 3 | 8 | 3 | 100 | 103 | 1 | 2 | −6 | 4 | 71 | 79 | 1 | 5 | 2 | 4 | 186 | 190 | 1 | −3 | 11 | 4 | 90 | 92 | 2 |
| −6 | 2 | 3 | 14 | 20 | 5 | 4 | 8 | 3 | 57 | 54 | 2 | 3 | −6 | 4 | 147 | 146 | 1 | 6 | 2 | 4 | 83 | 85 | 1 | −2 | 11 | 4 | 39 | 36 | 1 |
| −5 | 2 | 3 | 62 | 61 | 2 | −3 | 9 | 3 | 69 | 66 | 2 | 4 | −6 | 4 | 146 | 138 | 1 | −7 | 3 | 4 | 48 | 46 | 2 | −1 | 11 | 4 | 72 | 69 | 1 |
| −4 | 2 | 3 | 197 | 203 | 3 | −2 | 9 | 3 | 97 | 101 | 2 | 5 | −6 | 4 | 82 | 79 | 1 | −6 | 3 | 4 | 47 | 50 | 2 | 0 | 11 | 4 | 93 | 87 | 1 |
| −3 | 2 | 3 | 153 | 145 | 3 | −1 | 9 | 3 | 77 | 77 | 1 | 6 | −6 | 4 | 10 | 13 | 7 | −5 | 3 | 4 | 36 | 35 | 2 | 1 | 11 | 4 | 129 | 126 | 1 |
| −2 | 2 | 3 | 443 | 434 | 5 | 0 | 9 | 3 | 44 | 48 | 1 | −1 | −5 | 4 | 284 | 283 | 6 | −4 | 3 | 4 | 54 | 55 | 1 | 2 | 11 | 4 | 41 | 40 | 2 |
| −1 | 2 | 3 | 101 | 103 | 1 | 1 | 9 | 3 | 94 | 116 | 2 | 0 | −5 | 4 | 231 | 230 | 5 | −3 | 3 | 4 | 96 | 89 | 1 | −2 | 12 | 4 | 56 | 59 | 2 |
| 0 | 2 | 3 | 692 | 721 | 5 | 2 | 9 | 3 | 88 | 84 | 1 | 1 | −5 | 4 | 153 | 153 | 2 | −2 | 3 | 4 | 94 | 87 | 1 | −1 | 12 | 4 | 66 | 64 | 1 |
| 1 | 2 | 3 | 127 | 119 | 1 | 3 | 9 | 3 | 54 | 59 | 1 | 2 | −5 | 4 | 90 | 93 | 1 | −1 | 3 | 4 | 333 | 325 | 4 | 0 | 12 | 4 | 36 | 36 | 1 |
| 2 | 2 | 3 | 331 | 334 | 3 | −3 | 10 | 3 | 94 | 96 | 2 | 3 | −5 | 4 | 154 | 154 | 1 | 0 | 3 | 4 | 312 | 314 | 3 | 1 | 12 | 4 | 61 | 66 | 2 |
| 3 | 2 | 3 | 199 | 202 | 1 | −2 | 10 | 3 | 123 | 119 | 2 | 4 | −5 | 4 | 15 | 13 | 2 | 1 | 3 | 4 | 345 | 337 | 4 | −2 | −14 | 5 | 66 | 63 | 1 |
| 4 | 2 | 3 | 131 | 131 | 1 | −1 | 10 | 3 | 23 | 23 | 1 | 5 | −5 | 4 | 78 | 83 | 1 | 2 | 3 | 4 | 140 | 135 | 1 | −1 | −14 | 5 | 37 | 38 | 2 |
| 5 | 2 | 3 | 89 | 88 | 1 | 0 | 10 | 3 | 43 | 38 | 1 | 6 | −5 | 4 | 31 | 31 | 2 | 3 | 3 | 4 | 84 | 87 | 1 | 0 | −14 | 5 | 58 | 55 | 2 |
| 6 | 2 | 3 | 38 | 38 | 1 | 1 | 10 | 3 | 69 | 65 | 1 | −3 | −4 | 4 | 146 | 158 | 3 | 4 | 3 | 4 | 51 | 50 | 1 | 1 | −14 | 5 | 42 | 44 | 2 |
| −7 | 3 | 3 | 136 | 125 | 3 | 2 | 10 | 3 | 20 | 19 | 1 | −2 | −4 | 4 | 115 | 111 | 3 | 5 | 3 | 4 | 167 | 170 | 1 | 2 | −14 | 5 | 72 | 70 | 2 |
| −6 | 3 | 3 | 76 | 81 | 2 | 3 | 10 | 3 | 43 | 38 | 2 | −1 | −4 | 4 | 151 | 159 | 2 | 6 | 3 | 4 | 30 | 30 | 1 | −3 | −13 | 5 | 85 | 87 | 2 |
| −5 | 3 | 3 | 122 | 123 | 2 | −3 | 11 | 3 | 24 | 18 | 3 | 0 | −4 | 4 | 223 | 221 | 3 | −6 | 4 | 4 | 58 | 59 | 2 | −2 | −13 | 5 | 38 | 39 | 2 |
| −4 | 3 | 3 | 21 | 22 | 2 | −2 | 11 | 3 | 122 | 118 | 2 | 1 | −4 | 4 | 287 | 295 | 3 | −5 | 4 | 4 | 71 | 72 | 2 | −1 | −13 | 5 | 51 | 52 | 2 |
| −3 | 3 | 3 | 280 | 276 | 4 | −1 | 11 | 3 | 68 | 67 | 1 | 2 | −4 | 4 | 163 | 166 | 2 | −4 | 4 | 4 | 52 | 52 | 1 | 0 | −13 | 5 | 80 | 78 | 2 |
| −2 | 3 | 3 | 237 | 237 | 3 | 0 | 11 | 3 | 29 | 26 | 1 | 3 | −4 | 4 | 55 | 57 | 1 | −3 | 4 | 4 | 169 | 166 | 2 | 1 | −13 | 5 | 38 | 39 | 2 |
| −1 | 3 | 3 | 99 | 99 | 1 | 1 | 11 | 3 | 59 | 59 | 1 | 4 | −4 | 4 | 110 | 115 | 1 | −2 | 4 | 4 | 58 | 51 | 1 | 2 | −13 | 5 | 44 | 45 | 3 |
| 0 | 3 | 3 | 524 | 535 | 4 | 2 | 11 | 3 | 37 | 33 | 1 | 5 | −4 | 4 | 144 | 146 | 2 | −1 | 4 | 4 | 139 | 136 | 2 | 3 | −13 | 5 | 115 | 113 | 3 |
| 1 | 3 | 3 | 84 | 77 | 1 | 3 | 11 | 3 | 22 | 22 | 3 | 6 | −4 | 4 | 77 | 79 | 1 | 0 | 4 | 4 | 315 | 314 | 3 | −3 | −12 | 5 | 52 | 54 | 2 |
| 2 | 3 | 3 | 179 | 172 | 1 | −2 | 12 | 3 | 125 | 121 | 3 | −3 | −3 | 4 | 105 | 109 | 2 | 1 | 4 | 4 | 128 | 131 | 1 | −2 | −12 | 5 | 136 | 136 | 3 |
| 3 | 3 | 3 | 178 | 177 | 1 | −1 | 12 | 3 | 42 | 37 | 1 | −2 | −3 | 4 | 67 | 55 | 2 | 2 | 4 | 4 | 51 | 43 | 1 | −1 | −12 | 5 | 29 | 26 | 2 |
| 4 | 3 | 3 | 102 | 103 | 1 | 0 | 12 | 3 | 39 | 35 | 1 | −1 | −3 | 4 | 390 | 384 | 6 | 3 | 4 | 4 | 89 | 92 | 1 | 0 | −12 | 5 | 60 | 60 | 2 |
| 5 | 3 | 3 | 90 | 91 | 1 | 1 | 12 | 3 | 81 | 82 | 1 | 0 | −3 | 4 | 130 | 136 | 2 | 4 | 4 | 4 | 64 | 64 | 1 | 1 | −12 | 5 | 64 | 61 | 2 |
| 6 | 3 | 3 | 87 | 86 | 1 | −2 | −14 | 4 | 25 | 25 | 2 | 1 | −3 | 4 | 594 | 613 | 9 | 5 | 4 | 4 | 20 | 21 | 1 | 2 | −12 | 5 | 100 | 100 | 2 |
| −7 | 4 | 3 | 54 | 53 | 2 | 0 | −14 | 4 | 14 | 10 | 4 | 2 | −3 | 4 | 190 | 193 | 2 | 6 | 4 | 4 | 68 | 76 | 1 | 3 | −12 | 5 | 52 | 52 | 1 |
| −6 | 4 | 3 | 70 | 70 | 2 | 1 | −14 | 4 | 40 | 39 | 2 | 3 | −3 | 4 | 113 | 120 | 1 | −6 | 5 | 4 | 53 | 47 | 2 | 4 | −12 | 5 | 92 | 89 | 2 |
| −5 | 4 | 3 | 53 | 58 | 2 | −2 | −13 | 4 | 48 | 48 | 2 | 4 | −3 | 4 | 29 | 27 | 1 | −5 | 5 | 4 | 36 | 36 | 2 | −3 | −11 | 5 | 81 | 85 | 2 |
| −4 | 4 | 3 | 123 | 122 | 2 | −1 | −13 | 4 | 57 | 55 | 2 | 5 | −3 | 4 | 100 | 98 | 1 | −4 | 5 | 4 | 35 | 36 | 1 | −2 | −11 | 5 | 96 | 95 | 2 |
| −3 | 4 | 3 | 75 | 71 | 1 | 0 | −13 | 4 | 58 | 56 | 2 | 6 | −3 | 4 | 46 | 45 | 1 | −3 | 5 | 4 | 58 | 57 | 1 | −1 | −11 | 5 | 50 | 56 | 2 |
| −2 | 4 | 3 | 358 | 355 | 7 | 2 | −13 | 4 | 89 | 89 | 3 | 7 | −3 | 4 | 41 | 37 | 2 | −2 | 5 | 4 | 138 | 138 | 1 | 0 | −11 | 5 | 61 | 73 | 2 |
| −1 | 4 | 3 | 207 | 214 | 3 | 3 | −13 | 4 | 52 | 55 | 1 | −3 | −2 | 4 | 129 | 139 | 3 | −1 | 5 | 4 | 172 | 178 | 1 | 1 | −11 | 5 | 95 | 95 | 2 |
| 0 | 4 | 3 | 123 | 123 | 1 | −3 | −12 | 4 | 165 | 164 | 4 | −2 | −2 | 4 | 147 | 153 | 3 | 0 | 5 | 4 | 106 | 111 | 1 | 2 | −11 | 5 | 122 | 124 | 3 |
| 1 | 4 | 3 | 136 | 145 | 1 | −2 | −12 | 4 | 102 | 100 | 2 | −1 | −2 | 4 | 550 | 572 | 7 | 1 | 5 | 4 | 142 | 142 | 1 | 3 | −11 | 5 | 88 | 86 | 2 |
| 2 | 4 | 3 | 176 | 168 | 1 | −1 | −12 | 4 | 41 | 44 | 2 | 0 | −2 | 4 | 317 | 325 | 4 | 2 | 5 | 4 | 133 | 132 | 1 | 4 | −11 | 5 | 89 | 84 | 2 |
| 3 | 4 | 3 | 21 | 22 | 1 | 0 | −12 | 4 | 57 | 59 | 2 | 1 | −2 | 4 | 130 | 133 | 1 | 3 | 5 | 4 | 45 | 46 | 1 | −2 | −10 | 5 | 145 | 152 | 2 |
| 4 | 4 | 3 | 81 | 82 | 1 | 1 | −12 | 4 | 51 | 47 | 2 | 2 | −2 | 4 | 328 | 323 | 4 | 4 | 5 | 4 | 78 | 79 | 1 | −1 | −10 | 5 | 96 | 99 | 2 |
| 5 | 4 | 3 | 53 | 55 | 1 | 2 | −12 | 4 | 92 | 90 | 2 | 3 | −2 | 4 | 253 | 258 | 2 | 5 | 5 | 4 | 96 | 97 | 1 | 0 | −10 | 5 | 78 | 79 | 1 |
| 6 | 4 | 3 | 87 | 82 | 1 | 3 | −12 | 4 | 18 | 14 | 3 | 4 | −2 | 4 | 93 | 96 | 1 | 6 | 5 | 4 | 67 | 83 | 2 | 1 | −10 | 5 | 51 | 52 | 1 |
| −6 | 5 | 3 | 27 | 25 | 3 | 4 | −12 | 4 | 156 | 154 | 4 | 5 | −2 | 4 | 163 | 162 | 2 | −6 | 6 | 4 | 42 | 43 | 2 | 2 | −10 | 5 | 137 | 144 | 2 |
| −5 | 5 | 3 | 43 | 46 | 2 | −3 | −11 | 4 | 51 | 50 | 2 | 6 | −2 | 4 | 16 | 14 | 3 | −5 | 6 | 4 | 68 | 74 | 2 | 3 | −10 | 5 | 159 | 160 | 2 |
| −4 | 5 | 3 | 69 | 75 | 1 | −2 | −11 | 4 | 144 | 145 | 3 | 7 | −2 | 4 | 35 | 33 | 2 | −3 | 6 | 4 | 44 | 40 | 1 | 4 | −10 | 5 | 130 | 130 | 3 |
| −3 | 5 | 3 | 121 | 119 | 2 | 0 | −11 | 4 | 57 | 72 | 2 | −2 | −1 | 4 | 31 | 31 | 1 | −2 | 6 | 4 | 209 | 207 | 2 | 5 | −10 | 5 | 69 | 67 | 1 |

TABLE 7-continued

Observed and calculated structure factors for NEL

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −2 | 5 | 3 | 232 | 236 | 3 | 1 | −11 | 4 | 92 | 90 | 2 | −1 | −1 | 4 | 328 | 346 | 3 | −1 | 6 | 4 | 164 | 170 | 1 | −2 | −9 | 5 | 316 | 321 | 5 |
| −1 | 5 | 3 | 206 | 202 | 3 | 2 | −11 | 4 | 25 | 26 | 3 | 0 | −1 | 4 | 237 | 248 | 2 | 0 | 6 | 4 | 49 | 48 | 1 | −1 | −9 | 5 | 86 | 88 | 1 |
| 0 | 5 | 3 | 247 | 244 | 3 | 3 | −11 | 4 | 139 | 135 | 2 | 1 | −1 | 4 | 258 | 272 | 2 | 1 | 6 | 4 | 112 | 112 | 1 | 0 | −9 | 5 | 54 | 43 | 1 |
| 1 | 5 | 3 | 114 | 117 | 1 | 4 | −11 | 4 | 13 | 10 | 5 | 2 | −1 | 4 | 67 | 72 | 1 | 2 | 6 | 4 | 57 | 53 | 1 | 1 | −9 | 5 | 65 | 67 | 1 |
| 2 | 5 | 3 | 225 | 233 | 1 | −3 | −10 | 4 | 90 | 94 | 2 | 3 | −1 | 4 | 77 | 77 | 1 | 3 | 6 | 4 | 142 | 144 | 1 | 2 | −9 | 5 | 252 | 257 | 4 |
| 3 | 5 | 3 | 62 | 60 | 1 | −2 | −10 | 4 | 119 | 114 | 3 | 4 | −1 | 4 | 147 | 144 | 1 | 4 | 6 | 4 | 34 | 33 | 2 | 3 | −9 | 5 | 293 | 295 | 4 |
| 4 | 5 | 3 | 137 | 136 | 1 | −1 | −10 | 4 | 43 | 41 | 1 | 6 | −1 | 4 | 123 | 122 | 2 | −5 | 7 | 4 | 67 | 66 | 2 | 4 | −9 | 5 | 45 | 49 | 1 |
| 5 | 5 | 3 | 48 | 41 | 1 | 0 | −10 | 4 | 94 | 91 | 2 | 7 | −1 | 4 | 69 | 66 | 2 | −4 | 7 | 4 | 55 | 53 | 2 | 5 | −9 | 5 | 26 | 27 | 2 |
| 6 | 5 | 3 | 13 | 13 | 3 | 1 | −10 | 4 | 49 | 47 | 1 | −3 | 0 | 4 | 138 | 144 | 3 | −3 | 7 | 4 | 29 | 30 | 2 | −1 | −8 | 5 | 136 | 131 | 2 |
| −6 | 6 | 3 | 58 | 55 | 2 | 2 | −10 | 4 | 63 | 63 | 2 | −2 | 0 | 4 | 236 | 243 | 3 | −2 | 7 | 4 | 82 | 80 | 1 | 0 | −8 | 5 | 176 | 165 | 2 |
| −5 | 6 | 3 | 65 | 79 | 2 | 3 | −10 | 4 | 77 | 76 | 1 | −1 | 0 | 4 | 125 | 127 | 1 | −1 | 7 | 4 | 90 | 84 | 1 | 1 | −8 | 5 | 71 | 67 | 1 |
| −4 | 6 | 3 | 36 | 47 | 2 | 4 | −10 | 4 | 86 | 87 | 2 | 0 | 0 | 4 | 192 | 195 | 1 | 0 | 7 | 4 | 128 | 129 | 1 | 2 | −8 | 5 | 184 | 189 | 2 |
| −3 | 6 | 3 | 67 | 70 | 1 | 5 | −10 | 4 | 21 | 19 | 2 | 1 | 0 | 4 | 96 | 101 | 1 | 1 | 7 | 4 | 22 | 19 | 1 | 3 | −8 | 5 | 43 | 36 | 1 |
| −2 | 6 | 3 | 83 | 82 | 1 | −2 | −9 | 4 | 171 | 173 | 3 | 2 | 0 | 4 | 80 | 87 | 1 | 2 | 7 | 4 | 123 | 123 | 1 | 4 | −8 | 5 | 283 | 281 | 4 |
| −1 | 6 | 3 | 110 | 115 | 1 | −1 | −9 | 4 | 187 | 179 | 3 | 3 | 0 | 4 | 63 | 56 | 1 | 3 | 7 | 4 | 89 | 89 | 1 | 5 | −8 | 5 | 23 | 20 | 2 |
| 0 | 6 | 3 | 169 | 168 | 1 | 0 | −9 | 4 | 44 | 44 | 1 | 4 | 0 | 4 | 189 | 194 | 1 | 4 | 7 | 4 | 55 | 56 | 2 | 6 | −8 | 5 | 78 | 79 | 2 |
| 1 | 6 | 3 | 164 | 164 | 1 | 1 | −9 | 4 | 136 | 132 | 2 | 5 | 0 | 4 | 165 | 168 | 1 | −5 | 8 | 4 | 68 | 63 | 2 | −1 | −7 | 5 | 140 | 135 | 3 |
| 2 | 6 | 3 | 201 | 196 | 1 | 2 | −9 | 4 | 87 | 81 | 2 | 6 | 0 | 4 | 65 | 64 | 1 | −4 | 8 | 4 | 99 | 99 | 2 | 0 | −7 | 5 | 177 | 165 | 2 |
| 3 | 6 | 3 | 165 | 165 | 1 | 3 | −9 | 4 | 260 | 261 | 3 | 7 | 0 | 4 | 15 | 18 | 3 | −3 | 8 | 4 | 89 | 86 | 1 | 1 | −7 | 5 | 132 | 130 | 1 |
| 4 | 6 | 3 | 178 | 174 | 1 | 4 | −9 | 4 | 111 | 109 | 2 | −3 | 1 | 4 | 143 | 148 | 3 | −2 | 8 | 4 | 97 | 103 | 2 | 2 | −7 | 5 | 130 | 135 | 1 |
| 5 | 6 | 3 | 69 | 71 | 1 | 5 | −9 | 4 | 63 | 64 | 1 | −2 | 1 | 4 | 229 | 223 | 2 | −1 | 8 | 4 | 78 | 82 | 1 | 3 | −7 | 5 | 184 | 187 | 2 |
| −6 | 7 | 3 | 59 | 59 | 2 | −2 | −8 | 4 | 121 | 119 | 3 | −1 | 1 | 4 | 132 | 135 | 1 | 0 | 8 | 4 | 35 | 31 | 1 | 4 | −7 | 5 | 272 | 265 | 4 |
| −5 | 7 | 3 | 45 | 47 | 2 | −1 | −8 | 4 | 310 | 306 | 5 | 0 | 1 | 4 | 401 | 409 | 3 | 1 | 8 | 4 | 89 | 88 | 1 | 5 | −7 | 5 | 102 | 102 | 2 |
| −4 | 7 | 3 | 146 | 145 | 3 | 0 | −8 | 4 | 109 | 98 | 2 | 1 | 1 | 4 | 169 | 165 | 1 | 2 | 8 | 4 | 148 | 151 | 2 | 6 | −7 | 5 | 34 | 48 | 1 |
| −3 | 7 | 3 | 77 | 81 | 1 | 1 | −8 | 4 | 263 | 257 | 3 | 2 | 1 | 4 | 49 | 47 | 1 | 3 | 8 | 4 | 74 | 76 | 1 | −1 | −6 | 5 | 77 | 76 | 2 |
| −2 | 7 | 3 | 144 | 144 | 1 | 2 | −8 | 4 | 178 | 184 | 1 | 3 | 1 | 4 | 185 | 196 | 1 | 4 | 8 | 4 | 77 | 78 | 2 | 0 | −6 | 5 | 508 | 492 | 8 |
| −1 | 7 | 3 | 138 | 139 | 1 | 3 | −8 | 4 | 231 | 231 | 2 | 4 | 1 | 4 | 199 | 195 | 1 | −3 | 9 | 4 | 80 | 79 | 2 | 1 | −6 | 5 | 281 | 278 | 4 |
| 0 | 7 | 3 | 92 | 84 | 1 | 4 | −8 | 4 | 122 | 123 | 2 | 5 | 1 | 4 | 135 | 135 | 1 | −2 | 9 | 4 | 133 | 133 | 2 | 2 | −6 | 5 | 111 | 119 | 1 |
| 3 | −6 | 5 | 205 | 204 | 2 | −6 | 3 | 5 | 29 | 32 | 2 | −1 | −13 | 6 | 68 | 70 | 2 | −2 | −2 | 6 | 181 | 179 | 3 | 4 | 5 | 6 | 72 | 73 | 1 |
| 4 | −6 | 5 | 241 | 234 | 2 | −5 | 3 | 5 | 71 | 73 | 2 | 0 | −13 | 6 | 81 | 85 | 2 | −1 | −2 | 6 | 417 | 421 | 5 | 5 | 5 | 6 | 26 | 25 | 2 |
| 5 | −6 | 5 | 69 | 69 | 1 | −4 | 3 | 5 | 63 | 57 | 1 | 1 | −13 | 6 | 59 | 67 | 2 | 0 | −2 | 6 | 173 | 172 | 2 | −6 | 6 | 6 | 29 | 34 | 2 |
| 6 | −6 | 5 | 65 | 67 | 1 | −3 | 3 | 5 | 137 | 130 | 2 | 2 | −13 | 6 | 78 | 78 | 2 | 1 | −2 | 6 | 146 | 136 | 2 | −5 | 6 | 6 | 65 | 67 | 2 |
| −1 | −5 | 5 | 48 | 39 | 1 | −2 | 3 | 5 | 146 | 147 | 2 | 3 | −13 | 6 | 24 | 28 | 3 | 2 | −2 | 6 | 98 | 97 | 2 | −4 | 6 | 6 | 134 | 132 | 3 |
| 0 | −5 | 5 | 609 | 595 | 9 | −1 | 3 | 5 | 215 | 208 | 2 | −3 | −12 | 6 | 99 | 99 | 2 | 3 | −2 | 6 | 69 | 69 | 1 | −3 | 6 | 6 | 201 | 203 | 3 |
| 1 | −5 | 5 | 342 | 331 | 4 | 0 | 3 | 5 | 413 | 400 | 4 | −2 | −12 | 6 | 91 | 89 | 2 | 4 | −2 | 6 | 47 | 41 | 1 | −2 | 6 | 6 | 327 | 333 | 3 |
| 2 | −5 | 5 | 53 | 48 | 1 | 1 | 3 | 5 | 295 | 288 | 3 | −1 | −12 | 6 | 36 | 43 | 2 | 5 | −2 | 6 | 48 | 46 | 1 | −1 | 6 | 6 | 64 | 63 | 1 |
| 3 | −5 | 5 | 86 | 86 | 1 | 2 | 3 | 5 | 233 | 226 | 2 | 0 | −12 | 6 | 84 | 80 | 2 | 6 | −2 | 6 | 60 | 63 | 2 | 0 | 6 | 6 | 6 | 5 | 6 |
| 4 | −5 | 5 | 243 | 241 | 2 | 3 | 3 | 5 | 117 | 125 | 1 | 1 | −12 | 6 | 32 | 31 | 2 | −2 | −1 | 6 | 250 | 246 | 4 | 1 | 6 | 6 | 173 | 174 | 1 |
| 5 | −5 | 5 | 87 | 92 | 1 | 4 | 3 | 5 | 52 | 50 | 1 | 2 | −12 | 6 | 42 | 40 | 2 | −1 | −1 | 6 | 331 | 335 | 3 | 2 | 6 | 6 | 325 | 327 | 4 |
| 6 | −5 | 5 | 65 | 64 | 1 | 5 | 3 | 5 | 115 | 118 | 2 | 3 | −12 | 6 | 145 | 143 | 3 | 0 | −1 | 6 | 278 | 279 | 3 | 3 | 6 | 6 | 83 | 84 | 1 |
| −2 | −4 | 5 | 146 | 142 | 3 | −6 | 4 | 5 | 2 | 9 | 2 | 4 | −12 | 6 | 71 | 71 | 2 | 1 | −1 | 6 | 334 | 342 | 4 | 4 | 6 | 6 | 85 | 87 | 2 |
| −1 | −4 | 5 | 263 | 265 | 4 | −5 | 4 | 5 | 118 | 119 | 3 | −3 | −11 | 6 | 119 | 120 | 3 | 2 | −1 | 6 | 217 | 217 | 3 | −5 | 7 | 6 | 77 | 77 | 2 |
| 0 | −4 | 5 | 366 | 363 | 5 | −4 | 4 | 5 | 42 | 41 | 1 | −2 | −11 | 6 | 17 | 15 | 4 | 3 | −1 | 6 | 106 | 105 | 1 | −4 | 7 | 6 | 48 | 47 | 2 |
| 1 | −4 | 5 | 221 | 217 | 2 | −3 | 4 | 5 | 65 | 65 | 1 | −1 | −11 | 6 | 182 | 186 | 4 | 4 | −1 | 6 | 105 | 106 | 1 | −3 | 7 | 6 | 134 | 135 | 3 |
| 2 | −4 | 5 | 180 | 188 | 2 | −2 | 4 | 5 | 158 | 150 | 2 | 0 | −11 | 6 | 81 | 91 | 2 | 5 | −1 | 6 | 194 | 209 | 5 | −2 | 7 | 6 | 174 | 172 | 3 |
| 3 | −4 | 5 | 140 | 143 | 1 | −1 | 4 | 5 | 283 | 283 | 4 | 1 | −11 | 6 | 28 | 24 | 3 | 6 | −1 | 6 | 43 | 42 | 1 | −1 | 7 | 6 | 151 | 153 | 1 |
| 4 | −4 | 5 | 52 | 49 | 1 | 0 | 4 | 5 | 157 | 159 | 1 | 2 | −11 | 6 | 80 | 74 | 2 | −3 | 0 | 6 | 113 | 115 | 2 | 0 | 7 | 6 | 134 | 125 | 1 |
| 5 | −4 | 5 | 83 | 79 | 1 | 1 | 4 | 5 | 296 | 305 | 2 | 3 | −11 | 6 | 185 | 184 | 3 | −2 | 0 | 6 | 325 | 316 | 5 | 1 | 7 | 6 | 56 | 57 | 1 |
| 6 | −4 | 5 | 66 | 62 | 2 | 2 | 4 | 5 | 205 | 196 | 1 | 4 | −11 | 6 | 31 | 31 | 3 | −1 | 0 | 6 | 166 | 172 | 2 | 2 | 7 | 6 | 109 | 127 | 2 |

TABLE 7-continued

Observed and calculated structure factors for NEL

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −3 | −3 | 5 | 57 | 56 | 2 | 3 | 4 | 5 | 143 | 140 | 1 | −2 | −10 | 6 | 114 | 116 | 3 | 0 | 0 | 6 | 387 | 387 | 4 | 3 | 7 | 6 | 31 | 35 | 1 |
| −2 | −3 | 5 | 220 | 220 | 5 | 4 | 4 | 5 | 124 | 127 | 2 | −1 | −10 | 6 | 150 | 144 | 2 | 1 | 0 | 6 | 105 | 109 | 1 | 4 | 7 | 6 | 53 | 56 | 2 |
| −1 | −3 | 5 | 174 | 176 | 2 | −6 | 5 | 5 | 14 | 12 | 5 | 0 | −10 | 6 | 39 | 40 | 1 | 2 | 0 | 6 | 150 | 155 | 2 | −2 | 8 | 6 | 150 | 154 | 4 |
| 0 | −3 | 5 | 218 | 210 | 3 | −5 | 5 | 5 | 102 | 117 | 3 | 1 | −10 | 6 | 86 | 83 | 1 | 3 | 0 | 6 | 79 | 74 | 1 | −1 | 8 | 6 | 126 | 125 | 2 |
| 1 | −3 | 5 | 497 | 511 | 5 | −4 | 5 | 5 | 120 | 128 | 3 | 2 | −10 | 6 | 137 | 140 | 3 | 4 | 0 | 6 | 163 | 166 | 1 | 0 | 8 | 6 | 143 | 140 | 2 |
| 2 | −3 | 5 | 236 | 232 | 2 | −3 | 5 | 5 | 78 | 80 | 1 | 3 | −10 | 6 | 148 | 150 | 2 | 5 | 0 | 6 | 132 | 131 | 3 | 1 | 8 | 6 | 38 | 37 | 1 |
| 3 | −3 | 5 | 116 | 116 | 1 | −2 | 5 | 5 | 86 | 84 | 1 | 4 | −10 | 6 | 85 | 85 | 2 | 6 | 0 | 6 | 85 | 83 | 1 | 2 | 8 | 6 | 107 | 111 | 1 |
| 4 | −3 | 5 | 93 | 89 | 1 | −1 | 5 | 5 | 259 | 264 | 2 | 5 | −10 | 6 | 90 | 95 | 1 | −6 | 1 | 6 | 25 | 26 | 3 | 3 | 8 | 6 | 118 | 121 | 2 |
| 5 | −3 | 5 | 35 | 36 | 1 | 0 | 5 | 5 | 92 | 98 | 1 | −2 | −9 | 6 | 90 | 93 | 1 | −5 | 1 | 6 | 78 | 80 | 2 | 4 | 8 | 6 | 51 | 61 | 2 |
| 6 | −3 | 5 | 191 | 189 | 5 | 1 | 5 | 5 | 169 | 164 | 1 | −1 | −9 | 6 | 221 | 221 | 3 | −4 | 1 | 6 | 153 | 152 | 2 | −3 | 9 | 6 | 101 | 97 | 3 |
| −3 | −2 | 5 | 107 | 104 | 3 | 2 | 5 | 5 | 169 | 169 | 1 | 0 | −9 | 6 | 53 | 53 | 1 | −3 | 1 | 6 | 113 | 114 | 2 | −2 | 9 | 6 | 195 | 192 | 4 |
| −2 | −2 | 5 | 295 | 291 | 4 | 3 | 5 | 5 | 262 | 266 | 2 | 1 | −9 | 6 | 159 | 160 | 2 | −2 | 1 | 6 | 254 | 259 | 3 | −1 | 9 | 6 | 112 | 108 | 2 |
| −1 | −2 | 5 | 328 | 328 | 4 | 4 | 5 | 5 | 105 | 107 | 2 | 2 | −9 | 6 | 18 | 15 | 3 | −1 | 1 | 6 | 73 | 71 | 1 | 0 | 9 | 6 | 103 | 103 | 1 |
| 0 | −2 | 5 | 114 | 106 | 1 | −6 | 6 | 5 | 46 | 42 | 2 | 3 | −9 | 6 | 140 | 141 | 2 | 0 | 1 | 6 | 206 | 201 | 2 | 1 | 9 | 6 | 120 | 118 | 1 |
| 1 | −2 | 5 | 209 | 209 | 2 | −5 | 6 | 5 | 55 | 53 | 2 | 4 | −9 | 6 | 63 | 78 | 2 | 1 | 1 | 6 | 24 | 16 | 1 | 2 | 9 | 6 | 71 | 77 | 1 |
| 2 | −2 | 5 | 160 | 157 | 2 | −4 | 6 | 5 | 31 | 39 | 2 | 5 | −9 | 6 | 71 | 71 | 1 | 2 | 1 | 6 | 151 | 139 | 1 | 3 | 9 | 6 | 0 | 8 | 1 |
| 3 | −2 | 5 | 85 | 88 | 1 | −3 | 6 | 5 | 142 | 144 | 2 | −1 | −8 | 6 | 166 | 163 | 2 | 3 | 1 | 6 | 49 | 54 | 1 | −2 | 10 | 6 | 113 | 110 | 3 |
| 4 | −2 | 5 | 23 | 24 | 1 | −2 | 6 | 5 | 31 | 29 | 1 | 0 | −8 | 6 | 65 | 62 | 1 | 4 | 1 | 6 | 180 | 178 | 1 | −1 | 10 | 6 | 157 | 147 | 2 |
| 5 | −2 | 5 | 114 | 118 | 2 | −1 | 6 | 5 | 113 | 112 | 1 | 1 | −8 | 6 | 134 | 131 | 2 | 5 | 1 | 6 | 8 | 13 | 7 | 0 | 10 | 6 | 167 | 161 | 2 |
| 6 | −2 | 5 | 30 | 30 | 1 | 0 | 6 | 5 | 61 | 59 | 1 | 2 | −8 | 6 | 95 | 94 | 1 | 6 | 1 | 6 | 49 | 45 | 1 | 1 | 10 | 6 | 79 | 77 | 1 |
| 7 | −2 | 5 | 58 | 60 | 2 | 1 | 6 | 5 | 144 | 137 | 1 | 3 | −8 | 6 | 268 | 269 | 3 | −6 | 2 | 6 | 58 | 54 | 2 | 2 | 10 | 6 | 77 | 79 | 1 |
| −3 | −1 | 5 | 91 | 88 | 2 | 2 | 6 | 5 | 203 | 195 | 2 | 4 | −8 | 6 | 20 | 25 | 2 | −5 | 2 | 6 | 197 | 199 | 5 | −2 | 11 | 6 | 7 | 9 | 6 |
| −2 | −1 | 5 | 86 | 86 | 1 | 3 | 6 | 5 | 21 | 16 | 1 | 5 | −8 | 6 | 138 | 134 | 2 | −4 | 2 | 6 | 206 | 209 | 3 | −1 | 11 | 6 | 61 | 61 | 1 |
| −1 | −1 | 5 | 247 | 254 | 2 | 4 | 6 | 5 | 29 | 24 | 3 | 6 | −8 | 6 | 52 | 50 | 2 | −3 | 2 | 6 | 35 | 41 | 1 | 0 | 11 | 6 | 95 | 91 | 1 |
| 0 | −1 | 5 | 191 | 186 | 2 | −5 | 7 | 5 | 50 | 46 | 2 | −1 | −7 | 6 | 173 | 180 | 3 | −2 | 2 | 6 | 187 | 181 | 2 | 1 | 11 | 6 | 78 | 92 | 2 |
| 1 | −1 | 5 | 217 | 228 | 2 | −4 | 7 | 5 | 43 | 44 | 2 | 0 | −7 | 6 | 169 | 163 | 2 | −1 | 2 | 6 | 121 | 120 | 1 | −1 | −14 | 7 | 60 | 57 | 2 |
| 2 | −1 | 5 | 110 | 105 | 1 | −3 | 7 | 5 | 160 | 162 | 4 | 1 | −7 | 6 | 331 | 332 | 4 | 0 | 2 | 6 | 591 | 573 | 7 | 0 | −14 | 7 | 85 | 83 | 2 |
| 3 | −1 | 5 | 116 | 113 | 1 | −2 | 7 | 5 | 245 | 254 | 3 | 2 | −7 | 6 | 47 | 54 | 1 | 1 | 2 | 6 | 230 | 236 | 3 | 1 | −14 | 7 | 53 | 59 | 2 |
| 4 | −1 | 5 | 158 | 165 | 1 | −1 | 7 | 5 | 59 | 62 | 1 | 3 | −7 | 6 | 110 | 108 | 1 | 2 | 2 | 6 | 259 | 262 | 2 | −3 | −13 | 7 | 54 | 58 | 2 |
| 5 | −1 | 5 | 125 | 129 | 3 | 0 | 7 | 5 | 123 | 128 | 1 | 4 | −7 | 6 | 63 | 63 | 1 | 3 | 2 | 6 | 28 | 23 | 1 | −2 | −13 | 7 | 81 | 80 | 2 |
| 6 | −1 | 5 | 108 | 111 | 2 | 1 | 7 | 5 | 190 | 192 | 2 | 5 | −7 | 6 | 100 | 99 | 2 | 4 | 2 | 6 | 347 | 350 | 3 | −1 | −13 | 7 | 27 | 28 | 3 |
| −3 | 0 | 5 | 283 | 285 | 6 | 2 | 7 | 5 | 183 | 188 | 2 | 6 | −7 | 6 | 48 | 44 | 2 | 5 | 2 | 6 | 91 | 92 | 1 | 0 | −13 | 7 | 127 | 134 | 3 |
| −2 | 0 | 5 | 23 | 23 | 1 | 3 | 7 | 5 | 89 | 92 | 1 | −1 | −6 | 6 | 274 | 271 | 5 | 6 | 2 | 6 | 41 | 39 | 2 | 1 | −13 | 7 | 85 | 83 | 2 |
| −1 | 0 | 5 | 36 | 41 | 1 | 4 | 7 | 5 | 35 | 33 | 2 | 0 | −6 | 6 | 270 | 261 | 4 | −6 | 3 | 6 | 69 | 68 | 2 | 2 | −13 | 7 | 54 | 56 | 2 |
| 0 | 0 | 5 | 306 | 311 | 2 | −4 | 8 | 5 | 64 | 58 | 2 | 1 | −6 | 6 | 82 | 84 | 1 | −5 | 3 | 6 | 94 | 96 | 2 | 3 | −13 | 7 | 9 | 13 | 8 |
| 1 | 0 | 5 | 109 | 116 | 1 | −2 | 8 | 5 | 30 | 24 | 2 | 2 | −6 | 6 | 148 | 150 | 1 | −4 | 3 | 6 | 102 | 102 | 2 | −3 | −12 | 7 | 57 | 55 | 2 |
| 2 | 0 | 5 | 308 | 302 | 3 | −1 | 8 | 5 | 110 | 113 | 1 | 3 | −6 | 6 | 151 | 157 | 1 | −3 | 3 | 6 | 205 | 215 | 3 | −2 | −12 | 7 | 107 | 106 | 3 |
| 3 | 0 | 5 | 99 | 101 | 1 | 0 | 8 | 5 | 103 | 104 | 1 | 4 | −6 | 6 | 157 | 157 | 1 | −2 | 3 | 6 | 179 | 173 | 2 | −1 | −12 | 7 | 74 | 80 | 2 |
| 4 | 0 | 5 | 43 | 40 | 1 | 1 | 8 | 5 | 194 | 198 | 3 | 5 | −6 | 6 | 127 | 125 | 2 | −1 | 3 | 6 | 122 | 115 | 2 | 0 | −12 | 7 | 18 | 11 | 4 |
| 5 | 0 | 5 | 125 | 123 | 3 | 2 | 8 | 5 | 79 | 78 | 1 | 6 | −6 | 6 | 32 | 34 | 1 | 0 | 3 | 6 | 59 | 54 | 1 | 1 | −12 | 7 | 100 | 109 | 3 |
| 6 | 0 | 5 | 38 | 37 | 1 | 3 | 8 | 5 | 22 | 19 | 2 | −1 | −5 | 6 | 362 | 344 | 8 | 1 | 3 | 6 | 97 | 103 | 1 | 2 | −12 | 7 | 89 | 86 | 2 |
| −4 | 1 | 5 | 116 | 119 | 3 | 4 | 8 | 5 | 35 | 40 | 2 | 0 | −5 | 6 | 124 | 113 | 2 | 2 | 3 | 6 | 180 | 172 | 1 | 3 | −12 | 7 | 118 | 117 | 3 |
| −3 | 1 | 5 | 101 | 103 | 2 | −3 | 9 | 5 | 110 | 107 | 3 | 1 | −5 | 6 | 387 | 368 | 5 | 3 | 3 | 6 | 77 | 79 | 1 | 4 | −12 | 7 | 24 | 18 | 2 |
| −2 | 1 | 5 | 94 | 94 | 1 | −2 | 9 | 5 | 137 | 141 | 3 | 2 | −5 | 6 | 111 | 113 | 1 | 4 | 3 | 6 | 127 | 128 | 2 | −3 | −11 | 7 | 109 | 107 | 3 |
| −1 | 1 | 5 | 332 | 325 | 4 | −1 | 9 | 5 | 67 | 63 | 1 | 3 | −5 | 6 | 176 | 169 | 2 | 5 | 3 | 6 | 15 | 13 | 5 | −2 | −11 | 7 | 288 | 282 | 6 |
| 0 | 1 | 5 | 315 | 324 | 2 | 0 | 9 | 5 | 103 | 100 | 2 | 4 | −5 | 6 | 158 | 159 | 2 | −6 | 4 | 6 | 18 | 19 | 4 | −1 | −11 | 7 | 44 | 45 | 2 |
| 1 | 1 | 5 | 199 | 206 | 2 | 1 | 9 | 5 | 117 | 114 | 2 | 5 | −5 | 6 | 163 | 168 | 2 | −5 | 4 | 6 | 36 | 39 | 2 | 0 | −11 | 7 | 45 | 52 | 2 |
| 2 | 1 | 5 | 182 | 184 | 1 | 2 | 9 | 5 | 119 | 119 | 1 | 6 | −5 | 6 | 22 | 22 | 3 | −4 | 4 | 6 | 49 | 51 | 1 | 1 | −11 | 7 | 88 | 89 | 2 |
| 3 | 1 | 5 | 264 | 266 | 1 | 3 | 9 | 5 | 32 | 24 | 2 | −2 | −4 | 6 | 207 | 206 | 5 | −3 | 4 | 6 | 108 | 109 | 2 | 2 | −11 | 7 | 177 | 179 | 3 |

TABLE 7-continued

| Observed and calculated structure factors for NEL | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
| 4 | 1 | 5 | 100 | 101 | 1 | −3 | 10 | 5 | 23 | 20 | 3 | −1 | −4 | 6 | 305 | 297 | 7 | −2 | 4 | 6 | 266 | 265 | 3 | 3 | −11 | 7 | 44 | 43 | 2 |
| 5 | 1 | 5 | 129 | 127 | 3 | −2 | 10 | 5 | 54 | 52 | 2 | 0 | −4 | 6 | 296 | 280 | 6 | −1 | 4 | 6 | 127 | 130 | 1 | 4 | −11 | 7 | 94 | 89 | 2 |
| 6 | 1 | 5 | 43 | 40 | 1 | −1 | 10 | 5 | 49 | 47 | 1 | 1 | −4 | 6 | 339 | 333 | 5 | 0 | 4 | 6 | 82 | 86 | 1 | −2 | −10 | 7 | 21 | 11 | 3 |
| −7 | 2 | 5 | 51 | 48 | 2 | 0 | 10 | 5 | 51 | 46 | 1 | 2 | −4 | 6 | 64 | 57 | 1 | 1 | 4 | 6 | 106 | 97 | 1 | −1 | −10 | 7 | 52 | 55 | 1 |
| −6 | 2 | 5 | 77 | 76 | 2 | 1 | 10 | 5 | 107 | 108 | 1 | 3 | −4 | 6 | 88 | 88 | 1 | 2 | 4 | 6 | 113 | 115 | 1 | 0 | −10 | 7 | 99 | 100 | 2 |
| −5 | 2 | 5 | 106 | 109 | 2 | 2 | 10 | 5 | 90 | 89 | 1 | 4 | −4 | 6 | 29 | 26 | 2 | 3 | 4 | 6 | 46 | 45 | 1 | 1 | −10 | 7 | 63 | 58 | 1 |
| −4 | 2 | 5 | 139 | 143 | 2 | −2 | 11 | 5 | 21 | 19 | 2 | 5 | −4 | 6 | 186 | 192 | 3 | 4 | 4 | 6 | 187 | 187 | 3 | 2 | −10 | 7 | 125 | 123 | 3 |
| −3 | 2 | 5 | 210 | 213 | 3 | −1 | 11 | 5 | 98 | 94 | 1 | 6 | −4 | 6 | 34 | 30 | 2 | 5 | 4 | 6 | 37 | 36 | 2 | 3 | −10 | 7 | 19 | 10 | 3 |
| −2 | 2 | 5 | 89 | 90 | 1 | 0 | 11 | 5 | 71 | 67 | 1 | −2 | −3 | 6 | 263 | 262 | 4 | −6 | 5 | 6 | 75 | 74 | 2 | 4 | −10 | 7 | 68 | 67 | 2 |
| −1 | 2 | 5 | 213 | 204 | 2 | 1 | 11 | 5 | 73 | 71 | 1 | −1 | −3 | 6 | 255 | 254 | 4 | −5 | 5 | 6 | 102 | 101 | 3 | 5 | −10 | 7 | 137 | 139 | 3 |
| 0 | 2 | 5 | 68 | 69 | 1 | −2 | −14 | 6 | 45 | 42 | 1 | 0 | −3 | 6 | 168 | 155 | 3 | −3 | 5 | 6 | 89 | 88 | 1 | −2 | −9 | 7 | 229 | 235 | 3 |
| 1 | 2 | 5 | 178 | 174 | 2 | −1 | −14 | 6 | 78 | 74 | 2 | 1 | −3 | 6 | 286 | 281 | 3 | −2 | 5 | 6 | 224 | 221 | 2 | −1 | −9 | 7 | 79 | 76 | 1 |
| 2 | 2 | 5 | 165 | 162 | 1 | 0 | −14 | 6 | 47 | 46 | 2 | 2 | −3 | 6 | 124 | 112 | 1 | −1 | 5 | 6 | 51 | 51 | 1 | 0 | −9 | 7 | 67 | 69 | 1 |
| 3 | 2 | 5 | 262 | 268 | 1 | 1 | −14 | 6 | 84 | 85 | 2 | 3 | −3 | 6 | 8 | 2 | 3 | 0 | 5 | 6 | 71 | 76 | 1 | 1 | −9 | 7 | 66 | 62 | 1 |
| 4 | 2 | 5 | 256 | 263 | 1 | 2 | −14 | 6 | 9 | 12 | 9 | 4 | −3 | 6 | 21 | 19 | 2 | 1 | 5 | 6 | 36 | 38 | 1 | 2 | −9 | 7 | 315 | 319 | 5 |
| 5 | 2 | 5 | 98 | 97 | 1 | −3 | −13 | 6 | 166 | 168 | 4 | 5 | −3 | 6 | 42 | 41 | 1 | 2 | 5 | 6 | 196 | 190 | 2 | 3 | −9 | 7 | 131 | 122 | 2 |
| 6 | 2 | 5 | 39 | 36 | 2 | −2 | −13 | 6 | 80 | 78 | 2 | 6 | −3 | 6 | 93 | 92 | 2 | 3 | 5 | 6 | 116 | 121 | 1 | 4 | −9 | 7 | 50 | 50 | 1 |
| 5 | −9 | 7 | 44 | 41 | 1 | 1 | 1 | 7 | 435 | 439 | 6 | −1 | −14 | 8 | 52 | 51 | 2 | 2 | −3 | 8 | 117 | 119 | 1 | −2 | 5 | 8 | 74 | 80 | 1 |
| −1 | −8 | 7 | 77 | 71 | 1 | 2 | 1 | 7 | 61 | 53 | 1 | 0 | −14 | 8 | 99 | 95 | 2 | 3 | −3 | 8 | 58 | 54 | 1 | −1 | 5 | 8 | 39 | 43 | 1 |
| 0 | −8 | 7 | 139 | 135 | 2 | 3 | 1 | 7 | 275 | 274 | 2 | −3 | −13 | 8 | 60 | 62 | 2 | 4 | −3 | 8 | 81 | 80 | 1 | 0 | 5 | 8 | 68 | 61 | 1 |
| 1 | −8 | 7 | 117 | 116 | 1 | 4 | 1 | 7 | 88 | 91 | 1 | −2 | −13 | 8 | 134 | 131 | 3 | 5 | −3 | 8 | 95 | 93 | 1 | 1 | 5 | 8 | 31 | 34 | 1 |
| 2 | −8 | 7 | 155 | 155 | 2 | 5 | 1 | 7 | 78 | 75 | 2 | −1 | −13 | 8 | 146 | 142 | 3 | 6 | −3 | 8 | 113 | 107 | 3 | 2 | 5 | 8 | 89 | 106 | 2 |
| 3 | −8 | 7 | 92 | 85 | 1 | 6 | 1 | 7 | 54 | 54 | 1 | 0 | −13 | 8 | 50 | 51 | 2 | −3 | −2 | 8 | 62 | 56 | 2 | 3 | 5 | 8 | 38 | 37 | 1 |
| 4 | −8 | 7 | 77 | 79 | 1 | −6 | 2 | 7 | 50 | 47 | 2 | 3 | −13 | 8 | 56 | 58 | 2 | −2 | −2 | 8 | 142 | 136 | 3 | 4 | 5 | 8 | 44 | 46 | 2 |
| 5 | −8 | 7 | 145 | 147 | 2 | −5 | 2 | 7 | 162 | 162 | 4 | −3 | −12 | 8 | 59 | 60 | 2 | −1 | −2 | 8 | 159 | 151 | 2 | −5 | 6 | 8 | 13 | 18 | 6 |
| −1 | −7 | 7 | 194 | 188 | 3 | −4 | 2 | 7 | 95 | 93 | 1 | −2 | −12 | 8 | 112 | 112 | 3 | 0 | −2 | 8 | 36 | 34 | 2 | −4 | 6 | 8 | 24 | 23 | 3 |
| 0 | −7 | 7 | 224 | 213 | 3 | −3 | 2 | 7 | 181 | 177 | 3 | −1 | −12 | 8 | 143 | 150 | 4 | 1 | −2 | 8 | 140 | 134 | 1 | −3 | 6 | 8 | 86 | 84 | 2 |
| 1 | −7 | 7 | 42 | 39 | 1 | −2 | 2 | 7 | 178 | 176 | 2 | 0 | −12 | 8 | 82 | 73 | 2 | 2 | −2 | 8 | 184 | 188 | 1 | −2 | 6 | 8 | 120 | 118 | 3 |
| 2 | −7 | 7 | 43 | 46 | 1 | −1 | 2 | 7 | 111 | 110 | 1 | 1 | −12 | 8 | 61 | 61 | 2 | 3 | −2 | 8 | 74 | 66 | 1 | −1 | 6 | 8 | 6 | 3 | 6 |
| 3 | −7 | 7 | 59 | 51 | 1 | 0 | 2 | 7 | 84 | 85 | 1 | 2 | −12 | 8 | 168 | 172 | 4 | 4 | −2 | 8 | 103 | 105 | 2 | 0 | 6 | 8 | 95 | 91 | 1 |
| 4 | −7 | 7 | 160 | 159 | 2 | 1 | 2 | 7 | 56 | 50 | 1 | 3 | −12 | 8 | 48 | 51 | 2 | 5 | −2 | 8 | 36 | 38 | 1 | 1 | 6 | 8 | 107 | 108 | 1 |
| 5 | −7 | 7 | 121 | 118 | 2 | 2 | 2 | 7 | 149 | 149 | 1 | 4 | −12 | 8 | 18 | 20 | 3 | 6 | −2 | 8 | 138 | 138 | 2 | 2 | 6 | 8 | 131 | 133 | 2 |
| 6 | −7 | 7 | 128 | 128 | 3 | 3 | 2 | 7 | 48 | 44 | 1 | −3 | −11 | 8 | 64 | 62 | 2 | −3 | −1 | 8 | 111 | 112 | 2 | 3 | 6 | 8 | 69 | 70 | 1 |
| −1 | −6 | 7 | 143 | 140 | 3 | 4 | 2 | 7 | 32 | 31 | 1 | −2 | −11 | 8 | 122 | 115 | 3 | −2 | −1 | 8 | 69 | 63 | 1 | 4 | 6 | 8 | 19 | 14 | 3 |
| 0 | −6 | 7 | 40 | 41 | 1 | 5 | 2 | 7 | 44 | 41 | 1 | −1 | −11 | 8 | 46 | 47 | 2 | −1 | −1 | 8 | 446 | 443 | 6 | −2 | 7 | 8 | 114 | 109 | 3 |
| 1 | −6 | 7 | 35 | 28 | 1 | −6 | 3 | 7 | 48 | 48 | 2 | 0 | −11 | 8 | 24 | 29 | 3 | 0 | −1 | 8 | 96 | 86 | 1 | −1 | 7 | 8 | 83 | 82 | 2 |
| 2 | −6 | 7 | 204 | 204 | 2 | −5 | 3 | 7 | 136 | 135 | 3 | 1 | −11 | 8 | 39 | 33 | 2 | 1 | −1 | 8 | 244 | 247 | 3 | 0 | 7 | 8 | 157 | 158 | 2 |
| 3 | −6 | 7 | 93 | 89 | 1 | −4 | 3 | 7 | 75 | 74 | 1 | 2 | −11 | 8 | 46 | 47 | 2 | 2 | −1 | 8 | 76 | 75 | 1 | 1 | 7 | 8 | 102 | 107 | 1 |
| 4 | −6 | 7 | 42 | 44 | 1 | −3 | 3 | 7 | 114 | 122 | 2 | 3 | −11 | 8 | 36 | 31 | 2 | 3 | −1 | 8 | 163 | 160 | 1 | 2 | 7 | 8 | 70 | 70 | 1 |
| 5 | −6 | 7 | 164 | 162 | 2 | −2 | 3 | 7 | 192 | 186 | 3 | 4 | −11 | 8 | 93 | 87 | 2 | 4 | −1 | 8 | 123 | 120 | 2 | 3 | 7 | 8 | 47 | 47 | 1 |
| 6 | −6 | 7 | 31 | 31 | 1 | −1 | 3 | 7 | 23 | 24 | 1 | −2 | −10 | 8 | 155 | 148 | 3 | 5 | −1 | 8 | 59 | 59 | 1 | −2 | 8 | 8 | 105 | 105 | 3 |
| −2 | −5 | 7 | 98 | 103 | 2 | 0 | 3 | 7 | 48 | 54 | 1 | −1 | −10 | 8 | 195 | 199 | 3 | 6 | −1 | 8 | 33 | 29 | 1 | −1 | 8 | 8 | 46 | 46 | 1 |
| −1 | −5 | 7 | 189 | 179 | 4 | 1 | 3 | 7 | 99 | 88 | 1 | 0 | −10 | 8 | 45 | 42 | 1 | −5 | 0 | 8 | 38 | 35 | 2 | 0 | 8 | 8 | 19 | 22 | 2 |
| 0 | −5 | 7 | 238 | 212 | 5 | 2 | 3 | 7 | 108 | 103 | 1 | 1 | −10 | 8 | 105 | 100 | 2 | −4 | 0 | 8 | 167 | 173 | 3 | 1 | 8 | 8 | 122 | 121 | 1 |
| 1 | −5 | 7 | 47 | 48 | 1 | 3 | 3 | 7 | 322 | 324 | 3 | 2 | −10 | 8 | 219 | 214 | 5 | −3 | 0 | 8 | 68 | 68 | 1 | 2 | 8 | 8 | 31 | 27 | 1 |
| 2 | −5 | 7 | 89 | 84 | 1 | 4 | 3 | 7 | 83 | 84 | 1 | 3 | −10 | 8 | 61 | 62 | 2 | −2 | 0 | 8 | 115 | 110 | 2 | 3 | 8 | 8 | 90 | 91 | 2 |
| 3 | −5 | 7 | 224 | 230 | 2 | 5 | 3 | 7 | 80 | 81 | 2 | 4 | −10 | 8 | 87 | 80 | 2 | −1 | 0 | 8 | 123 | 121 | 1 | −2 | 9 | 8 | 27 | 22 | 3 |
| 4 | −5 | 7 | 133 | 137 | 1 | −6 | 4 | 7 | 79 | 80 | 2 | 5 | −10 | 8 | 54 | 52 | 2 | 0 | 0 | 8 | 427 | 414 | 5 | −1 | 9 | 8 | 136 | 130 | 2 |
| 5 | −5 | 7 | 108 | 112 | 1 | −5 | 4 | 7 | 145 | 149 | 3 | −2 | −9 | 8 | 214 | 219 | 3 | 1 | 0 | 8 | 138 | 135 | 1 | 0 | 9 | 8 | 52 | 52 | 1 |

TABLE 7-continued

Observed and calculated structure factors for NEL

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 6 | −5 | 7 | 32 | 31 | 2 | −4 | 4 | 7 | 22 | 26 | 3 | −1 | −9 | 8 | 261 | 256 | 4 | 2 | 0 | 8 | 149 | 143 | 1 | 1 | 9 | 8 | 58 | 57 | 1 |
| −2 | −4 | 7 | 50 | 49 | 1 | −3 | 4 | 7 | 118 | 110 | 2 | 0 | −9 | 8 | 135 | 135 | 2 | 3 | 0 | 8 | 58 | 60 | 1 | −1 | 10 | 8 | 14 | 6 | 3 |
| −1 | −4 | 7 | 462 | 435 | 10 | −2 | 4 | 7 | 54 | 50 | 1 | 1 | −9 | 8 | 94 | 96 | 2 | 4 | 0 | 8 | 145 | 139 | 2 | 0 | 10 | 8 | 33 | 36 | 1 |
| 0 | −4 | 7 | 97 | 106 | 2 | −1 | 4 | 7 | 204 | 206 | 2 | 2 | −9 | 8 | 248 | 252 | 6 | 5 | 0 | 8 | 49 | 50 | 2 | −2 | −14 | 9 | 10 | 9 | 8 |
| 1 | −4 | 7 | 111 | 115 | 1 | 0 | 4 | 7 | 63 | 62 | 1 | 3 | −9 | 8 | 83 | 78 | 2 | 6 | 0 | 8 | 68 | 62 | 1 | −1 | −14 | 9 | 23 | 23 | 3 |
| 2 | −4 | 7 | 98 | 94 | 1 | 1 | 4 | 7 | 347 | 344 | 3 | 4 | −9 | 8 | 105 | 107 | 2 | −6 | 1 | 8 | 56 | 54 | 2 | 0 | −14 | 9 | 66 | 65 | 2 |
| 3 | −4 | 7 | 59 | 58 | 1 | 2 | 4 | 7 | 89 | 81 | 1 | 5 | −9 | 8 | 95 | 94 | 2 | −5 | 1 | 8 | 22 | 19 | 3 | −3 | −13 | 9 | 17 | 17 | 3 |
| 4 | −4 | 7 | 121 | 124 | 1 | 3 | 4 | 7 | 231 | 230 | 3 | −2 | −8 | 8 | 100 | 96 | 2 | −4 | 1 | 8 | 292 | 296 | 4 | −2 | −13 | 9 | 45 | 42 | 2 |
| 5 | −4 | 7 | 31 | 29 | 1 | 4 | 4 | 7 | 142 | 141 | 2 | −1 | −8 | 8 | 49 | 45 | 1 | −3 | 1 | 8 | 63 | 64 | 1 | −1 | −13 | 9 | 58 | 56 | 2 |
| 6 | −4 | 7 | 84 | 82 | 2 | 5 | 4 | 7 | 54 | 48 | 2 | 0 | −8 | 8 | 130 | 123 | 2 | −2 | 1 | 8 | 150 | 148 | 2 | 0 | −13 | 9 | 61 | 59 | 2 |
| −2 | −3 | 7 | 99 | 97 | 1 | −6 | 5 | 7 | 85 | 87 | 2 | 1 | −8 | 8 | 76 | 79 | 1 | −1 | 1 | 8 | 269 | 265 | 3 | −3 | −12 | 9 | 0 | 6 | 1 |
| −1 | −3 | 7 | 145 | 147 | 2 | −5 | 5 | 7 | 138 | 137 | 3 | 2 | −8 | 8 | 89 | 92 | 2 | 0 | 1 | 8 | 99 | 90 | 1 | −2 | −12 | 9 | 49 | 45 | 2 |
| 0 | −3 | 7 | 198 | 182 | 4 | −3 | 5 | 7 | 189 | 187 | 4 | 3 | −8 | 8 | 136 | 135 | 2 | 1 | 1 | 8 | 99 | 93 | 1 | −1 | −12 | 9 | 105 | 111 | 3 |
| 1 | −3 | 7 | 87 | 87 | 1 | −2 | 5 | 7 | 61 | 59 | 1 | 4 | −8 | 8 | 78 | 81 | 2 | 2 | 1 | 8 | 66 | 65 | 1 | 0 | −12 | 9 | 0 | 13 | 1 |
| 2 | −3 | 7 | 92 | 92 | 1 | −1 | 5 | 7 | 80 | 85 | 1 | 5 | −8 | 8 | 44 | 42 | 1 | 3 | 1 | 8 | 76 | 75 | 1 | 1 | −12 | 9 | 44 | 44 | 2 |
| 3 | −3 | 7 | 118 | 123 | 1 | 0 | 5 | 7 | 86 | 81 | 1 | −2 | −7 | 8 | 97 | 95 | 2 | 4 | 1 | 8 | 105 | 103 | 1 | 3 | −12 | 9 | 60 | 57 | 2 |
| 4 | −3 | 7 | 46 | 41 | 1 | 1 | 5 | 7 | 103 | 107 | 1 | −1 | −7 | 8 | 43 | 45 | 1 | 5 | 1 | 8 | 37 | 37 | 2 | −3 | −11 | 9 | 60 | 60 | 2 |
| 5 | −3 | 7 | 106 | 104 | 1 | 2 | 5 | 7 | 77 | 74 | 1 | 0 | −7 | 8 | 107 | 104 | 2 | −6 | 2 | 8 | 60 | 57 | 2 | −2 | −11 | 9 | 43 | 38 | 2 |
| 6 | −3 | 7 | 52 | 46 | 2 | 3 | 5 | 7 | 207 | 203 | 2 | 1 | −7 | 8 | 70 | 63 | 1 | −5 | 2 | 8 | 88 | 87 | 2 | −1 | −11 | 9 | 90 | 90 | 2 |
| −2 | −2 | 7 | 76 | 75 | 1 | 4 | 5 | 7 | 22 | 19 | 2 | 2 | −7 | 8 | 41 | 40 | 1 | −4 | 2 | 8 | 200 | 199 | 3 | 0 | −11 | 9 | 63 | 71 | 2 |
| −1 | −2 | 7 | 309 | 308 | 4 | −5 | 6 | 7 | 50 | 49 | 2 | 3 | −7 | 8 | 120 | 113 | 1 | −3 | 2 | 8 | 187 | 188 | 3 | 1 | −11 | 9 | 104 | 102 | 3 |
| 0 | −2 | 7 | 216 | 205 | 3 | −4 | 6 | 7 | 81 | 80 | 2 | 4 | −7 | 8 | 70 | 70 | 2 | −2 | 2 | 8 | 42 | 38 | 1 | 2 | −11 | 9 | 126 | 124 | 3 |
| 1 | −2 | 7 | 260 | 252 | 3 | −3 | 6 | 7 | 72 | 72 | 2 | 5 | −7 | 8 | 83 | 83 | 1 | −1 | 2 | 8 | 33 | 33 | 1 | 3 | −11 | 9 | 77 | 80 | 2 |
| 2 | −2 | 7 | 177 | 173 | 2 | −2 | 6 | 7 | 237 | 238 | 3 | 6 | −7 | 8 | 10 | 8 | 10 | 0 | 2 | 8 | 254 | 246 | 2 | 4 | −11 | 9 | 101 | 100 | 2 |
| 3 | −2 | 7 | 33 | 40 | 1 | −1 | 6 | 7 | 141 | 142 | 1 | −2 | −6 | 8 | 180 | 184 | 4 | 1 | 2 | 8 | 83 | 84 | 1 | −3 | −10 | 9 | 63 | 63 | 2 |
| 4 | −2 | 7 | 77 | 82 | 1 | 0 | 6 | 7 | 167 | 161 | 1 | −1 | −6 | 8 | 71 | 75 | 1 | 2 | 2 | 8 | 113 | 104 | 1 | −2 | −10 | 9 | 118 | 107 | 3 |
| 5 | −2 | 7 | 124 | 118 | 2 | 1 | 6 | 7 | 34 | 33 | 1 | 0 | −6 | 8 | 416 | 414 | 5 | 3 | 2 | 8 | 139 | 141 | 1 | −1 | −10 | 9 | 99 | 96 | 2 |
| 6 | −2 | 7 | 54 | 52 | 2 | 2 | 6 | 7 | 70 | 81 | 1 | 1 | −6 | 8 | 91 | 92 | 1 | 4 | 2 | 8 | 33 | 33 | 1 | 1 | −10 | 9 | 113 | 115 | 3 |
| −3 | −1 | 7 | 94 | 92 | 2 | 3 | 6 | 7 | 32 | 30 | 1 | 2 | −6 | 8 | 120 | 127 | 1 | 5 | 2 | 8 | 55 | 54 | 2 | 2 | −10 | 9 | 36 | 33 | 3 |
| −2 | −1 | 7 | 302 | 296 | 5 | 4 | 6 | 7 | 56 | 55 | 2 | 3 | −6 | 8 | 101 | 99 | 1 | −6 | 3 | 8 | 32 | 31 | 2 | 3 | −10 | 9 | 23 | 24 | 3 |
| −1 | −1 | 7 | 177 | 166 | 2 | −4 | 7 | 7 | 24 | 28 | 3 | 4 | −6 | 8 | 107 | 109 | 2 | −4 | 3 | 8 | 205 | 235 | 6 | 4 | −10 | 9 | 16 | 11 | 5 |
| 0 | −1 | 7 | 12 | 10 | 1 | −3 | 7 | 7 | 113 | 115 | 2 | 5 | −6 | 8 | 65 | 65 | 1 | −3 | 3 | 8 | 67 | 64 | 1 | −2 | −9 | 9 | 95 | 97 | 2 |
| 1 | −1 | 7 | 494 | 499 | 7 | −2 | 7 | 7 | 84 | 85 | 2 | 6 | −6 | 8 | 6 | 9 | 6 | −2 | 3 | 8 | 94 | 94 | 1 | −1 | −9 | 9 | 73 | 73 | 1 |
| 2 | −1 | 7 | 99 | 95 | 1 | −1 | 7 | 7 | 101 | 103 | 2 | −2 | −5 | 8 | 77 | 72 | 2 | −1 | 3 | 8 | 169 | 171 | 1 | 0 | −9 | 9 | 67 | 66 | 1 |
| 3 | −1 | 7 | 27 | 25 | 1 | 0 | 7 | 7 | 81 | 79 | 1 | −1 | −5 | 8 | 83 | 85 | 2 | 0 | 3 | 8 | 100 | 91 | 1 | 1 | −9 | 9 | 73 | 72 | 1 |
| 4 | −1 | 7 | 149 | 152 | 1 | 1 | 7 | 7 | 26 | 28 | 1 | 0 | −5 | 8 | 95 | 96 | 1 | 1 | 3 | 8 | 158 | 151 | 1 | 2 | −9 | 9 | 108 | 100 | 3 |
| 5 | −1 | 7 | 109 | 114 | 2 | 2 | 7 | 7 | 58 | 58 | 1 | 1 | −5 | 8 | 168 | 161 | 2 | 2 | 3 | 8 | 176 | 168 | 1 | 3 | −9 | 9 | 73 | 74 | 2 |
| 6 | −1 | 7 | 11 | 14 | 4 | 3 | 7 | 7 | 150 | 153 | 2 | 2 | −5 | 8 | 102 | 97 | 1 | 3 | 3 | 8 | 215 | 220 | 2 | 4 | −9 | 9 | 36 | 35 | 3 |
| −3 | 0 | 7 | 105 | 102 | 1 | 4 | 7 | 7 | 64 | 62 | 2 | 3 | −5 | 8 | 36 | 34 | 1 | 4 | 3 | 8 | 159 | 157 | 2 | 5 | −9 | 9 | 58 | 57 | 1 |
| −2 | 0 | 7 | 137 | 137 | 2 | −2 | 8 | 7 | 67 | 66 | 2 | 4 | −5 | 8 | 151 | 149 | 2 | 5 | 3 | 8 | 71 | 72 | 2 | −2 | −8 | 9 | 89 | 85 | 1 |
| −1 | 0 | 7 | 333 | 332 | 4 | −1 | 8 | 7 | 115 | 112 | 2 | 5 | −5 | 8 | 36 | 39 | 1 | −6 | 4 | 8 | 38 | 39 | 2 | −1 | −8 | 9 | 81 | 80 | 1 |
| 0 | 0 | 7 | 139 | 135 | 1 | 0 | 8 | 7 | 33 | 36 | 1 | 6 | −5 | 8 | 33 | 37 | 2 | −5 | 4 | 8 | 109 | 107 | 3 | 0 | −8 | 9 | 151 | 150 | 2 |
| 1 | 0 | 7 | 115 | 123 | 2 | 1 | 8 | 7 | 76 | 76 | 1 | −2 | −4 | 8 | 64 | 62 | 1 | −4 | 4 | 8 | 75 | 83 | 2 | 1 | −8 | 9 | 201 | 205 | 3 |
| 2 | 0 | 7 | 85 | 87 | 1 | 2 | 8 | 7 | 59 | 60 | 1 | −1 | −4 | 8 | 173 | 164 | 3 | −3 | 4 | 8 | 105 | 111 | 1 | 2 | −8 | 9 | 74 | 78 | 2 |
| 3 | 0 | 7 | 124 | 123 | 1 | 3 | 8 | 7 | 111 | 115 | 2 | 0 | −4 | 8 | 136 | 144 | 2 | −2 | 4 | 8 | 192 | 188 | 2 | 3 | −8 | 9 | 65 | 60 | 2 |
| 4 | 0 | 7 | 158 | 162 | 1 | −2 | 9 | 7 | 33 | 26 | 2 | 1 | −4 | 8 | 55 | 53 | 1 | −1 | 4 | 8 | 235 | 242 | 2 | 4 | −8 | 9 | 21 | 23 | 2 |
| 5 | 0 | 7 | 59 | 60 | 2 | −1 | 9 | 7 | 99 | 96 | 2 | 2 | −4 | 8 | 44 | 45 | 1 | 0 | 4 | 8 | 16 | 14 | 1 | 5 | −8 | 9 | 64 | 63 | 1 |
| 6 | 0 | 7 | 36 | 35 | 1 | 0 | 9 | 7 | 5 | 5 | 5 | 3 | −4 | 8 | 138 | 138 | 1 | 1 | 4 | 8 | 223 | 225 | 2 | −2 | −7 | 9 | 90 | 92 | 1 |
| −6 | 1 | 7 | 89 | 91 | 2 | 1 | 9 | 7 | 50 | 50 | 1 | 4 | −4 | 8 | 91 | 96 | 1 | 2 | 4 | 8 | 164 | 160 | 1 | −1 | −7 | 9 | 154 | 152 | 2 |

TABLE 7-continued

Observed and calculated structure factors for NEL

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −5 | 1 | 7 | 177 | 180 | 4 | 2 | 9 | 7 | 73 | 70 | 1 | 5 | −4 | 8 | 69 | 68 | 1 | 3 | 4 | 8 | 68 | 68 | 1 | 0 | −7 | 9 | 113 | 108 | 2 |
| −4 | 1 | 7 | 117 | 119 | 2 | −2 | 10 | 7 | 43 | 35 | 2 | 6 | −4 | 8 | 85 | 79 | 2 | 4 | 4 | 8 | 40 | 38 | 1 | 1 | −7 | 9 | 135 | 131 | 1 |
| −3 | 1 | 7 | 149 | 156 | 2 | −1 | 10 | 7 | 45 | 40 | 1 | −2 | −3 | 8 | 83 | 74 | 2 | 5 | 4 | 8 | 16 | 14 | 4 | 2 | −7 | 9 | 185 | 182 | 2 |
| −2 | 1 | 7 | 284 | 285 | 3 | 0 | 10 | 7 | 103 | 104 | 1 | −1 | −3 | 8 | 104 | 101 | 1 | −5 | 5 | 8 | 21 | 21 | 3 | 3 | −7 | 9 | 13 | 14 | 4 |
| −1 | 1 | 7 | 241 | 225 | 2 | 1 | 10 | 7 | 22 | 22 | 1 | 0 | −3 | 8 | 189 | 164 | 4 | −4 | 5 | 8 | 21 | 20 | 3 | 4 | −7 | 9 | 84 | 84 | 2 |
| 0 | 1 | 7 | 78 | 83 | 1 | −2 | −14 | 8 | 89 | 92 | 2 | 1 | −3 | 8 | 230 | 230 | 2 | −3 | 5 | 8 | 114 | 110 | 3 | 5 | −7 | 9 | 8 | 7 | 8 |
| −2 | −6 | 9 | 56 | 59 | 1 | 0 | 2 | 9 | 227 | 221 | 2 | −2 | −9 | 10 | 41 | 37 | 2 | 3 | 0 | 10 | 155 | 162 | 2 | 3 | −11 | 11 | 7 | 10 | 7 |
| −1 | −6 | 9 | 71 | 75 | 1 | 1 | 2 | 9 | 70 | 70 | 1 | −1 | −9 | 10 | 60 | 66 | 1 | 4 | 0 | 10 | 44 | 47 | 1 | 4 | −11 | 11 | 44 | 45 | 2 |
| 0 | −6 | 9 | 99 | 100 | 2 | 2 | 2 | 9 | 121 | 120 | 1 | 0 | −9 | 10 | 55 | 55 | 1 | 5 | 0 | 10 | 151 | 148 | 4 | −3 | −10 | 11 | 30 | 30 | 2 |
| 1 | −6 | 9 | 124 | 127 | 1 | 3 | 2 | 9 | 66 | 77 | 1 | 1 | −9 | 10 | 75 | 80 | 1 | −6 | 1 | 10 | 40 | 39 | 2 | −2 | −10 | 11 | 99 | 102 | 3 |
| 2 | −6 | 9 | 186 | 190 | 2 | 4 | 2 | 9 | 106 | 107 | 1 | 2 | −9 | 10 | 98 | 91 | 3 | −5 | 1 | 10 | 41 | 42 | 2 | −1 | −10 | 11 | 152 | 174 | 4 |
| 3 | −6 | 9 | 78 | 74 | 1 | 5 | 2 | 9 | 24 | 23 | 3 | 3 | −9 | 10 | 58 | 58 | 2 | −4 | 1 | 10 | 78 | 78 | 2 | 0 | −10 | 11 | 37 | 43 | 2 |
| 4 | −6 | 9 | 121 | 122 | 2 | −6 | 3 | 9 | 81 | 75 | 2 | 4 | −9 | 10 | 50 | 48 | 2 | −3 | 1 | 10 | 53 | 55 | 1 | 1 | −10 | 11 | 148 | 151 | 4 |
| 5 | −6 | 9 | 29 | 27 | 1 | −5 | 3 | 9 | 46 | 42 | 2 | 5 | −9 | 10 | 33 | 35 | 2 | −2 | 1 | 10 | 112 | 115 | 1 | 2 | −10 | 11 | 148 | 156 | 4 |
| 6 | −6 | 9 | 34 | 33 | 2 | −4 | 3 | 9 | 126 | 137 | 3 | −2 | −8 | 10 | 74 | 78 | 1 | −1 | 1 | 10 | 71 | 68 | 1 | 3 | −10 | 11 | 17 | 20 | 4 |
| −2 | −5 | 9 | 49 | 42 | 1 | −3 | 3 | 9 | 262 | 267 | 3 | −1 | −8 | 10 | 157 | 156 | 2 | 0 | 1 | 10 | 68 | 67 | 1 | 4 | −10 | 11 | 58 | 57 | 2 |
| −1 | −5 | 9 | 249 | 259 | 4 | −2 | 3 | 9 | 115 | 114 | 1 | 0 | −8 | 10 | 143 | 139 | 2 | 1 | 1 | 10 | 86 | 86 | 1 | −3 | −9 | 11 | 103 | 102 | 3 |
| 0 | −5 | 9 | 89 | 93 | 1 | −1 | 3 | 9 | 40 | 37 | 1 | 1 | −8 | 10 | 114 | 109 | 2 | 2 | 1 | 10 | 95 | 96 | 1 | −2 | −9 | 11 | 148 | 141 | 3 |
| 1 | −5 | 9 | 163 | 176 | 2 | 0 | 3 | 9 | 34 | 30 | 1 | 2 | −8 | 10 | 30 | 31 | 2 | 3 | 1 | 10 | 81 | 83 | 3 | −1 | −9 | 11 | 48 | 51 | 2 |
| 2 | −5 | 9 | 63 | 68 | 1 | 1 | 3 | 9 | 141 | 142 | 1 | 3 | −8 | 10 | 89 | 88 | 2 | 4 | 1 | 10 | 70 | 69 | 1 | 1 | −9 | 11 | 135 | 145 | 3 |
| 3 | −5 | 9 | 110 | 112 | 1 | 2 | 3 | 9 | 45 | 45 | 1 | 4 | −8 | 10 | 42 | 40 | 1 | 5 | 1 | 10 | 71 | 71 | 2 | 2 | −9 | 11 | 116 | 117 | 3 |
| 4 | −5 | 9 | 118 | 116 | 2 | 3 | 3 | 9 | 101 | 115 | 2 | 5 | −8 | 10 | 26 | 24 | 2 | −6 | 2 | 10 | 26 | 27 | 2 | 3 | −9 | 11 | 50 | 49 | 2 |
| 5 | −5 | 9 | 54 | 56 | 1 | 4 | 3 | 9 | 89 | 89 | 1 | −2 | −7 | 10 | 252 | 251 | 4 | −5 | 2 | 10 | 45 | 47 | 2 | 4 | −9 | 11 | 22 | 21 | 4 |
| 6 | −5 | 9 | 21 | 18 | 3 | 5 | 3 | 9 | 24 | 22 | 3 | −1 | −7 | 10 | 114 | 118 | 2 | −4 | 2 | 10 | 66 | 66 | 2 | −3 | −8 | 11 | 34 | 31 | 2 |
| −2 | −4 | 9 | 61 | 61 | 1 | −5 | 4 | 9 | 87 | 84 | 2 | 0 | −7 | 10 | 275 | 271 | 4 | −3 | 2 | 10 | 88 | 97 | 2 | −2 | −8 | 11 | 121 | 121 | 2 |
| −1 | −4 | 9 | 150 | 142 | 2 | −3 | 4 | 9 | 138 | 137 | 3 | 1 | −7 | 10 | 158 | 164 | 2 | −2 | 2 | 10 | 54 | 57 | 1 | −1 | −8 | 11 | 207 | 213 | 3 |
| 0 | −4 | 9 | 94 | 92 | 1 | −2 | 4 | 9 | 57 | 58 | 1 | 2 | −7 | 10 | 237 | 241 | 4 | −1 | 2 | 10 | 96 | 97 | 1 | 0 | −8 | 11 | 160 | 157 | 2 |
| 1 | −4 | 9 | 58 | 64 | 1 | −1 | 4 | 9 | 57 | 61 | 1 | 3 | −7 | 10 | 117 | 125 | 2 | 0 | 2 | 10 | 56 | 55 | 1 | 1 | −8 | 11 | 56 | 64 | 1 |
| 2 | −4 | 9 | 50 | 57 | 1 | 0 | 4 | 9 | 44 | 46 | 1 | 4 | −7 | 10 | 46 | 47 | 2 | 1 | 2 | 10 | 63 | 64 | 1 | 2 | −8 | 11 | 101 | 97 | 3 |
| 3 | −4 | 9 | 188 | 192 | 2 | 1 | 4 | 9 | 88 | 86 | 1 | 5 | −7 | 10 | 82 | 82 | 1 | 2 | 2 | 10 | 56 | 59 | 1 | 3 | −8 | 11 | 76 | 76 | 2 |
| 4 | −4 | 9 | 155 | 166 | 2 | 2 | 4 | 9 | 114 | 123 | 1 | −2 | −6 | 10 | 67 | 66 | 1 | 3 | 2 | 10 | 14 | 14 | 3 | 4 | −8 | 11 | 92 | 90 | 2 |
| 5 | −4 | 9 | 96 | 96 | 1 | 3 | 4 | 9 | 84 | 84 | 1 | −1 | −6 | 10 | 90 | 85 | 1 | 4 | 2 | 10 | 31 | 27 | 1 | −3 | −7 | 11 | 38 | 35 | 2 |
| 6 | −4 | 9 | 37 | 38 | 2 | 4 | 4 | 9 | 23 | 21 | 3 | 0 | −6 | 10 | 139 | 132 | 2 | 5 | 2 | 10 | 24 | 23 | 3 | −2 | −7 | 11 | 279 | 288 | 4 |
| −2 | −3 | 9 | 171 | 172 | 2 | −5 | 5 | 9 | 103 | 101 | 2 | 1 | −6 | 10 | 110 | 103 | 1 | −5 | 3 | 10 | 20 | 18 | 3 | −1 | −7 | 11 | 78 | 83 | 1 |
| −1 | −3 | 9 | 21 | 15 | 1 | −4 | 5 | 9 | 20 | 19 | 4 | 2 | −6 | 10 | 71 | 67 | 1 | −4 | 3 | 10 | 58 | 65 | 2 | 0 | −7 | 11 | 86 | 84 | 1 |
| 0 | −3 | 9 | 127 | 121 | 1 | −3 | 5 | 9 | 138 | 130 | 3 | 3 | −6 | 10 | 211 | 219 | 2 | −2 | 3 | 10 | 67 | 70 | 1 | 1 | −7 | 11 | 50 | 51 | 1 |
| 1 | −3 | 9 | 241 | 247 | 2 | −2 | 5 | 9 | 82 | 80 | 1 | 4 | −6 | 10 | 56 | 58 | 2 | −1 | 3 | 10 | 155 | 164 | 1 | 2 | −7 | 11 | 248 | 264 | 4 |
| 2 | −3 | 9 | 107 | 107 | 1 | −1 | 5 | 9 | 113 | 116 | 2 | 5 | −6 | 10 | 120 | 121 | 2 | 0 | 3 | 10 | 110 | 110 | 1 | 3 | −7 | 11 | 31 | 30 | 2 |
| 3 | −3 | 9 | 67 | 66 | 1 | 0 | 5 | 9 | 11 | 6 | 5 | −2 | −5 | 10 | 13 | 14 | 3 | 1 | 3 | 10 | 79 | 82 | 1 | 4 | −7 | 11 | 113 | 116 | 2 |
| 4 | −3 | 9 | 81 | 78 | 1 | 1 | 5 | 9 | 114 | 118 | 1 | −1 | −5 | 10 | 55 | 64 | 1 | 2 | 3 | 10 | 79 | 82 | 1 | 5 | −7 | 11 | 78 | 78 | 1 |
| 5 | −3 | 9 | 100 | 95 | 1 | 2 | 5 | 9 | 106 | 102 | 2 | 0 | −5 | 10 | 75 | 72 | 1 | 3 | 3 | 10 | 36 | 35 | 1 | −3 | −6 | 11 | 138 | 141 | 3 |
| 6 | −3 | 9 | 81 | 78 | 2 | 3 | 5 | 9 | 63 | 57 | 1 | 1 | −5 | 10 | 90 | 95 | 1 | 4 | 3 | 10 | 53 | 50 | 2 | −2 | −6 | 11 | 117 | 108 | 2 |
| −3 | −2 | 9 | 97 | 100 | 1 | 4 | 5 | 9 | 38 | 38 | 2 | 2 | −5 | 10 | 110 | 107 | 1 | −5 | 4 | 10 | 85 | 84 | 2 | −1 | −6 | 11 | 204 | 206 | 3 |
| −2 | −2 | 9 | 98 | 104 | 1 | −5 | 6 | 9 | 18 | 18 | 3 | 3 | −5 | 10 | 82 | 87 | 1 | −4 | 4 | 10 | 60 | 58 | 2 | 0 | −6 | 11 | 123 | 112 | 2 |
| −1 | −2 | 9 | 193 | 194 | 2 | −4 | 6 | 9 | 51 | 52 | 2 | 4 | −5 | 10 | 151 | 149 | 4 | −3 | 4 | 10 | 110 | 107 | 3 | 1 | −6 | 11 | 140 | 145 | 1 |
| 0 | −2 | 9 | 92 | 99 | 1 | −3 | 6 | 9 | 59 | 59 | 2 | 5 | −5 | 10 | 92 | 92 | 1 | −2 | 4 | 10 | 219 | 231 | 3 | 2 | −6 | 11 | 150 | 152 | 2 |
| 1 | −2 | 9 | 106 | 113 | 1 | −2 | 6 | 9 | 75 | 71 | 2 | −2 | −4 | 10 | 97 | 99 | 1 | −1 | 4 | 10 | 29 | 31 | 2 | 3 | −6 | 11 | 93 | 96 | 1 |
| 2 | −2 | 9 | 18 | 14 | 1 | −1 | 6 | 9 | 126 | 128 | 2 | −1 | −4 | 10 | 95 | 99 | 1 | 0 | 4 | 10 | 177 | 176 | 3 | 4 | −6 | 11 | 100 | 101 | 2 |
| 3 | −2 | 9 | 17 | 19 | 2 | 0 | 6 | 9 | 48 | 52 | 1 | 0 | −4 | 10 | 125 | 124 | 1 | 1 | 4 | 10 | 46 | 44 | 1 | 5 | −6 | 11 | 40 | 38 | 1 |

TABLE 7-continued

Observed and calculated structure factors for NEL

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 4 | −2 | 9 | 99 | 117 | 3 | 1 | 6 | 9 | 70 | 73 | 1 | 1 | −4 | 10 | 71 | 66 | 1 | 2 | 4 | 10 | 79 | 79 | 1 | −3 | −5 | 11 | 33 | 33 | 2 |
| 5 | −2 | 9 | 138 | 134 | 2 | 2 | 6 | 9 | 114 | 115 | 1 | 2 | −4 | 10 | 75 | 77 | 1 | 3 | 4 | 10 | 50 | 47 | 1 | −2 | −5 | 11 | 159 | 158 | 2 |
| 6 | −2 | 9 | 59 | 60 | 1 | 3 | 6 | 9 | 7 | 5 | 7 | 3 | −4 | 10 | 98 | 103 | 1 | 4 | 4 | 10 | 23 | 18 | 3 | −1 | −5 | 11 | 125 | 125 | 2 |
| −4 | −1 | 9 | 137 | 138 | 3 | 4 | 6 | 9 | 64 | 71 | 2 | 4 | −4 | 10 | 19 | 16 | 2 | −5 | 5 | 10 | 22 | 25 | 3 | 0 | −5 | 11 | 111 | 110 | 2 |
| −3 | −1 | 9 | 134 | 139 | 2 | −2 | 7 | 9 | 92 | 91 | 2 | 5 | −4 | 10 | 75 | 72 | 1 | −4 | 5 | 10 | 51 | 52 | 2 | 1 | −5 | 11 | 86 | 86 | 1 |
| −2 | −1 | 9 | 85 | 83 | 1 | −1 | 7 | 9 | 106 | 106 | 2 | −3 | −3 | 10 | 29 | 27 | 1 | −3 | 5 | 10 | 61 | 61 | 2 | 2 | −5 | 11 | 93 | 96 | 1 |
| −1 | −1 | 9 | 245 | 244 | 2 | 0 | 7 | 9 | 34 | 30 | 1 | −2 | −3 | 10 | 86 | 83 | 1 | −2 | 5 | 10 | 91 | 95 | 2 | 3 | −5 | 11 | 103 | 110 | 1 |
| 0 | −1 | 9 | 26 | 24 | 1 | 1 | 7 | 9 | 73 | 72 | 1 | −1 | −3 | 10 | 201 | 209 | 3 | −1 | 5 | 10 | 120 | 118 | 3 | 4 | −5 | 11 | 85 | 85 | 2 |
| 1 | −1 | 9 | 113 | 118 | 1 | 2 | 7 | 9 | 91 | 89 | 1 | 0 | −3 | 10 | 14 | 8 | 2 | 0 | 5 | 10 | 22 | 23 | 2 | 5 | −5 | 11 | 22 | 21 | 2 |
| 2 | −1 | 9 | 72 | 68 | 1 | 3 | 7 | 9 | 39 | 38 | 2 | 1 | −3 | 10 | 23 | 25 | 1 | 1 | 5 | 10 | 148 | 145 | 2 | −3 | −4 | 11 | 60 | 61 | 1 |
| 3 | −1 | 9 | 44 | 42 | 1 | −2 | 8 | 9 | 57 | 51 | 2 | 2 | −3 | 10 | 129 | 125 | 1 | 2 | 5 | 10 | 76 | 76 | 1 | −2 | −4 | 11 | 81 | 81 | 1 |
| 4 | −1 | 9 | 25 | 20 | 2 | −1 | 8 | 9 | 29 | 29 | 2 | 3 | −3 | 10 | 57 | 57 | 1 | 3 | 5 | 10 | 128 | 122 | 1 | −1 | −4 | 11 | 15 | 19 | 3 |
| 5 | −1 | 9 | 87 | 89 | 1 | 0 | 8 | 9 | 43 | 42 | 1 | 4 | −3 | 10 | 179 | 184 | 3 | 4 | 5 | 10 | 30 | 29 | 2 | 0 | −4 | 11 | 106 | 105 | 1 |
| 6 | −1 | 9 | 48 | 48 | 1 | 1 | 8 | 9 | 27 | 27 | 1 | 5 | −3 | 10 | 231 | 224 | 3 | −2 | 6 | 10 | 67 | 68 | 2 | 1 | −4 | 11 | 164 | 167 | 2 |
| −6 | 0 | 9 | 58 | 53 | 2 | 2 | 8 | 9 | 86 | 81 | 1 | −4 | −2 | 10 | 118 | 119 | 3 | −1 | 6 | 10 | 68 | 69 | 2 | 2 | −4 | 11 | 60 | 60 | 2 |
| −5 | 0 | 9 | 78 | 77 | 2 | −1 | 9 | 9 | 66 | 68 | 1 | −3 | −2 | 10 | 94 | 95 | 1 | 0 | 6 | 10 | 65 | 62 | 1 | 3 | −4 | 11 | 64 | 63 | 1 |
| −4 | 0 | 9 | 103 | 104 | 2 | 0 | 9 | 9 | 32 | 31 | 1 | −2 | −2 | 10 | 41 | 44 | 1 | 1 | 6 | 10 | 55 | 52 | 1 | 4 | −4 | 11 | 203 | 194 | 3 |
| −3 | 0 | 9 | 235 | 237 | 4 | 1 | 9 | 9 | 63 | 62 | 2 | −1 | −2 | 10 | 50 | 58 | 1 | 2 | 6 | 10 | 79 | 77 | 1 | 5 | −4 | 11 | 39 | 36 | 1 |
| −2 | 0 | 9 | 163 | 167 | 2 | −1 | −14 | 10 | 62 | 59 | 2 | 0 | −2 | 10 | 70 | 64 | 1 | 3 | 6 | 10 | 101 | 96 | 1 | −4 | −3 | 11 | 183 | 184 | 4 |
| −1 | 0 | 9 | 237 | 243 | 2 | −3 | −13 | 10 | 44 | 49 | 2 | 1 | −2 | 10 | 110 | 115 | 1 | −2 | 7 | 10 | 100 | 98 | 3 | −3 | −3 | 11 | 94 | 99 | 1 |
| 0 | 0 | 9 | 79 | 77 | 1 | −2 | −13 | 10 | 19 | 15 | 3 | 2 | −2 | 10 | 67 | 66 | 1 | −1 | 7 | 10 | 62 | 61 | 1 | −2 | −3 | 11 | 114 | 114 | 2 |
| 1 | 0 | 9 | 330 | 332 | 3 | −1 | −13 | 10 | 69 | 65 | 2 | 3 | −2 | 10 | 77 | 79 | 1 | 0 | 7 | 10 | 69 | 65 | 1 | −1 | −3 | 11 | 60 | 62 | 1 |
| 2 | 0 | 9 | 107 | 110 | 1 | 0 | −13 | 10 | 100 | 93 | 2 | 4 | −2 | 10 | 129 | 131 | 2 | 1 | 7 | 10 | 72 | 72 | 1 | 0 | −3 | 11 | 462 | 460 | 5 |
| 3 | 0 | 9 | 7 | 14 | 6 | −3 | −12 | 10 | 20 | 20 | 3 | 5 | −2 | 10 | 152 | 155 | 3 | 2 | 7 | 10 | 53 | 51 | 1 | 1 | −3 | 11 | 128 | 134 | 1 |
| 4 | 0 | 9 | 23 | 22 | 2 | −2 | −12 | 10 | 25 | 25 | 3 | −5 | −1 | 10 | 112 | 116 | 3 | −2 | 8 | 10 | 29 | 27 | 2 | 2 | −3 | 11 | 97 | 98 | 1 |
| 5 | 0 | 9 | 116 | 122 | 3 | −1 | −12 | 10 | 44 | 43 | 2 | −4 | −1 | 10 | 192 | 190 | 4 | −1 | 8 | 10 | 29 | 28 | 2 | 3 | −3 | 11 | 87 | 88 | 2 |
| −6 | 1 | 9 | 18 | 19 | 3 | 0 | −12 | 10 | 67 | 64 | 2 | −3 | −1 | 10 | 18 | 16 | 2 | 0 | 8 | 10 | 86 | 87 | 1 | 4 | −3 | 11 | 143 | 145 | 2 |
| −5 | 1 | 9 | 31 | 27 | 2 | 1 | −12 | 10 | 41 | 45 | 2 | −2 | −1 | 10 | 116 | 115 | 1 | 1 | 8 | 10 | 62 | 60 | 1 | 5 | −3 | 11 | 36 | 36 | 1 |
| −4 | 1 | 9 | 156 | 153 | 4 | 3 | −12 | 10 | 33 | 36 | 2 | −1 | −1 | 10 | 277 | 282 | 3 | −1 | −14 | 11 | 98 | 98 | 2 | −5 | −2 | 11 | 92 | 94 | 2 |
| −3 | 1 | 9 | 213 | 213 | 3 | −3 | −11 | 10 | 33 | 34 | 2 | 0 | −1 | 10 | 84 | 86 | 1 | −2 | −13 | 11 | 25 | 18 | 2 | −4 | −2 | 11 | 118 | 112 | 3 |
| −2 | 1 | 9 | 111 | 106 | 1 | −2 | −11 | 10 | 103 | 102 | 2 | 1 | −1 | 10 | 135 | 133 | 1 | −1 | −13 | 11 | 58 | 55 | 2 | −3 | −2 | 11 | 115 | 119 | 2 |
| −1 | 1 | 9 | 35 | 32 | 1 | −1 | −11 | 10 | 26 | 29 | 2 | 2 | −1 | 10 | 155 | 147 | 1 | 0 | −13 | 11 | 27 | 25 | 3 | −2 | −2 | 11 | 19 | 14 | 2 |
| 0 | 1 | 9 | 94 | 85 | 1 | 0 | −11 | 10 | 110 | 128 | 3 | 3 | −1 | 10 | 161 | 166 | 1 | −3 | −12 | 11 | 88 | 85 | 2 | −1 | −2 | 11 | 91 | 89 | 1 |
| 1 | 1 | 9 | 137 | 129 | 1 | 1 | −11 | 10 | 92 | 94 | 2 | 4 | −1 | 10 | 77 | 77 | 1 | −2 | −12 | 11 | 21 | 19 | 3 | 0 | −2 | 11 | 196 | 194 | 2 |
| 2 | 1 | 9 | 117 | 121 | 1 | 2 | −11 | 10 | 56 | 56 | 2 | 5 | −1 | 10 | 164 | 153 | 4 | −1 | −12 | 11 | 68 | 71 | 2 | 1 | −2 | 11 | 139 | 136 | 1 |
| 3 | 1 | 9 | 127 | 130 | 1 | 3 | −11 | 10 | 81 | 77 | 2 | −6 | 0 | 10 | 80 | 76 | 2 | 0 | −12 | 11 | 58 | 55 | 2 | 2 | −2 | 11 | 57 | 57 | 1 |
| 4 | 1 | 9 | 147 | 150 | 2 | 4 | −11 | 10 | 47 | 43 | 2 | −5 | 0 | 10 | 47 | 47 | 2 | 1 | −12 | 11 | 62 | 62 | 2 | 3 | −2 | 11 | 39 | 41 | 2 |
| 5 | 1 | 9 | 50 | 47 | 2 | −3 | −10 | 10 | 14 | 13 | 6 | −4 | 0 | 10 | 163 | 158 | 4 | 3 | −12 | 11 | 53 | 54 | 2 | 4 | −2 | 11 | 84 | 83 | 1 |
| −6 | 2 | 9 | 111 | 103 | 3 | −2 | −10 | 10 | 152 | 148 | 3 | −3 | 0 | 10 | 45 | 41 | 1 | −3 | −11 | 11 | 34 | 33 | 2 | 5 | −2 | 11 | 21 | 24 | 1 |
| −5 | 2 | 9 | 15 | 19 | 5 | −1 | −10 | 10 | 95 | 104 | 3 | −2 | 0 | 10 | 102 | 104 | 1 | −2 | −11 | 11 | 141 | 145 | 3 | −6 | −1 | 11 | 86 | 82 | 2 |
| −4 | 2 | 9 | 88 | 90 | 2 | 1 | −10 | 10 | 135 | 142 | 3 | −1 | 0 | 10 | 171 | 171 | 2 | −1 | −11 | 11 | 91 | 99 | 3 | −5 | −1 | 11 | 126 | 127 | 3 |
| −3 | 2 | 9 | 159 | 157 | 2 | 2 | −10 | 10 | 64 | 64 | 2 | 0 | 0 | 10 | 33 | 31 | 1 | 0 | −11 | 11 | 67 | 73 | 2 | −4 | −1 | 11 | 39 | 36 | 2 |
| −2 | 2 | 9 | 207 | 205 | 2 | 3 | −10 | 10 | 59 | 57 | 2 | 1 | 0 | 10 | 111 | 108 | 1 | 1 | −11 | 11 | 50 | 46 | 2 | −3 | −1 | 11 | 93 | 97 | 1 |
| −1 | 2 | 9 | 58 | 60 | 1 | 4 | −10 | 10 | 85 | 82 | 2 | 2 | 0 | 10 | 100 | 96 | 1 | 2 | −11 | 11 | 123 | 124 | 3 | −2 | −1 | 11 | 174 | 164 | 3 |
| −1 | −1 | 11 | 13 | 11 | 3 | 0 | −11 | 12 | 25 | 25 | 3 | −4 | −1 | 12 | 97 | 95 | 2 | 3 | −9 | 13 | 108 | 109 | 3 | −5 | 1 | 13 | 31 | 32 | 2 |
| 0 | −1 | 11 | 117 | 117 | 1 | 1 | −11 | 12 | 81 | 84 | 2 | −3 | −1 | 12 | 90 | 93 | 2 | 4 | −9 | 13 | 63 | 60 | 2 | −4 | 1 | 13 | 33 | 34 | 2 |
| 1 | −1 | 11 | 160 | 166 | 1 | 2 | −11 | 12 | 0 | 1 | 1 | −2 | −1 | 12 | 110 | 112 | 2 | −3 | −8 | 13 | 42 | 42 | 2 | −3 | 1 | 13 | 106 | 108 | 3 |

TABLE 7-continued

| Observed and calculated structure factors for NEL | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
| 2 | −1 | 11 | 58 | 52 | 1 | 3 | −11 | 12 | 48 | 56 | 2 | −1 | −1 | 12 | 260 | 259 | 4 | −2 | −8 | 13 | 66 | 60 | 2 | −2 | 1 | 13 | 11 | 9 | 9 |
| 3 | −1 | 11 | 72 | 72 | 1 | −3 | −10 | 12 | 32 | 28 | 2 | 0 | −1 | 12 | 53 | 52 | 1 | −1 | −8 | 13 | 64 | 67 | 2 | −1 | 1 | 13 | 137 | 130 | 3 |
| 4 | −1 | 11 | 42 | 40 | 1 | −2 | −10 | 12 | 39 | 36 | 2 | 1 | −1 | 12 | 144 | 145 | 1 | 0 | −8 | 13 | 62 | 63 | 2 | 0 | 1 | 13 | 108 | 103 | 3 |
| 5 | −1 | 11 | 53 | 54 | 2 | −1 | −10 | 12 | 44 | 50 | 2 | 2 | −1 | 12 | 57 | 57 | 1 | 1 | −8 | 13 | 102 | 104 | 2 | 1 | 1 | 13 | 32 | 26 | 1 |
| −6 | 0 | 11 | 84 | 86 | 2 | 0 | −10 | 12 | 25 | 19 | 3 | 3 | −1 | 12 | 178 | 178 | 3 | 2 | −8 | 13 | 128 | 131 | 3 | 2 | 1 | 13 | 161 | 170 | 2 |
| −5 | 0 | 11 | 62 | 62 | 2 | 1 | −10 | 12 | 8 | 4 | 8 | 4 | −1 | 12 | 33 | 27 | 1 | 3 | −8 | 13 | 18 | 16 | 5 | 3 | 1 | 13 | 26 | 26 | 2 |
| −4 | 0 | 11 | 35 | 36 | 2 | 2 | −10 | 12 | 60 | 63 | 2 | −5 | 0 | 12 | 147 | 142 | 3 | 4 | −8 | 13 | 88 | 89 | 2 | 4 | 1 | 13 | 23 | 24 | 2 |
| −3 | 0 | 11 | 88 | 89 | 1 | 3 | −10 | 12 | 63 | 65 | 2 | −4 | 0 | 12 | 22 | 23 | 3 | −4 | −7 | 13 | 91 | 93 | 2 | −5 | 2 | 13 | 31 | 32 | 2 |
| −2 | 0 | 11 | 66 | 61 | 1 | 4 | −10 | 12 | 38 | 36 | 2 | −3 | 0 | 12 | 98 | 108 | 3 | −3 | −7 | 13 | 26 | 24 | 3 | −4 | 2 | 13 | 111 | 108 | 2 |
| −1 | 0 | 11 | 154 | 149 | 2 | −3 | −9 | 12 | 13 | 15 | 6 | −2 | 0 | 12 | 65 | 70 | 1 | −2 | −7 | 13 | 161 | 166 | 4 | −3 | 2 | 13 | 110 | 110 | 2 |
| 0 | 0 | 11 | 218 | 221 | 2 | −2 | −9 | 12 | 66 | 65 | 2 | −1 | 0 | 12 | 120 | 119 | 2 | −1 | −7 | 13 | 74 | 81 | 2 | −2 | 2 | 13 | 43 | 38 | 2 |
| 1 | 0 | 11 | 134 | 133 | 1 | −1 | −9 | 12 | 99 | 122 | 3 | 0 | 0 | 12 | 87 | 88 | 1 | 0 | −7 | 13 | 171 | 159 | 4 | −1 | 2 | 13 | 82 | 79 | 2 |
| 2 | 0 | 11 | 136 | 143 | 1 | 0 | −9 | 12 | 68 | 75 | 2 | 1 | 0 | 12 | 90 | 85 | 1 | 1 | −7 | 13 | 35 | 32 | 1 | 0 | 2 | 13 | 26 | 24 | 3 |
| 3 | 0 | 11 | 115 | 120 | 2 | 1 | −9 | 12 | 54 | 54 | 2 | 2 | 0 | 12 | 46 | 44 | 1 | 2 | −7 | 13 | 89 | 93 | 3 | 1 | 2 | 13 | 44 | 41 | 1 |
| 4 | 0 | 11 | 43 | 41 | 1 | 2 | −9 | 12 | 57 | 54 | 2 | 3 | 0 | 12 | 80 | 82 | 1 | 3 | −7 | 13 | 100 | 103 | 3 | 2 | 2 | 13 | 51 | 51 | 1 |
| 5 | 0 | 11 | 61 | 62 | 2 | 3 | −9 | 12 | 67 | 69 | 2 | 4 | 0 | 12 | 45 | 41 | 1 | 4 | −7 | 13 | 88 | 82 | 2 | 3 | 2 | 13 | 77 | 76 | 1 |
| −6 | 1 | 11 | 52 | 50 | 2 | 4 | −9 | 12 | 39 | 32 | 2 | −5 | 1 | 12 | 93 | 92 | 2 | −4 | −6 | 13 | 103 | 105 | 2 | −4 | 3 | 13 | 37 | 32 | 2 |
| −5 | 1 | 11 | 39 | 40 | 2 | −3 | −8 | 12 | 153 | 153 | 4 | −4 | 1 | 12 | 42 | 43 | 2 | −3 | −6 | 13 | 113 | 111 | 3 | −3 | 3 | 13 | 54 | 53 | 2 |
| −4 | 1 | 11 | 140 | 141 | 3 | −2 | −8 | 12 | 87 | 89 | 2 | −2 | 1 | 12 | 201 | 209 | 3 | −2 | −6 | 13 | 60 | 64 | 2 | −1 | 3 | 13 | 52 | 60 | 2 |
| −3 | 1 | 11 | 118 | 135 | 2 | −1 | −8 | 12 | 198 | 208 | 4 | −1 | 1 | 12 | 81 | 82 | 1 | −1 | −6 | 13 | 143 | 148 | 4 | 0 | 3 | 13 | 53 | 52 | 1 |
| −2 | 1 | 11 | 154 | 157 | 2 | 0 | −8 | 12 | 106 | 109 | 3 | 0 | 1 | 12 | 234 | 249 | 4 | 0 | −6 | 13 | 312 | 317 | 4 | 1 | 3 | 13 | 43 | 40 | 1 |
| −1 | 1 | 11 | 236 | 238 | 2 | 1 | −8 | 12 | 218 | 222 | 5 | 1 | 1 | 12 | 37 | 33 | 1 | 1 | −6 | 13 | 105 | 102 | 2 | 2 | 3 | 13 | 86 | 82 | 1 |
| 0 | 1 | 11 | 87 | 85 | 1 | 2 | −8 | 12 | 44 | 54 | 3 | 2 | 1 | 12 | 99 | 101 | 1 | 2 | −6 | 13 | 105 | 109 | 3 | 3 | 3 | 13 | 64 | 64 | 1 |
| 1 | 1 | 11 | 167 | 167 | 1 | 3 | −8 | 12 | 109 | 105 | 3 | 3 | 1 | 12 | 78 | 78 | 1 | 3 | −6 | 13 | 52 | 53 | 2 | −1 | 4 | 13 | 81 | 81 | 2 |
| 2 | 1 | 11 | 239 | 244 | 3 | 4 | −8 | 12 | 54 | 53 | 2 | 4 | 1 | 12 | 27 | 28 | 1 | 4 | −6 | 13 | 79 | 78 | 1 | 0 | 4 | 13 | 43 | 40 | 1 |
| 3 | 1 | 11 | 100 | 95 | 2 | −3 | −7 | 12 | 115 | 117 | 3 | −5 | 2 | 12 | 71 | 72 | 2 | −4 | −5 | 13 | 124 | 122 | 3 | 1 | 4 | 13 | 87 | 85 | 1 |
| 4 | 1 | 11 | 24 | 21 | 1 | −2 | −7 | 12 | 135 | 129 | 3 | −4 | 2 | 12 | 79 | 78 | 2 | −3 | −5 | 13 | 99 | 98 | 2 | 2 | 4 | 13 | 33 | 31 | 1 |
| 5 | 1 | 11 | 15 | 20 | 4 | −1 | −7 | 12 | 160 | 158 | 2 | −3 | 2 | 12 | 157 | 158 | 4 | −2 | −5 | 13 | 50 | 49 | 2 | −1 | 5 | 13 | 109 | 106 | 3 |
| −5 | 2 | 11 | 52 | 49 | 2 | 0 | −7 | 12 | 127 | 124 | 2 | −1 | 2 | 12 | 104 | 109 | 2 | −1 | −5 | 13 | 193 | 204 | 3 | 0 | 5 | 13 | 42 | 42 | 1 |
| −4 | 2 | 11 | 117 | 121 | 3 | 1 | −7 | 12 | 186 | 186 | 2 | 0 | 2 | 12 | 233 | 230 | 4 | 0 | −5 | 13 | 427 | 428 | 7 | 1 | 5 | 13 | 89 | 84 | 1 |
| −3 | 2 | 11 | 20 | 28 | 3 | 2 | −7 | 12 | 69 | 65 | 2 | 1 | 2 | 12 | 125 | 124 | 1 | 1 | −5 | 13 | 226 | 232 | 5 | −1 | 6 | 13 | 37 | 38 | 2 |
| −2 | 2 | 11 | 75 | 72 | 1 | 3 | −7 | 12 | 123 | 130 | 3 | 2 | 2 | 12 | 68 | 65 | 1 | 2 | −5 | 13 | 101 | 103 | 2 | 0 | 6 | 13 | 39 | 37 | 2 |
| −1 | 2 | 11 | 83 | 88 | 1 | 4 | −7 | 12 | 80 | 81 | 1 | 3 | 2 | 12 | 120 | 119 | 1 | 3 | −5 | 13 | 100 | 101 | 3 | −2 | −12 | 14 | 8 | 12 | 7 |
| 0 | 2 | 11 | 76 | 71 | 1 | −3 | −6 | 12 | 154 | 157 | 3 | 4 | 2 | 12 | 51 | 47 | 2 | 4 | −5 | 13 | 112 | 112 | 2 | −1 | −12 | 14 | 17 | 20 | 4 |
| 1 | 2 | 11 | 98 | 97 | 1 | −2 | −6 | 12 | 66 | 61 | 1 | −5 | 3 | 12 | 45 | 43 | 2 | −5 | −4 | 13 | 121 | 117 | 3 | 0 | −12 | 14 | 57 | 55 | 2 |
| 2 | 2 | 11 | 126 | 129 | 2 | −1 | −6 | 12 | 160 | 164 | 2 | −4 | 3 | 12 | 81 | 75 | 2 | −4 | −4 | 13 | 28 | 22 | 3 | −3 | −11 | 14 | 32 | 36 | 2 |
| 3 | 2 | 11 | 160 | 161 | 2 | 0 | −6 | 12 | 121 | 117 | 2 | −3 | 3 | 12 | 76 | 79 | 2 | −3 | −4 | 13 | 31 | 31 | 2 | −2 | −11 | 14 | 65 | 68 | 2 |
| 4 | 2 | 11 | 31 | 33 | 1 | 1 | −6 | 12 | 147 | 153 | 2 | −1 | 3 | 12 | 126 | 121 | 3 | −2 | −4 | 13 | 82 | 83 | 2 | −1 | −11 | 14 | 60 | 61 | 2 |
| −5 | 3 | 11 | 39 | 38 | 2 | 2 | −6 | 12 | 147 | 152 | 2 | 0 | 3 | 12 | 91 | 85 | 1 | −1 | −4 | 13 | 16 | 14 | 2 | 0 | −11 | 14 | 22 | 22 | 3 |
| −4 | 3 | 11 | 15 | 13 | 5 | 3 | −6 | 12 | 67 | 69 | 2 | 1 | 3 | 12 | 73 | 83 | 1 | 0 | −4 | 13 | 65 | 69 | 1 | −3 | −10 | 14 | 14 | 14 | 5 |
| −3 | 3 | 11 | 96 | 94 | 2 | 4 | −6 | 12 | 75 | 73 | 1 | 2 | 3 | 12 | 54 | 52 | 1 | 1 | −4 | 13 | 129 | 131 | 2 | −2 | −10 | 14 | 73 | 73 | 2 |
| −2 | 3 | 11 | 88 | 89 | 2 | 5 | −6 | 12 | 56 | 59 | 1 | 3 | 3 | 12 | 25 | 22 | 1 | 2 | −4 | 13 | 137 | 138 | 2 | −1 | −10 | 14 | 55 | 50 | 2 |
| −1 | 3 | 11 | 55 | 53 | 1 | −3 | −5 | 12 | 184 | 183 | 4 | −4 | 4 | 12 | 32 | 27 | 2 | 3 | −4 | 13 | 93 | 101 | 2 | 0 | −10 | 14 | 26 | 24 | 3 |
| 0 | 3 | 11 | 37 | 29 | 1 | −2 | −5 | 12 | 111 | 113 | 2 | −3 | 4 | 12 | 63 | 66 | 2 | 4 | −4 | 13 | 69 | 62 | 2 | 2 | −10 | 14 | 67 | 76 | 2 |
| 1 | 3 | 11 | 77 | 73 | 1 | −1 | −5 | 12 | 145 | 147 | 2 | −1 | 4 | 12 | 89 | 92 | 2 | −5 | −3 | 13 | 124 | 118 | 3 | 3 | −10 | 14 | 102 | 100 | 2 |
| 2 | 3 | 11 | 75 | 81 | 1 | 0 | −5 | 12 | 122 | 113 | 2 | 0 | 4 | 12 | 47 | 43 | 1 | −4 | −3 | 13 | 132 | 134 | 3 | −4 | −9 | 14 | 63 | 64 | 2 |

TABLE 7-continued

Observed and calculated structure factors for NEL

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 3 | 3 | 11 | 104 | 102 | 1 | 1 | −5 | 12 | 217 | 225 | 3 | 1 | 4 | 12 | 81 | 76 | 1 | −3 | −3 | 13 | 105 | 103 | 2 | −3 | −9 | 14 | 70 | 67 | 2 |
| 4 | 3 | 11 | 18 | 12 | 3 | 2 | −5 | 12 | 54 | 53 | 2 | 2 | 4 | 12 | 69 | 69 | 1 | −2 | −3 | 13 | 122 | 127 | 3 | −2 | −9 | 14 | 33 | 27 | 2 |
| −5 | 4 | 11 | 21 | 20 | 3 | 3 | −5 | 12 | 129 | 133 | 2 | 3 | 4 | 12 | 76 | 74 | 1 | −1 | −3 | 13 | 23 | 21 | 2 | −1 | −9 | 14 | 26 | 26 | 2 |
| −4 | 4 | 11 | 23 | 23 | 3 | 4 | −5 | 12 | 100 | 99 | 2 | −1 | 5 | 12 | 86 | 88 | 2 | 0 | −3 | 13 | 308 | 309 | 4 | 0 | −9 | 14 | 115 | 115 | 3 |
| −3 | 4 | 11 | 11 | 14 | 10 | 5 | −5 | 12 | 110 | 110 | 1 | 0 | 5 | 12 | 27 | 28 | 2 | 1 | −3 | 13 | 33 | 35 | 2 | 2 | −9 | 14 | 92 | 89 | 2 |
| −2 | 4 | 11 | 142 | 139 | 3 | −4 | −4 | 12 | 29 | 27 | 2 | 1 | 5 | 12 | 26 | 24 | 2 | 2 | −3 | 13 | 54 | 52 | 2 | 3 | −9 | 14 | 28 | 28 | 3 |
| −1 | 4 | 11 | 62 | 64 | 2 | −3 | −4 | 12 | 60 | 62 | 2 | 2 | 5 | 12 | 48 | 44 | 1 | 3 | −3 | 13 | 117 | 119 | 2 | −4 | −8 | 14 | 49 | 50 | 2 |
| 0 | 4 | 11 | 93 | 91 | 1 | −2 | −4 | 12 | 92 | 95 | 1 | −1 | 6 | 12 | 57 | 58 | 2 | 4 | −3 | 13 | 57 | 57 | 1 | −3 | −8 | 14 | 142 | 139 | 3 |
| 1 | 4 | 11 | 65 | 67 | 1 | −1 | −4 | 12 | 181 | 178 | 3 | 0 | 6 | 12 | 34 | 35 | 1 | −5 | −2 | 13 | 125 | 122 | 3 | −2 | −8 | 14 | 70 | 70 | 2 |
| 2 | 4 | 11 | 82 | 80 | 1 | 0 | −4 | 12 | 40 | 42 | 1 | 1 | 6 | 12 | 48 | 46 | 1 | −4 | −2 | 13 | 34 | 27 | 2 | −1 | −8 | 14 | 102 | 120 | 3 |
| 3 | 4 | 11 | 58 | 57 | 1 | 1 | −4 | 12 | 130 | 131 | 1 | 2 | 6 | 12 | 77 | 77 | 2 | −3 | −2 | 13 | 117 | 121 | 3 | 0 | −8 | 14 | 88 | 84 | 2 |
| 4 | 4 | 11 | 49 | 50 | 2 | 2 | −4 | 12 | 18 | 19 | 6 | −1 | 7 | 12 | 23 | 24 | 3 | −2 | −2 | 13 | 52 | 56 | 2 | 2 | −8 | 14 | 29 | 27 | 3 |
| −3 | 5 | 11 | 56 | 55 | 2 | 3 | −4 | 12 | 101 | 107 | 2 | 0 | 7 | 12 | 43 | 43 | 2 | −1 | −2 | 13 | 161 | 158 | 2 | 3 | −8 | 14 | 60 | 55 | 2 |
| −1 | 5 | 11 | 83 | 77 | 2 | 4 | −4 | 12 | 30 | 27 | 3 | −2 | −13 | 13 | 70 | 74 | 2 | 0 | −2 | 13 | 143 | 139 | 2 | 4 | −8 | 14 | 28 | 32 | 2 |
| 0 | 5 | 11 | 26 | 25 | 2 | 5 | −4 | 12 | 97 | 98 | 1 | −1 | −13 | 13 | 54 | 51 | 2 | 1 | −2 | 13 | 59 | 58 | 1 | −4 | −7 | 14 | 69 | 64 | 2 |
| 1 | 5 | 11 | 86 | 83 | 1 | −5 | −3 | 12 | 115 | 117 | 3 | 0 | −13 | 13 | 0 | 9 | 1 | 2 | −2 | 13 | 175 | 185 | 2 | −3 | −7 | 14 | 116 | 115 | 3 |
| 2 | 5 | 11 | 51 | 47 | 1 | −4 | −3 | 12 | 200 | 204 | 5 | −3 | −12 | 13 | 38 | 40 | 2 | 3 | −2 | 13 | 141 | 141 | 2 | −2 | −7 | 14 | 85 | 87 | 2 |
| 3 | 5 | 11 | 113 | 114 | 1 | −3 | −3 | 12 | 27 | 29 | 3 | −2 | −12 | 13 | 22 | 16 | 3 | 4 | −2 | 13 | 56 | 52 | 1 | 0 | −7 | 14 | 140 | 143 | 3 |
| −2 | 6 | 11 | 66 | 67 | 2 | −2 | −3 | 12 | 86 | 84 | 1 | −1 | −12 | 13 | 86 | 80 | 2 | −5 | −1 | 13 | 134 | 129 | 3 | 1 | −7 | 14 | 164 | 171 | 4 |
| −1 | 6 | 11 | 39 | 38 | 2 | −1 | −3 | 12 | 190 | 194 | 3 | 0 | −12 | 13 | 64 | 61 | 2 | −4 | −1 | 13 | 44 | 44 | 2 | 2 | −7 | 14 | 79 | 74 | 2 |
| 0 | 6 | 11 | 92 | 87 | 2 | 0 | −3 | 12 | 124 | 127 | 1 | −3 | −11 | 13 | 56 | 53 | 2 | −3 | −1 | 13 | 73 | 83 | 2 | 3 | −7 | 14 | 47 | 44 | 2 |
| 1 | 6 | 11 | 59 | 55 | 1 | 1 | −3 | 12 | 90 | 95 | 1 | −2 | −11 | 13 | 124 | 121 | 3 | −2 | −1 | 13 | 20 | 24 | 3 | 4 | −7 | 14 | 33 | 30 | 2 |
| 2 | 6 | 11 | 100 | 97 | 1 | 2 | −3 | 12 | 98 | 102 | 1 | −1 | −11 | 13 | 77 | 77 | 2 | −1 | −1 | 13 | 149 | 155 | 3 | −4 | −6 | 14 | 34 | 34 | 2 |
| −2 | 7 | 11 | 78 | 80 | 2 | 3 | −3 | 12 | 46 | 51 | 1 | 0 | −11 | 13 | 27 | 22 | 3 | 0 | −1 | 13 | 49 | 46 | 1 | −3 | −6 | 14 | 99 | 97 | 2 |
| −1 | 7 | 11 | 36 | 37 | 2 | 4 | −3 | 12 | 37 | 31 | 2 | 3 | −11 | 13 | 21 | 25 | 3 | 1 | −1 | 13 | 74 | 78 | 1 | −2 | −6 | 14 | 81 | 87 | 2 |
| 0 | 7 | 11 | 61 | 61 | 1 | 5 | −3 | 12 | 81 | 96 | 1 | −3 | −10 | 13 | 60 | 63 | 2 | 2 | −1 | 13 | 98 | 97 | 1 | −1 | −6 | 14 | 41 | 47 | 2 |
| 1 | 7 | 11 | 53 | 50 | 1 | −5 | −2 | 12 | 179 | 178 | 4 | −2 | −10 | 13 | 87 | 81 | 2 | 3 | −1 | 13 | 153 | 156 | 2 | 0 | −6 | 14 | 209 | 203 | 5 |
| −1 | 8 | 11 | 65 | 67 | 2 | −4 | −2 | 12 | 64 | 62 | 2 | −1 | −10 | 13 | 36 | 36 | 2 | 4 | −1 | 13 | 48 | 46 | 1 | 1 | −6 | 14 | 14 | 5 | 9 |
| −2 | −13 | 12 | 39 | 38 | 2 | −3 | −2 | 12 | 29 | 26 | 2 | 0 | −10 | 13 | 67 | 69 | 2 | −5 | 0 | 13 | 89 | 90 | 2 | 2 | −6 | 14 | 36 | 29 | 3 |
| −1 | −13 | 12 | 33 | 31 | 2 | −2 | −2 | 12 | 33 | 29 | 1 | 1 | −10 | 13 | 35 | 37 | 2 | −4 | 0 | 13 | 10 | 10 | 10 | 3 | −6 | 14 | 46 | 45 | 2 |
| 0 | −13 | 12 | 59 | 52 | 2 | −1 | −2 | 12 | 81 | 83 | 1 | 2 | −10 | 13 | 65 | 68 | 2 | −3 | 0 | 13 | 60 | 75 | 2 | 4 | −6 | 14 | 119 | 115 | 3 |
| −3 | −12 | 12 | 27 | 24 | 2 | 0 | −2 | 12 | 47 | 46 | 1 | 3 | −10 | 13 | 26 | 26 | 3 | −2 | 0 | 13 | 14 | 20 | 5 | −4 | −5 | 14 | 63 | 63 | 2 |
| −2 | −12 | 12 | 67 | 66 | 2 | 1 | −2 | 12 | 104 | 105 | 1 | −3 | −9 | 13 | 45 | 43 | 2 | −1 | 0 | 13 | 159 | 153 | 4 | −3 | −5 | 14 | 76 | 69 | 2 |
| −1 | −12 | 12 | 17 | 15 | 4 | 2 | −2 | 12 | 139 | 140 | 1 | −2 | −9 | 13 | 138 | 141 | 3 | 0 | 0 | 13 | 37 | 39 | 3 | −2 | −5 | 14 | 154 | 173 | 4 |
| 0 | −12 | 12 | 62 | 61 | 2 | 3 | −2 | 12 | 37 | 41 | 1 | −1 | −9 | 13 | 55 | 62 | 2 | 1 | 0 | 13 | 28 | 30 | 2 | 1 | −5 | 14 | 60 | 54 | 3 |
| −3 | −11 | 12 | 72 | 67 | 2 | 4 | −2 | 12 | 42 | 40 | 1 | 0 | −9 | 13 | 98 | 99 | 3 | 2 | 0 | 13 | 116 | 121 | 1 | 2 | −5 | 14 | 46 | 51 | 3 |
| −2 | −11 | 12 | 60 | 63 | 2 | 5 | −2 | 12 | 95 | 91 | 2 | 1 | −9 | 13 | 31 | 26 | 2 | 3 | 0 | 13 | 75 | 72 | 1 | 3 | −5 | 14 | 98 | 100 | 3 |
| −1 | −11 | 12 | 40 | 46 | 2 | −5 | −1 | 12 | 88 | 88 | 2 | 2 | −9 | 13 | 139 | 144 | 4 | 4 | 0 | 13 | 21 | 18 | 1 | 4 | −5 | 14 | 25 | 24 | 2 |
| −5 | −4 | 14 | 49 | 49 | 2 | 3 | 1 | 14 | 8 | 8 | 8 | 3 | −6 | 15 | 52 | 50 | 2 | 0 | 3 | 15 | 113 | 106 | 3 | −3 | −2 | 16 | 108 | 102 | 2 |
| −4 | −4 | 14 | 64 | 65 | 2 | −4 | 2 | 14 | 92 | 85 | 2 | −4 | −5 | 15 | 86 | 85 | 2 | 1 | 3 | 15 | 65 | 58 | 2 | −2 | −2 | 16 | 66 | 63 | 2 |
| −2 | −4 | 14 | 110 | 123 | 3 | −3 | 2 | 14 | 44 | 41 | 2 | −3 | −5 | 15 | 125 | 120 | 3 | −2 | −11 | 16 | 85 | 85 | 2 | −1 | −2 | 16 | 65 | 64 | 2 |
| −1 | −4 | 14 | 126 | 138 | 3 | −2 | 2 | 14 | 30 | 35 | 2 | −1 | −5 | 15 | 107 | 107 | 3 | −1 | −11 | 16 | 45 | 44 | 2 | 0 | −2 | 16 | 99 | 101 | 3 |
| 0 | −4 | 14 | 331 | 325 | 8 | −1 | 2 | 14 | 42 | 41 | 3 | 1 | −5 | 15 | 179 | 181 | 4 | −2 | −10 | 16 | 123 | 121 | 3 | 1 | −2 | 16 | 87 | 83 | 2 |
| 1 | −4 | 14 | 186 | 190 | 4 | 0 | 2 | 14 | 38 | 43 | 3 | 2 | −5 | 15 | 23 | 25 | 4 | −1 | −10 | 16 | 124 | 116 | 2 | 2 | −2 | 16 | 26 | 23 | 3 |
| 2 | −4 | 14 | 69 | 63 | 2 | 1 | 2 | 14 | 35 | 35 | 2 | 3 | −5 | 15 | 39 | 39 | 2 | 0 | −10 | 16 | 21 | 17 | 3 | 3 | −2 | 16 | 34 | 35 | 2 |

TABLE 7-continued

Observed and calculated structure factors for NEL

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 3 | −4 | 14 | 41 | 40 | 2 | 2 | 2 | 14 | 38 | 37 | 1 | −4 | −4 | 15 | 46 | 43 | 2 | −3 | −9 | 16 | 55 | 58 | 2 | −3 | −1 | 16 | 44 | 44 | 2 |
| 4 | −4 | 14 | 80 | 77 | 1 | −1 | 3 | 14 | 34 | 29 | 3 | −3 | −4 | 15 | 71 | 73 | 2 | −2 | −9 | 16 | 69 | 65 | 2 | −2 | −1 | 16 | 39 | 40 | 2 |
| −5 | −3 | 14 | 10 | 15 | 10 | 0 | 3 | 14 | 22 | 18 | 3 | −1 | −4 | 15 | 87 | 87 | 2 | −1 | −9 | 16 | 42 | 37 | 2 | 0 | −1 | 16 | 130 | 127 | 3 |
| −4 | −3 | 14 | 58 | 56 | 2 | 1 | 3 | 14 | 64 | 61 | 1 | 0 | −4 | 15 | 46 | 44 | 2 | 0 | −9 | 16 | 36 | 31 | 2 | 1 | −1 | 16 | 49 | 45 | 2 |
| −3 | −3 | 14 | 196 | 197 | 4 | 2 | 3 | 14 | 61 | 54 | 1 | 2 | −4 | 15 | 41 | 42 | 2 | −3 | −8 | 16 | 53 | 44 | 2 | 2 | −1 | 16 | 73 | 69 | 2 |
| −1 | −3 | 14 | 121 | 125 | 3 | −1 | 4 | 14 | 80 | 82 | 2 | 3 | −4 | 15 | 57 | 54 | 2 | −2 | −8 | 16 | 62 | 61 | 2 | 0 | 0 | 16 | 128 | 125 | 3 |
| 0 | −3 | 14 | 238 | 244 | 5 | 0 | 4 | 14 | 41 | 38 | 1 | −4 | −3 | 15 | 54 | 53 | 2 | −1 | −8 | 16 | 20 | 22 | 3 | 1 | 0 | 16 | 94 | 91 | 2 |
| 1 | −3 | 14 | 228 | 227 | 5 | 1 | 4 | 14 | 16 | 12 | 3 | −3 | −3 | 15 | 9 | 13 | 8 | 0 | −8 | 16 | 61 | 57 | 2 | 0 | 1 | 16 | 59 | 59 | 2 |
| 2 | −3 | 14 | 145 | 149 | 6 | 0 | 5 | 14 | 39 | 49 | 2 | −2 | −3 | 15 | 106 | 121 | 3 | 2 | −8 | 16 | 67 | 64 | 2 | 1 | 1 | 16 | 17 | 21 | 3 |
| 3 | −3 | 14 | 19 | 18 | 3 | −1 | −12 | 15 | 74 | 67 | 2 | −1 | −3 | 15 | 199 | 198 | 5 | −4 | −7 | 16 | 59 | 59 | 2 | 0 | 2 | 16 | 38 | 37 | 2 |
| 4 | −3 | 14 | 69 | 67 | 2 | −2 | −11 | 15 | 30 | 27 | 2 | 1 | −3 | 15 | 62 | 58 | 2 | −3 | −7 | 16 | 38 | 35 | 2 | −1 | −10 | 17 | 26 | 20 | 2 |
| −5 | −2 | 14 | 22 | 21 | 3 | −1 | −11 | 15 | 95 | 87 | 2 | 2 | −3 | 15 | 83 | 75 | 2 | −2 | −7 | 16 | 93 | 86 | 2 | −2 | −9 | 17 | 68 | 64 | 2 |
| −4 | −2 | 14 | 20 | 16 | 3 | 0 | −11 | 15 | 41 | 37 | 2 | 3 | −3 | 15 | 84 | 81 | 2 | −1 | −7 | 16 | 107 | 106 | 2 | −1 | −9 | 17 | 49 | 49 | 2 |
| −3 | −2 | 14 | 69 | 76 | 2 | −3 | −10 | 15 | 105 | 100 | 2 | −4 | −2 | 15 | 59 | 55 | 2 | 0 | −7 | 16 | 30 | 33 | 2 | −3 | −8 | 17 | 18 | 18 | 3 |
| −1 | −2 | 14 | 91 | 88 | 2 | −2 | −10 | 15 | 61 | 62 | 2 | −3 | −2 | 15 | 39 | 39 | 2 | 2 | −7 | 16 | 23 | 25 | 3 | −2 | −8 | 17 | 30 | 30 | 2 |
| 0 | −2 | 14 | 226 | 229 | 4 | −1 | −10 | 15 | 49 | 46 | 2 | −2 | −2 | 15 | 72 | 75 | 2 | 3 | −7 | 16 | 74 | 76 | 2 | −1 | −8 | 17 | 76 | 75 | 2 |
| 1 | −2 | 14 | 95 | 93 | 2 | 0 | −10 | 15 | 57 | 56 | 2 | −1 | −2 | 15 | 87 | 83 | 2 | −4 | −6 | 16 | 58 | 62 | 2 | −3 | −7 | 17 | 14 | 16 | 4 |
| 2 | −2 | 14 | 103 | 108 | 1 | 2 | −10 | 15 | 60 | 60 | 2 | 0 | −2 | 15 | 51 | 47 | 2 | −3 | −6 | 16 | 34 | 34 | 2 | −2 | −7 | 17 | 29 | 30 | 2 |
| 3 | −2 | 14 | 46 | 44 | 1 | −3 | −9 | 15 | 54 | 52 | 2 | 1 | −2 | 15 | 76 | 74 | 2 | −2 | −6 | 16 | 18 | 14 | 3 | −1 | −7 | 17 | 17 | 17 | 3 |
| 4 | −2 | 14 | 43 | 46 | 1 | −2 | −9 | 15 | 112 | 107 | 3 | 3 | −2 | 15 | 56 | 54 | 2 | −1 | −6 | 16 | 92 | 90 | 2 | −3 | −6 | 17 | 24 | 19 | 2 |
| −5 | −1 | 14 | 25 | 24 | 2 | −1 | −9 | 15 | 55 | 56 | 2 | −4 | −1 | 15 | 29 | 28 | 2 | 0 | −6 | 16 | 120 | 118 | 3 | −2 | −6 | 17 | 69 | 68 | 2 |
| −4 | −1 | 14 | 11 | 19 | 10 | 0 | −9 | 15 | 65 | 60 | 2 | −3 | −1 | 15 | 73 | 75 | 2 | 1 | −6 | 16 | 42 | 42 | 3 | −1 | −6 | 17 | 104 | 108 | 2 |
| −3 | −1 | 14 | 109 | 116 | 3 | 2 | −9 | 15 | 34 | 37 | 3 | −2 | −1 | 15 | 96 | 96 | 2 | 2 | −6 | 16 | 89 | 87 | 2 | 2 | −6 | 17 | 78 | 78 | 2 |
| −2 | −1 | 14 | 95 | 101 | 2 | 3 | −9 | 15 | 43 | 43 | 2 | −1 | −1 | 15 | 71 | 69 | 2 | 3 | −6 | 16 | 42 | 41 | 2 | −3 | −5 | 17 | 19 | 17 | 3 |
| −1 | −1 | 14 | 7 | 7 | 6 | −4 | −8 | 15 | 107 | 102 | 2 | 0 | −1 | 15 | 40 | 38 | 3 | −4 | −5 | 16 | 52 | 53 | 2 | −2 | −5 | 17 | 37 | 34 | 2 |
| 0 | −1 | 14 | 50 | 51 | 3 | −3 | −8 | 15 | 91 | 86 | 2 | 1 | −1 | 15 | 92 | 98 | 2 | −3 | −5 | 16 | 87 | 88 | 2 | −1 | −5 | 17 | 59 | 60 | 2 |
| 1 | −1 | 14 | 69 | 72 | 1 | −2 | −8 | 15 | 82 | 78 | 2 | 2 | −1 | 15 | 64 | 64 | 1 | −2 | −5 | 16 | 57 | 56 | 2 | 1 | −5 | 17 | 37 | 36 | 3 |
| 2 | −1 | 14 | 57 | 60 | 1 | −1 | −8 | 15 | 33 | 27 | 2 | 3 | −1 | 15 | 34 | 33 | 2 | −1 | −5 | 16 | 46 | 46 | 2 | 2 | −5 | 17 | 43 | 39 | 2 |
| 3 | −1 | 14 | 26 | 24 | 2 | 0 | −8 | 15 | 122 | 122 | 3 | −4 | 0 | 15 | 0 | 9 | 1 | 1 | −5 | 16 | 96 | 96 | 3 | −3 | −4 | 17 | 10 | 9 | 9 |
| 4 | −1 | 14 | 20 | 27 | 2 | 2 | −8 | 15 | 42 | 44 | 2 | −3 | 0 | 15 | 32 | 28 | 2 | 2 | −5 | 16 | 26 | 20 | 3 | −2 | −4 | 17 | 52 | 51 | 2 |
| −5 | 0 | 14 | 74 | 67 | 2 | 3 | −8 | 15 | 89 | 85 | 2 | −2 | 0 | 15 | 127 | 131 | 3 | 3 | −5 | 16 | 40 | 35 | 2 | −1 | −4 | 17 | 17 | 16 | 4 |
| −4 | 0 | 14 | 68 | 66 | 2 | −4 | −7 | 15 | 40 | 40 | 2 | 0 | 0 | 15 | 26 | 26 | 3 | −4 | −4 | 16 | 23 | 26 | 3 | 1 | −4 | 17 | 48 | 46 | 2 |
| −3 | 0 | 14 | 111 | 111 | 3 | −3 | −7 | 15 | 67 | 69 | 2 | 1 | 0 | 15 | 10 | 7 | 9 | −3 | −4 | 16 | 56 | 56 | 2 | 2 | −4 | 17 | 50 | 51 | 2 |
| −2 | 0 | 14 | 98 | 101 | 2 | −2 | −7 | 15 | 58 | 58 | 2 | 2 | 0 | 15 | 55 | 56 | 1 | −2 | −4 | 16 | 21 | 22 | 3 | −3 | −3 | 17 | 32 | 34 | 2 |
| −1 | 0 | 14 | 46 | 46 | 2 | −1 | −7 | 15 | 50 | 52 | 2 | 3 | 0 | 15 | 34 | 40 | 2 | −1 | −4 | 16 | 98 | 96 | 2 | −2 | −3 | 17 | 13 | 7 | 6 |
| 0 | 0 | 14 | 87 | 86 | 2 | 0 | −7 | 15 | 55 | 54 | 2 | −4 | 1 | 15 | 23 | 27 | 3 | 1 | −4 | 16 | 46 | 43 | 2 | 1 | −3 | 17 | 40 | 35 | 2 |
| 1 | 0 | 14 | 64 | 63 | 1 | 2 | −7 | 15 | 128 | 127 | 3 | −2 | 1 | 15 | 7 | 11 | 6 | 2 | −4 | 16 | 37 | 31 | 2 | 2 | −3 | 17 | 49 | 48 | 2 |
| 2 | 0 | 14 | 125 | 128 | 2 | 3 | −7 | 15 | 35 | 31 | 2 | 0 | 1 | 15 | 37 | 36 | 3 | 3 | −4 | 16 | 0 | 10 | 1 | −2 | −2 | 17 | 50 | 49 | 2 |
| 3 | 0 | 14 | 11 | 10 | 6 | −4 | −6 | 15 | 110 | 107 | 2 | 1 | 1 | 15 | 72 | 65 | 1 | −4 | −3 | 16 | 72 | 71 | 2 | 2 | −2 | 17 | 63 | 61 | 2 |
| −4 | 1 | 14 | 57 | 52 | 2 | −3 | −6 | 15 | 86 | 84 | 2 | 2 | 1 | 15 | 45 | 47 | 1 | −3 | −3 | 16 | 15 | 14 | 5 | 0 | 0 | 17 | 30 | 35 | 3 |
| −3 | 1 | 14 | 43 | 42 | 2 | −2 | −6 | 15 | 38 | 42 | 2 | −1 | 2 | 15 | 50 | 51 | 2 | −2 | −3 | 16 | 35 | 32 | 2 | −2 | −6 | 18 | 12 | 11 | 6 |
| −2 | 1 | 14 | 114 | 117 | 3 | −1 | −6 | 15 | 27 | 24 | 2 | 0 | 2 | 15 | 110 | 103 | 3 | −1 | −3 | 16 | 51 | 51 | 2 | | | | | | |
| 0 | 1 | 14 | 55 | 53 | 2 | 0 | −6 | 15 | 158 | 158 | 4 | 1 | 2 | 15 | 58 | 60 | 1 | 2 | −3 | 16 | 59 | 60 | 2 | | | | | | |
| 1 | 1 | 14 | 69 | 69 | 1 | 1 | −6 | 15 | 66 | 68 | 2 | 2 | 2 | 15 | 21 | 21 | 2 | 3 | −3 | 16 | 26 | 29 | 3 | | | | | | |
| 2 | 1 | 14 | 85 | 82 | 1 | 2 | −6 | 15 | 46 | 52 | 2 | −1 | 3 | 15 | 48 | 48 | 2 | −4 | −2 | 16 | 28 | 28 | 2 | | | | | | |

EXAMPLE 3

Synthesis of NEL

The preparation of NEL having the basic structure I can be accomplished by a common general method, i.e. the condensation of a bicyclic Windaus-Grundmann type ketone II with the allylic phosphine oxide III to the corresponding 2-methylene-19-nor-vitamin D analog IV followed by deprotection at C-1, C-3 and C-25 in the latter compound IV to obtain compound I, i.e. NEL.

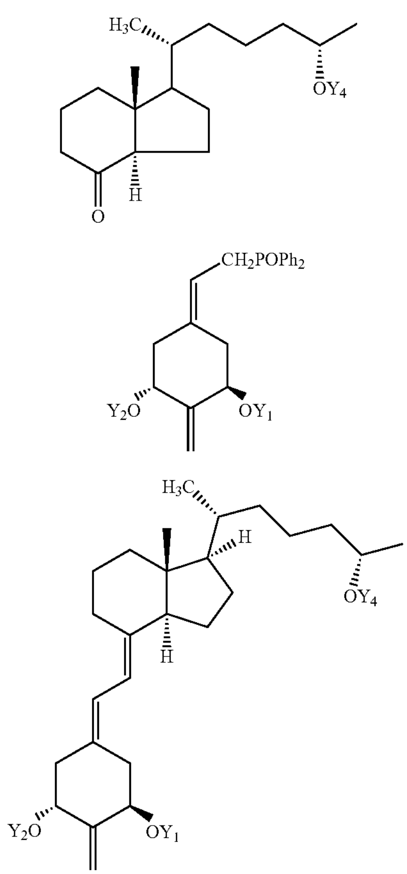

In ketone II, $Y_4$ is preferably a hydroxy-protecting group such as a silyl protecting group. The t-butyldimethyl-silyl (TBDMS) group is an example of a particularly useful hydroxy-protecting group. In phosphine oxide III, $Y_1$ and $Y_2$ are preferably hydroxy-protecting groups such as silyl protecting groups. The t-butyldimethylsilyl (TMDMS) group is an example of a particularly useful hydroxy-protecting group. The process described above represents an application of the convergent synthesis concept, which has been applied effectively to the preparation of numerous vitamin D compounds (see Lythgoe et al., *J. Chem. Soc. Perkin Trans. I,* 590 (1978); Lythgoe, *Chem. Soc. Rev.* 9, 449 (1983); Toh et al., *J. Org. Chem.* 48, 1414 (1983); Baggiolini et al., *J. Org. Chem.* 51, 3098 (1986); Sardina et al., *J. Org. Chem.* 51, 1264 (1986); *J. Org. Chem.* 51, 1269 (1986); DeLuca et al., U.S. Pat. No. 5,086,191; DeLuca et al., U.S. Pat. No. 5,536,713; and DeLuca et al, U.S. Pat. No. 5,843,928 all of which are hereby incorporated by reference in their entirety and for all purposes as if fully set forth herein.

Phosphine oxide III is a convenient reagent that can be used to prepare a large number of 19-nor-vitamin D compounds and is prepared according to the procedures described by Sicinski et al., *J. Med. Chem.,* 41, 4662 (1998), DeLuca et al., U.S. Pat. No. 5,843,928; Perlman et al., *Tetrahedron Lett.* 32, 7663 (1991); and DeLuca et al., U.S. Pat. No. 5,086,191 which, are hereby incorporated by reference in their entirety as if fully set forth herein.

The overall process of the synthesis of compound I is illustrated and described more completely in U.S. Pat. No. 5,843,928 entitled "2-Alkylidene-19-Nor-Vitamin D Compounds" and in U.S. Pat. No. 7,528,122 entitled "Vitamin D Analog—NEL, Methods and Uses Thereof," the specifications of which are specifically incorporated herein by reference.

We claim:

1. (20R,25S)-2-methylene-19,26-dinor-1α,25-dihydroxyvitamin $D_3$ in crystalline form.

2. The crystalline form of (20R,25S)-2-methylene-19,26-dinor-1α,25-dihydroxyvitamin $D_3$ having molecular packing arrangement defined by space group P1 and unit cell dimensions a=6.4 Å, b=12.6 Å, c=16.0 Å, α=110.9°, β=95.3° and γ=90.6°.

3. A three dimensional structure for (20R,25S)-2-methylene-19,26-dinor-1α,25-dihydroxyvitamin $D_3$ as defined by the molecular packing arrangement set forth in claim 2.

4. A method of purifying (20R,25S)-2-methylene-19,26-dinor, 1α,25-dihydroxyvitamin $D_3$, comprising the steps of:

(a) preparing a solvent comprising water and methanol;

(b) dissolving a product containing (20R,25S)-2-methylene-19,26-dinor-1α,25-dihydroxyvitamin $D_3$ to be purified in said solvent;

(c) cooling said solvent and dissolved product below ambient temperature for a sufficient amount of time to form a precipitate of (20R,25S)-2-methylene-19,26-dinor-1α,25-dihydroxyvitamin $D_3$ crystals; and (d) separating the (20R,25S)-2-methylene-19,26-dinor-1α,25-dihydroxyvitamin $D_3$ crystals from the solvent.

5. The method of claim 4 including the further step of maintaining said solvent and dissolved product at ambient temperature for a period of time prior to cooling below ambient temperature.

6. The method of claim 4 wherein said solvent comprises 20% water and 80% methanol, by volume.

7. The method of claim 4 wherein said solvent and dissolved product are cooled to about −20° C.

8. The method of claim 4 wherein the step of separating comprises filtering the solvent and precipitate to obtain the crystals.

9. The method of claim 4 including a further step (e) comprising repeating steps (a) through (d) using the recovered crystals from step (d) as the product of step (b).

10. The method of claim 7 wherein said solvent and dissolved product are maintained at −20° C. for up to 7 weeks.

11. A method of purifying (20R,25S)-2-methylene-19,26-dinor-1α,25-dihydroxyvitamin $D_3$, comprising the steps of (a) preparing a solvent comprising 80% methanol and 20% water, by volume;

(b) dissolving a product containing (20R,25S)-2-methylene-19,26-dinor-1α,25-dihydroxyvitamin $D_3$ to be purified in said solvent;

(c) cooling said solvent and dissolved product below ambient temperature for a sufficient amount of time to form a precipitate of (20R,25S)-2-methylene-19,26-dinor-1α,25-dihydroxyvitamin $D_3$ crystals; and (d) recovering the (20R,25S)-2-methylene-19,26-dinor-1α,25-dihydroxyvitamin $D_3$ crystals having a molecular packing arrangement defined by space group P1 and unit cell dimensions a=6.4 Å, b=12.6 Å c=16.0 Å, α=110.9°, β=95.3° and γ=90.6°, or any other space group that yields substantially the same crystalline packing arrangement.

12. The method of claim 11 wherein said solvent and dissolved product is maintained at ambient temperature for a period of time prior to cooling below ambient temperature.

13. The method of claim 11 wherein said solvent and dissolved product are cooled to about −20° C.

14. The method of claim 13 wherein said solvent and dissolved product are maintained at about −20° C. for up to 7 weeks.

15. The method of claim 11 wherein the step of recovering comprises filtering.

16. The method of claim 11 further including the step of (e) repeating steps (a) through (d) using the recovered crystals from step (d) as the product of step (b).

* * * * *